United States Patent
Gallego et al.

(10) Patent No.: US 11,142,525 B2
(45) Date of Patent: Oct. 12, 2021

(54) AZALACTAM COMPOUNDS AS HPK1 INHIBITORS

(71) Applicant: Pfizer Inc., New York, NY (US)

(72) Inventors: Rebecca Anne Gallego, San Diego, CA (US); Sajiv Krishnan Nair, Vista, CA (US); Robert Steven Kania, Del Mar, CA (US); Omar Khaled Ahmad, Cambridge, MA (US); Ted William Johnson, Carlsbad, CA (US); Jamison Bryce Tuttle, Marblehead, MA (US); Mehran Jalaie, San Diego, CA (US); Michele Ann McTigue, Encinitas, CA (US); Dahui Zhou, Groton, CT (US); Matthew L. Del Bel, San Diego, CA (US); Ru Zhou, Carlsbad, CA (US); Mingying He, San Diego, CA (US); Anne-Marie Dechert Schmitt, Westerly, RI (US)

(73) Assignee: PFIZER INC., New York, NY (US)

( * ) Notice: Subject to any disclaimer, the term of this patent is extended or adjusted under 35 U.S.C. 154(b) by 30 days.

(21) Appl. No.: 16/679,820

(22) Filed: Nov. 11, 2019

(65) Prior Publication Data
US 2020/0172539 A1    Jun. 4, 2020

Related U.S. Application Data

(60) Provisional application No. 62/909,970, filed on Oct. 3, 2019, provisional application No. 62/767,602, filed on Nov. 15, 2018.

(51) Int. Cl.
*C07D 471/04*    (2006.01)
*A61P 35/00*    (2006.01)

(52) U.S. Cl.
CPC ............ *C07D 471/04* (2013.01); *A61P 35/00* (2018.01)

(58) Field of Classification Search
CPC ................................ C07D 471/04; A61P 35/00
See application file for complete search history.

(56) References Cited

U.S. PATENT DOCUMENTS

2011/0230482 A1    9/2011    Zhang et al.

FOREIGN PATENT DOCUMENTS

| WO | 2018/049324 | 3/2018 |
|---|---|---|
| WO | 2018/167147 | 9/2018 |
| WO | 2019/015559 | 1/2019 |
| WO | 2019/148005 | 8/2019 |

*Primary Examiner* — John M Mauro
(74) *Attorney, Agent, or Firm* — Pfizer Inc.

(57) ABSTRACT

This invention relates to compounds of general Formula (I)

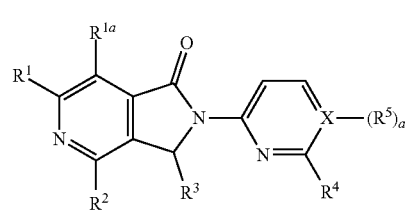

and pharmaceutically acceptable salts thereof, in which $R^1$, $R^{1a}$, $R^2$, $R^3$, $R^4$, and $(R^5)_a$ are as defined herein, to pharmaceutical compositions comprising such compounds and pharmaceutically acceptable salts thereof, and to methods of using such compounds, pharmaceutically acceptable salts and compositions for the treatment of abnormal cell growth, including cancer.

40 Claims, No Drawings

AZALACTAM COMPOUNDS AS HPK1 INHIBITORS

CROSS-REFERENCE TO RELATED APPLICATIONS

This application claims the benefits of U.S. Provisional Application No. 62/767,602 filed Nov. 15, 2018, and U.S. Provisional Application No. 62/909,970 filed Oct. 3, 2019, which are both hereby incorporated by reference in their entireties.

FIELD OF THE INVENTION

The present invention relates to compounds of Formulae I, II, or III, and their pharmaceutically acceptable salts, to pharmaceutical compositions comprising such compounds and salts, and to the uses thereof. The compounds, salts and compositions of the present invention are useful for treating or ameliorating abnormal cell proliferative disorders, such as cancer.

BACKGROUND

Hematopoietic progenitor kinase 1 (HPK1), also known as mitogen activated protein kinase kinase kinase kinase 1 (MAP4K1), is a member of the mammalian Ste20-like family of serine/threonine kinases that operates via the JNK and ERK signalling pathways. HPK1 is mainly expressed in hematopoietic organs and cells (e.g., T-cells, B-cells, and dendritic cells), suggesting potential involvement of HPK1 in the regulation of signaling in hematopoietic lineages, including lymphocytes. (Shui, et al, "Hematoppietic progenitor kinase 1 negatively regulates T cell receptor signaling and T cell-mediated immune responses", Nature Immunology 8, 84-91 (2006)).

For example, upon activation of T-Cell Receptor (TCR), HPK1 kinase is employed to the plasma membrane resulting in full kinase activation. This full kinase activation leads to HPK1 phosphorylation of adaptor protein SLP76 ultimately leading to the destabilization of the TCR signaling complex which impedes downstream mitogen-activated protein (MAP) kinase signaling events necessary for T-cell activation and proliferation. (Hernandez, et al., "The kinase activity of hematopoietic progenitor kinase 1 is essential for the regulation of T cell function", Open Cell Reports 25, 80-94, Oct. 2, 2018). HPK1 kinase has also been shown to negatively regulate T-cell signaling by the $PGE_2$ receptor in a PKA-dependent manner. Furthermore, HPK1 kinase has been reported to play roles in: i) activation-induced cell death (AICD) and JNK activation; ii) regulation of leukocyte function-associated antigen-1 (LFA-1) integrin activation on T-cells by direct competition with adhesion and degranulation promoting adaptor protein (ADAP) for binding of the SLP76 SH2-domain; and iii) regulation of activation via nuclear factor κB (NF-κB) signaling by interacting with IKK-α and -ß. Studies have also shown HPK1 negatively regulates MAP kinase pathway signaling and Ap-1 transcription in T-cells. (Hernandez, et al. 2018).

The research conducted to date on HPK1 kinases suggests that HPK1 plays a role in enhancing T-cell responses and heightening anti-tumor immunity.

SUMMARY

The present invention provides, in part, compounds of Formulae I, II, and III, and pharmaceutically acceptable salts thereof. Such compounds can inhibit the activity of HPK1 kinase, thereby effecting biological functions. Also provided are pharmaceutical compositions and medicaments, comprising the compounds or salts of the invention, alone or in combination with additional anticancer therapeutic agents or palliative agents.

The present invention also provides, in part, methods for preparing the compounds, pharmaceutically acceptable salts and compositions of the invention, and methods of using the foregoing.

In one embodiment, the invention provides a compound of Formula I:

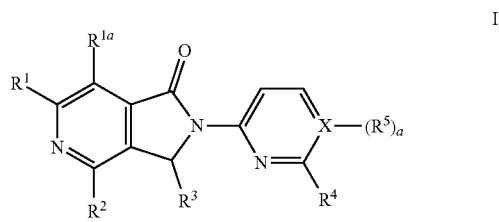

or a pharmaceutically acceptable salt thereof, wherein:

$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, —N$(R^6)(R^7)$, and $(C_3-C_6)$cycloalkyl, wherein said $(C_1-C_6)$alkyl, halo$(C_1-C_6)$alkyl, and $(C_3-C_6)$cycloalkyl are optionally substituted with one to three substituents selected from the group consisting of halogen, hydroxy, cyano, $(C_1-C_6)$alkyl, and $(C_1-C_6)$alkoxy;

$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl, and halo$(C_1-C_6)$alkyl are optionally substituted with one to three substituents selected from the group consisting of halogen, hydroxy, cyano, $(C_1-C_6)$alkyl, and $(C_1-C_6)$alkoxy;

$R^{1a}$ is selected from the group consisting of hydrogen and halogen;

$R^2$ is:
i) —$(CH_2)_m$N$(R^8)(R^9)$, wherein m is an integer selected from 0, 1, 2, or 3, and $R^8$ and $R^9$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^8$ and $R^9$ taken together with the nitrogen to which they are attached form a (4- to 6-membered) heterocycloalkyl that is optionally substituted with one to three substituents selected from the group consisting of halogen, hydroxy, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy;

ii) $(C_1-C_6)$alkyl, wherein said $(C_1-C_6)$alkyl is optionally substituted with 1 to 3 substituents selected from the group consisting of halogen, $(C_1-C_6)$alkoxy, $-N(R^6)$$(R^7)$, cyano, and hydroxy, wherein $R^6$ and $R^7$ are each independently selected from the group consisting of hydrogen and $(C_1-C_6)$alkyl; or iii) a (4- to 6-membered)heterocycloalkyl, wherein said heterocycloalkyl is optionally substituted with one to three substituents selected from the group consisting of halogen, hydroxy, cyano, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy;

$R^3$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy;

X is carbon or nitrogen;

$R^4$ is a (4- to 6-membered)heterocycloalkyl or a (5- to 10-membered)heteroaryl, wherein said (4- to 6-membered) heterocycloalkyl and (5- to 10-membered)heteroaryl are optionally substituted with 1 to 3 substituents selected from the group consisting of halogen, cyano, oxo, hydroxy, $-N(R^{10})(R^{11})$, $(C_1-C_6)$alkyl, halo$(C_1-C_6)$alkyl, $(C_1-C_6)$alkoxy, halo$(C_1-C_6)$alkoxy, and $-(CH_2)_n(C_3-C_6)$cycloalkyl, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy, and wherein n is an integer selected from 0, 1, or 2; and wherein $R^{10}$ and $R^{11}$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy;

$R^5$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy; and a is an integer selected from 0 or 1, provided that when X is nitrogen a is 0.

In another embodiment, the invention provides a pharmaceutical composition comprising a compound of any one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof.

In another embodiment, the invention provides a method for the treatment of abnormal cell growth, in particular cancer, in a subject in need thereof, comprising administering to the subject a therapeutically effective amount of a compound of the invention, or a pharmaceutically acceptable salt thereof. Compounds of the invention may be administered as single agents, or may be administered in combination with other anti-cancer therapeutic agents, in particular standard of care agents appropriate for the particular cancer.

In a further embodiment, the invention provides a method for the treatment of abnormal cell growth, in particular cancer, in a subject in need thereof, comprising administering to the subject an amount of a compound of the invention, or a pharmaceutically acceptable salt thereof, in combination with an amount of an additional anti-cancer therapeutic agent, which amounts are together effective in treating said abnormal cell growth.

In another embodiment, the invention relates to a compound of the invention, or a pharmaceutically acceptable salt thereof, for use as a medicament, in particular a medicament for treatment of cancer.

In another embodiment, the invention relates to a compound of the invention, or a pharmaceutically acceptable salt thereof, for use in the treatment of abnormal cell growth, in particular cancer, in a subject.

In a further embodiment, the invention provides the use of a compound of the invention, or a pharmaceutically acceptable salt thereof, for the treatment of abnormal cell growth, in particular cancer, in a subject.

In another embodiment, the invention relates to a pharmaceutical composition for use in the treatment of abnormal cell growth in a subject in need thereof, which composition comprises a compound of the invention, or a pharmaceutically acceptable salt thereof, and a pharmaceutically acceptable carrier or excipient.

In yet another embodiment, the invention provides the use of a compound of any one of the formulae described herein, or a pharmaceutically acceptable salt thereof, for the preparation of a medicament for the treatment of abnormal cell growth in a subject.

In frequent embodiments of the foregoing compounds, methods and uses, the abnormal cell growth is cancer.

In some embodiments, the methods and uses provided result in one or more of the following effects: (1) inhibiting cancer cell proliferation; (2) inhibiting cancer cell invasiveness; (3) inducing apoptosis of cancer cells; (4) inhibiting cancer cell metastasis; (5) inhibiting angiogenesis; (6) enhancing T-cell responses; or (7) heightening of anti-tumor activity.

In another embodiment, the invention provides a method for the treatment of HPK1-dependent disorders and enhancing an immune response in a subject, comprising administering to the subject a compound of the invention, or a pharmaceutically acceptable salt thereof, in an amount that is effective for treating said disorder, in particular cancer. In some embodiments, the disorder is cancer that is characterized by amplification or overexpression of HPK1 kinase.

In some embodiments, the methods and uses described herein further comprise administering to the subject an amount of an additional anticancer therapeutic agent or a palliative agent, which amounts are together effective in treating said abnormal cell growth. Each of the embodiments of the compounds of the present invention described below can be combined with one or more other embodiments of the compounds of the present invention described herein not inconsistent with the embodiment(s) with which it is combined.

It is to be understood that both the foregoing general description and the following detailed description are exemplary and explanatory only and are not restrictive of the invention, as claimed.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein.

DETAILED DESCRIPTION

Definitions and Exemplifications

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl ring.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 6-membered heteroaryl group" is specifically intended to include any 5-, 6-membered heteroaryl group.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount. For example, a compound of the present invention may decrease HPK1 activity by at least about 2.5% to about 100%, from about 10% to about 90%, from about 20% to about 70%, from about 30% to about 60%, from about 40% to about 50% compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

The term "$(C_1-C_6)$alkyl", as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl. The $(C_1-C_6)$alkyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl. For example, a $(C_1-C_6)$alkyl moiety can be substituted with one or more halogen atoms to form a "halo$(C_1-C_6)$alkyl". Representative examples of a halo$(C_1-C_6)$alkyl include, but are not limited to, fluoromethyl, 2-fluoroethyl, difluoromethyl, trifluoromethyl, and pentafluoroethyl. Other representative examples of a substituted $(C_1-C_6)$alkyl include, but are not limited to cyanobutyl and ethoxyethyl.

The term "halo$(C_1-C_6)$alkyl" as used herein, refers to a $(C_1-C_6)$alkyl group as defined above wherein the alkyl group is substituted with one or more halogen atoms. For example, a halo$(C_1-C_6)$alkyl may be selected from fluoromethyl, fluoroethyl, difluoromethyl, difluoroethyl, trifluoromethyl, trifluoroethyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $(C_2-C_6)$alkenyl group, the compound may exist as the pure E (entgegen) form, the pure Z (zusammen) form, or any mixture thereof. The $(C_2-C_6)$alkenyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl. The $(C_2-C_6)$alkynyl can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy. The $(C_1-C_6)$alkoxy can be optionally substituted in which one or more hydrogen atoms are replaced by a substituent selected from the group consisting of halogen, cyano, hydroxy, —$SF_5$, nitro, —$(C_1-C_6)$alkoxy, and —$N(R^6)(R^7)$, in which $R^6$ and $R^7$ are each independently selected from hydrogen and $(C_1-C_6)$alkyl. For example, a $(C_1-C_6)$alkoxy can be substituted with one or more halogen atoms to form a "halo$(C_1-C_6)$alkoxy". Representative examples of a halo$(C_1-C_6)$alkoxy include, but are not limited to, fluoromethoxy, difluoromethoxy, 2-fluoroethoxy, trifluoromethoxy, and pentafluoroethoxy.

The term "halo$(C_1-C_6)$alkoxy" as used herein, refers to a $(C_1-C_6)$alkoxy group as defined above wherein the alkoxy group is substituted with one or more halogen atoms. For example, a halo$(C_1-C_6)$alkoxy may be selected from fluoromethoxy, fluoroethoxy, difluoromethoxy, difluoroethoxy, trifluoromethoxy, trifluoroethoxy.

The term "($C_1$-$C_6$)alkythio", as used herein, refers to a ($C_1$-$C_6$)alkyl group, as defined above, attached to the parent molecular moiety through a sulfur atom. Representative examples of a ($C_1$-$C_6$)alkylthio include, but are not limited to, methylthio, ethylthio, propylthio, and the like.

The ($C_1$-$C_6$)alkythio can be optionally substituted in which one or more hydrogen atoms are replaced by a substituent selected from the group consisting of halogen, cyano, hydroxy, —$SF_5$, nitro, —($C_1$-$C_6$)alkoxy, and —N($R^6$)($R^7$), in which $R^6$ and $R^7$ are each independently selected from hydrogen and ($C_1$-$C_6$)alkyl.

As used herein, the term "($C_3$-$C_6$)cycloalkyl" refers to a carbocyclic substituent obtained by removing hydrogen from a saturated carbocyclic molecule having from 3 to 6 carbon atoms.

A "cycloalkyl' may be a monocyclic ring, examples of which include cyclopropyl, cyclobutyl, cyclopentyl, and cyclohexyl. The ($C_3$-$C_6$)cycloalkyl can be optionally substituted in which one or more hydrogen atoms are replaced by a substituent selected from the group consisting of halogen, cyano, hydroxy, —$SF_5$, nitro, —($C_1$-$C_6$)alkoxy, and —N($R^6$)($R^7$), in which $R^6$ and $R^7$ are each independently selected from hydrogen and ($C_1$-$C_6$)alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered)heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. The heterocycloalkyl substituent may be attached via a nitrogen atom having the appropriate valence, or via any ring carbon atom. The heterocycloalkyl moiety may be optionally substituted with one or more substituents at a nitrogen atom having the appropriate valence, or at any available carbon atom.

Examples of heterocycloalkyl rings include, but are not limited to, azetidinyl, dihydrofuranyl, dihydrothiophenyl, tetrahydrothiophenyl, tetrahydrofuranyl, tetrahydro-triazinyl, tetrahydropyrazolyl, tetrahydrooxazinyl, tetrahydropyrimidinyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, 2-oxo-piperidinyl (e.g., 2-oxo-piperidin-1-yl), azabicyclo[2.2.1]heptyl and the like. Once specific example of heterocycloalkyl is 2-oxo-1,3-oxazolidin-3-yl. The heterocycloalkyl can be optionally substituted in which one or more hydrogen atoms are replaced by a substituent selected from the group consisting of halogen, cyano, hydroxy, —$SF_5$, nitro, —($C_1$-$C_6$)alkoxy, and —N($R^6$)($R^7$), in which $R^6$ and $R^7$ are each independently selected from hydrogen and ($C_1$-$C_6$)alkyl.

A "($C_6$-$C_{10}$)aryl" refers to an all-carbon monocyclic or fused-ring polycyclic aromatic group having a conjugated pi-electron system containing from 6 to 10 carbon atoms, such as phenyl or naphthyl.

As used herein, the term "heteroaryl" refers to an aromatic carbocyclic system containing one, two, three or four heteroatoms selected independently from oxygen, nitrogen and sulfur and having one, two or three rings wherein such rings may be fused, wherein fused is defined above. A "(5- to 10-membered) heteroaryl" ring refers to a heteroaryl ring having from 5 to 10 ring atoms in which at least one of the ring atoms is nitrogen, with the remaining ring atoms being independently selected from the group consisting of carbon, oxygen, sulfur, and nitrogen. A "(5- to 6-membered) heteroaryl" ring refers to a heteroaryl ring having from 5 to 6 ring atoms in which at least one of the ring atoms is nitrogen, with the remaining ring atoms being independently selected from the group consisting of carbon, oxygen, sulfur, and nitrogen. Examples of heteroaryls include, but are not limited to, imidazolyl, pyrazolyl, pyrimidinyl, pyridazinyl, thiazolyl, triazolyl (e.g., 1,2,3-triazol or 1,2,4-triazol), pyrazinyl, oxazolyl, thiadiazolyl, pyridinyl, imidazopyridinyl, triazolopyridinyl, dihydropyrrolotriazolyl, and oxadiazolyl. More specific examples of heteroaryls include imidazolyl, 1H-pyrazolyl, thiadiazolyl, or triazolyl.

It is to be understood that the heteroaryl may be optionally fused to a cycloalkyl group, or to a heterocycloalkyl group, as defined herein.

The heteroaryl substituent may be attached via a nitrogen atom having the appropriate valence, or via any carbon atom. The heteroaryl moiety may be optionally substituted with one or more substituents at a nitrogen atom having the appropriate valence, or at any available carbon atom. The (5- to 6-membered)heteroaryl can be optionally substituted in which one or more hydrogen atoms are replaced by a substituent selected from the group consisting of halogen, cyano, hydroxy, —$SF_5$, nitro, —($C_1$-$C_6$)alkoxy, and —N($R^6$)($R^7$), in which $R^6$ and $R^7$ are each independently selected from hydrogen and ($C_1$-$C_6$)alkyl. The substituent can be attached to the heteroaryl moiety at any available carbon atom or to a heteroatom when the heteroatom is nitrogen having the appropriate valence.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

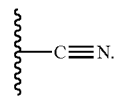

"nitro", as used herein, means an —$NO_2$ group.

"Optionally substituted", as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —CH$_3$) is optionally substituted, then up to 3 hydrogen atoms on the carbon atom can be replaced with substituent groups.

"Patient" or "subject" refers to warm-blooded animals such as, for example, pigs, cows, chickens, horses, guinea pigs, mice, rats, gerbils, cats, rabbits, dogs, monkeys, chimpanzees, and humans.

"Pharmaceutically acceptable" indicates that the substance or composition must be compatible, chemically and/or toxicologically, with the other ingredients comprising a formulation, and/or the mammal being treated therewith.

The term "therapeutically effective amount" as used herein refers to that amount of the compound being administered which will relieve to some extent one or more of the symptoms of the disorder being treated. In reference to the treatment of an HPK1 kinase-mediated disorder (e.g., cancer), a therapeutically effective amount refers to that amount which has the effect of relieving to some extent (or, for example, eliminating) one or more symptoms associated with the HPK1 kinase-mediated disorder. For example, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a substituted or optionally substituted moiety is described without indicating the atom via which such moiety is bonded to a substituent, then the substituent may be bonded via any appropriate atom in such moiety. For example in an optionally substituted (5- to 10-membered) heteroaryl, a substituent on the heteroaryl can be bonded to any carbon atom on the heteroaryl part or on the heteroatom of the heteroaryl, valency permitting. Combinations of substituents and/or variables are permissible only if such combinations result in stable compounds.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

Compounds

The compounds of Formula I, as described above, contain an azalactam (2,3-dihydro-1H-pyrrolo[3,4-c]pyridin-1-one) core wherein the pyrrolo ring is attached via its nitrogen atom to a 6-membered heteroaryl (pyridine or pyrimidine) that is substituted with $R^4$ and an optional $R^5$ substituent.

In one embodiment, in Formula I as described above, $R^1$ is —N($R^6$)($R^7$), and $R^6$ and $R^7$ are each independently selected from the group consisting of hydrogen and ($C_1$-$C_6$)alkyl, wherein said ($C_1$-$C_6$)alkyl is optionally substituted with 1 to 3 halogen.

In another embodiment, $R^1$ is —N($R^6$)($R^7$), and $R^6$ and $R^7$ are each methyl.

In another embodiment, $R^1$ is —N($R^6$)($R^7$), and $R^6$ and $R^7$ are each ethyl.

In another embodiment, $R^1$ is —N($R^6$)($R^7$), and one of $R^6$ and $R^7$ is hydrogen and the other is methyl.

In another embodiment, $R^1$ is —N($R^6$)($R^7$), and one of $R^6$ and $R^7$ is methyl and the other is ethyl.

In yet another embodiment, $R^1$ is —N($R^6$)($R^7$) and $R^6$ and $R^7$ taken together with the nitrogen to which they are attached form a (4- to 8-membered)heterocycloalkyl that is optionally substituted with one to three substituents selected from the group consisting of halogen, ($C_1$-$C_6$)alkyl, halo ($C_1$-$C_6$)alkyl, ($C_1$-$C_6$)alkoxy, and halo($C_1$-$C_6$)alkoxy. When $R^6$ and $R^7$ taken together form a (4- to 8-membered)heterocycloalkyl, the heterocycloalkyl may be selected from the group consisting of azetidinyl, pyrrolidinyl, and azabicyclo [2.2.1]heptyl.

In certain embodiments, $R^1$ is azetidinyl optionally substituted with one to three substituents selected from the group consisting of halogen, ($C_1$-$C_6$)alkyl, halo($C_1$-$C_6$)alkyl, ($C_1$-$C_6$)alkoxy, and halo($C_1$-$C_6$)alkoxy.

In certain embodiments, $R^1$ is pyrrolidinyl optionally substituted with one to three substituents selected from the group consisting of halogen, ($C_1$-$C_6$)alkyl, halo($C_1$-$C_6$)alkyl, ($C_1$-$C_6$)alkoxy, and halo($C_1$-$C_6$)alkoxy.

In certain other embodiments, $R^1$ is a ($C_3$-$C_6$)cycloalkyl, wherein said ($C_3$-$C_6$)cycloalkyl is optionally substituted with one to three substituents selected from the group consisting of halogen, hydroxy, ($C_1$-$C_6$)alkyl, and ($C_1$-$C_6$) alkoxy. When $R^1$ is a ($C_3$-$C_6$)cycloalkyl, the ($C_3$-$C_6$)cycloalkyl is cyclopropyl.

In yet another embodiment, $R^1$ is a ($C_1$-$C_6$)alkyl selected from the group consisting of methyl, ethyl, propyl, isopropyl, butyl, and tert-butyl.

In another embodiment, $R^1$ is hydrogen.

It is to be understood that any of the above-mentioned subgenuses (embodiments) of $R^1$ can be combined together with any of the subgenuses for $R^{1a}$, $R^2$, $R^3$, $R^4$, $R^5$, a, and X as described above and hereinafter.

In another embodiment, in Formula I as described above, $R^2$ is —(CH$_2$)$_m$N($R^8$)($R^9$), wherein m is 1 and one of $R^8$ and $R^9$ is hydrogen and the other is methyl.

In another embodiment, $R^2$ is —(CH$_2$)$_m$N($R^8$)($R^9$), wherein m is 1 and $R^8$ and $R^9$ are both hydrogen.

In certain other embodiments, $R^2$ is a (4- to 6-membered) heterocycloalkyl and the heterocycloalkyl is azetidinyl.

It is to be understood that any of the above-mentioned subgenuses (embodiments) of $R^2$ can be combined together with any of the subgenuses for $R^1$, $R^{1a}$, $R^3$, $R^4$, $R^5$, a, and X as described above and hereinafter.

In another embodiment, in Formula I as described above, $R^3$ is hydrogen.

In yet another embodiment, in Formula I as described above, $R^4$ is a (5- to 6-membered)heteroaryl optionally substituted with 1 to 3 substituents selected from the group consisting of halogen, cyano, hydroxy, —N($R^{10}$)($R^{11}$), ($C_1$-$C_6$)alkyl, halo($C_1$-$C_6$)alkyl, ($C_1$-$C_6$)alkoxy, halo($C_1$-$C_6$)alkoxy, and —(CH$_2$)$_n$($C_3$-$C_6$)cycloalkyl, wherein n is an integer selected from 0, 1, or 2; and wherein $R^{10}$ and $R^{11}$ are each independently selected from the group consisting of hydrogen and ($C_1$-$C_6$)alkyl, wherein said ($C_1$-$C_6$)alkyl is optionally substituted with 1 to 3 substituents selected from the group consisting of halogen and hydroxy. When $R^4$ is a (5- to 6-membered)heteroaryl, the heteroaryl may be 1, 2, 3-triazolyl, 1, 2, 4-triazolyl or pyrazolyl.

In another embodiment, $R^4$ is a (4- to 6-membered)heterocycloalkyl optionally substituted with 1 to 3 substituents selected from the group consisting of halogen, cyano, oxo, hydroxy, —N($R^{10}$)($R^{11}$), ($C_1$-$C_6$)alkyl, halo($C_1$-$C_6$)alkyl, ($C_1$-$C_6$)alkoxy, halo($C_1$-$C_6$)alkoxy, and —(CH$_2$)$_n$($C_3$-$C_6$)cycloalkyl, wherein n is an integer selected from 0, 1, or 2; and wherein $R^{10}$ and $R^{11}$ are each independently selected from the group consisting of hydrogen and ($C_1$-$C_6$)alkyl, wherein said ($C_1$-$C_6$)alkyl is optionally substituted with 1 to 3 substituents selected from the group consisting of halogen and hydroxy. When $R^4$ is a (4- to 6-membered)heterocycloalkyl, the heterocycloalkyl may be oxazolidinyl optionally substituted with an oxo substituent.

It is to be understood that any of the above-mentioned subgenuses (embodiments) of $R^4$ can be combined together with any of the subgenuses for $R^1$, $R^{1a}$, $R^2$, $R^3$, $R^5$, a, and X as described above and hereinafter.

In yet another embodiment, in Formula I as described above, X is nitrogen, and a is 0.

In another embodiment, X is carbon, a is 1 and $R^5$ is hydrogen or halogen. When $R^5$ is a halogen, $R^5$ can be a fluorine atom.

It is to be understood that any of the above-mentioned subgenuses (embodiments) of X can be combined together with any of the subgenuses for $R^1$, $R^{1a}$, $R^2$, $R^3$, $R^4$, $R^5$, and a as described above and hereinafter.

In another embodiments, the invention provides a compound of Formula I, or a pharmaceutically acceptable salt thereof, wherein:

$R^{1a}$ is H;

$R^1$ is of ($C_1$-$C_6$)alkyl, halo($C_1$-$C_6$)alkyl, —N($R^6$)($R^7$), and ($C_3$-$C_4$)cycloalkyl, wherein said ($C_3$-$C_4$)cycloalkyl is optionally substituted with one ($C_1$-$C_6$)alkyl;

$R^6$ and $R^7$ are each independently selected from the group consisting of hydrogen and ($C_1$-$C_6$)alkyl, or $R^6$ and $R^7$ are taken together with the nitrogen to which they are attached form a (4- to 8-membered)heterocycloalkyl that is optionally substituted with one to three ($C_1$-$C_6$)alkyl or halo($C_1$-$C_6$)alkyl;

$R^2$ is —(CH$_2$)$_m$N($R^8$)($R^9$) wherein m is 1 and $R^8$ and $R^9$ are each independently selected from the group consisting of hydrogen and ($C_1$-$C_6$)alkyl;

$R^3$ is H;

X is carbon;

$R^5$ is hydrogen;

a is 1; and $R^4$ is a (5-membered)heterocycloalkyl or a (5-membered) heteroaryl, each optionally substituted with 1 to 3 substituents selected from oxo, ($C_1$-$C_6$)alkyl optionally substituted with hydroxy, halo($C_1$-$C_6$)alkyl and —(CH$_2$)$_n$($C_3$-$C_6$)cycloalkyl wherein n is 0 or 1.

In another embodiment, the invention provides a compound of Formula I,

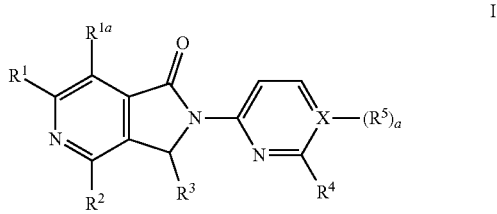

or a pharmaceutically acceptable salt thereof, wherein:

$R^1$ is selected from the group consisting of hydrogen, halogen, ($C_1$-$C_6$)alkyl, halo($C_1$-$C_6$)alkyl, ($C_1$-$C_6$)alkoxy, halo($C_1$-$C_6$)alkoxy, —N($R^6$)($R^7$), and ($C_3$-$C_6$)cycloalkyl, wherein said ($C_1$-$C_6$)alkyl, halo($C_1$-$C_6$)alkyl, and ($C_3$-$C_6$)cycloalkyl are optionally substituted with one to three substituents selected from the group consisting of halogen, hydroxy, cyano, ($C_1$-$C_6$)alkyl, and ($C_1$-$C_6$)alkoxy;

$R^6$ and $R^7$ are each independently selected from the group consisting of hydrogen and ($C_1$-$C_6$)alkyl, wherein said ($C_1$-$C_6$)alkyl is optionally substituted with 1 to 3 substituents selected from the group consisting of halogen, ($C_1$-$C_6$)alkoxy, cyano, and hydroxy, or $R^6$ and $R^7$ taken together with the nitrogen to which they are attached form a (4- to 8-membered)heterocycloalkyl that is optionally substituted with one to three substituents selected from the group consisting of halogen, ($C_1$-$C_6$)alkyl, halo($C_1$-$C_6$)alkyl, ($C_1$-$C_6$)alkoxy, and halo($C_1$-$C_6$)alkoxy, wherein said ($C_1$-$C_6$)alkyl, and halo($C_1$-$C_6$)alkyl are optionally substituted with one to three substituents selected from the group consisting of halogen, hydroxy, cyano, ($C_1$-$C_6$)alkyl, and ($C_1$-$C_6$)alkoxy;

$R^{1a}$ is H;

$R^2$ is CH$_2$N($R^8$)($R^9$), wherein $R^8$ and $R^9$ are each independently selected from the group consisting of hydrogen and ($C_1$-$C_6$)alkyl, wherein said ($C_1$-$C_6$)alkyl is optionally substituted with 1 to 3 substituents selected from the group consisting of halogen, ($C_1$-$C_6$)alkoxy, cyano, and hydroxy, or $R^8$ and $R^9$ taken together with the nitrogen to which they are attached form a (4- to 6-membered)heterocycloalkyl that is optionally substituted with one to three substituents selected from the group consisting of halogen, hydroxy, ($C_1$-$C_6$)alkyl, halo($C_1$-$C_6$)alkyl, ($C_1$-$C_6$)alkoxy, and halo($C_1$-$C_6$)alkoxy, wherein said ($C_1$-$C_6$)alkyl and halo($C_1$-$C_6$)alkyl are optionally substituted with one to three substituents selected from the group consisting of halogen, hydroxy, cyano, and ($C_1$-$C_6$)alkoxy; and $R^3$ is H;

X is carbon;

$R^5$ is hydrogen;

a is 1; and $R^4$ is a (4- to 6-membered)heterocycloalkyl or a (5- to 10-membered)heteroaryl, wherein said (4- to 6-membered) heterocycloalkyl and (5- to 10-membered)heteroaryl are optionally substituted with 1 to 3 substituents selected from the group consisting of halogen, cyano, oxo, hydroxy, —N($R^{10}$)($R^{11}$), ($C_1$-$C_6$)alkyl, halo($C_1$-$C_6$)alkyl, ($C_1$-$C_6$)alkoxy, halo($C_1$-$C_6$)alkoxy, and —(CH$_2$)$_n$($C_3$-$C_6$)cycloalkyl, wherein said ($C_1$-$C_6$)alkyl and halo($C_1$-$C_6$)alkyl are optionally substituted with one to three substituents selected from the group consisting of halogen, hydroxy, cyano, and ($C_1$-$C_6$)alkoxy, and wherein n is an integer selected from 0, 1, or 2; and wherein $R^{10}$ and $R^{11}$ are each independently selected from the group consisting of hydrogen and ($C_1$-$C_6$) alkyl, wherein said ($C_1$-$C_6$)alkyl is optionally substituted with 1 to 3 substituents selected from the group consisting of halogen and hydroxy.

In another embodiment, the invention provides a compound of Formula I, or a pharmaceutically acceptable salt thereof, wherein:

$R^1$ is selected from the group consisting of ($C_1$-$C_4$)alkyl, $CF_3$, —N($R^6$)($R^7$), and ($C_3$-$C_4$)cycloalkyl, wherein said ($C_3$-$C_4$)cycloalkyl is optionally substituted with one $CH_3$;

$R^6$ and $R^7$ are each independently selected from the group consisting of hydrogen and ($C_1$-$C_3$)alkyl, or $R^6$ and $R^7$ taken together with the nitrogen to which they are attached form a (4- to 5-membered)heterocycloalkyl that is optionally substituted with one to two $CH_3$ substituents;

$R^2$ is $CH_2N(R^8)(R^9)$, wherein $R^8$ is hydrogen and $R^9$ is selected from the group consisting of hydrogen and $CH_3$; and $R^4$ is a (5-membered)heterocycloalkyl or a (5-membered)heteroaryl, wherein said (5-membered)heterocycloalkyl is 1,3-oxazolidin-3-yl and said (5-membered)heteroaryl is 1H-pyrazolyl or triazolyl, each optionally substituted with 1 to 2 substituents selected from the group consisting of oxo, ($C_1$-$C_5$)alkyl, halo($C_1$-$C_5$)alkyl, and —$CH_2$-cyclopropyl.

In another embodiment, the invention provides a compound of Formula I, or a pharmaceutically acceptable salt thereof, wherein:

$R^1$ is selected from the group consisting of ($C_1$-$C_4$)alkyl, $CF_3$, —N($R^6$)($R^7$), and ($C_3$-$C_4$)cycloalkyl, wherein said ($C_3$-$C_4$)cycloalkyl is optionally substituted with one $CH_3$;

$R^6$ and $R^7$ are each independently selected from the group consisting of hydrogen and ($C_1$-$C_3$)alkyl, or $R^6$ and $R^7$ taken together with the nitrogen to which they are attached form a (4- to 5-membered)heterocycloalkyl that is optionally substituted with one to two $CH_3$ substituents;

$R^2$ is $CH_2N(R^8)(R^9)$, wherein $R^8$ is hydrogen and $R^9$ is selected from the group consisting of hydrogen and $CH_3$; and $R^4$ is a (5-membered)heterocycloalkyl or a (5-membered)heteroaryl, wherein said (5-membered)heterocycloalkyl is 2-oxo-1,3-oxazolidin-3-yl, optionally substituted with 1 $CH_3$, $CH_2F$, $CHF_2$, or $CF_3$, and said (5-membered)heteroaryl is 1H-pyrazolyl or triazolyl, optionally substituted with 1 to 2 substituents selected from the group consisting of ($C_1$-$C_5$)alkyl, halo($C_1$-$C_5$)alkyl, and —$CH_2$-cyclopropyl.

In another embodiment, the invention provides a compound of Formula I, or a pharmaceutically acceptable salt thereof, wherein $R^1$ is —N($R^6$)($R^7$), wherein $R^6$ and $R^7$ are each independently selected from the group consisting of hydrogen and ($C_1$-$C_3$)alkyl.

In another embodiment, the invention provides a compound of Formula I, or a pharmaceutically acceptable salt thereof, wherein $R^1$ is —N($R^6$)($R^7$), wherein $R^6$ and $R^7$ taken together with the nitrogen to which they are attached form a (4- to 5-membered)heterocycloalkyl that is azetidinyl or pyrrolidinyl, and said heterocycloalkyl is optionally substituted with one to two $CH_3$ substituents.

In another embodiment, the invention provides a compound of Formula I, or a pharmaceutically acceptable salt thereof, wherein:

$R^1$ is selected from the group consisting of —N($R^6$)($R^7$), and ($C_3$-$C_4$)cycloalkyl, wherein said ($C_3$-$C_4$)cycloalkyl is optionally substituted with one $CH_3$;

$R^6$ and $R^7$ are each independently selected from the group consisting of hydrogen and ($C_1$-$C_3$)alkyl, or $R^6$ and $R^7$ taken together with the nitrogen to which they are attached form a (4- to 5-membered)heterocycloalkyl that is optionally substituted with one to two substituents selected from the group consisting of $CH_3$, or halo($C_1$)alkyl;

$R^2$ is —$CH_2N(R^8)(R^9)$, wherein $R^8$ and $R^9$ are each independently selected from the group consisting of hydrogen and $CH_3$; and $R^4$ is a (5-membered)heterocycloalkyl or a (5-membered)heteroaryl, wherein said (5-membered)heterocycloalkyl is 2-oxo-1,3-oxazolidin-3-yl, optionally substituted with 1 substituent selected from the group consisting of $CH_3$, $CHF_2$—, and $CH_2F$, and said (5-membered)heteroaryl is imidazolyl, 1H-pyrazolyl, thiadiazolyl, or triazolyl, optionally substituted with 1 to 2 substituents independently selected from the group consisting of ($C_1$-$C_5$)alkyl, halo($C_1$-$C_6$)alkyl, and —($C_4$-$C_5$)cycloalkyl, wherein said ($C_1$-$C_5$)alkyl is optionally substituted with one hydroxy.

In another embodiment, the invention provides a compound of Formula I, or a pharmaceutically acceptable salt thereof, wherein:

$R^1$ is —N($R^6$)($R^7$);

$R^6$ and $R^7$ are each independently selected from the group consisting of hydrogen and ($C_1$-$C_3$)alkyl, or $R^6$ and $R^7$ taken together with the nitrogen to which they are attached form pyrrolidin-1-yl, optionally substituted with 1 to 2 $CH_3$;

$R^2$ is —$CH_2N(R^8)(R^9)$, wherein $R^8$ and $R^9$ are each independently selected from the group consisting of hydrogen and $CH_3$; and $R^4$ is triazol-3-yl, substituted with 1 to 2 substituents independently selected from the group consisting of $CH_3$—, $CH_3$—$CH_2$—, and $CH_3$—$CH_2$—$CH_2$—.

The compounds of the invention concerning a compound of Formula I, or a pharmaceutically acceptable salt thereof, wherein:

$R^{1a}$ is H;
$R^3$ is H;
a is 1;
X is carbon; and
$R^5$ is hydrogen; provides a structure represented by

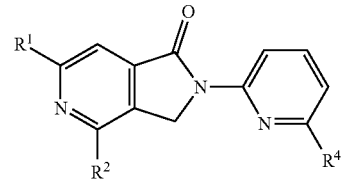

and wherein $R^1$, $R^2$, and $R^4$ are as defined herein.

In another embodiment, the present invention is directed to any one or more of the following compounds:

6-(dimethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-[(methylamino)methyl]-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one;

4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one;

4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one;

4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one;

4-(aminomethyl)-2-[6-(4-ethyl-5-methyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one;

or a pharmaceutically acceptable salt thereof.

In another embodiment, the present invention is directed to compounds of Formula II

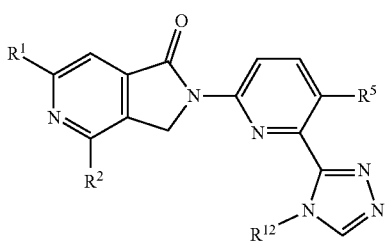

or a pharmaceutically acceptable salt thereof, wherein:

$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, —N$(R^6)(R^7)$, and $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy;

$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy;

$R^2$ is:
i) a —(CH$_2)_m$N$(R^8)(R^9)$, wherein m is an integer selected from 0, 1, 2, or 3, and $R^8$ and $R^9$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy, or $R^8$ and $R^9$ taken together with the nitrogen to which they are attached form a (4- to 6-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy; or
ii) a (4- to 6-membered)heterocycloalkyl, wherein said heterocycloalkyl is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy;

$R^5$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy; and $R^{12}$ is selected from the group consisting of $(C_1-C_6)$alkyl, halo$(C_1-C_6)$alkyl, and —(CH$_2)_n$(C$_3$-C$_6$)cycloalkyl, wherein n is an integer 0 or 1.

In another embodiment, in Formula II as described above, $R^1$ is —N$(R^6)(R^7)$, and $R^6$ and $R^7$ are each independently selected from the group consisting of hydrogen and $(C_1-C_6)$alkyl, wherein said $(C_1-C_6)$alkyl is optionally substituted with 1 to 3 halogen.

In another embodiment of Formula II, $R^1$ is —N$(R^6)(R^7)$, and $(R^6)$ and $(R^7)$ are each independently methyl.

In another embodiment of Formula II, $R^1$ is —N$(R^6)(R^7)$, and $(R^6)$ and $(R^7)$ are each independently ethyl.

In another embodiment of Formula II, $R^1$ is —N$(R^6)(R^7)$, and one of $(R^6)$ and $(R^7)$ is hydrogen and the other is methyl.

In another embodiment of Formula II, $R^1$ is —N$(R^6)(R^7)$, and one of $(R^6)$ and $(R^7)$ is methyl and the other is ethyl.

In yet another embodiment of Formula II, $R^1$ is —N$(R^6)(R^7)$ and $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy. When $R^6$ and $R^7$ taken together form a (4- to 8-membered)heterocycloalkyl, the heterocycloalkyl may be selected from the group consisting of azetidinyl, pyrrolidinyl, and azabicyclo[2.2.1]heptyl.

In certain embodiments of Formula II, $R^1$ is azetidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

In certain embodiments of Formula II, $R^1$ is pyrrolidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

In certain other embodiments of Formula II, $R^1$ is a $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy. When $R^1$ is a $(C_3-C_6)$cycloalkyl, the $(C_3-C_6)$cycloalkyl is cyclopropyl.

In yet another embodiment of Formula II, $R^1$ is a $(C_1-C_6)$alkyl selected from the group consisting of methyl, ethyl, propyl, isopropyl, butyl, and tert-butyl.

In another embodiment of Formula II, $R^1$ is hydrogen.

It is to be understood that any of the above-mentioned subgenuses (embodiments of Formula II) of $R^1$ can be combined together with any of the subgenuses for $R^2$, $R^5$, and $R^{12}$ as described above and hereinafter for Formula II.

In another embodiment, in Formula II as described above, $R^2$ is —(CH$_2)_m$N$(R^8)(R^9)$, wherein m is 1 and one of $(R^8)$ and $(R^9)$ is hydrogen and the other is methyl.

In another embodiment of Formula II, $R^2$ is —(CH$_2)_m$N$(R^8)(R^9)$, wherein m is 1 and $(R^8)$ and $(R^9)$ are both hydrogen.

In certain other embodiments of Formula II, $R^2$ is a (4- to 6-membered)heterocycloalkyl and the heterocycloalkyl is azetidinyl.

It is to be understood that any of the above-mentioned subgenuses (embodiments of Formula II) of $R^2$ can be combined together with any of the subgenuses for $R^1$, $R^5$, and $R^{12}$ as described above and hereinafter of Formula II.

In another embodiment, in Formula II as described above, $R^{12}$ is $(C_1-C_6)$alkyl selected from the group consisting of ethyl, ethyl, propyl, propyl, isopropyl, butyl, and tert-butyl.

In another embodiment of Formula II, $R^{12}$ is halo$(C_1-C_6)$alkyl selected from the group consisting of fluoromethyl, fluoroethyl, difluoromethyl, difluoroethyl, trifluoromethyl, triflourobutanyl, and trifluoropentanyl.

In yet another embodiment of Formula II, $R^{12}$ is —(CH$_2)_n$(C$_3$-C$_6$)cycloalkyl, wherein n is 1 and the (C$_3$-C$_6$) cycloalkyl is cyclopropyl.

In some embodiments, the compound of Formula II has the absolute stereochemistry as shown in Formula II-A or II-B:

II-A

II-B

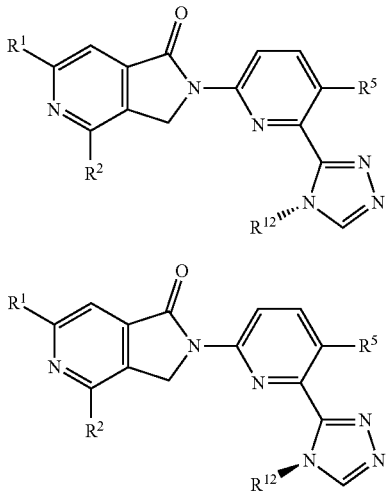

or a pharmaceutically acceptable salt thereof, where $R^1$, $R^2$, $R^5$, and $R^{12}$ are defined as for Formula II.

Each of the embodiments described herein with respect to Formula II is also applicable to compounds of Formula II-A and II-B.

In another embodiment, the present invention is directed to compounds of Formula III

III

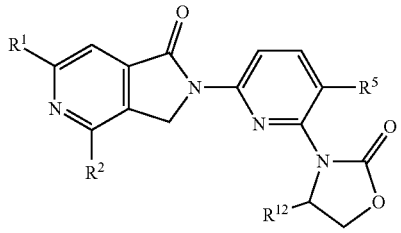

or a pharmaceutically acceptable salt thereof, wherein:

$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, —$N(R^6)(R^7)$, and $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy;

$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy;

$R^2$ is:

i) a —$(CH_2)_m N(R^8)(R^9)$, wherein m is an integer selected from 0, 1, 2, or 3, and $R^8$ and $R^9$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy, or $R^8$ and $R^9$ taken together with the nitrogen to which they are attached form a (4- to 6-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy; or ii) a (4- to 6-membered)heterocycloalkyl, wherein said heterocycloalkyl is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy;

$R^5$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy; and $R^{12}$ is selected from the group consisting of $(C_1-C_6)$alkyl, halo$(C_1-C_6)$alkyl, and —$(CH_2)_n(C_3-C_6)$cycloalkyl.

In another embodiment, in Formula III as described above, $R^1$ is —$N(R^6)(R^7)$, and $R^6$ and $R^7$ are each independently selected from the group consisting of hydrogen and $(C_1-C_6)$alkyl, wherein said $(C_1-C_6)$alkyl is optionally substituted with 1 to 3 halogen.

In another embodiment of Formula III, $R^1$ is —$N(R^6)(R^7)$, and $R^6$ and $R^7$ are each methyl.

In another embodiment of Formula III, $R^1$ is —$N(R^6)(R^7)$, and $R^6$ and $R^7$ are each is ethyl.

In another embodiment of Formula III, $R^1$ is —$N(R^6)(R^7)$, and one of $R^6$ and $R^7$ is hydrogen and the other is methyl.

In another embodiment of Formula III, $R^1$ is —$N(R^6)(R^7)$, and one of $R^6$ and $R^7$ is methyl and the other is ethyl.

In yet another embodiment of Formula III, $R^1$ is —$N(R^6)(R^7)$ and $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy. When $R^6$ and $R^7$ taken together form a (4- to 8-membered)heterocycloalkyl, the heterocycloalkyl may be selected from the group consisting of azetidinyl, pyrrolidinyl, and azabicyclo[2.2.1]heptyl.

In certain embodiments of Formula III, $R^1$ is azetidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

In certain embodiments of Formula III, $R^1$ is pyrrolidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

In certain other embodiments of Formula III, $R^1$ is a $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy. When $R^1$ is a $(C_3-C_6)$cycloalkyl, the $(C_3-C_6)$cycloalkyl is cyclopropyl.

In yet another embodiment of Formula III, $R^1$ is a $(C_1-C_6)$alkyl selected from the group consisting of methyl, ethyl, propyl, isopropyl, butyl, and tert-butyl.

In another embodiment of Formula III, $R^1$ is hydrogen.

It is to be understood that any of the above-mentioned subgenuses (embodiments of Formula III) of $R^1$ can be combined together with any of the subgenuses for $R^2$, $R^5$, and $R^{12}$ as described above and hereinafter for Formula III.

In another embodiment, in Formula III as described above, $R^2$ is —$(CH_2)_m N(R^8)(R^9)$, wherein m is 1 and one of $(R^8)$ and $(R^9)$ is hydrogen and the other is methyl.

In another embodiment of Formula III, $R^2$ is —$(CH_2)_m N(R^8)(R^9)$, wherein m is 1 and $R^8$ and $R^9$ are both hydrogen.

In certain other embodiments of Formula III, R² is a (4- to 6-membered)heterocycloalkyl and the heterocycloalkyl is azetidinyl.

It is to be understood that any of the above-mentioned subgenuses (embodiments of Formula III) of R² can be combined together with any of the subgenuses for R¹, R⁵, and R¹² as described above and hereinafter for Formula III.

In another embodiment, in Formula III as described above, R¹² is (C₁-C₆)alkyl selected from the group consisting of ethyl, ethyl, propyl, propyl, isopropyl, butyl, and tert-butyl.

In another embodiment of Formula III, R¹² is halo(C₁-C₆)alkyl selected from the group consisting of fluoromethyl, fluoroethyl, difluoromethyl, difluoroethyl, trifluoromethyl, triflourobutanyl, and trifluoropentanyl.

In yet another embodiment of Formula III, R¹² is —(CH₂)ₙ(C₃-C₆)cycloalkyl, wherein n is 1 and the (C₃-C₆)cycloalkyl is cyclopropyl.

In some embodiments, the compound of Formula III has the absolute stereochemistry as shown in Formula III-A or III-B:

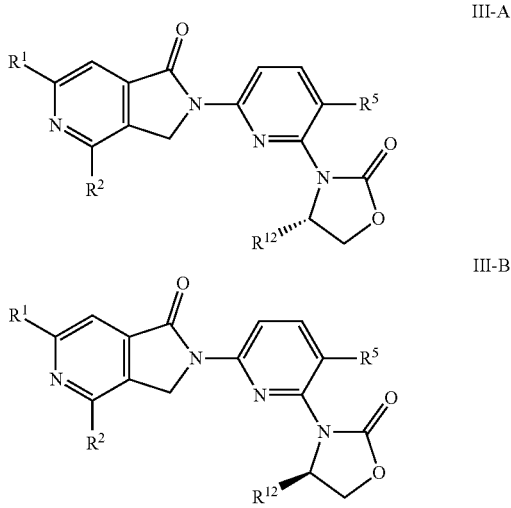

or a pharmaceutically acceptable salt thereof, where R¹, R², R⁵, and R¹² are defined as for Formula Ill.

Each of the embodiments described herein with respect to Formula III is also applicable to compounds of Formula III-A and III-B.

In another aspect, the invention provides a compound selected from the group consisting of:

4-[(methylamino)methyl]-6-(pyrrolidin-1-yl)-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one;

6-(dimethylamino)-4-[(methylamino)methyl]-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one;

2-{6-[4-(cyclopropylmethyl)-4H-1,2,4-triazol-3-yl]pyridin-2-yl}-6-(dimethylamino)-4-[(methylamino)methyl]-2,3-dihydro-1H-pyrrolo[3,4-c]pyridin-1-one;

6-(dimethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

2-(6-{4-[(2S)-butan-2-yl]-4H-1,2,4-triazol-3-yl}pyridin-2-yl)-6-(dimethylamino)-4-[(methylamino)methyl]-2,3-dihydro-1H-pyrrolo[3,4-c]pyridin-1-one;

6-(dimethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one;

6-(dimethylamino)-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one;

4-(aminomethyl)-2-{6-[4-(cyclopropylmethyl)-4H-1,2,4-triazol-3-yl]pyridin-2-yl}-6-(dimethylamino)-2,3-dihydro-1H-pyrrolo[3,4-c]pyridin-1-one;

4-(aminomethyl)-6-(dimethylamino)-2-{6-[5-(propan-2-yl)-1H-pyrazol-4-yl]pyridin-2-yl}-2,3-dihydro-1H-pyrrolo[3,4-c]pyridin-1-one;

4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(dimethylamino)-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(dimethylamino)-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one;

6-(dimethylamino)-4-[(methylamino)methyl]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one;

6-(dimethylamino)-4-[(methylamino)methyl]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one;

6-(dimethylamino)-2-{5-fluoro-6-[5-(propan-2-yl)-1H-pyrazol-4-yl]pyridin-2-yl}-4-[(methylamino)methyl]-2,3-dihydro-1H-pyrrolo[3,4-c]pyridin-1-one;

4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

6-(azetidin-1-yl)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-[(2R,4R)-2,4-dimethylazetidin-1-yl]-2-{6-[4-(propan-2-yl)-4H-1,2,4-triazol-3-yl]pyridin-2-yl}-2,3-dihydro-1H-pyrrolo[3,4-c]pyridin-1-one;

6-[(1s,4s)-7-azabicyclo[2.2.1]hept-7-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-cyclopropyl-2-{6-[(4S)-4-methyl-2-oxo-1,3-oxazolidin-3-yl]pyridin-2-yl}-2,3-dihydro-1H-pyrrolo[3,4-c]pyridin-1-one;

6-[(2R,5S)-2,5-dimethylpyrrolidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

6-(diethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one;

6-[(2R,4R)-2,4-dimethylazetidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(dimethylamino)-2-{6-[(4S)-4-methyl-2-oxo-1,3-oxazolidin-3-yl]pyridin-2-yl}-2,3-dihydro-1H-pyrrolo[3,4-c]pyridin-1-one;

4-(aminomethyl)-6-cyclopropyl-2-{6-[4-(propan-2-yl)-4H-1,2,4-triazol-3-yl]pyridin-2-yl}-2,3-dihydro-1H-pyrrolo[3,4-c]pyridin-1-one;

6-(azetidin-1-yl)-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one;

4-(aminomethyl)-6-[(2R,4S)-2,4-dimethylazetidin-1-yl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(dimethylamino)-2-{6-[5-(propan-2-yl)-1H-1,2,3-triazol-1-yl]pyridin-2-yl}-2,3-dihydro-1H-pyrrolo[3,4-c]pyridin-1-one;

4-[(methylamino)methyl]-6-(propan-2-yl)-2-{6-[4-(propan-2-yl)-4H-1,2,4-triazol-3-yl]pyridin-2-yl}-2,3-dihydro-1H-pyrrolo[3,4-c]pyridin-1-one;

6-cyclopropyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-[(2R,4R)-2,4-dimethylazetidin-1-yl]-2-{6-[(4S)-4-methyl-2-oxo-1,3-oxazolidin-3-yl]pyridin-2-yl}-2,3-dihydro-1H-pyrrolo[3,4-c]pyridin-1-one;

6-cyclopropyl-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one;

4-(aminomethyl)-6-(diethylamino)-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-2-{6-[(4S)-4-methyl-2-oxo-1,3-oxazolidin-3-yl]pyridin-2-yl}-6-(propan-2-yl)-2,3-dihydro-1H-pyrrolo[3,4-c]pyridin-1-one;

6-(diethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(azetidin-1-yl)-2-{6-[(4S)-4-methyl-2-oxo-1,3-oxazolidin-3-yl]pyridin-2-yl}-2,3-dihydro-1H-pyrrolo[3,4-c]pyridin-1-one;

6-[(2R,5R)-2,5-dimethylpyrrolidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-(1-methylcyclopropyl)-2-{6-[(4S)-4-methyl-2-oxo-1,3-oxazolidin-3-yl]pyridin-2-yl}-2,3-dihydro-1H-pyrrolo[3,4-c]pyridin-1-one;

4-[(methylamino)methyl]-6-(1-methylcyclopropyl)-2-{6-[(4S)-4-methyl-2-oxo-1,3-oxazolidin-3-yl]pyridin-2-yl}-2,3-dihydro-1H-pyrrolo[3,4-c]pyridin-1-one;

6-[ethyl(methyl)amino]-4-[(methylamino)]-2-{6-[4-(propan-2-yl)-4H-1,2,4-triazol-3-yl]pyridin-2-yl}-2,3-dihydro-1H-pyrrolo[3,4-c]pyridin-1-one;

6-(dimethylamino)-2-{6-[(4R)-4-(fluoromethyl)-2-oxo-1,3-oxazolidin-3-yl]pyridin-2-yl}-4-[(methylamino)methyl]-2,3-dihydro-1H-pyrrolo[3,4-c]pyridin-1-one;

6-methyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

6-(dimethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one;

4-[(methylamino)methyl]-6-(1-methylcyclopropyl)-2-{6-[4-(propan-2-yl)-4H-1,2,4-triazol-3-yl]pyridin-2-yl}-2,3-dihydro-1H-pyrrolo[3,4-c]pyridin-1-one;

4-[(methylamino)methyl]-6-[methyl(propan-2-yl)amino]-2-{6-[4-(propan-2-yl)-4H-1,2,4-triazol-3-yl]pyridin-2-yl}-2,3-dihydro-1H-pyrrolo[3,4-c]pyridin-1-one;

2-{6-[(4R)-4-(difluoromethyl)-2-oxo-1,3-oxazolidin-3-yl]pyridin-2-yl}-6-(dimethylamino)-4-[(methylamino)methyl]-2,3-dihydro-1H-pyrrolo[3,4-c]pyridin-1-one;

6-tert-butyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

4-(aminomethyl)-6-tert-butyl-2-{6-[(4S)-4-methyl-2-oxo-1,3-oxazolidin-3-yl]pyridin-2-yl}-2,3-dihydro-1H-pyrrolo[3,4-c]pyridin-1-one;

6-tert-butyl-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one;

6-amino-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

6-tert-butyl-4-[(methylamino)methyl]-2-(6-{4-[(3)-1,1,1-trifluoropentan-3-yl]-4H-1,2,4-triazol-3-yl}pyridin-2-yl)-2,3-dihydro-1H-pyrrolo[3,4-c]pyridin-1-one;

4-[(methylamino)methyl]-2-{6-[4-(propan-2-yl)-4H-1,2,4-triazol-3-yl]pyridin-2-yl}-6-(trifluoromethyl)-2,3-dihydro-1H-pyrrolo[3,4-c]pyridin-1-one;

6-[(2R,4S)-2,4-dimethylazetidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one;

or a pharmaceutically acceptable salt thereof.

In another aspect, the invention provides a compound selected from the group consisting of the compounds exemplified in Table 1 and 53, comprising Examples 1 and 53, inclusive, or a pharmaceutically acceptable salt thereof. In another aspect, the invention provides a compound selected from the group consisting of the compounds exemplified in Examples 1 to 53 herein, or a pharmaceutically acceptable salt thereof. In another aspect, the invention concerns any one or more compounds exemplified herein, or pharmaceutically acceptable salt thereof.

The compounds of the invention were optimized for selectivity against HPK1 kinase.

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients. In other embodiments, the pharmaceutical composition further comprises at least one additional anticancer therapeutic agent.

In another embodiment the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent or a palliative agent. In some such embodiments, the at least one additional agent is an anti-cancer therapeutic agent as described below. In some such embodiments, the combination provides an additive, greater than additive, or synergistic anti-cancer effect.

In one embodiment, the invention provides a method for the treatment of abnormal cell growth in a subject in need thereof, comprising administering to the subject a therapeutically effective amount of a compound of the invention, or a pharmaceutically acceptable salt thereof.

In another embodiment, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In frequent embodiments of the methods provided herein, the abnormal cell growth is cancer. Compounds of the invention may be administered as single agents, or may be administered in combination with other anti-cancer therapeutic agents, in particular standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; (5) inhibiting angiogenesis; (6) enhancing T-cell responses; or (7) heightening of anti-tumor activity.

In another aspect, the invention provides a method for the treatment of a disorder mediated by HPK1 kinase activity, in a subject, such as certain cancers, comprising administering to the subject a compound of the invention, or a pharmaceutically acceptable salt thereof, in an amount that is effective for treating said disorder.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminium and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent.

In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_5)$alkyl;

(ii) where the compound contains an alcohol functionality (—OH), an ether thereof, for example, replacement of the hydrogen with $(C_1-C_6)$alkanoyloxymethyl, or with a phosphate ether group; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms.

The carbon-carbon bonds of the compounds of the invention may be depicted herein using a solid line ( ——— ), a solid wedge ( ◼◼◼ ), or a dotted wedge ( ·······||||| ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety. The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de).

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl. Certain isotopically-labeled compounds of the invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering the compounds of the invention, or pharmaceutically acceptable salts thereof, alone or in combination with other therapeutic agents or palliative agents.

In one embodiment, the invention provides a method for the treatment of abnormal cell growth in a subject comprising administering to the subject a therapeutically effective amount of a compound of the invention, or a pharmaceutically acceptable salt thereof. In frequent embodiments, the abnormal cell growth is cancer.

In another embodiment, the invention provides a method for the treatment of cancer in a subject comprising administering to the subject an amount of a compound of the invention, or a pharmaceutically acceptable salt thereof, in combination with an amount of an additional anticancer therapeutic agent, which amounts are together effective in treating said cancer.

Compounds of the invention include compounds of any of the formulae described herein, or a pharmaceutically acceptable salt thereof.

In still another embodiment, the invention provides a method of inhibiting cancer cell proliferation in a subject, comprising administering to the subject a compound of the invention, or a pharmaceutically acceptable salt thereof, in an amount effective to inhibit cell proliferation.

In another embodiment, the invention provides a method of inhibiting cancer cell invasiveness in a subject, comprising administering to the subject a compound of the invention, or a pharmaceutically acceptable salt thereof, in an amount effective to inhibit cell invasiveness.

In another embodiment, the invention provides a method of inducing apoptosis in cancer cells in a subject, comprising administering to the subject a compound of the invention, or a pharmaceutically acceptable salt thereof, in an amount effective to induce apoptosis.

The presently disclosed compounds find use in inhibiting the activity of the HPK1 kinase. HPK1, also referred to as mitogen activated protein kinase kinase kinase kinase 1 or MAP4K1, is a member of the germinal center kinase subfamily of Ste20-related serine/threnonine kinases. HPK1 kinase functions as a MAP4K by phosphorylating and activating MAP3K proteins, including MEKKI, MLK3 and TAK1, leading to the activation of the MAPK Jnk.

HPK1 polynucleotides and polypeptides are known in the art (Hu et al. (1996) Genes Dev. 10: 2251-2264, which is herein incorporated by reference in its entirety). HPK1 polypeptides comprise a variety of conserved structural motifs. HPK1 polypeptides comprise an amino-terminal Ste20-like kinase domain that spans amino acid residues 17-293, which includes the ATP-binding site from amino acid residues 23-46. The kinase domain is followed by four pro line-rich (PR) motifs that serve as binding sites for SH3-containing proteins, such as CrkL, Grb2, HIP-55, Gads, Nek, and Crk. The four PR motifs span amino acid residues 308-407, 394-402, 432-443, and 468-477, respectively. HPK1 becomes phosphorylated and activated in response to TCR or BCR stimulation. TCR- and BCR-induced phosphorylation of the tyrosine at position 381, located between PR1 and PR2, mediates binding to SLP-76 in T cells or BLNK in B cells via a SLP-76 or BLNK SH2 domain, and is required for activation of the kinase. A citron homology domain found in the C-terminus of HPK1, approximately spanning residues 495-800, may act as a regulatory domain and may be involved in macromolecular interactions.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads. The presently disclosed compounds may or may not be a specific HPK1 inhibitor. A specific HPK1 inhibitor reduces the biological activity of HPK1 by an amount that is statistically greater than the inhibitory effect of the inhibitor on any other protein (e.g., other serine/threonine kinases). In certain embodiments, the presently disclosed compounds specifically inhibit the serine/threonine kinase activity of HPK1.

The presently disclosed compounds can be used in a method for inhibiting HPK1. Such methods comprise contacting HPK1 with an effective amount of a presently disclosed compound.

The term "contacting" means bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder (e.g., cancer). As used herein, a "HPK1-dependent disorder" is a pathological condition in which HPK1 activity is necessary for the genesis or maintenance of the pathological condition.

The presently disclosed compounds also find use in enhancing an immune response in a subject in need thereof. Such methods comprise administering an effective amount of a presently disclosed compound (i.e., compound of Formula I, II, or Ill or a pharmaceutically acceptable salt, prodrug, metabolite, or derivative thereof). The term "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells. In some embodiments, the CD8 T cells in the subject have enhanced priming, activation, proliferation and/or cytolytic activity relative to prior to the administration of the compound of Formula I, 11, III or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of y-IFN+ CD8 T cells. In some embodiments, the CD8 T cell is an antigen-specific T-cell.

In some embodiments, the antigen presenting cells in the subject have enhanced maturation and activation relative to prior to the administration of the compound of Formula I, II, III or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83+ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I, II, III or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signalling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) J Cell Biol 195(5):839-853). The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, gamma-IFN) and/or target cell killing.

The term "anergy" refers to the state of unresponsiveness to antigen stimulation resulting from incomplete or insufficient signals delivered through the T-cell receptor {e.g. increase in intracellular Ca in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of Interleukin-2. Anergic T-cells do not undergo clonal expansion and/or acquire effector functions.

The term "exhaustion" refers to T cell exhaustion as a state of T cell dysfunction that arises from sustained TCR signalling that occurs during many chronic infections and cancer. It is distinguished from anergy in that it arises not through incomplete or deficient signalling, but from sustained signalling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., gamma-interferon, IL-2, IL-12, and TNFa), increased proliferation, increased antigen responsiveness (e.g., viral, pathogen, or tumor clearance) relative to such levels before the intervention, and increased effector granule production by CD8 T cells, such as granzyme B.

Accordingly, the presently disclosed compounds of Formula I, II, III or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity.

In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer. "Immunogenecity" refers to the ability of a particular substance to provoke an immune response. Tumors are immunogenic and enhancing tumor immunogenicity aids in the clearance of the tumor cells by the immune response.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

In one aspect, provided herein is a method for treating of cancer in a subject in need thereof comprising administering to the subject an effective amount of a compound of Formula I, II, III or a pharmaceutically acceptable salt, prodrug, metabolite, or derivative thereof. In some embodiments, the subject has melanoma. The melanoma may be at early stage or at late stage.

In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, the treatment results in a sustained response in the subject after cessation of the treatment.

"Sustained response" refers to the sustained effect on reducing tumor growth after cessation of a treatment. For example, the tumor size may remain the same or smaller as compared to the size at the beginning of the administration phase.

The treatment methods disclosed herein may result in a partial or complete response. As used herein, "complete response" or "CR" refers to disappearance of all target lesions; "partial response" or "PR" refers to at least a 30 percent decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the HPKI antagonist. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In frequent embodiments of the methods provided herein, the abnormal cell growth is cancer characterized by amplification or overexpression of HPK1 kinase. In some embodiments of the methods provided herein, the subject is identified as having a cancer characterized by amplification or overexpression of HPK1 kinase.

In frequent embodiments of the methods provided herein, the abnormal cell growth is cancer, wherein the cancer is selected from the group consisting of breast cancer, ovarian cancer, bladder cancer, uterine cancer, prostate cancer, lung cancer (including NSCLC, SCLC, squamous cell carcinoma or adenocarcinoma), esophageal cancer, head and neck cancer, colorectal cancer, kidney cancer (including RCC), liver cancer (including HCC), pancreatic cancer, stomach (i.e., gastric) cancer and thyroid cancer. In further embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer. In some such embodiments, the cancer is characterized by amplification or overexpression of HPK1 kinase.

In some embodiments, the cancer is selected from the group consisting of breast cancer and ovarian cancer. In some such embodiments, the cancer is breast cancer or ovarian cancer characterized by amplification or overexpression of HPK1 kinase. In some such embodiments, the cancer is (a) breast cancer or ovarian cancer; (b) characterized by amplification or overexpression of HPK1 kinase.

In some embodiments, the cancer is ovarian cancer. In some such embodiments, the ovarian cancer is characterized by amplification or overexpression of HPK1 kinase.

In other embodiments, the cancer is breast cancer, including, e.g., ER-positive/HR-positive breast cancer, HER2-negative breast cancer; ER-positive/HR-positive breast cancer, HER2-positive breast cancer; triple negative breast cancer (TNBC); or inflammatory breast cancer. In some embodiments, the breast cancer is endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification or overexpression of HPK1 kinase.

In some embodiments, the compound of the invention is administered as first line therapy. In other embodiments, the compound of the invention is administered as second (or later) line therapy. In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent. In some embodiments, the compound of the invention is administered as second (or later) line therapy following treatment with a CDK4/CDK6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with HER2 targeted agents, e.g., trastuzumab.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of: (1) tumor cells (tumors) that show increased expression of HPK1 kinase; (2) tumors that proliferate by aberrant HPK1 kinase; (3) tumors characterized by amplification or overexpression of HPK1 kinase and (4) tumors that are resistant to endocrine therapy, HER2 antagonists or CDK4/6 inhibition.

The term "additional anticancer therapeutic agent" as used herein means any one or more therapeutic agent, other than a compound of the invention, that is or can be used in the treatment of cancer, such as agents derived from the following classes: mitotic inhibitors, alkylating agents, antimetabolites, antitumor antibiotics, topoisomerase I and II inhibitors, plant alkaloids, hormonal agents and antagonists, growth factor inhibitors, radiation, inhibitors of protein tyrosine kinases and/or serine/threonine kinases, cell cycle inhibitors, biological response modifiers, enzyme inhibitors, antisense oligonucleotides or oligonucleotide derivatives, cytotoxics, and immuno-oncology agents.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is selected from the group consisting of breast cancer, ovarian cancer, bladder cancer, uterine cancer, prostate cancer, lung cancer, esophageal cancer, liver cancer, pancreatic cancer and stomach cancer. In some such embodiments, the cancer is characterized by amplification or overexpression of HPK1 kinase.

Dosage Forms and Regimens

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 antagonists and the like.

When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) anti-cancer therapeutic agents.

In particular embodiments, a compound of the invention may be administered in combination with one or more: targeted agents, such as inhibitors of PI3 kinase, mTOR, PARP, IDO, TDO, ALK, ROS, MEK, VEGF, FLT3, AXL, ROR2, EGFR, FGFR, Src/Abl, RTK/Ras, Myc, Raf, PDGF, AKT, c-Kit, erbB, CDK4/CDK6, CDK5, CDK7, CDK9, SMO, CXCR4, HER2, GLS1, EZH2 or Hsp90, or immunomodulatory agents, such as PD-1 or PD-L1 antagonists, OX40 agonists or 4-1BB agonists.

In other embodiments, a compound of the invention may be administered in combination with a standard of care agent, such as tamoxifen, docetaxel, paclitaxel, cisplatin, capecitabine, gemcitabine, vinorelbine, exemestane, letrozole, fulvestrant, anastrozole or trastuzumab.

Synthetic Methods

The compounds of Formula I, II and III may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XIII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, II and III or their pharmaceutically acceptable salts, can be prepared according to the reaction Schemes discussed herein below. Unless otherwise indicated, the substituents in the Schemes are defined as above. One of ordinary skill in the art will recognize that $R^{13}$ is a substituent that occurs off of $R^4$. Non-limiting examples of $R^{13}$ include $(C_1-C_6)$alkyl optionally substituted with hydroxy, halo$(C_1-C_6)$alkyl and $—(CH_2)_n(C_3-C_6)$cycloalkyl wherein n is 0 or 1. Non-limiting examples of $(C_1-C_6)$alkyl for $R^{13}$ in the schemes below include $CH_3—$, $CH_3—CH_2—$, and $CH_3—CH_2—CH_2—$.

Isolation and purification of the products is accomplished by standard procedures, which are known to a chemist of ordinary skill.

It will be understood by one skilled in the art that the various symbols, superscripts, and subscripts used in the schemes, methods, and examples are used for convenience of representation and/or to reflect the order in which they are introduced in the schemes, and are not intended to necessarily correspond to the symbols, superscripts, or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed-phase chromatography, and chiral chromatography, to afford single enantiomers. The schemes are representative of methods useful in synthesizing the compounds of the present invention. They are not to constrain the scope of the invention in any way.

Compounds of the invention are prepared according to the exemplary procedures provided herein and modifications thereof known to those of skill in the art.

The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "DBU" means 1,8-diazabicyclo[5.4.0]undec-7-ene, "Cbz" means benzyloxycarbonyl, "DCM" ($CH_2Cl_2$) means methylene chloride, "de" means diastereomeric excess, "DEA" means diethylamine, "DIPEA" means diisopropyl ethyl amine, "DMA" means N,N-dimethylacetamide, "DME" means 1,2-dimethoxyethane, "DMF" means N,N-dimethyl formamide, "DMSO" means dimethylsulfoxide, "EDTA" means ethylenediaminetetraacetic acid, "ee" means enantiomeric excess, "Et" means ethyl, "EtOAc" means ethyl acetate, "EtOH" means ethanol, "HOAc" or "AcOH" means acetic acid, "i-Pr" or "iPr" means isopropyl, "IPA" means isopropyl alcohol, "LAH" means lithium aluminum hydride, "LHMDS" means lithium hexamethyldisilazide (lithium bis(trimethylsilyl)amide), "mCPBA" means meta-chloroperoxy-benzoic acid, "Me" means methyl, "MeOH" means methanol, "MS" means mass spectrometry, "MTBE" means methyl tert-butyl ether, "NCS" means N-chlorosuccinimide, "Ph" means phenyl, "TBHP" means tert-butyl hydroperoxide, "TBME" means tert-Butyl methyl ether, "TFA" means trifluoroacetic acid, "THF" means tetrahydrofuran, "SFC" means supercritical fluid chromatography, "TLC" means thin layer chromatography, "Rf" means retention factor, "~" means approximately, "rt" means retention time, "h" means hours, "min" means minutes, "equiv" means equivalents, "sat." means saturated.

Preparation of Synthetic Intermediates

Intermediate 1: 2-bromo-6-[4-(propan-2-yl)-4H-1,2,4-triazol-3-yl]pyridine

Step 1: 6-bromopyridine-2-carbohydrazide (1a)

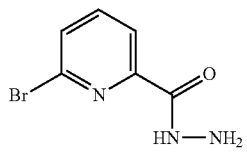

To a solution of methyl 6-bromo-2-pyridinecarboxylate (16.0 g, 74.0 mmol) in methanol (120 mL) was added hydrazine monohydrate (5.23 g, 88.8 mmol, 85%) and the mixture was stirred for 16 hours at ambient temperature. The resultant solution was concentrated to approximately half the volume and then triturated by adding 40 mL of methyl tert-butyl ether and stirring for 10 minutes. The resultant white solid was filtered and dried under vacuum to provide the title compound (15 g, 94%). $^1$H NMR (400 MHz, CDCl$_3$) δ 8.82 (br. s., 1H), 8.13 (dd, J=0.9, 7.5 Hz, 1H), 7.76-7.71 (m, 1H), 7.64 (dd, J=0.9, 8.0 Hz, 1H), 4.08 (br. s., 2H). m/z (ESI) for ($C_6H_6BrN_3O$) 217.5 (M+H)$^+$ Step 2: N'-[(6-bromopyridin-2-yl)carbonyl]-N,N-dimethylhydrazonoformamide (1b)

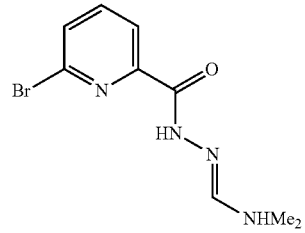

A solution of 6-bromopyridine-2-carbohydrazide (1a) (15.0 g, 69.4 mmol) in dimethyl formamide dimethyl acetal (80 mL) was stirred at 80° C. for 16 hours. The resulting mixture was concentrated under reduced pressure to give a residue. Methyl tert-butyl ether (60 mL) was added to this residue and it was stirred for 40 min, the resultant yellow solid was filtered and dried to provide the title compound (16 g, 85%). $^1$H NMR (400 MHz, DMSO-d$_6$) δ 10.74 (s, 1H), 8.06 (s, 1H), 8.01-7.97 (m, 1H), 7.91 (t, J=7.7 Hz, 1H), 7.80 (dd, J=1.0, 7.8 Hz, 1H), 2.84 (s, 6H). m/z (ESI) for ($C_9H_{11}BrN_4O$) 272.7 (M+H)$^+$ Step 3: 2-bromo-6-[4-(propan-2-yl)-4H-1,2,4-triazol-3-yl]pyridine (Intermediate 1)

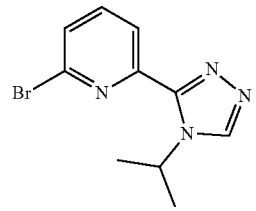

N'-[(6-bromopyridin-2-yl)carbonyl]-N,N-dimethylhydrazonoformamide (1b) (16.0 g, 59.0 mmol) and iso-propylamine (12.0 g, 200 mmol) were dissolved in acetic acid (33 mL) and acetonitrile (130 mL). After observed smoke evolution subsided, the resultant solution was stirred at 95° C. for 16 hours. The reaction mixture was combined with another batch of this reaction (5 g scale) and concentrated in vacuo. The resulting material was diluted with water (130 mL) and adjusted to pH=7 with 1N aqueous sodium hydroxide (120 mL). The resulting mixture was then extracted with ethyl acetate (2×150 mL) and the combined organic layer was washed with water (2×130 mL) and concentrated in vacuo. The crude product was purified using column chromatography (0-100% ethyl acetate in petroleum ether) to provide the title compound as a yellow solid (16.9 g, average yield 82%). $^1$H NMR (400 MHz, CDCl$_3$) δ 8.42-8.34 (m, 1H), 8.28 (d, J=7.8 Hz, 1H), 7.69 (t, J=7.8 Hz, 1H), 7.52 (d, J=7.8 Hz, 1H), 5.57 (spt, J=6.7 Hz, 1H), 1.56 (d, J=6.5 Hz, 6H). m/z (ESI) for ($C_{10}H_{11}BrN_4$) 268.8 (M+H)$^+$ Intermediate 2: tert-butyl ((6-chloro-1-oxo-2,3-dihydro-1H-pyrrolo[3,4-c]pyridin-4-yl)methyl)(methyl)carbamate Step 1: 4-chloro-2,3-dihydro-1H-pyrrolo[3,4-c]pyridin-1-one (2a)

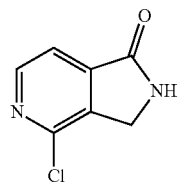

2a

N-bromosuccinimide (5.43 g, 30.5 mmol) and azobisisobutyronitrile (453 mg, 2.76 mmol) were added to a solution of methyl 2-chloro-3-methylpyridine-4-carboxylate (5.12 g, 27.61 mmol) in carbon tetrachloride (35 mL, 0.8 M). The resulting mixture was heated at 80° C. for 18 h. The mixture was cooled to room temperature, filtered and solid was washed with carbon tetrachloride (10 mL). The filtrate was diluted with DCM (100 mL) and washed with a saturated solution of aqueous sodium bicarbonate (100 mL). The aqueous layer was extracted with DCM (100 mL). The combined organic layers were dried over anhydrous sodium sulfate, filtered and concentrated to give a pale brown oil, which was dissolved in 7 N ammonia in methanol (39 mL, 276 mmol). The reaction was allowed to stir at room temperature for 3 h. The solvent was removed under reduced pressure. The residue was dissolved in DCM (100 mL) and washed with a saturated solution of aqueous sodium bicarbonate (100 mL). The aqueous layer was extracted with DCM (100 mL). The combined organic layer was dried over anhydrous sodium sulfate, filtered and concentrated to provide the title compound as off-white solid (4.58 g, 98%). $^1$H NMR (400 MHz, CDCl$_3$) δ 8.62 (d, J=4.89 Hz, 1H), 7.75 (d, J=5.01 Hz, 1H), 6.70 (br. s., 1H), 4.54 (s, 2H). m/z (APCI+) for (C$_7$H5ClN$_2$O) 168.7 (M+H)$^+$ Step 2: methyl 1-oxo-2,3-dihydro-1H-pyrrolo[3,4-c]pyridine-4-carboxylate (2b)

2b

Into a 100 mL pressure tank reactor was placed 4-chloro-2,3-dihydro-1H-pyrrolo[3,4-c]pyridin-1-one (2a) (787 mg, 4.67 mmol), methanol (30 mL), potassium acetate (913 mg, 9.30 mol), and palladium-tetrakis(triphenylphosphine) (168 mg, 0.145 mmol). The vessel was pressurized with carbon monoxide gas (4 bar) and the reaction was heated for 4 h at 100° C. The resulting mixture was filtered and the resulting solid was washed with methanol. The solid was then collected and dried to provide the title compound as brown solid (744 mg, 83%) which was used without purification. $^1$H NMR (400 MHz, DMSO-d$_6$) δ 9.13 (s, 1H), 8.87 (d, J=4.77 Hz, 1H), 7.93 (d, J=4.77 Hz, 1H), 4.71 (s, 2H), 3.93 (s, 3H). m/z (APCI+) for (C$_9$H$_8$N$_2$O$_3$) 193.0 (M+H)$^+$ Step 3: 2-(tert-Butyl) 4-methyl 1-oxo-1,3-dihydro-2H-pyrrolo[3,4-c]pyridine-2,4-dicarboxylate (2c)

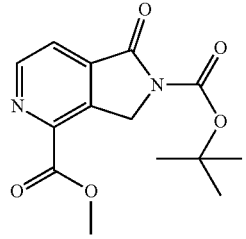

2c

Triethylamine (0.81 mL, 5.81 mmol), di-tert-butyl dicarbonate (1.07 g, 4.65 mmol) and 4-dimethylamine pyridine (48.3 mg, 0.387 mmol) were added to a suspension of methyl 1-oxo-2,3-dihydro-1H-pyrrolo[3,4-c]pyridine-4-carboxylate (2b) (744 mg, 3.87 mmol) in DCM (4.0 mL, 1 M). The mixture was stirred at room temperature for 4 h. The reaction was diluted with water (30 mL) and extracted with DCM (2×30 mL). The combined organic layer was dried over anhydrous sodium sulfate, filtered and concentrated. The crude material was purified using column chromatography (30-100% ethyl acetate in heptane) to provide the title compound as pale yellow solid (74 mg, 66%). $^1$H NMR (400 MHz, CDCl$_3$) δ 8.98 (d, J=4.89 Hz, 1H), 8.02 (d, J=4.89 Hz, 1H), 5.21 (s, 2H), 4.11 (s, 3H), 1.65 (s, 9H). m/z (APCI+) for (C$_{14}$H$_{16}$N$_2$O$_5$) 293.3 (M+H)$^+$ Step 4: 2-(tert-Butoxycarbonyl)-4-(methoxycarbonyl)-1-oxo-2,3-dihydro-1H-pyrrolo[3,4-c]pyridine 5-oxide (2d)

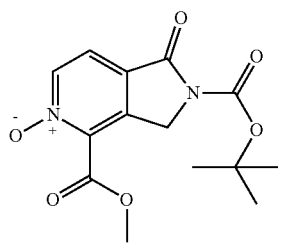

2d

Urea-hydrogen peroxide (1.14 g, 12.1 mmol) was added to a solution of 2-(tert-butyl) 4-methyl 1-oxo-1,3-dihydro-2H-pyrrolo[3,4-c]pyridine-2,4-dicarboxylate 2c (1.68 g, 5.76 mmol) in acetonitrile (38 mL, 0.15 M). The mixture was cooled to 0° C., then trifluoroacetic anhydride (1.6 mL, 11.5 mmol) was added dropwise. The resulting mixture was stirred at 0° C. and then was allowed warm to room temperature and stir for 2 h. The mixture was quenched with 10% aqueous sodium thiosulfate (80 mL) and extracted with DCM (2×80 mL). The combined organic layer was dried over anhydrous sodium sulfate, filtered and concentrated to provide the title compound as a white solid (2.23 g, 125%-80% pure by weight). m/z (APCI+) for ($C_{14}H_{16}N_2O_6$) 308.9 (M+H)+

Step 5: 2-(tert-Butyl) 4-methyl 6-chloro-1-oxo-1,3-dihydro-2H-pyrrolo[3,4-c]pyridine-2,4-dicarboxylate (2e)

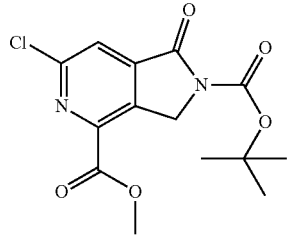

2e 2,6-lutidine (0.34 mL, 2.90 mmol) was added to a solution of 2-(tert-butoxycarbonyl)-4-(methoxycarbonyl)-1-oxo-2,3-dihydro-1H-pyrrolo[3,4-c]pyridine 5-oxide (2d) (1.05 g, 2.90 mmol) in DCM (29 mL, 0.1 M) at 0° C., then phosphorous(V)oxychloride (0.54 mL, 5.79 mmol) and DMF (0.14 mL, 1.74 mmol) were added. The resulting mixture was stirred at 0° C. then allowed to warm to room temperature. After 2 h, LCMS show only starting material and phosphorous(V)oxychloride (0.32 mL, 3.47 mmol) and DMF (0.14 mL, 1.74 mmol) were added and the reaction and the mixture was allowed to stir at room temperature for 18 h. The reaction was quenched with a saturated solution of aqueous sodium bicarbonate (100 mL) and extracted with DCM (2×100 mL). The combined organic layer was dried over anhydrous sodium sulfate, filtered and concentrated. The crude material was purified using column chromatography (30-100% ethyl acetate in heptane) to provide the title compound as white solid (722 mg, 76%). (Contained about 8% methyl 6-chloro-2-formyl-1-oxo-2,3-dihydro-1H-pyrrolo[3,4-c]pyridine-4-carboxylate by $^1$H NMR). $^1$H NMR (400 MHz, CDCl$_3$) δ 7.92 (s, 1H) 5.07 (s, 2H) 4.00 (s, 3H) 1.55 (s, 9H). m/z (APCI+) for ($C_{14}H_{15}ClN_2O_5$) 328.9 (M+H)+

Step 6: methyl 6-chloro-1-oxo-2,3-dihydro-1H-pyrrolo[3,4-c]pyridine-4-carboxylate (2f)

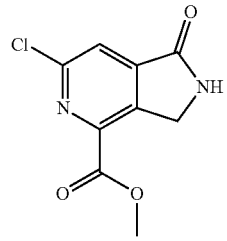

2f

A solution of 4 N HCl in dioxane (7.0 mL, 29.0 mmol) was added to a solution of 2-(tert-butyl) 4-methyl 6-chloro-1-oxo-1,3-dihydro-2H-pyrrolo[3,4-c]pyridine-2,4-dicarboxylate (2e) (722 mg, 2.21 mmol) in DCM (20 mL) and methanol (5 mL). The mixture was stirred at room temperature for 3 h. The volatile material was removed under reduced pressure and the resulting material was azeotroped with toluene then further concentrated in vacuo to provide the title compound as an off-white solid (520 mg, 90%). $^1$H NMR (400 MHz, DMSO-d$_6$) δ 9.28 (s, 1H) 8.04 (s, 1H) 4.68 (s, 2H) 3.94 (s, 3H). m/z (APCI+) for ($C_9H_7ClN_2O_3$) 226.90 (M+H)+

Step 7: 6-chloro-4-(hydroxymethyl)-2,3-dihydro-1H-pyrrolo[3,4-c]pyridin-1-one (2g)

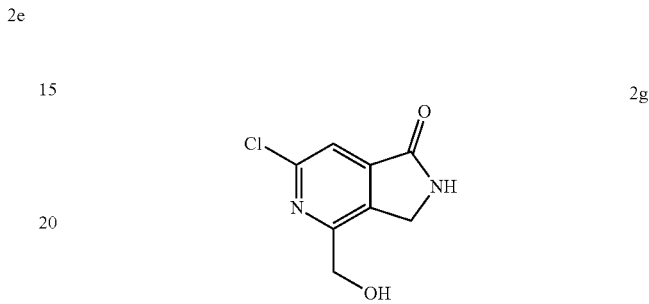

2g

A 2.0 M solution of lithium borohydride in THF (8.8 mL, 17.7 mmol) was added to a suspension of methyl 6-chloro-1-oxo-2,3-dihydro-1H-pyrrolo[3,4-c]pyridine-4-carboxylate (2f) (1.0 g, 3.80 mmol) in THF (60 mL, 0.074 M) at 0° C. The mixture was stirred at 0° C. for 1 h, then was quenched with an aqueous solution of 1N HCl (0.5 mL). The mixture was diluted with water (100 mL) and extracted with 20% isopropanol in DCM (4×100 mL). The combined organic layer was dried over anhydrous sodium sulfate, filtered and concentrated to provide the title compound as a white solid (795 mg, 91%). $^1$H NMR (400 MHz, DMSO-d$_6$) δ 9.05 (br. s., 1H) 7.60 (s, 1H) 5.59 (t, J=5.93 Hz, 1H) 4.72 (d, J=5.75 Hz, 2H) 4.56 (s, 2H). m/z (APCI+) for ($C_8H_7ClN_2O_2$) 199.0 (M+H)+

Step 8: tert-butyl ((6-chloro-1-oxo-2,3-dihydro-1H-pyrrolo[3,4-c]pyridin-4-yl)methyl)(methyl)carbamate (Intermediate 2)

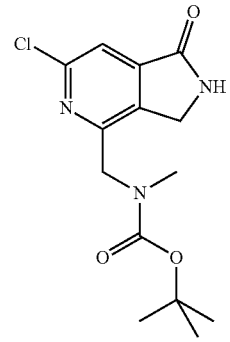

Intermediate 2

Methanesulfonyl chloride (0.04 mL, 0.483 mmol) was added to a suspension of 6-chloro-4-(hydroxymethyl)-2,3-dihydro-1H-pyrrolo[3,4-c]pyridin-1-one (2g) (48.0 mg, 0.240 mmol) in DCM (6.0 mL, 0.02 M) at 0° C. The resulting mixture was stirred at 0° C. for 30 min. A 2 M solution of methylamine in THF (1.21 mL, 2.42 mmol) was added and the mixture was stirred at room temperature for 2 h. The volatile material was removed under reduced pressure and the residue was taken into DCM (6 mL). Di-tert-butyl dicarbonate (66.6 mg, 0.290 mmol) and triethylamine (0.10 mL, 0.725 mmol) were added and the mixture was stirred at room temperature for 3 h. The reaction was diluted with water (20 mL) and extracted with DCM (2×20 mL). The combined organic layer was dried over anhydrous sodium sulfate, filtered and concentrated. The crude material was purified using column chromatography (50-100% ethyl acetate in heptane) to provide the title compound as an off-white solid (40 mg, 53%). ¹H NMR (400 MHz, CDCl₃) δ 7.72 (s, 1H), 4.68 (s, 2H), 4.54 (br. s., 2H), 2.94 (s, 3H), 1.50 (br. s., 9H). m/z (APCI+) for ($C_{14}H_{18}ClN_3O_3$) 312.0 (M+H)⁺.

Intermediate 3: tert-butyl ((6-(dimethylamino)-1-oxo-2,3-dihydro-1H-pyrrolo[3,4-c]pyridin-4-yl)methyl)(methyl)carbamate Step 1: methyl 6-(dimethylamino)-1-oxo-2,3-dihydro-1H-pyrrolo[3,4-c]pyridine-4-carboxylate (3a)

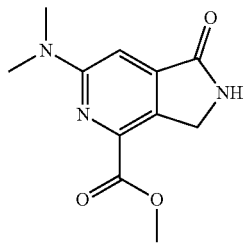

3a

A mixture of dimethylamine hydrochloride (30.8 mg, 0.377 mmol) triethylamine (0.14 mL, 1.03 mmol) and methyl 6-chloro-1-oxo-2,3-dihydro-1H-pyrrolo[3,4-c]pyridine-4-carboxylate 2f (77.7 mg, 0.34 mmol) in DMF (2 mL) was heated to 80° C. After stirring at that temperature for 24 h, the reaction was not complete. Dimethylamine hydrochloride (30.8 mg, 0.377 mmol) and trimethylamine (0.14 mL, 1.03 mmol) were added and the mixture was allowed to stir at 80° C. for 24 h. The volatile material was removed under reduced pressure. The residue was taken into water (10 mL) and extracted with DCM (2×10 mL). The combined organic layer was dried over anhydrous sodium sulfate, filtered and concentrated. The crude material was purified using column chromatography (0-10% methanol in DCM) to provide the title compound as pale brown oil (35 mg, 43%). ¹H NMR (400 MHz, CDCl₃) δ 7.17 (s, 1H) 4.71 (s, 2H) 4.06 (s, 3H) 3.22 (s, 6H). m/z (APCI+) for ($C_{11}H_{13}N_3O_3$) 236.0 (M+H)⁺

Step 2: 6-(dimethylamino)-4-(hydroxymethyl)-2,3-dihydro-1H-pyrrolo[3,4-c]pyridin-1-one (3b)

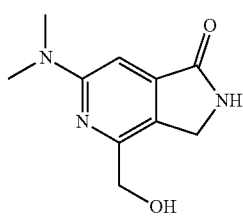

3b

Lithium borohydride (0.27 mL, 0.536 mmol, 2.0 M in THF) was added to a solution of methyl 6-(dimethylamino)-1-oxo-2,3-dihydro-1H-pyrrolo[3,4-c]pyridine-4-carboxylate (3a) (35 mg, 0.130 mmol) in THF (5.0 mL, 0.03 M) at 0° C. The resulting mixture was stirred at 0° C. then allowed warmed to room temperature and stirred for 18 h. The mixture was quenched with water (15 mL) and extracted with 10% methanol in DCM (2×15 mL). The combined organic layers were dried over anhydrous sodium sulfate, filtered and concentrated to provide the title compound as an off-white solid (24 mg, 78%) which was used without purification. m/z (APCI+) for ($C_{10}H_{13}N_3O_2$) 208.1 (M+H)⁺

Step 3: tert-butyl ((6-(dimethylamino)-1-oxo-2,3-dihydro-1H-pyrrolo[3,4-c]pyridin-4-yl)methyl)(methyl)carbamate (Intermediate 3)

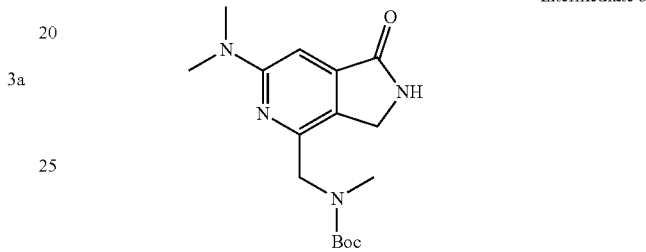

Intermediate 3

To a solution of 6-(dimethylamino)-4-(hydroxymethyl)-2,3-dihydro-1H-pyrrolo[3,4-c]pyridin-1-one (3b) (24 mg, 0.120 mmol) in DCM (16.0 mL) was added triethylamine (0.08 mL, 0.579 mmol) and methanesulfonyl chloride (0.02 mL, 0.232 mmol) at 0° C. The mixture was stirred at 0° C. for 30 min, a 1 M solution of methylamine in THF (1.2 mL, 1.16 mmol) was added and the reaction was stirred at room temperature for 2 h. The volatile material was removed under reduced pressure. The residue was taken into DCM (10 mL) and triethylamine (0.08 mL, 0.579 mmol) and di-tert-butyl dicarbonate (39.1 mg, 0.174 mmol) were added. The resulting mixture was stirred at room temperature for 18 h. The mixture was quenched with water (15 mL) and extracted with 10% methanol in DCM (2×15 mL). The combined organic layer was dried over anhydrous sodium sulfate, filtered and concentrated. The crude material was purified using column chromatography (0-10% methanol in DCM) to provide the title compound as white foam (17 mg, 46%). ¹H NMR (400 MHz, CDCl₃) δ 6.83 (s, 1H), 6.61-6.44 (m, 1H), 4.50 (br s, 2H), 4.41-4.31 (m, 2H), 3.12 (s, 6H), 2.97-2.89 (m, 3H), 1.51-1.39 (s, 9H). m/z (APCI+) for ($C_{16}H_{24}N_4O_3$) 321.0 (M+H)⁺.

Alternatively, Intermediate 3 was prepared as follows:

Step 1: 2-chloro-6-(dimethylamino)-N,N-dimethylpyridine-4-carboxamide (3c)

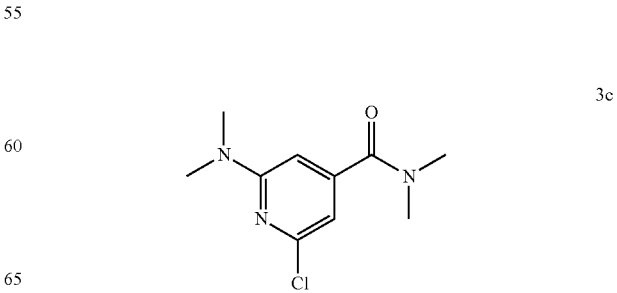

3c

To a 3.0 L round-bottom flask charged with methyl 2,6-dichloropyridine-4-carboxylate (58.0 g, 281 mmol) under an atmosphere of $N_2$ was added N,N-dimethylamine (38.1 g, 845 mmol) at 0-10° C. THF (200 mL) was added. A solution of i-PrMgCl (2.0 M in THF, 352 mL, 704 mmol) was added over 3 h, maintaining the reaction temperature at 0-10° C. The reaction was stirred a further 10 min at 0° C. and then at 25° C. for 18 h. LCMS analysis showed consumption of the starting material with formation of the desired product mass. The reaction was cooled in an ice bath and quenched by addition of cold saturated aqueous $NH_4Cl$ (500 mL), maintaining the reaction temperature <20° C. EtOAc (500 mL) was added and the layers were separated. The aqueous layer was extracted with EtOAc (500 mL). The combined organics were washed with brine, dried over $Na_2SO_4$, filtered, and concentrated. The resultant oil was taken up in heptane (200 mL) and concentrated on a rotary evaporator until solids formed. The suspension was stirred for 0.5 h and the solids were collected by filtration. The filter cake was washed with hexanes (3×50 mL). The filter cake was slurried in 1:20 EtOAc/petroleum ether (100 mL) and the solids were collected by filtration. The filter cake was washed with 1:20 EtOAc/petroleum ether (3×30 mL) and then dried under vacuum to provide 2-chloro-6-(dimethylamino)-N,N-dimethylpyridine-4-carboxamide (51 g, 80% yield) as a light-yellow solid. $^1$H NMR (400 MHz, CDCl$_3$) δ 6.49 (d, J=0.7 Hz, 1H), 6.35 (d, J=0.9 Hz, 1H), 3.13-3.09 (m, 9H), 2.98 (s, 3H); m/z (ESI+) for ($C_{10}H_{14}ClN_3O$), 227.9 (M+H)$^+$.

Step 2: 2-chloro-6-(dimethylamino)-3-formyl-N,N-dimethylpyridine-4-carboxamide (3d)

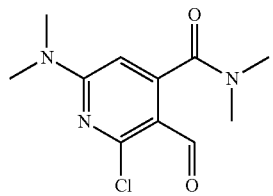

3d

This transformation was run in two parallel reactions. To a round-bottom flask containing DMF (250 mL), with stirring, was added POCl$_3$ (85.9 g, 560 mmol) at 15-25° C. The mixture was stirred at 15-25° C. for 15 min and then 2-chloro-6-(dimethylamino)-N,N-dimethylpyridine-4-carboxamide (25.5 g, 112 mmol) was added. The mixture was stirred at 50° C. for 16 h. LCMS analysis showed consumption of the starting material with formation of the desired product mass. The two reactions were combined and then quenched by slowly pouring into cold aqueous saturated $Na_2CO_3$, maintaining the pH ~9. The mixture was extracted with EtOAc (4×1.0 L). The combined organics were washed with brine (5×600 mL), dried over $Na_2SO_4$, filtered, and concentrated. The crude product was combined with two additional reactions run in identical fashion with 7.5 g and 5.0 g 2-chloro-6-(dimethylamino)-N,N-dimethylpyridine-4-carboxamide. The material was taken up in EtOAc (200 mL) and slurried for 20 min. The suspension was filtered. The filter cake was washed with EtOAc (2×50 mL). The filter cake was slurried in 1:1 petroleum ether/EtOAc (80 mL) for 20 min. The suspension was filtered and the filter cake was washed with 1:1 petroleum ether/EtOAc (60 mL). The filter cake was dried under vacuum. The combined filtrate was concentrated to dryness. The residue was slurried with 1:1 petroleum ether/EtOAc (100 mL) for 30 min. The suspension was filtered and the filter cake was washed with 1:1 petroleum ether/EtOAc (2×50 mL) and dried under vacuum. The combined dried solids were slurried in petroleum either (200 mL) for 10 min and the solids were collected by filtration. The filter cake was washed with petroleum ether (100 mL) and then concentrated under vacuum. The combined filtrate was concentrated under vacuum to ~50 mL and then let stand for 2 d. The resultant solids were collected by filtration and the filter cake was washed with 3:2 petroleum ether/EtOAc (2×50 mL). The solids were combined to provide 2-chloro-6-(dimethylamino)-3-formyl-N,N-dimethylpyridine-4-carboxamide (52 g, 73% yield) as a yellow solid. $^1$H NMR (400 MHz, CDCl$_3$) δ 10.21 (d, J=0.6 Hz, 1H), 6.28 (d, J=0.6 Hz, 1H), 3.19 (s, 6H), 3.13 (s, 3H), 2.77 (s, 3H); m/z (ESI+) for ($C_{11}H_{14}ClN_3O_2$), 255.9 (M+H)$^+$.

Step 3: tert-butyl {[6-(dimethylamino)-4-(dimethylcarbamoyl)-3-formylpyridin-2-yl]methyl}methylcarbamate (3e)

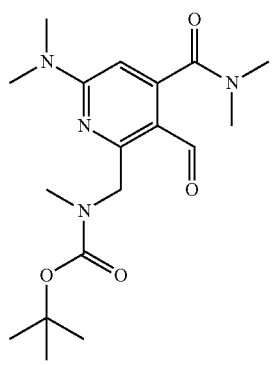

3e

A mixture of tert-butyl dimethylcarbamate (3.41 g, 23.5 mmol) and N,N,N,N-tetramethylenediamine (3.27 g, 28.2 mmol) in 135 mL THF was cooled to −55° C. under an atmosphere of $N_2$. A solution of s-BuLi (1.4 M in cyclohexane, 20.1 mL, 28.2 mmoL) was added slowly maintaining the solution temperature <−52° C. (internal). The mixture was stirred for an additional 30 min at −55° C. and then treated with a solution of $ZnCl_2$ (1.9 M in 2-methyltetrahydrofuran, 14.8 mL, 28.2 mmol), maintaining the reaction temperature <−52° C. The solution was stirred for an additional 40 min at −55° C. and then warmed to room temperature to provide a solution of {[(tert-butoxycarbonyl)(methyl)amino]methyl}(chlorido)zinc (c=0.195 M). A portion of the pre-formed zincate solution (90.2 mL, 17.6 mmoL) was transferred to an oven-dried 250 mL round bottom under an atmosphere of $N_2$ and concentrated to dryness to provide a white foam. The flash was back-filled with $N_2$. A separate flask was charged with 2-chloro-6-(dimethylamino)-3-formyl-N,N-dimethylpyridine-4-carboxamide (3.0 g, 10 mmol), PdCl$_2$(dppf) (0.858 g, 1.17 mmol), 1,4-dioxane (50 mL) and $H_2O$ (0.159 g, 8.8 mmol). The suspension was transferred to via cannulation to the flask containing the zincate and then the mixture was stirred at 80° C. for 80 min. LCMS showed formation of the desired product mass with some remaining starting material. An additional aliquot of {[(tert-butoxycarbonyl)(methyl)amino]methyl}(chlorido)zinc solution (2.0 mL) was added and the mixture was stirred at 80° C. for 20 min. No additional conversion was observed. The reaction was cooled to 0° C. and quenched by addition of saturated aqueous NH$_4$Cl (10 mL) and H$_2$O (20 mL). The mixture was stirred at 0° C. for 20 min and then filtered through a pad of celite. The filtrate was extracted with EtOAc (4×). The combined organics were dried over Na$_2$SO$_4$, filtered, and concentrated. The residue was purified by flash chromatography (80 g SiO$_2$, 0-100% EtOAc/heptane. The resultant white foam was triturated with MTBE and concentrated under vacuum to provide tert-butyl {[6-(dimethylamino)-4-(dimethylcarbamoyl)-3-formylpyridin-2-yl]methyl}methylcarbamate (3.8 g, 95% yield) as a light-yellow solid. $^1$H NMR (400 MHz, DMSO-d$_6$) δ 9.84 (d, J=6.8 Hz, 1H), 6.45 (s, 1H), 4.71 (s, 2H), 3.15 (s, 6H), 2.99 (s, 3H), 2.90 (s, 3H), 2.75 (s, 3H), 1.33 (d, J=69.8 Hz, 9H); m/z (ESI+) for (C$_{18}$H$_{28}$N$_4$O$_4$), 365.3 (M+H)$^+$.

Step 4: tert-butyl {[6-(dimethylamino)-4-(dimethylcarbamoyl)-3-{(E)-[(2-methylpropane-2-sulfinyl)imino]methyl}pyridin-2-yl]methyl}methylcarbamate (3f)

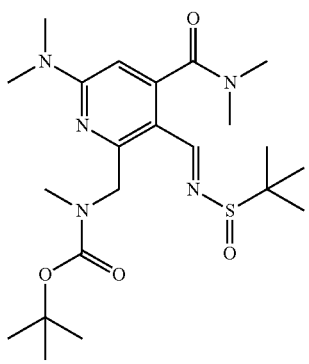

3f

To a solution of tert-butyl {[6-(dimethylamino)-4-(dimethylcarbamoyl)-3-formylpyridin-2-yl]
methyl}methylcarbamate (3.0 g, 8.0 mmol) and (R)-(+)-2-methyl-2-propanesulfinamide (1.2 g, 9.88 mmol) in THF (40 mL) was added titanium(IV) ethoxide (5.63 g, 24.7 mmol). The mixture was stirred at 50° C. overnight. The reaction was cooled to room temperature, diluted with DCM (50 mL), and quenched by addition of saturated aqueous NaHCO$_3$ (20 mL). The solution was vigorously stirred for 20 min and then filtered through a pad of celite. The celite was washed with DCM (3×). The combined filtrate was dried over Na$_2$SO$_4$, filtered, and concentrated. The residue was purified by flash chromatography (80 g SiO$_2$, 0-100% EtOAc/heptane) to provide tert-butyl {[6-(dimethylamino)-4-(dimethylcarbamoyl)-3-{(E)-[(2-methylpropane-2-sulfinyl)imino]methyl}pyridin-2-yl]methyl}methylcarbamate (3.89 g, 97% yield) as a colorless foam. $^1$H NMR (400 MHz, DMSO-d$_6$) δ 8.39 (s, 1H), 6.46 (s, 1H), 4.77-4.55 (m, 2H), 3.12 (s, 6H), 2.95 (s, 3H), 2.93 (s, 3H), 2.74 (s, 3H), 1.41 (s, 4H), 1.20 (s, 5H), 1.12 (s, 9H); m/z (ESI+) for (C$_{22}$H$_{37}$N$_5$O$_4$S), 468.4 (M+H)$^+$ Step 5: tert-butyl {[6-(dimethylamino)-1-oxo-2,3-dihydro-1H-pyrrolo[3,4-c]pyridin-4-yl]methyl}methylcarbamate

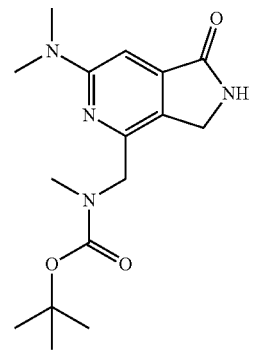

Intermediate 3

To round-bottom flask charged with tert-butyl {[6-(dimethylamino)-4-(dimethylcarbamoyl)-3-{(E)-[(2-methylpropane-2-sulfinyl)imino]methyl}pyridin-2-yl]
methyl}methylcarbamate (3.89, 8.32 mmol) under an atmosphere of N$_2$ was added THF (42 mL). The mixture was cooled to 0° C. and then treated with a solution of LiBH$_4$ (2.0 M in THF, 4.37 mL, 8.73 mmol). The mixture was stirred at 0° C. for 1 h and then a solution of NaOMe (25% in MeOH, 17.1 mL, 74.9 mmol) was added at the same temperature. The reaction was allowed to warm slowly to room temperature and stirred for 16 h. LCMS analysis indicated consumption of the starting material with formation of the desired product mass. The mixture was diluted with DCM and washed with saturated aqueous NH$_4$Cl and brine. The organic layer was dried over Na$_2$SO$_4$, filtered, and concentrated. The residue was purified by flash chromatography (80 g SiO$_2$, 0-100% EtOAc/heptanes) to provide Intermediate 3 (1.7 g, 64% yield) as a colorless foam. $^1$H NMR (400 MHz, DMSO-d$_6$) δ 8.68 (s, 1H), 6.68 (s, 1H), 4.42 (s, 2H), 4.23 (s, 2H), 3.06 (s, 6H), 2.86 (s, 3H), 1.36 (m, 9H); LCMS m/z (ESI+) for (C$_{16}$H$_{24}$N$_4$O$_3$), 321.2 (M+H)$^+$.

Intermediate 4:
2-bromo-6-(5-methyl-1,3,4-oxadiazol-2-yl)pyridine

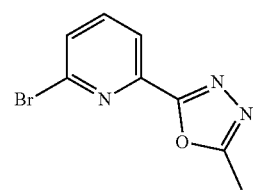

Step 1: N'-acetyl-6-bromopyridine-2-carbohydrazide (4a)

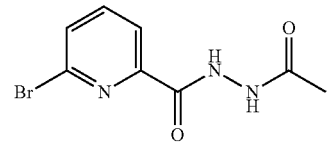

4a

To a solution of 6-bromopyridine-2-carbohydrazide (1a) (1.5 g, 6.94 mmol) in DCM (23 mL) at 0° C. were added TEA (1.4 mL, 10.4 mmol) and acetyl chloride (0.56 mL, 7.8 mmol). The resulting solution stirred at 20° C. for 58 h. The reaction was concentrated dryness and the residue was purified by flash chromatography (SiO$_2$, 0-100% ethyl acetate/petroleum ether) to provide N-acetyl-6-bromopyridine-2-carbohydrazide as a white solid (1.0 g, 56%). $^1$H NMR (400 MHz, DMSO-d$_6$) δ 10.41 (d, J=1.6 Hz, 1H), 10.02 (d, J=1.6 Hz, 1H), 8.04 (dd, J=7.5, 1.2 Hz, 1H), 7.97 (t, J=7.7 Hz, 1H), 7.91 (dd, J=7.9, 1.2 Hz, 1H), 1.92 (s, 3H); m/z (ESI) for (C$_8$H$_8$BrN$_3$O$_2$), 257.9 (M+H)$^+$.

Step 2: 2-bromo-6-(5-methyl-1,3,4-oxadiazol-2-yl)pyridine

Intermediate 4

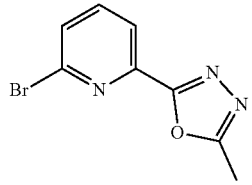

To a solution of N'-acetyl-6-bromopyridine-2-carbohydrazide (4a) (240 mg, 0.93 mmol) in DCM (6 mL) and MeCN (6 mL) was added TEA (0.78 mL, 5.6 mmol) and p-toluenesulfonyl chloride (195 mg, 1.0 mmol). The resulting solution stirred stir at 20° C. for 5 h. The reaction was concentrated in vacuo and the resulting material was purified flash chromatography (SiO$_2$, 0-10% methanol/DCM) to provide 2-bromo-6-(5-methyl-1,3,4-oxadiazol-2-yl)pyridine as a white solid (80 mg, 36%). $^1$H NMR (400 MHz, DMSO-d$_6$) δ 8.18 (d, J=7.6 Hz, 1H), 8.00 (t, J=7.8 Hz, 1H), 7.90 (d, J=8.0 Hz, 1H), 2.63 (s, 3H); m/z (ESI) for (C$_8$H$_6$BrN$_3$O), 241.5 (M+H)$^+$.

Intermediate 5:
2-bromo-6-(1,3,4-oxadiazol-2-yl)pyridine

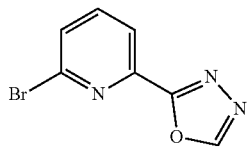 [SMILES: Brc1cccc(-c2nnco2)n1]

A solution of 6-bromopyridine-2-carbohydrazinde (1a) (1.0 g, 4.63 mmol) in HC(OEt)$_3$ (4.0 mL) was stirred at 120° C. for 18 h. The reaction was cooled to room temperature and HC(OEt)$_3$ (4.0 mL) was added. The reaction was allowed to stir at 140° C. for 3 h, then 135° C. for 16 h, 150° C. for 16 h, and 135° C. for 19 h. LCMS analysis minimal remaining starting material with formation of the desired product mass. The reaction was concentrated to dryness. The residue as purified by flash chromatography (SiO$_2$, 1:10 EtOAc/petroleum ether) to provide Intermediate 5 (400 mg, 38% yield) as a white solid. $^1$H NMR (400 MHz, DMSO-d$_6$) δ 9.46 (s, 1H), 8.23 (d, J=7.5 Hz, 1H), 8.05-7.98 (m, 1H), 7.92 (d, J=8.0 Hz, 1H); m/z (ESI) for (C$_7$H4BrN$_3$O), 225.8, 227.8 (M+H)$^+$.

Intermediate 6:
2-bromo-6-(1,3,4-thiadiazol-2-yl)pyridine

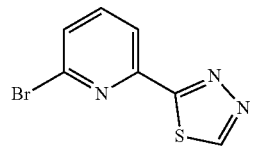 [SMILES: Brc1cccc(-c2nncs2)n1]

Step 1:
6-bromo-N-formylpyridine-2-carbohydrazide (6a)

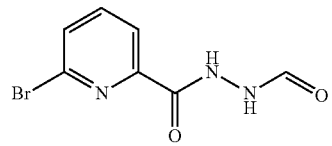

6a

Neat formic acid (3.2 g, 69.4 mmol) was added to Ac$_2$O (5.9 g, 57.9 mmol) under an atmosphere of N$_2$. The mixture was stirred at 60° C. for 1 h and then cooled to room temperature. THF (20.0 mL) was added. The solution was transferred to a solution of 6-bromopyridine-2-carbohydrazinde (1a) (5.0 g, 23.1 mmol) in THF (40 mL) at 0° C. The mixture was stirred at 15° C. for 3 h. LCMS analysis showed consumption of the starting material with formation of the desired product mass. The reaction was concentrated to dryness. The residue was slurried with DCM (50 mL) and the solids were collected by filtration. The filter cake was washed with DCM (50 mL) and dried under vacuum to provide 6-bromo-N-formylpyridine-2-carbohydrazide (6a) (3.7 g, 65% yield) as a white solid. $^1$H NMR (400 MHz, DMSO-d$_6$) δ 10.17 (s, 2H), 8.13-8.00 (m, 2H), 7.98-7.90 (m, 1H), 7.86 (dd, J=7.9, 1.0 Hz, 1H); m/z (ESI) for (C$_7$H$_6$BrN$_3$O$_2$), 245.7 (M+H)$^+$.

Step 2: 2-bromo-6-(1,3,4-thiadiazol-2-yl)pyridine

Intermediate 6

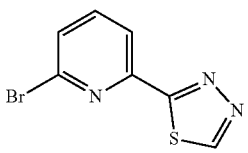

To a solution of 6-bromo-N-formylpyridine-2-carbohydrazide (6a) (4.2 g, 17.4 mmol) in xylenes (420 mL) was added phosphorus pentasulfide (2.3 g, 10.4 mmol). The mixture was stirred at 140° C. for 45 min. LCMS analysis showed consumption of the starting material with formation of the desired product mass. The reaction was concentrated to dryness. The residue was purified by flash chromatography (SiO$_2$, 1:1 petroleum ether/EtOAc). The product was re-purified by flash chromatography (SiO$_2$, 1:3 EtOAc/petroleum ether) to provide Intermediate 6 (587 mg, 14% yield) as a white solid. $^1$H NMR (400 MHz, DMSO-d$_6$) δ

9.75 (s, 1H), 8.32 (dd, J=7.7, 0.9 Hz, 1H), 8.03-7.97 (m, 1H), 7.86 (dd, J=7.9, 0.9 Hz, 1H); m/z (ESI) for (C₇H4BrN₃S), 243.8 (M+H)⁺.

Intermediate 7: tert-butyl [(6-chloro-1-oxo-2,3-dihydro-1H-pyrrolo[3,4-c]pyridin-4-yl)methyl]carbamate

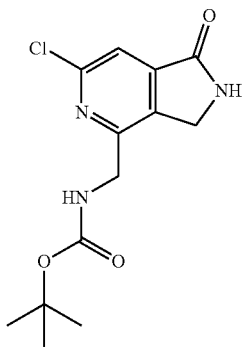 [SMILES: CC(C)(C)OC(=O)NCc1nc(Cl)cc2c1CNC2=O]

Step 1: (6-chloro-1-oxo-2,3-dihydro-1H-pyrrolo[3,4-c]pyridin-4-yl)methyl methanesulfonate (7a)

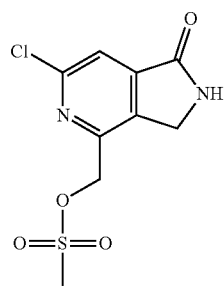

A solution of 6-chloro-4-(hydroxymethyl)-2,3-dihydro-1H-pyrrolo[3,4-c]pyridin-1-one (2.0 g, 10.1 mmol) and TEA (3.1 mg, 30.2 mmol) in THF (50.0 mL) under an atmosphere of N₂ was cooled to 0° C. and then treated dropwise with MsCl (1.73 g, 15.1 mmol). The mixture was stirred at 0° C. for 2 h. LCMS analysis indicated consumption of the starting material. The reaction was diluted with EtOAc (150 mL). The mixture was washed with H₂O (50 mL), saturated aqueous NaHCO₃ (50 mL), and brine (2×50 mL), dried over Na₂SO₄, filtered, and concentrated to provide (6-chloro-1-oxo-2,3-dihydro-1H-pyrrolo[3,4-c]pyridin-4-yl)methyl methanesulfonate (2.0 g, 72% yield) as a grey solid. m/z (ESI+) for (C₉H₉ClN₂O₄S), 276.9 (M+H)⁺.

Step 2: 4-(azidomethyl)-6-chloro-2,3-dihydro-1H-pyrrolo[3,4-c]pyridin-1-one (7b)

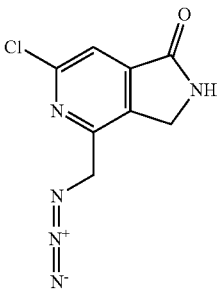

A solution of (6-chloro-1-oxo-2,3-dihydro-1H-pyrrolo[3,4-c]pyridin-4-yl)methyl methanesulfonate (2.0 g, 7.23 mmol), 18-crown-6 (191 mg, 0.723 mmol), and NaN₃ (705 mg, 10.8 mmol) in MeCN (70 mL) was stirred at 10° C. for 20 h. LMCS analysis showed consumption of the starting material with formation of the desired product mass. The reaction was diluted with H₂O (50 mL) and extracted with EtOAc (2×50 mL). The combined organics were washed with brine (50 mL), dried over Na₂SO₄, filtered, and concentrated to provide 4-(azidomethyl)-6-chloro-2,3-dihydro-1H-pyrrolo[3,4-c]pyridin-1-one (1.62 g, >99% yield) as a light brown solid. m/z (ESI+) for (C₈H₆ClN₅O), 223.7 (M+H)⁺.

Step 3: 4-(aminomethyl)-6-chloro-2,3-dihydro-1H-pyrrolo[3,4-c]pyridin-1-one (7c)

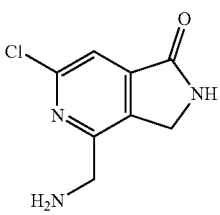

A solution of 4-(azidomethyl)-6-chloro-2,3-dihydro-1H-pyrrolo[3,4-c]pyridin-1-one (1.62 g, 7.23 mmol) and PPh₃ (2.84 mg, 10.8 mmol) in a mixture of THF (40.0 mL) and H₂O (4.0 mL) was stirred at 20° C. for 6 h. LCMS analysis showed consumption of the starting material. A solution of HCl (4.0 M in EtOAc, 50 mL) was added and the mixture was extracted with H₂O (2×30 mL). The combined aqueous layers were basified with solid NaHCO₃ to pH ~8 to provide an aqueous solution of 4-(aminomethyl)-6-chloro-2,3-dihydro-1H-pyrrolo[3,4-c]pyridin-1-one (c 0.12 M, 60 mL), which was taken on directly to the next step.

Step 4: tert-butyl [(6-chloro-1-oxo-2,3-dihydro-1H-pyrrolo[3,4-c]pyridin-4-yl)methyl]carbamate Intermediate 7

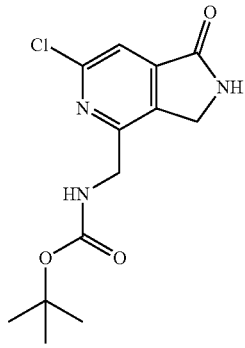

To a solution of 4-(aminomethyl)-6-chloro-2,3-dihydro-1H-pyrrolo[3,4-c]pyridin-1-one (0.12 M in aqueous NaHCO$_3$, 25 mL) was added TEA (620 mg, 6.03 mmol) and DCM (10 mL). The mixture was cooled to 10° C. and Boc$_2$O (790 mg, 3.62 mmol) was added. The mixture was stirred at 15° C. for 1.5 h. LCMS analysis showed consumption of the starting material with formation of the desired product mass. The mixture was diluted with DCM (50 mL) and washed with H$_2$O (25 mL). The organic layer was dried over Na$_2$SO$_4$, filtered, and concentrated. The residue was diluted with DCM (5 mL). Petroleum ether (15 mL) was added and the mixture was stirred at 10° C. for 15 min to provide a suspension. The solids were collected by filtration and The filter cake was dried under vacuum to provide Intermediate 7 (809 mg, 90% yield) as an off-white solid. $^1$H NMR (400 MHz, DMSO-d$_6$) δ 9.08 (s, 1H), 7.62 (s, 1H), 7.50 (br. t, J=6.0 Hz, 1H), 4.46 (s, 2H), 4.34 (d, J=6.0 Hz, 2H), 1.40 (s, 9H); m/z (ESI+) for (C$_{13}$H$_{16}$ClN$_3$O$_3$), 197.9 (M-Boc+H)$^+$.

Intermediate 8: tert-butyl methyl{[6-(1-methylcyclopropyl)-1-oxo-2,3-dihydro-1H-pyrrolo[3,4-c]pyridin-4-yl]methyl}carbamate

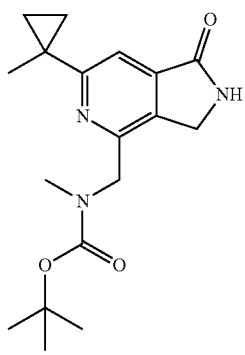 [SMILES: CN(Cc1nc(C2(C)CC2)cc2c1CNC2=O)C(=O)OC(C)(C)C]

Step 1: ethyl 3-cyano-2-hydroxy-6-(1-methylcyclopropyl)pyridine-4-carboxylate (8a)

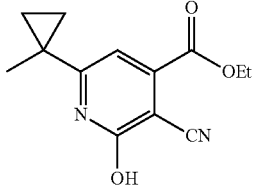

A mixture of 2-cyanoacetamide (10.0 g, 119 mmol) and TEA (12.0 g, 119 mmol) in EtOH (50 mL) was heated to 65° C. (internal) until the solids dissolved and then ethyl 3-(1-methylcyclopropyl)-3-oxopropanoate (24.6 g, 124 mmol) was added. The mixture was stirred at 65° C. for 2 h. TLC analysis (1:10 EtOAc/petroleum ether) showed consumption of the starting material. The reaction was cooled to 10° C. The resultant precipitate was collected by filtration. The filter cake was washed with MTBE (3×10 mL) and dried under vacuum. The filtrate was concentrated to dryness. The residue was diluted with EtOH (10 mL) and MTBE (30 mL) was added. The resultant solids were collected by filtration. The filter cake was washed with EtOH (5 mL) and MTBE (2×10 mL) and dried under vacuum. The solids were combined to provide ethyl 3-cyano-2-hydroxy-6-(1-methylcyclopropyl)pyridine-4-carboxylate (25.0 g, 85% yield) as a yellow solid. $^1$H NMR (400 MHz, DMSO-d$_6$) δ 12.74 (br. s, 1H), 6.63 (br. s, 1H), 4.36 (q, J=7.1 Hz, 2H), 1.45-1.27 (m, 6H), 1.16-1.06 (m, 2H), 0.92-0.75 (m, 2H).

Step 2: ethyl 2-chloro-3-cyano-6-(1-methylcyclopropyl)pyridine-4-carboxylate (8b)

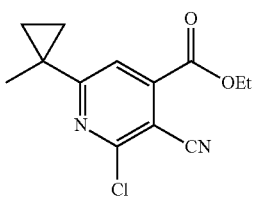

To a solution of ethyl 3-cyano-2-hydroxy-6-(1-methylcyclopropyl)pyridine-4-carboxylate (24.0 g, 97.5 mmol) in MeCN (487 mL) was added POCl$_3$ (74.7 g, 487 mmol) dropwise at 30° C. The mixture was stirred at 65° C. for 60 h. TLC analysis (EtOAc) showed consumption of the starting material. The solution was concentrated to remove residual POCl$_3$. The residue was poured onto ice and basified with NaHCO$_3$ to pH 8. The mixture was extracted with EtOAc (2×100 mL). The combined organics were dried over Na$_2$SO$_4$, filtered, and concentrated. The residue was purified by flash chromatography (1:10 EtOAc/petroleum ether) to provide ethyl 2-chloro-3-cyano-6-(1-methylcyclopropyl)pyridine-4-carboxylate (21.9 g, 85% yield) as a light yellow solid. $^1$H NMR (400 MHz, Chloroform-d) δ 7.79 (s, 1H), 4.50 (q, J=7.2 Hz, 2H), 1.55 (s, 3H), 1.50-1.40 (m, 5H), 1.03 (q, J=3.9 Hz, 2H); m/z (ESI+) for (C$_{13}$H$_{13}$ClN$_2$O$_2$), 264.9 (M+H)$^+$.

Step 3: 4-chloro-6-(1-methylcyclopropyl)-2,3-dihydro-1H-pyrrolo[3,4-c]pyridin-1-one (8c)

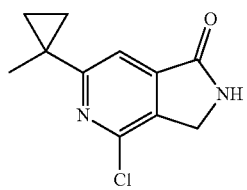

8c

To a solution of ethyl 2-chloro-3-cyano-6-(1-methylcyclopropyl)pyridine-4-carboxylate (2.5 g, 9.44 mmol) in EtOH (500 mL) was added Raney Ni (2.0 g 34.1 mmol). The black mixture was stirred at 30° C. under an atmosphere of H$_2$ at 30 psi for 48 h. TLC analysis (1:10 EtOAc/petroleum ether) showed consumption of the starting material. The mixture was filtered through a pad of celite. The filter cake was washed with MeOH (250 mL). The combined filtrate was concentrated to dryness. The residue was slurried in EtOAc (5 mL) for 20 min and the suspension was filtered. The filter cake was washed with EtOAc (2 mL) and dried under vacuum to provide 4-chloro-6-(1-methylcyclopropyl)-2,3-dihydro-1H-pyrrolo[3,4-c]pyridin-1-one (1.1 g, 52% yield) as a grey solid. $^1$H NMR (400 MHz, CDCl$_3$) δ7.66 (br. s, 1H), 7.23-7.05 (m, 1H), 4.56-4.34 (m, 2H), 1.55 (br. s, 3H), 1.39-1.11 (m, 2H), 0.99-0.66 (m, 2H); m/z (ESI+) for (C$_{11}$H$_{11}$ClN$_2$O), 222.8 (M+H)$^+$.

Step 4: tert-butyl methyl{[6-(1-methylcyclopropyl)-1-oxo-2,3-dihydro-1H-pyrrolo[3,4-c]pyridin-4-yl]methyl}carbamate

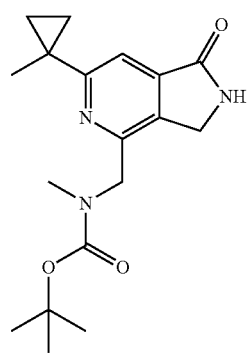

Intermediate 8

A mixture of 4-chloro-6-(1-methylcyclopropyl)-2,3-dihydro-1H-pyrrolo[3,4-c]pyridin-1-one (1.0 g, 4.49 mmol), sodium [(tert-butoxycarbonyl)(methyl)amino]acetate (1.9 g, 8.98 mmol), NiCl$_2$.glyme (197 mg, 0.898 mmol), pyridine-2-yl-N-cyanoamidine (131 mg, 0.898 mmol), and iridium (III) bis[2-(2,4-difluorophenyl)-5-methylpyridine-N,C$_{20}$]-4,40-di-tert-butyl-2,20-bipyridine hexafluorophosphate (22.8 mg, 0.0225 mmol) in DMF (135 mL) was evacuated and backfilled with N$_2$ (3×). The mixture was irradiated with two 72 W purple LED strips under flow (8 mL/min) at ambient temperature for 7 h with fan cooling. The mixture was further irradiated with one 72 W purple LED strip under flow (3 mL/min) for 16 h with fan cooling. The reaction mixture was concentrated to dryness. The residue was purified by flash chromatography (5 g SiO$_2$, 30-80% EtOAc/petroleum ether) to provide Intermediate 8 (856 mg, 58% yield) as an off-white solid. $^1$H NMR (400 MHz, DMSO-d$_6$) δ 8.86 (br. s, 1H), 7.45 (s, 1H), 4.59-4.40 (m, 2H), 4.35 (s, 2H), 2.84 (s, 3H), 1.52 (s, 3H), 1.47-1.31 (m, 5H), 1.31-1.10 (m, 6H), 0.86-0.81 (m, 2H); m/z (ESI+) for (C$_{18}$H$_{25}$N$_3$O$_3$), 332.1 (M+H)$^+$.

Intermediate 9: 4-chloro-6-[ethyl(methyl)amino]-2,3-dihydro-1H-pyrrolo[3,4-c]pyridin-1-one

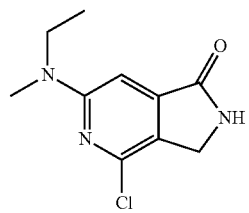

Step 1: ethyl 2-chloro-6-[ethyl(methyl)amino]pyridine-4-carboxylate (9a)

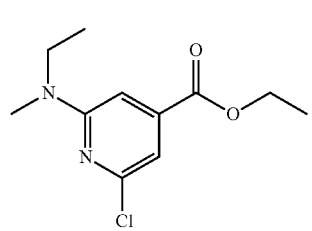

9a

A solution of ethyl 2,6-dichloropyridine-4-carboxylate (1.61 g, 7.34 mmol) and N-methylethanamine (1.30 g, 22.0 mmol) in DMF (3.0 mL) was stirred at 80° C. for 3 h. LCMS analysis showed consumption of the starting material. The reaction was concentrated to dryness. The residue was purified by flash chromatography (12 g SiO$_2$, 0-100% EtOAc/heptane) to provide ethyl 2-chloro-6-[ethyl(methyl)amino]pyridine-4-carboxylate (1.65 g, 93% yield) as a colorless oil.

$^1$H NMR (400 MHz, CDCl$_3$) δ 7.03 (d, J=0.9 Hz, 1H), 6.96 (d, J=0.9 Hz, 1H), 4.39 (q, J=7.1 Hz, 2H), 3.61 (q, J=7.1 Hz, 2H), 3.09 (s, 3H), 1.41 (t, J=7.2 Hz, 3H), 1.19 (t, J=7.1 Hz, 3H); m/z (APCI+) for (C$_{11}$H$_{15}$ClN$_2$O$_2$), 243.1 (M+H)$^+$.

Step 2: ethyl 2-chloro-6-[ethyl(methyl)amino]-3-formylpyridine-4-carboxylate (9b)

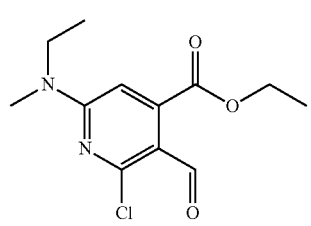

9b

To DMF (508 mg, 6.95 mmol), under an atmosphere of N₂, was added POCl₃ (800 mg, 5.22 mmol). The mixture was stirred at room temperature for 20 min and then a solution of ethyl 2-chloro-6-[ethyl(methyl)amino]pyridine-4-carboxylate (1.65 g, 6.39 mmol) in DCM (25.5 mL) was added. The mixture was stirred at reflux for 20 h under N₂. The mixture was cooled to room temperature and quenched by pouring slowly into aqueous saturated NaHCO₃ (100 mL). The mixture was stirred for 10 min and then extracted with EtOAc (2×80 mL). The combined organics were dried over Na₂SO₄, filtered, and concentrated. The residue was purified by flash chromatography (24 g SiO₂, 0-100% EtOAc/heptane) to provide ethyl 2-chloro-6-[ethyl(methyl) amino]-3-formylpyridine-4-carboxylate (1.51 g, 82% yield) as a pale-yellow solid. $^1$H NMR (400 MHz, CDCl₃) δ 10.17 (s, 1H) 6.37 (s, 1H) 4.43 (q, J=7.09 Hz, 2H) 3.67 (br. d, J=4.03 Hz, 2H) 3.16 (d, J=9.29 Hz, 3H) 1.39 (t, J=7.15 Hz, 3H) 1.23 (t, J=7.09 Hz, 3H); m/z (APCI+) for (C₁₂H₁₅ClN₂O₃), 271.1 (M+H)⁺.

Step 3: 4-chloro-6-[ethyl(methyl)amino]-2,3-di-hydro-1H-pyrrolo[3,4-c]pyridin-1-one Intermediate 9

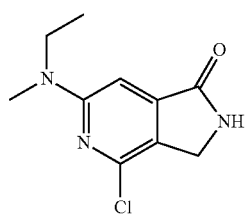

A mixture of ethyl 2-chloro-6-[ethyl(methyl)amino]-3-formylpyridine-4-carboxylate (1.33 g, 4.91 mmol) and a solution of NH₃ (7.0 N in MeOH, 7.01 mL, 49.1 mmol) was stirred for 1 h at room temperature. The mixture was concentrated to dryness. The residue was dissolved in DCM (10.0 mL) and TFA (5.59 g, 49.1 mmol) and Et₃SiH (1.14 g, 1.57 mmol) were added. The mixture was stirred at room temperature for 90 min. The reaction was concentrated to dryness. The residue was dissolved in DCM (100 mL) and washed with saturated aqueous NaHCO₃. The aqueous layer was extracted with DCM. The combined organics were dried over Na₂SO₄, filtered, and concentrated to provide Intermediate 9 (823 mg, 74% yield) as a yellow solid. 1H NMR (400 MHz, CDCl₃) δ 6.82 (s, 1H) 6.41 (br. s, 1H) 4.37 (s, 2H) 3.63 (q, J=7.09 Hz, 2H) 3.10 (s, 3H) 1.19 (t, J=7.09 Hz, 3H); m/z (APCI+) for (C₁₀H₁₂ClN₃O), 226.1 (M+H)⁺.

Intermediate 10: 4-chloro-6-[(2R)-2-methylpyrroli-din-1-yl]-2,3-dihydro-1H-pyrrolo[3,4-c]pyridin-1-one

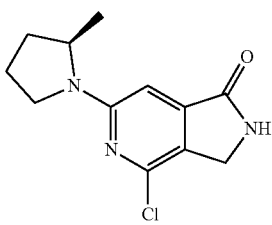 [SMILES: C[C@@H]1CCCN1c1cc2c(c(Cl)n1)CNC2=O]

Step 1: {2-chloro-6-[(2R)-2-methylpyrrolidin-1-yl] pyridin-4-yl}(piperidin-1-yl)methanone (10a)

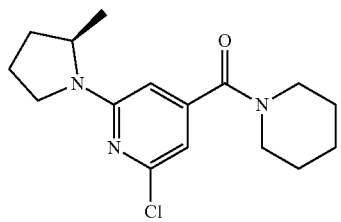

10a

A solution of (2,6-dichloropyridin-4-yl)(piperidin-1-yl) methanone (600 mg, 2.32 mmol) and (2R)-2-methylpyrrolidine (591 mg, 6.95 mmol) in DMF (1.5 mL) was stirred at 100° C. for 16 h. LCMS analysis showed consumption of the starting material with formation of the desired product mass. The reaction was cooled to room temperature, diluted with H₂O, and extracted with DCM (3×). The combined organic layers were dried over Na₂SO₄, filtered, and concentrated. The residue was purified by flash chromatography (24 g SiO₂, 0-20% EtOAc/heptane) to provide {2-chloro-6-[(2R)-2-methylpyrrolidin-1-yl]pyridin-4-yl}(piperidin-1-yl) methanone (664 mg, 93% yield). $^1$H NMR (400 MHz, Chloroform-d) δ 6.44 (d, J=1.0 Hz, 1H), 6.21 (d, J=1.0 Hz, 1H), 4.12 (q, J=7.1 Hz, 1H), 3.72-3.62 (m, 2H), 3.54 (ddd, J=10.5, 7.6, 2.9 Hz, 1H), 3.40-3.28 (m, 2H), 2.10-2.04 (m, 2H), 1.75-1.62 (m, 4H), 1.26 (t, J=7.2 Hz, 1H), 1.21 (d, J=6.3 Hz, 2H); m/z (APCI+) for (C₁₆H₂₂ClN₃O), 308.2 (M+H)⁺.

Step 2: 2-chloro-6-[(2R)-2-methylpyrrolidin-1-yl]-4-(piperidine-1-carbonyl)pyridine-3-carbaldehyde (10b)

10b

To a solution of DMF (473 mg, 6.47 mmol) in DCM (3.0 mL) was added POCl₃ (992 mg, 6.47 mmol). The mixture was stirred for 10 min and then a solution of {2-chloro-6-[(2R)-2-methylpyrrolidin-1-yl]pyridin-4-yl}(piperidin-1-yl) methanone (664 mg, 2.16 mmol) in DCM (3.0 mL) was added. The mixture was stirred at reflux for 15 h. LCMS analysis showed consumption of the starting material with formation of the desired product mass. The reaction was concentrated to dryness and slowly poured into saturated aqueous NaHCO₃ (30 mL). The mixture was extracted with DCM (3×30 mL). The combined organics were dried over Na₂SO₄, filtered, and concentrated. The residue was purified by flash chromatography (24 g SiO₂, 0-40% EtOAc/heptane) to provide 2-chloro-6-[(2R)-2-methylpyrrolidin-1-yl]-4-(piperidine-1-carbonyl)pyridine-3-carbaldehyde (568 mg, 78% yield). $^1$H NMR (400 MHz, CDCl₃) δ 10.07 (s, 1H), 5.99 (s, 1H), 4.13-4.65 (m, 1H), 3.68-3.83 (m, 1H), 3.55-3.68 (m, 2H), 3.35-3.55 (m, 1H), 2.98-3.20 (m, 2H), 1.88-2.17 (m, 3H), 1.71-1.83 (m, 2H), 1.55-1.67 (m, 3H), 1.46-1.55 (m, 1H), 1.31-1.42 (m, 1H), 1.17-1.26 (m, 3H); m/z (APCI+) for ($C_{17}H_{22}ClN_3O_2$), 336.1 (M+H)$^+$.

Step 3: N-[(E)-{2-chloro-6-[(2R)-2-methylpyrrolidin-1-yl]-4-(piperidine-1-carbonyl)pyridin-3-yl}methylidene]-2-methylpropane-2-sulfinamide (10c)

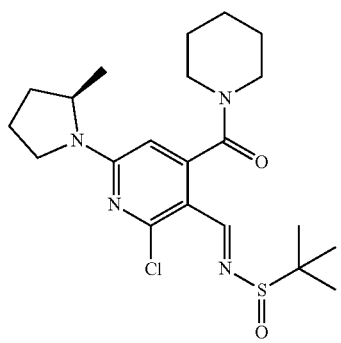

10c

A mixture of 2-chloro-6-[(2R)-2-methylpyrrolidin-1-yl]-4-(piperidine-1-carbonyl)pyridine-3-carbaldehyde (432 mg, 1.29 mmol), (R)-(+)-2-methyl-2-propanesulfinamide (187 mg, 1.54 mmol), and titanium(IV) ethoxide (880 mg, 3.86 mmol) in THF (10.0 mL) was stirred at 45° C. for 16 h. LCMS analysis showed ~25% remaining starting material. Additional batches of (R)-(+)-2-methyl-2-propanesulfinamide (62.4 mg, 0.515 mmol), and titanium(IV) ethoxide (293 mg, 1.29 mmol) were added and the mixture was stirred at 50° C. for 16 h. LCMS analysis showed consumption of the starting material. The reaction was cooled to room temperature. The mixture was diluted with DCM and washed with NaHCO$_3$ and brine. The organic layer was dried over Na$_2$SO$_4$, filtered, and concentrated to provide N-[(E)-{2-chloro-6-[(2R)-2-methylpyrrolidin-1-yl]-4-(piperidine-1-carbonyl)pyridin-3-yl}methylidene]-2-methylpropane-2-sulfinamide (495 mg, 88% yield) as a white gum, which was taken on without further purification. m/z (APCI+) for ($C_{21}H_{31}ClN_4O_2S$), 440.2 (M+H)$^+$.

Step 4: 4-chloro-6-[(2R)-2-methylpyrrolidin-1-yl]-2,3-dihydro-1H-pyrrolo[3,4-c]pyridin-1-one Intermediate 10

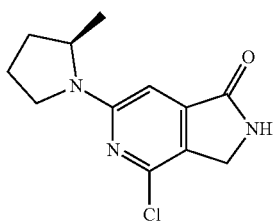

A solution of N-[(E)-{2-chloro-6-[(2R)-2-methylpyrrolidin-1-yl]-4-(piperidine-1-carbonyl)pyridin-3-yl}methylidene]-2-methylpropane-2-sulfinamide (495 mg, 1.13 mmol) in THF (15.0 mL) was cooled to 0° C. and then a solution of LiBH$_4$ (2.0 M in THF, 620 mL, 1.24 mmol) was added. The mixture was stirred at 0° C. for 2 h and then a solution of NaOMe (25% in MeOH, 2.5 mL, 10.1 mmol) was added. The reaction was allowed to warm to room temperature and then stirred for 16 h. The reaction was diluted with DCM (60 mL) and washed with saturated aqueous NH$_4$Cl (60 mL) and brine (60 mL). The organic layer was dried over Na$_2$SO$_4$, filtered, and concentrated. The residue was purified by flash chromatography (24 g SiO$_2$, 50-100% EtOAc/heptane) to provide Intermediate 10 (199 mg, 70% yield) as a colorless foam. $^1$H NMR (400 MHz, Chloroform-d) δ 6.68 (s, 1H), 6.45 (s, 1H), 4.35 (s, 2H), 4.21-4.14 (m, 1H), 3.58 (ddd, J=10.5, 7.6, 2.8 Hz, 1H), 3.39 (q, J=8.9 Hz, 1H), 2.13-1.97 (m, 2H), 1.75 (dt, J=5.2, 2.6 Hz, 1H), 1.23 (d, J=6.3 Hz, 3H). One hydrogen atom assumed obscured by water peak; m/z (APCI+) for ($C_{12}H_{14}ClN_3O$), 252.3 (M+H)$^+$.

Intermediate 11: 4-chloro-6-[methyl(propan-2-yl)amino]-2,3-dihydro-1H-pyrrolo[3,4-c]pyridin-1-one

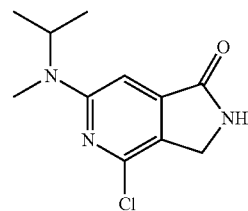 [SMILES: CC(C)N(C)c1cc2c(c(Cl)n1)CNC2=O]

Step 1: 2-chloro-N,N-dimethyl-6-[methyl(propan-2-yl)amino]pyridine-4-carboxamide (11a)

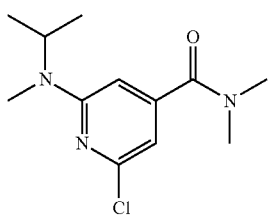

11a

A mixture of 2,6-dichloro-N,N-dimethylpyridine-4-carboxamide (30.0 g, 137 mmol) and N-methylpropan-2-amine (50.1 g, 685 mmol) in MeCN (120 mL) was partitioned between three sealed reaction vessels and each was stirred at 100° C. for 60 h. LCMS analysis showed consumption of the starting material with formation of the desired product mass. The reaction mixtures were combined and concentrated to dryness. The residue was purified by flash chromatography (SiO$_2$, 1:1 EtOAc/petroleum ether) to provide 2-chloro-N,N-dimethyl-6-[methyl(propan-2-yl)amino]pyridine-4-carboxamide (30.5 g, 87% yield) as a yellow solid. $^1$H NMR (400 MHz, Chloroform-d) δ 6.45 (d, J=0.9 Hz, 1H), 6.31 (d, J=1.0 Hz, 1H), 4.82 (p, J=6.8 Hz, 1H), 3.08 (s, 3H), 2.97 (s, 3H), 2.83 (s, 3H), 1.16 (d, J=6.7 Hz, 6H); m/z (ESI+) for ($C_{12}H_{18}ClN_3O$), 255.9 (M+H)$^+$.

Step 2: 2-chloro-3-formyl-N,N-dimethyl-6-[methyl(propan-2-yl)amino]pyridine-4-carboxamide (11b)

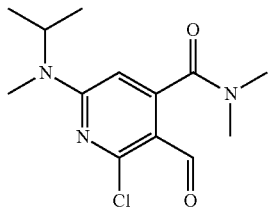

11b

To a solution of DMF (21.9 g, 299 mmol) in DCE (120 mL) was added POCl$_3$ (45.9 g, 299 mmol) dropwise at 5–15° C. The mixture was stirred at room temperature for 15 min and 2-chloro-N,N-dimethyl-6-[methyl(propan-2-yl)amino]pyridine-4-carboxamide (25.5 g, 99.7 mmol) was added. The reaction was stirred at 65° C. for 16 h. LCMS analysis showed consumption of the starting material with formation of the desired product mass. The reaction was cooled to room temperature and added dropwise to saturated aqueous Na$_2$CO$_3$ (900 mL). The mixture was extracted with DCM (2×300 mL). The combined organic layers were washed with brine (5×500 mL), dried over Na$_2$SO$_4$, filtered, and concentrated. The residue was purified by flash chromatography (SiO$_2$, 1:1 EtOAc/petroleum ether) to provide 2-chloro-3-formyl-N,N-dimethyl-6-[methyl(propan-2-yl)amino]pyridine-4-carboxamide (23.7 g, 84% yield) as a brown solid. $^1$H NMR (400 MHz, CDCl$_3$) δ 10.19 (s, 1H), 6.25 (br. s, 1H), 3.12 (s, 3H), 3.02–2.85 (m, 3H), 2.77 (s, 3H), 1.22 (br. d, J=6.5 Hz, 6H); m/z (ESI+) for (C$_{13}$H$_{18}$ClN$_3$O$_2$), 283.9 (M+H)$^+$.

Step 3: 2-chloro-N,N-dimethyl-3-{(E)-[(2-methylpropane-2-sulfinyl)imino]methyl}-6-[methyl(propan-2-yl)amino]pyridine-4-carboxamide (11c)

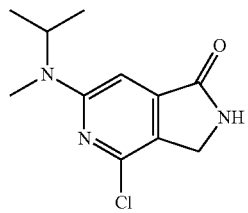

11c

A mixture of 2-chloro-3-formyl-N,N-dimethyl-6-[methyl(propan-2-yl)amino]pyridine-4-carboxamide (23.7 g, 83.5 mmol), (R)-(+)-2-methyl-2-propanesulfinamide (12.1 g, 100 mmol), and titanium(IV) ethoxide (38.1 g, 167 mmol) in THF (250 mL) was stirred at 50° C. for 20 h. LMCS analysis showed consumption of the starting material with formation of the desired product mass. The reaction was concentrated to dryness. The residue was stirred with saturated aqueous NaHCO$_3$ (300 mL) for 30 min. The mixture was filtered. The filter cake was rinsed with H$_2$O (3×80 mL) and petroleum ether (3×50 mL) and dried under vacuum to provide 2-chloro-N,N-dimethyl-3-{(E)-[(2-methylpropane-2-sulfinyl)imino]methyl}-6-[methyl(propan-2-yl)amino]pyridine-4-carboxamide (32.3 g, >99% yield) as a yellow solid. $^1$H NMR (400 MHz, DMSO-d$_6$) δ 9.07 (s, 1H), 6.74 (s, 1H), 5.36–5.10 (m, 1H), 3.30 (s, 3H), 3.26 (s, 3H), 3.10 (s, 3H), 1.54 (d, J=6.7 Hz, 6H), 1.49 (s, 9H); m/z (ESI+) for (C$_{17}$H$_{27}$ClN$_4$O$_2$S), 387.2 (M+H)$^+$.

Step 4: 4-chloro-6-[methyl(propan-2-yl)amino]-2,3-dihydro-1H-pyrrolo[3,4-c]pyridin-1-one

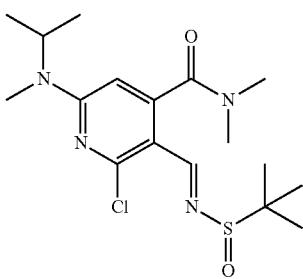

Intermediate 11

A solution of 2-chloro-N,N-dimethyl-3-{(E)-[(2-methylpropane-2-sulfinyl)imino]methyl}-6-[methyl(propan-2-yl)amino]pyridine-4-carboxamide (32.3 g, 83.5 mmol) in THF (200 mL) was cooled to 0° C. and LiBH$_4$ (1.82 g, 83.5 mmol) was added. The mixture was stirred at room temperature for 1 h. LCMS analysis showed consumption of the starting material. NaOMe (165 g, 919 mmol) was added and the mixture was stirred at room temperature for 16 h. The reaction mixture was filtered and the filter cake was washed with EtOAc (3×200 mL). The combined filtrate was concentrated to dryness. The residue was dissolved in DCM (300 mL) and washed with H$_2$O (500 mL). The aqueous layer was extracted with DCM (2×300 mL). The combined organic layers were washed with brine (500 mL), dried over Na$_2$SO$_4$, filtered, and concentrated. The solid was slurried in a mixture of DCM (50 mL) and petroleum ether (120 mL) for 30 min. The solids were collected by filtration. The filter cake was dried under vacuum to provide Intermediate 11 (11.3 g, 56% yield) as an off-white solid. $^1$H NMR (400 MHz, Chloroform-d) δ 7.19 (s, 1H), 6.79 (s, 1H), 4.82 (p, J=6.7 Hz, 1H), 4.35 (d, J=1.2 Hz, 2H), 2.88 (s, 3H), 1.18 (d, J=6.7 Hz, 6H); m/z (ESI+) for (C$_{11}$H$_{14}$ClN$_3$O), 239.9 (M+H)$^+$.

Intermediate 12: 2-bromo-6-(4-ethyl-4H-1,2,4-triazol-3-yl)pyridine

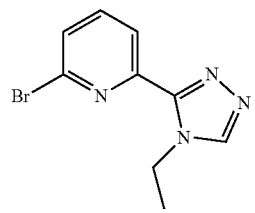

A flask was charged with N'-[(6-bromopyridin-2-yl)carbonyl]-N,N dimethylhydrazonoformamide (2.0 g, 7.4 mmol), ethylamine (0.5 mL, 333 mg, 7.4 mmol), acetic acid (3 mL) and MeCN (15 mL, 0.5 M). The solution was heated for 16 h at 95° C. The reaction was diluted with EtOAc (10 mL) and H$_2$O (10 mL). Solid K$_2$CO$_3$ was added until the pH of the aqueous layer was ~pH 8. The layers were separated and the aqueous layer was extracted with EtOAc (3×30 mL). The combined organic layers were washed with brine (30 mL), dried over Na$_2$SO$_4$, filtered, and concentrated to dryness. The residue was slurried with EtOAc (0.3 mL) and petroleum ether (3 mL) for 5 min. The solids were collected by filtration to provide Intermediate 12 (1.5 g, 80%) as a pale-yellow solid. $^1$H NMR (400 MHz, DMSO-d$_6$) δ 8.75 (s, 1H), 8.19 (dd, J=7.7, 0.9 Hz, 1H), 7.99-7.90 (m, 1H), 7.79 (dd, J=8.0, 0.9 Hz, 1H), 4.47 (q, J=7.2 Hz, 2H), 1.38 (t, J=7.2 Hz, 3H); m/z (APCI+) for (C$_9$H$_9$BrN$_4$), 252.7 (M+H)+.

Intermediate 13: 2-bromo-6-(4-propyl-4H-1,2,4-triazol-3-yl)pyridine

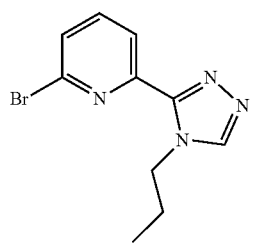

A mixture of N'-[(6-bromopyridin-2-yl)carbonyl]-N,N-dimethylhydrazonoformamide (1b) (29.0 g, 106.8 mmol) and propan-1-amine (31.6 g, 534 mmoL) in MeCN (440 mL) and acetic acid (110 mL) was stirred at 95° C. for 16 h. LCMS analysis showed consumption of the starting material with formation of the desired product mass. The reaction was concentrated to dryness. The residue was taken up in H$_2$O (50 mL) and basified to pH ~9 with 1 N NaOH (~500 mL). The mixture was extracted with EtOAc (3×150 mL). The combined organic layers were washed with brine (150 mL), dried over Na$_2$SO$_4$, filtered, and concentrated. The residue was slurried with EtOAc (50 mL) for 10 min and the solid was collected by filtration. The filter cake was washed with petroleum ether (2×50 mL) and dried in vacuum to provide Intermediate 13 (21.0 g, 74% yield) as a yellow solid. $^1$H NMR (400 MHz, DMSO-d$_6$) δ 8.74 (s, 1H), 8.20 (dd, J=0.7, 7.8 Hz, 1H), 7.98-7.91 (m, 1H), 7.78 (dd, J=0.7, 8.0 Hz, 1H), 4.45-4.36 (m, 2H), 1.77 (sxt, J=7.4 Hz, 2H), 0.87 (t, J=7.4 Hz, 3H); m/z (ESI+) for (C$_{10}$H$_{11}$BrN$_4$), 266.7 (M+H)$^+$.

Intermediate 14: 2-bromo-6-[4-(pentan-3-yl)-4H-1,2,4-triazol-3-yl]pyridine

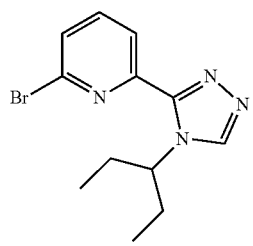 [SMILES: CCC(CC)n1cnnc1-c1cccc(Br)n1]

A mixture of N'-[(6-bromopyridin-2-yl)carbonyl]-N,N-dimethylhydrazonoformamide (1b) (3.10 g, 11.4 mmol) and pentan-3-amine (2.99 g, 34.4 mmoL) in MeCN (24 mL) and acetic acid (6 mL) was stirred at 95° C. for 16 h. LCMS analysis showed consumption of the starting material with formation of the desired product mass. The solution was concentrated to dryness. The residue was taken up in EtOAc (100 mL) and washed with saturated aqueous NaHCO$_3$ (50 mL). The organic layer was dried over Na$_2$SO$_4$, filtered, and concentrated. The residue was purified by flash chromatography (SiO$_2$, 1:1 DCM/EtOAc) to provide Intermediate 14 (2.3 g, 68% yield) as a white solid. $^1$H NMR (400 MHz, DMSO-d$_6$) δ 8.92 (s, 1H), 8.16 (d, J=7.7 Hz, 1H), 7.98-7.92 (m, 1H), 7.78 (d, J=7.9 Hz, 1H), 5.01 (tt, J=8.5, 5.8 Hz, 1H), 1.85 (ddt, J=14.1, 8.5, 7.2 Hz, 4H), 0.73 (t, J=7.4 Hz, 6H); m/z (ESI+) for (C$_{12}$H$_{15}$BrN$_4$), 295.0 (M+H)$^+$.

Intermediate 15: 2-bromo-6-{4-[(2S)-butan-2-yl]-4H-1,2,4-triazol-3-yl}pyridine

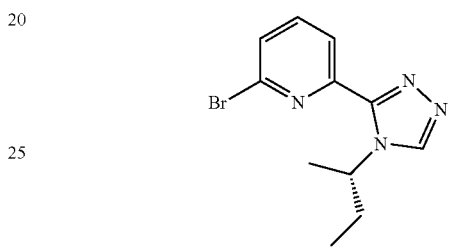

A mixture of N'-[(6-bromopyridin-2-yl)carbonyl]-N,N-dimethylhydrazonoformamide (1b) (4.40 g, 16.2 mmol) and (2S)-butan-2-amine (1.25 g, 17.0 mmoL) in MeCN (100 mL) and acetic acid (25 mL) was stirred at 90° C. for 16 h. LCMS analysis showed consumption of the starting material. The solution was concentrated to dryness. The residue was partitioned between EtOAc (50 mL) and Na$_2$CO$_3$ (50 mL). The organic layer was washed with brine (2×30 mL), dried over Na$_2$SO$_4$, filtered, and concentrated. The residue was purified by flash chromatography (120 g SiO$_2$, 1-5% MeOH/EtOAc) to provide Intermediate 15 (3.0 g, 66% yield) as a light yellow oil. $^1$H NMR (400 MHz, Chloroform-d) δ 8.33 (s, 1H), 8.30 (dd, J=7.8, 0.9 Hz, 1H), 7.72-7.67 (m, 1H), 7.53 (dd, J=7.9, 0.9 Hz, 1H), 5.42 (h, J=6.9 Hz, 1H), 1.87 (ddq, J=30.1, 14.1, 7.2 Hz, 2H), 1.56 (d, J=6.9 Hz, 3H), 0.94 (t, J=7.4 Hz, 3H); m/z (ESI+) for (C$_{11}$H$_{13}$BrN$_4$), 282.8 (M+H)$^+$.

Intermediate 16: 6-(4-propyl-4H-1,2,4-triazol-3-yl)pyridin-2-amine

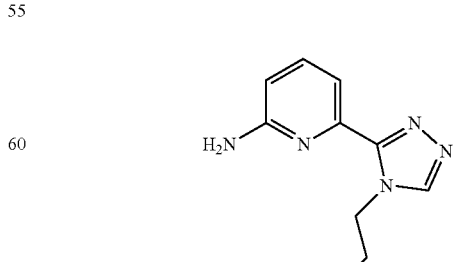

Step 1: 6-aminopyridine-2-carbohydrazide (16a)

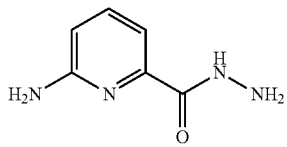

16a

To a solution of methyl 6-aminopyridine-2-carboxylate (100 g, 657 mmol) in MeOH (1.0 L) was added N₂H4.H₂O (69.7 g, 1.18 mol). The mixture was stirred at reflux for 5 h. Significant amounts of a white precipitate were formed. TLC analysis (1:10 MeOH/DCM) showed consumption of the starting material. The reaction mixture was filtered. The filter cake was washed with EtOAc (3×100 mL) and dried under vacuum to provide 6-aminopyridine-2-carbohydrazide (95.4 g, 95% yield) as a white solid. $^1$H NMR (400 MHz, DMSO-$d_6$) δ 9.11 (s, 1H), 7.53-7.46 (m, 1H), 7.08 (dd, J=7.3, 0.9 Hz, 1H), 6.58 (dd, J=8.4, 0.9 Hz, 1H), 6.06 (s, 2H), 4.45 (d, J=4.7 Hz, 2H); m/z (ESI) for ($C_6H_8N_4O$), 152.8 (M+H)$^+$.

Step 2: N'-(6-{(2E)-2-[(dimethylamino)methylidene]hydrazinecarbonyl}pyridin-2-yl)-N,N-dimethylmethanimidamide (16b)

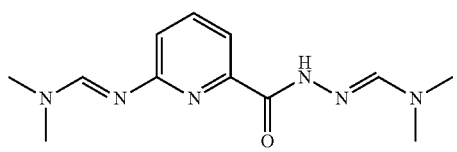

16b

A mixture of 6-aminopyridine-2-carbohydrazide (95.4 g, 627 mmol) in N,N-dimethyldimethoxymethylamine (500 mL) was stirred at reflux for 18 h. TLC analysis (1:10 MeOH/DCM) showed consumption of the starting material. The reaction was concentrated to dryness. The residue was slurried in a mixture of EtOAc (100 mL) and petroleum ether (200 mL) at 15° C. for 5 min. The solids were collected by filtration and the filter cake was dried under vacuum to provide N'-(6-{(2E)-2-[(dimethylamino)methylidene]hydrazinecarbonyl}pyridin-2-yl)-N,N-dimethylmethanimidamide (156 g, 95% yield) as a white solid. $^1$H NMR (400 MHz, Chloroform-d) δ 9.94 (s, 1H), 8.33 (s, 1H), 8.14 (s, 1H), 7.77 (dd, J=7.4, 0.9 Hz, 1H), 7.69-7.62 (m, 1H), 7.03 (dd, J=8.4, 0.9 Hz, 1H), 3.11 (s, 3H), 3.10 (s, 3H), 2.95 (s, 6H); m/z (ESI) for ($C_{12}H_{18}N_6O$), 263.0 (M+H)$^+$.

Step 3: 6-(4-propyl-4H-1,2,4-triazol-3-yl)pyridin-2-amine

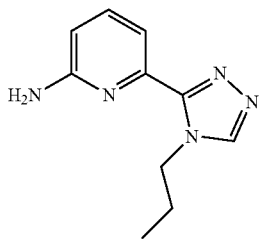

Intermediate 16

To a solution of N'-(6-{(2E)-2-[(dimethylamino)methylidene]hydrazinecarbonyl}pyridin-2-yl)-N,N-dimethylmethanimidamide (100 g, 381 mmol) in PhMe (800 mL) was added propan-1-amine (113 g, 1.91 mol) and acetic acid (160 g, 2.67 mol). The mixture was stirred at 90-100° C. (internal) for 24 h. LCMS analysis showed consumption of the starting material. The reaction was cooled to room temperature. The mixture was adjusted to pH ~10-11 by added of 50% aqueous NaOH and then washed with H₂O. The aqueous layer was extracted with 5:1 DCM/THF (3×). The combined organic layers were concentrated to dryness. The residue was concentrated EtOAc (3×). The solids were slurried in 1:2 EtOAc/heptanes for 30 min. The solids were collected by filtration. The filter cake was dried under vacuum to provide Intermediate 16 (25.6 g, 76% yield) as a white solid. $^1$H NMR (400 MHz, DMSO-$d_6$) δ 8.57 (s, 1H), 7.53-7.47 (m, 1H), 7.22 (d, J=7.0 Hz, 1H), 6.52 (d, J=8.0 Hz, 1H), 6.15 (s, 2H), 4.48 (t, J=7.2 Hz, 2H), 1.67 (h, J=7.4 Hz, 2H), 0.81 (t, J=7.4 Hz, 3H); m/z (ESI) for ($C_{10}H_{13}N_5$), 204.2 (M+H)$^+$.

Intermediate 17: 2-bromo-6-(5-methyl-4-propyl-4H-1,2,4-triazol-3-yl)pyridine

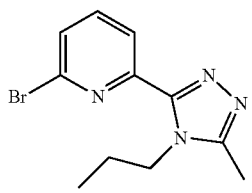 [SMILES: CCCn1c(C)nnc1-c1cccc(Br)n1]

This transformation was carried out in 5 parallel batches. Pyridine (20.0 mL) was cooled in an ice bath to 0° C. TFA (950 mg, 8.33 mmol), propan-1-amine (1.48 g, 25.0 mmol), and 2-bromo-6-(5-methyl-1,3,4-oxadiazol-2-yl)pyridine (Intermediate 4) (2.00 g, 8.33 mmol) were added successively. The mixture was sealed and stirred at 100° C. for 3.5 d with addition of more propan-1-amine (1.48 g, 25.0 mmol) to the reaction after 1.5 and 2.5 d, respectively. LCMS analysis showed consumption of the starting material with formation of the desired product mass.

The parallel reactions were combined and concentrated to dryness. The residue was purified by flash chromatography (SiO₂, 0-100% EtOAc/petroleum ether). The desired fractions were re-purified by preparative HPLC with a YMC Triart C18 column (250×50 mm, 7 μm particle size), which was eluted with 30-70% MeCN/H$_2$O (+0.225% formic acid) with a flow rate of 25 mL/min.

The desired fractions were basified by addition of saturated aqueous NaHCO$_3$ to pH ~8. The solution was concentrated to remove the MeCN and then extracted with DCM (3×50 mL). The combined organic layers were washed with brine, dried over Na$_2$SO$_4$, filtered, and concentrated to provide Intermediate 17 (6.11 g, 52% yield) as a white solid. $^1$H NMR (400 MHz, CDCl$_3$) δ 8.31-8.24 (m, 1H), 7.70-7.63 (m, 1H), 7.51-7.47 (m, 1H), 4.40-4.32 (m, 2H), 2.53 (s, 3H), 1.86-1.74 (m, 2H), 1.00 (td, J=7.4, 2.9 Hz, 3H). m/z (ESI+) for (C$_{11}$H$_{13}$BrN$_4$), 282.9 (M+H)$^+$.

Intermediate 18: 2-bromo-6-(4,5-diethyl-4H-1,2,4-triazol-3-yl)pyridine

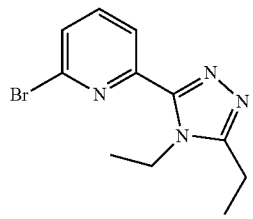 [SMILES: CCc1nnc(-c2cccc(Br)n2)n1CC]

Step 1: 6-bromo-N'-propanoylpyridine-2-carbohydrazide

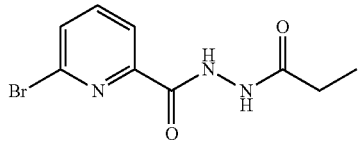

To a stirred mixture of 6-bromopyridine-2-carbohydrazide (Intermediate 1a) (3.00 g, 13.9 mmol) in DCM (46.3 mL) at 0° C. were added TEA (2.11 g, 20.8 mmol) and propanoyl chloride (1.35 g, 15.7 mmol). The mixture was stirred at 0° C. for 20 min and then at 20° C. for 16 h. TLC analysis (1:1 EtOAc/petroleum ether) showed remaining starting material. The mixture was cooled to 0° C. and additional TEA (2.11 g, 20.8 mmol) and propanoyl chloride (1.45 g, 15.7 mmol) were added. The mixture was stirred at 0° C. for 20 min and then at 20° C. for 16 h. TLC analysis (1:1 EtOAc/petroleum ether) showed consumption of the starting material. The reaction was quenched by addition of H$_2$O (60 mL) and extracted with DCM (2×30 mL). The combined organic layers were washed with brine (80 mL), dried over Na$_2$SO$_4$, filtered, and concentrated. The crude material was slurried with EtOAc (10 mL) and petroleum ether (30 mL) for 10 min at 20° C. The solids were collected by filtration and dried under vacuum to provide 6-bromo-N'-propanoylpyridine-2-carbohydrazide (3.0 g, 79% yield) as a white solid. $^1$H NMR (400 MHz, CDCl$_3$) δ 9.96 (br.d, J=5.4 Hz, 1H), 8.36 (br.d, J=5.4 Hz, 1H), 8.10 (dd, J=7.5, 1.0 Hz, 1H), 7.47-7.70 (m, 1H), 7.65 (dd, J=7.9, 1.1 Hz, 1H), 2.38 (q, J=7.6 Hz, 2H), 1.25 (t, J=7.6 Hz, 3H).

Step 2: 2-bromo-6-(5-ethyl-1,3,4-oxadiazol-2-yl)pyridine

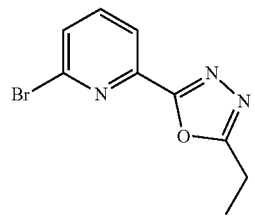

To a stirred solution of 6-bromo-N'-propanoylpyridine-2-carbohydrazide (3.00 g, 11.0 mmol) in DCM (50.0 mL) and MeCN (50.0 mL) were added TEA (6.69 g, 66.2 mmol) and p-toluenesulfonyl chloride (2.31 g, 12.1 mmol). The mixture was stirred at ambient temperature for 60 h. TLC analysis (EtOAc) showed consumption of the starting material. The mixture was concentrated to dryness. The residue was dissolved in H$_2$O (50 mL) and extracted with DCM (2×30 mL). The combined organic layers were washed with brine (50 mL), dried over Na$_2$SO$_4$, filtered, and concentrated. The crude material was slurried with EtOAc (3 mL) and petroleum ether (6 mL) at ambient temperature for 30 min. The solids were collected by filtration and dried under vacuum to provide 2-bromo-6-(5-ethyl-1,3,4-oxadiazol-2-yl)pyridine (1.34 g, 48% yield) as a yellow solid. $^1$H NMR (400 MHz, CDCl$_3$) δ 8.21 (dd, J=7.6, 1.0 Hz, 1H), 7.80-7.68 (m, 1H), 7.64 (dd, J=8.0, 0.9 Hz, 1H), 3.00 (q, J=7.6 Hz, 2H), 1.46 (t, J=7.6 Hz, 3H). m/z (ESI+) for (C$_9$H$_8$BrN$_3$O), 256.0 (M+H)$^+$.

Step 3: 2-bromo-6-(4,5-diethyl-4H-1,2,4-triazol-3-yl)pyridine

Intermediate 18

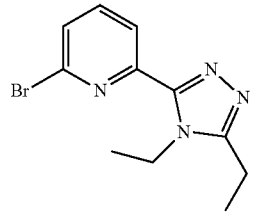

Pyridine (8.0 mL) was cooled in an ice bath to 0° C. TFA (301 mg, 2.64 mmol), 2-bromo-6-(5-ethyl-1,3,4-oxadiazol-2-yl)pyridine (670 mg, 2.64 mmol), and ethylamine (476 mg, 10.5 mmol) were added successively. The mixture was stirred at 95° C. for 20 h and then at 100° C. for 7 h. The reaction was concentrated to dryness. The residue was purified by flash chromatography (SiO$_2$, 1:10 MeOH/EtOAc) to provide Intermediate 18 (500 mg, 67% yield) as a yellow gum. $^1$H NMR (400 MHz, CDCl$_3$) δ 8.28 (dd, J=7.8, 0.9 Hz, 1H), 7.71-7.62 (m, 1H), 7.61-7.37 (m, 1H), 4.47 (q, J=7.1 Hz, 2H), 2.84 (q, J=7.6 Hz, 2H), 1.57-1.34 (m, 6H). m/z (ESI+) for (C$_{11}$H$_{13}$BrN$_4$), 280.7 (M+H)$^+$.

Intermediate 19: tert-butyl methyl({6-[(2R)-2-methylpyrrolidin-1-yl]-1-oxo-2,3-dihydro-1H-pyrrolo[3,4-c]pyridin-4-yl}methyl)carbamate

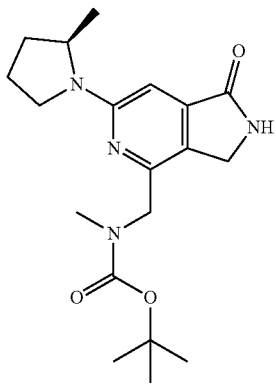 [SMILES: C[C@@H]1CCCN1c1cc2c(c(CN(C)C(=O)OC(C)(C)C)n1)CNC2=O]

Step 1: tert-butyl ({3-formyl-6-[(2R)-2-methylpyrrolidin-1-yl]-4-(piperidine-1-carbonyl)pyridin-2-yl}methyl)methylcarbamate

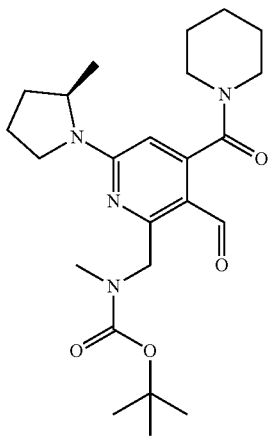 [SMILES: C[C@@H]1CCCN1c1cc(C(=O)N2CCCCC2)c(C=O)c(CN(C)C(=O)OC(C)(C)C)n1]

A solution of 2-chloro-6-[(2R)-2-methylpyrrolidin-1-yl]-4-(piperidine-1-carbonyl)pyridine-3-carbaldehyde (Intermediate 10b) (600 mg, 1.79 mmol) and PdCl$_2$(dppf) (261 mg, 0.357 mmol) in 1,4-dioxane (25.0 mL) was sparged with N$_2$ for 5 min and then heated to 80° C. A solution of {[(tert-butoxycarbonyl)(methyl)amino]methyl}(chlorido) zinc (0.158 M in THF, 39.6 mL) was added at 80° C. and the mixture was stirred a further 35 min at the same temperature. LCMS analysis showed consumption of the starting material with formation of the desired product mass. The mixture was cooled to 30° C. and filtered through celite. The filter cake was washed with DCM (5×10 mL) and the filtrate was concentrated to dryness. The residue was combined with the crude material obtained from a parallel reaction run in identical fashion with 100 mg 2-chloro-6-[(2R)-2-methylpyrrolidin-1-yl]-4-(piperidine-1-carbonyl)pyridine-3-carbaldehyde. The mixture purified by flash chromatography (SiO$_2$, 1:1 EtOAc/petroleum ether) to provide tert-butyl ({3-formyl-6-[(2R)-2-methylpyrrolidin-1-yl]-4-(piperidine-1-carbonyl)pyridin-2-yl}methyl)methylcarbamate (900 mg, 97% yield) as a yellow gum. $^1$H NMR (400 MHz, DMSO-d$_6$) δ 9.84 (s, 1H), 6.40-6.06 (m, 1H), 4.91-4.45 (m, 2H), 4.52-3.92 (m, 1H), 3.69-3.47 (m, 3H), 3.21-3.00 (m, 2H), 2.98-2.84 (m, 3H), 2.22-1.82 (m, 3H), 1.83-1.66 (m, 1H), 1.59 (s, 4H), 1.41 (s, 7H), 1.19 (d, J=18.2 Hz, 8H). m/z (ESI+) for (C$_{24}$H$_{36}$N$_4$O$_4$), 445.4 (M+H)$^+$.

Step 2: tert-butyl methyl{[3-{(E)-[(2-methylpropane-2-sulfinyl)imino]methyl}-6-[(2R)-2-methylpyrrolidin-1-yl]-4-(piperidine-1-carbonyl)pyridin-2-yl]methyl}carbamate

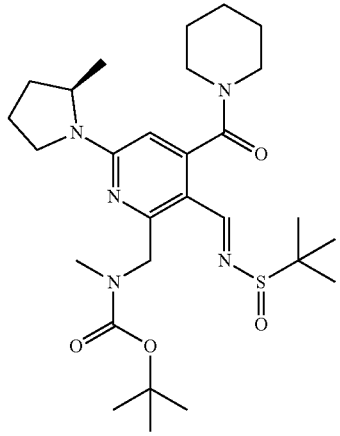 [SMILES: C[C@@H]1CCCN1c1cc(C(=O)N2CCCCC2)c(/C=N/S(=O)C(C)(C)C)c(CN(C)C(=O)OC(C)(C)C)n1]

A mixture of tert-butyl ({3-formyl-6-[(2R)-2-methylpyrrolidin-1-yl]-4-(piperidine-1-carbonyl)pyridin-2-yl}methyl)methylcarbamate (1.40 g, 3.15 mmol), titanium(IV) ethoxide (1.44 g, 6.30 mmol), and (S)-(−)-2-methyl-2-propanesulfinamide (573 mg, 4.72 mmol) in THF (50.0 mL) was stirred at 50° C. for 18 h. Additional batches of titanium(IV) ethoxide (359 mg, 1.57 mmol) and (S)-(−)-2-methyl-2-propanesulfinamide (115 mg, 0.945 mmol) were added and the mixture was stirred at 50° C. for an additional 20 h. LCMS analysis showed consumption of the starting material with formation of the desired product mass. The reaction was quenched with saturated aqueous Na$_2$CO$_3$ (150 mL) and diluted with DCM (100 mL). The mixture was filtered through celite and the layers were separated. The aqueous layer was extracted with DCM (100 mL). The combined organic layers were washed with brine (150 mL), dried over Na$_2$SO$_4$, filtered, and concentrated to provide tert-butyl methyl{[3-{(E)-[(2-methylpropane-2-sulfinyl)imino]methyl}-6-[(2R)-2-methylpyrrolidin-1-yl]-4-(piperidine-1-carbonyl)pyridin-2-yl]methyl}carbamate (1.7 g, >99% yield) as a yellow solid. m/z (ESI+) for (C$_{28}$H$_{45}$N$_5$O$_4$S), 548.5 (M+H)$^+$.

Step 3: tert-butyl methyl({6-[(2R)-2-methylpyrrolidin-1-yl]-1-oxo-2,3-dihydro-1H-pyrrolo[3,4-c]pyridin-4-yl}methyl)carbamate

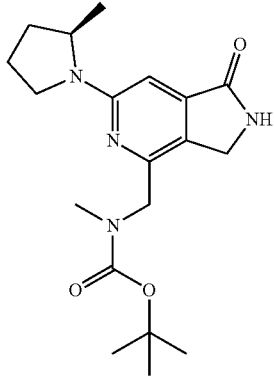

Intermediate 19

To a solution of tert-butyl methyl{[3-{(E)-[(2-methylpropane-2-sulfinyl)imino]methyl}-6-[(2R)-2-methylpyrrolidin-1-yl]-4-(piperidine-1-carbonyl)pyridin-2-yl]methyl}carbamate (1.72 g. 3.41 mmol) in THF (20.0 mL) at 0° C. was added LiBH$_4$ (68.6 mg, 3.15 mmol). The reaction was stirred at 0° C. for 1 h. TLC analysis showed consumption of the starting material. The mixture was warmed to ambient temperature and a solution of NaOMe (30% in MeOH, 6.24 g, 34.6 mmol) was added. The mixture was stirred for 16 h. LCMS analysis showed formation of the desired product mass. The reaction was concentrated to dryness. The residue was dissolved in EtOAc (40 mL) and washed with H$_2$O (40 mL). The aqueous layer was extracted with EtOAc (30 mL). The combined organic layers were washed with brine (60 mL), dried over Na$_2$SO$_4$, filtered, and concentrated. The residue was purified by flash chromatography (SiO$_2$, EtOAc) to provide Intermediate 19 (750 mg, 66% yield) as a white solid. $^1$H NMR (400 MHz, CDCl$_3$) δ 7.04-6.79 (m, 1H), 6.68 (s, 1H), 4.56-4.43 (m, 2H), 4.43-4.33 (m, 2H), 4.27-4.16 (m, 1H), 3.58 (ddd, J=2.5, 7.3, 10.0 Hz, 1H), 3.45-3.30 (m, 1H), 3.01-2.91 (m, 3H), 2.17-1.96 (m, 3H), 1.80-1.72 (m, 1H), 1.53-1.37 (m, 9H), 1.26-1.23 (m, 3H); m/z (ESI+) for (C$_{19}$H$_{28}$N$_4$O$_3$), 361.2 (M+H)$^+$.

Intermediate 20: (4R)-3-(6-bromopyridin-2-yl)-4-(fluoromethyl)-1,3-oxazolidin-2-one

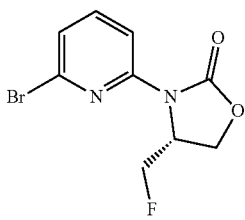 [SMILES: O=C1OC[C@H](CF)N1c1cccc(Br)n1]

Step 1: methyl (4R)-2-oxo-3-(triphenylmethyl)-1,3-oxazolidine-4-carboxylate

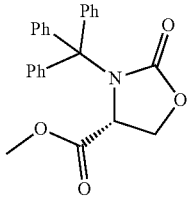 [SMILES: COC(=O)[C@H]1COC(=O)N1C(c1ccccc1)(c1ccccc1)c1ccccc1]

A solution of methyl N-(triphenylmethyl)-D-serinate (90.0 g, 249 mmol) and TEA (69.8 g, 690 mmol) in PhMe (1.8 L) was added dropwise to a solution of triphosgene (69.8 g, 41.5 mmol) in PhMe (300 mL) under an atmosphere of N$_2$, maintaining the temperature at −5-10° C. (internal). The mixture was stirred at ambient temperature for 30 min. TLC analysis (1:2 EtOAc/petroleum ether) showed consumption of the starting material. The reaction was quenched by dropwise addition of 1 N HCl (600 mL) and the mixture was stirred for 10 min. The layers were separated. The aqueous layer was basified to pH ~8-9 by addition of 2 N NaOH and then extracted with DCM/PhMe (1:5, 1.5 L). The combined organic layers were washed with saturated aqueous NaHCO$_3$ (500 mL) and brine (500 mL), dried over Na$_2$SO$_4$, filtered, and concentrated. The solids were slurried in EtOAc/petroleum ether (1:3, 400 mL) at room temperature for 30 min. The solids were collected by filtration and dried under vacuum to provide methyl (4R)-2-oxo-3-(triphenylmethyl)-1,3-oxazolidine-4-carboxylate (71 g, 74% yield) as a white solid. $^1$H NMR (400 MHz, CDCl$_3$) δ 7.38-7.27 (m, 15H), 4.61-4.50 (m, 1H), 4.50-4.38 (m, 1H), 4.21 (dd, J=3.3, 8.9 Hz, 1H), 3.49 (s, 3H).

Step 2: (4S)-4-(hydroxymethyl)-3-(triphenylmethyl)-1,3-oxazolidin-2-one

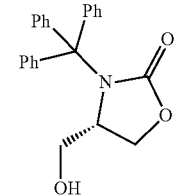

A solution of methyl (4R)-2-oxo-3-(triphenylmethyl)-1,3-oxazolidine-4-carboxylate (158 g, 409 mmol) in THF (2.4 L) was cooled to −65° C. (internal) and LiAlH$_4$ (18.6 g, 490 mmol) was added portion-wise, maintaining the temperature below −60° C. (internal). The mixture was stirred at −10° C. (internal) for 1.5 h. TLC analysis (1:2 EtOAc/petroleum ether) indicated consumption of the starting material. The mixture was quenched by careful addition of Na$_2$SO$_4$*10H$_2$O until gas emission was no longer observed. The suspension was filtered through a pad of celite. The filter cake was suspended in EtOAc (500 mL), stirred for 10 min, and then filtered. This process was repeated 3×. The combined filtrate was concentrated to dryness. The residue was purified by flash chromatography (660 g SiO$_2$, 0-80% EtOAc/petroleum ether) to provide (4S)-4-(hydroxymethyl)-3-(triphenylmethyl)-1,3-oxazolidin-2-one (29.9 g, 20% yield) as a white solid. ¹H NMR (400 MHz, CDCl₃) δ 7.31-7.10 (m, 15H), 4.36-4.12 (m, 2H), 3.73-3.58 (m, 1H), 3.22-2.94 (m, 2H).

Step 3: (4R)-4-(fluoromethyl)-3-(triphenylmethyl)-1,3-oxazolidin-2-one

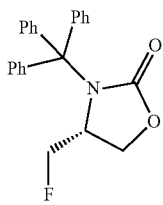 [SMILES: O=C1OC[C@H](CF)N1C(c1ccccc1)(c1ccccc1)c1ccccc1]

A solution of (4S)-4-(hydroxymethyl)-3-(triphenylmethyl)-1,3-oxazolidin-2-one (29.9 g, 83.3 mmol) and TEA (75.9 g, 750 mmol) in MeCN (400 mL) was cooled with an ice-water bath to 0° C. (internal) and nonafluorobutanesulfonyl fluoride (75.5 g, 250 mmol) was added slowly, maintaining the reaction temperature at 5-10° C. (internal). The solution was stirred at 0° C. (internal) for 5 min. TLC analysis (1:2 EtOAc/petroleum ether) showed consumption of the starting material. Triethylamine trihydrofluoride (40.3 g, 250 mmol) was added dropwise and the solution was stirred at 5-10° C. (internal) for 2 h. The mixture was partitioned between EtOAc (200 mL) and H₂O (200 mL). The aqueous phase was extracted with EtOAc (200 mL). The combined organic layers were washed with saturated aqueous NaHCO₃ (200 mL) and brine (200 mL), dried over Na₂SO₄, filtered, and concentrated. The residue was slurried with petroleum ether (200 mL) and EtOAc (100 mL) for 2 h at ambient temperature and the solids were collected by filtration. The filtrate was concentrated to dryness and purified by flash chromatography (80 g SiO₂, 30-50% EtOAc/petroleum ether). The desired fractions were concentrated to dryness and combined with the previously-isolated filter cake to provide (4R)-4-(fluoromethyl)-3-(triphenylmethyl)-1,3-oxazolidin-2-one (26.7 g, 89% yield) as a white solid. ¹H NMR (400 MHz, CDCl₃) δ 7.39-7.22 (m, 15H), 4.54-4.46 (m, 1H), 4.41-4.35 (m, 1H), 4.08-3.82 (m, 3H); ¹⁹F NMR (377 MHz, CDCl₃) 5-231.64 (s, 1F).

Step 4: (4R)-4-(fluoromethyl)-1,3-oxazolidin-2-one

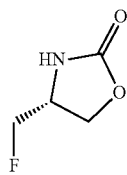

A suspension of (4R)-4-(fluoromethyl)-3-(triphenylmethyl)-1,3-oxazolidin-2-one (26.7 g, 74.0 mmol) in DCM (90.0 mL) was cooled to 0° C. (internal) and treated dropwise with TFA (90.0 mL). The reaction was stirred at room temperature for 1.5 h. LCMS analysis showed consumption of the starting material. The mixture was concentrated to dryness. The residue was dissolved in DCM (200 mL) and solution was cooled to 0° C. (internal) with an ice-water bath. The mixture was basified with concentrated aqueous NH₄OH to pH ~9, maintaining the internal temperature at 5-15° C. (internal). The mixture was dried over Na₂SO₄, filtered, and concentrated through a pad of celite. The filter cake was washed with DCM. The combined filtrate was concentrated to dryness. The residue was purified by flash chromatography (80 g SiO₂, EtOAc) to provide (4R)-4-(fluoromethyl)-3-(triphenylmethyl)-1,3-oxazolidin-2-one (3.86 g, 44% yield) as a pale-yellow oil. ¹H NMR (400 MHz, CDCl₃) δ 6.41 (br s, 1H), 4.57-4.44 (m, 2H), 4.42-4.31 (m, 1H), 4.29-4.23 (m, 1H), 4.22-4.10 (m, 1H); ¹⁹F NMR (377 MHz, CDCl₃) δ -229.49 (s, 1F).

Step 5: (4R)-3-(6-bromopyridin-2-yl)-4-(fluoromethyl)-1,3-oxazolidin-2-one

Intermediate 20

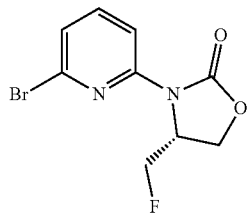

A mixture of (4R)-4-(fluoromethyl)-3-(triphenylmethyl)-1,3-oxazolidin-2-one (4.70 g, 39.5 mmol), 2,6-dibromopyridine (14.5 g, 61.2 mmol), and Cs₂CO₃ (32.1 g, 98.7 mmol) in 1,4-dioxane (250.0 mL) was sparged with N₂ for 2 min. Pd(OAc)₂ (886 mg, 3.95 mmol) and Xantphos (2.74 g, 4.74 mmol) were added and the mixture was sparged with N₂. The mixture was stirred at 80° C. for 3 h, cooled to room temperature, and filtered. The filter cake was washed with EtOAc (5×30 mL). The combined filtrate was concentrated to dryness. The residue was purified by flash chromatography (330 g SiO₂, 0-30% EtOAc/petroleum ether) to provide Intermediate 20 (3.72 g, 34% yield) as a white solid. ¹H NMR (400 MHz, CDCl₃) δ 8.21 (dd, J=8.3, 0.7 Hz, 1H), 7.75-7.49 (m, 1H), 7.26 (dd, J=7.6, 0.7 Hz, 1H), 5.12-4.98 (m, 1H), 4.96-4.61 (m, 2H), 4.60-4.48 (m, 2H); ¹⁹F NMR (377 MHz, CDCl₃) δ -237.04; m/z (ESI+) for (C₉H₈BrFN₂O₂), 276.7 (M+H)+; [α]$_D^{30}$=+97.3° (C=1.0, MeOH).

EXAMPLES

General Methods

Unless stated otherwise, the variables in Schemes have the same meanings as defined herein. The amines mentioned herein may constitute protected amines that are deprotected under standard conditions known in the art.

Method A

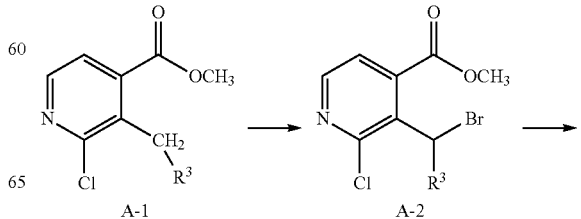

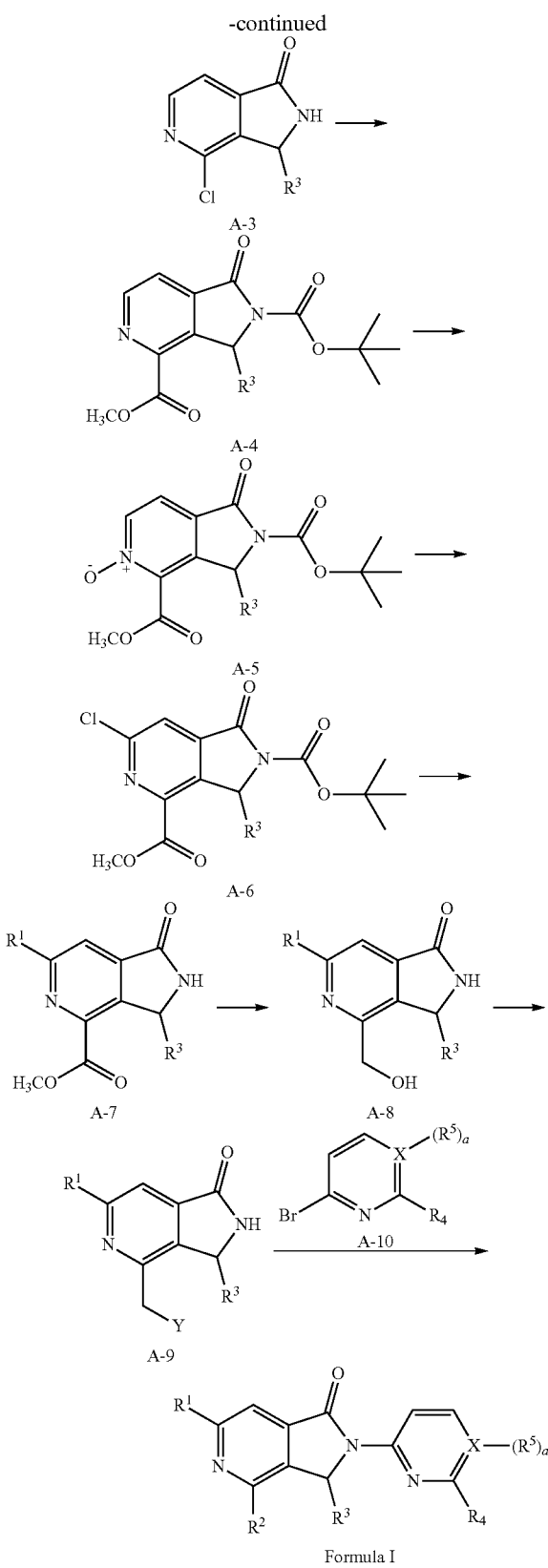

sonicotinate) (J. Med. Chem., 47(25), 6363-6372; 2004) using N-bromosuccinimide yields a compound of formula A-2. During this step, the $R^3$ substituent should be represented by the same moiety as is desired in the final product, Formula I, or a protected variation thereof. In a next step, the compound of formula A-2 undergoes ammonolysis with ammonia to form the 4-chloro-2,3-dihydro-1H-pyrrolo[3,4-c]pyridin-1-one compound of formula A-3. The compound of formula A-3 then undergoes carbonylation of the chloride using carbon monoxide and methanol under palladium catalysis followed by protection to provide the ester of formula A-4. In a next step, N-oxide formation of the compound of formula A-4 under standard conditions (urea hydrogen peroxide) followed by chlorination of the compound of formula A-5 using phosphorous oxychloride provides the chloride of formula A-6. Next, deprotection of the carbamate protecting group of formula A-6 is followed by reaction of the chloride with $R^1$ (e.g., an amine) to give the compound of formula A-7 (e.g., an aminopyridine).

During this step, the $R^1$ substituent should be represented by the same moiety as is desired in the final product, Formula I, or a protected variation thereof. In a next step, reduction of the ester functionality in formula A-7 provides the alcohol of formula A-8. Activation of the alcohol functionality of formula A-8, as a mesylate (A-9, $Y=OSO_2CH_3$) followed by either:

i) azidation (A-9, $Y=N_3$) and reduction of the azide functionality under standard conditions to provide primary amines (formula A-9, $Y=NH_2$); or ii) direct displacement of the mesylate (formula A-9, $Y=OSO_2CH_3$) with primary amines to give the corresponding secondary amines (formula A-9, $Y=N(R^8)(R^9)$, $R^8$ and $R^9=H$ and/or alkyl) to yield the compound of formula A-9.

Protection of the amino functionality as the corresponding tert-butyl carbamate, formula A-9 ($Y=N(R^8)$ Boc, $R^8=H$ or alkyl) is followed by coupling with the bromo pyridine of formula A-10 under palladium or copper catalysis to provide protected pyrrolo[3,4-c]pyridin-1-ones ($R^2=CH_2N(R^8)$ Boc, $R^8=H$ or alkyl). During this step, the $R^4$ and $(R^5)_a$ substituents of formula A-10 should be represented by the same moiety as is desired in the final product, Formula I, or a protected variation thereof. Next, a deprotection of the carbamate protecting group under standard conditions yields pyrrolo[3,4-c]pyridin-1-ones of Formula I ($R^2=CH_2N(R^8)(R^9)$, $R^8$ and $R^9=H$ and/or alkyl).

Method B

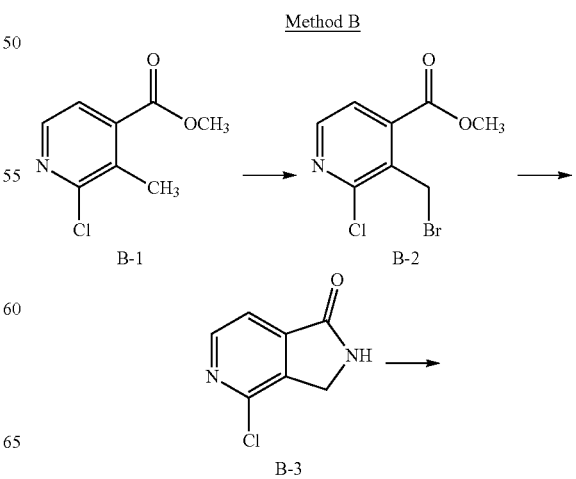

Method A refers to one synthetic sequence for the preparation of compounds of Formula I, as depicted above. Referring to Method A, in a first step a bromination of compound of formula A-1 (e.g., ethyl 2-chloro-3-methyli-

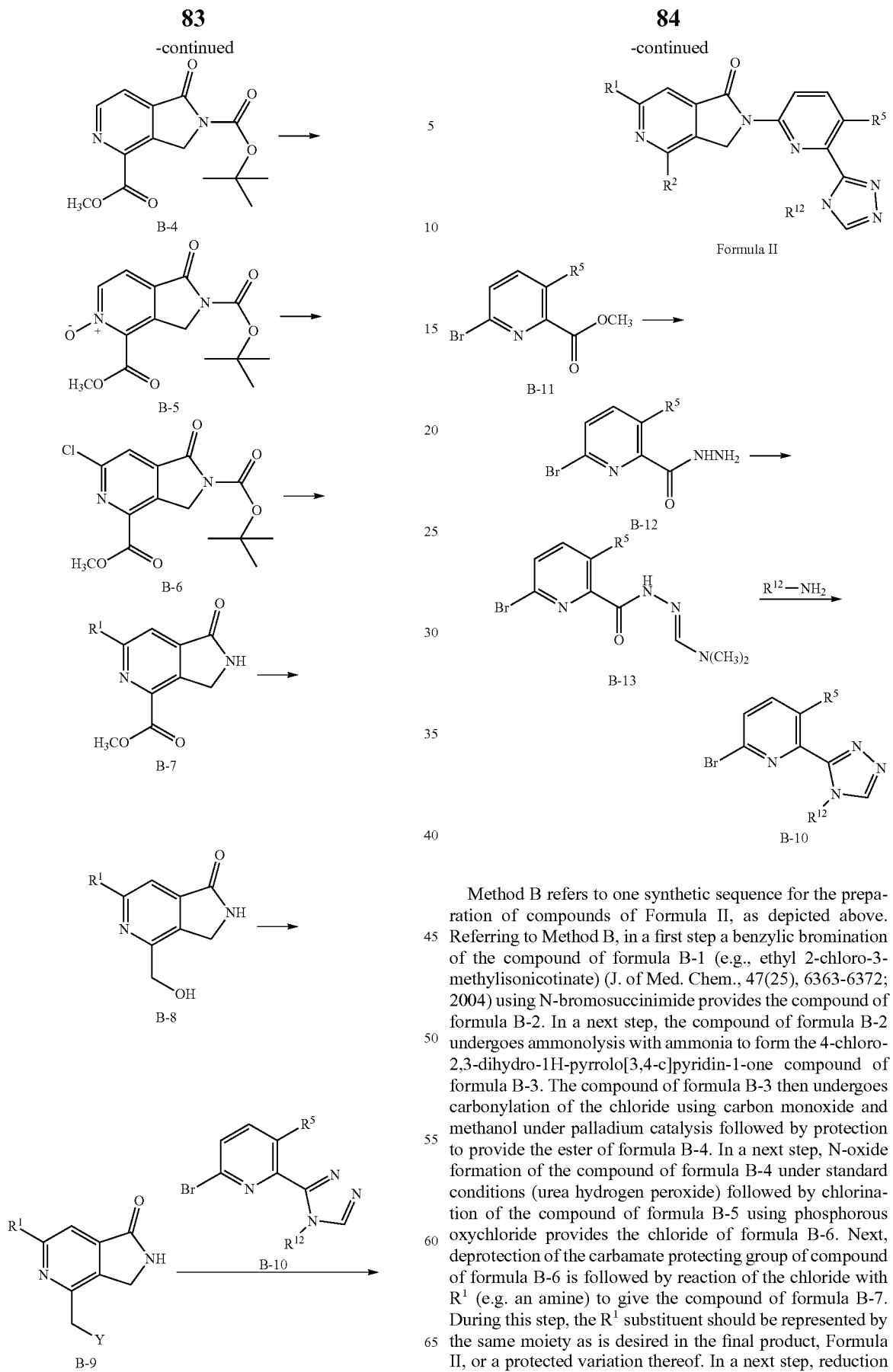

Method B refers to one synthetic sequence for the preparation of compounds of Formula II, as depicted above. Referring to Method B, in a first step a benzylic bromination of the compound of formula B-1 (e.g., ethyl 2-chloro-3-methylisonicotinate) (J. of Med. Chem., 47(25), 6363-6372; 2004) using N-bromosuccinimide provides the compound of formula B-2. In a next step, the compound of formula B-2 undergoes ammonolysis with ammonia to form the 4-chloro-2,3-dihydro-1H-pyrrolo[3,4-c]pyridin-1-one compound of formula B-3. The compound of formula B-3 then undergoes carbonylation of the chloride using carbon monoxide and methanol under palladium catalysis followed by protection to provide the ester of formula B-4. In a next step, N-oxide formation of the compound of formula B-4 under standard conditions (urea hydrogen peroxide) followed by chlorination of the compound of formula B-5 using phosphorous oxychloride provides the chloride of formula B-6. Next, deprotection of the carbamate protecting group of compound of formula B-6 is followed by reaction of the chloride with $R^1$ (e.g. an amine) to give the compound of formula B-7. During this step, the $R^1$ substituent should be represented by the same moiety as is desired in the final product, Formula II, or a protected variation thereof. In a next step, reduction of the ester functionality of formula B-7 provides the alcohol compound of formula B-8. Activation of the alcohol functionality of formula B-8, as a mesylate (B-9, Y=OSO$_2$CH$_3$) followed by either:

i) azidation (B-9, Y=N$_3$) and reduction of the azide functionality under standard conditions to provide primary amines (formula B-9, Y=NH$_2$); or ii) direct displacement of the mesylate (formula B-9, Y=OSO$_2$CH$_3$) with primary amines to give the corresponding secondary amines (formula B-9, Y=N(R$^8$)(R$^9$), R$^8$ and R$^9$=H and/or alkyl) to yield a compound of formula B-9.

Protection of the amino functionality as the corresponding tert-butyl carbamate, formula B-9 (Y=N(R$^8$) Boc, R$^8$=H or alkyl) is followed by coupling with the bromo pyridine of formula B-10 under palladium or copper catalysis to provide protected pyrrolo[3,4-c]pyridin-1-ones (R$^2$=CH$_2$N(R$^8$) Boc, R$^8$=H and/or alkyl). During this step, the R$^5$ and R$^{12}$ substituents of formula B-10 should be represented by the same moiety as is desired in the final product, Formula II, or a protected variation thereof.

Next, a deprotection of the carbamate protecting group under standard conditions yields pyrrolo[3,4-c]pyridin-1-ones Formula II (R$^2$=CH$_2$N(R$^8$)(R$^9$), R$^8$ and R$^9$=H and/or alkyl).

Preparation of the compound of formula B-10 can be accomplished by hydrazinolysis of the bromopyridine ester of formula B-11 (J. of Med. Chem., 60(2), 722-748; 2017) to form the compound of formula B-12. During this step, the R$^5$ substituent of formula B-11 should be represented by the same moiety as is desired in the final product, Formula II, or a protected variation thereof. Next, reaction of the hydrazide of formula B-12 with dimethylformamide dimethyl acetal provides the compound of formula B-13. Condensation of the compound of formula B-13 with an amine (e.g., R$^{12}$—NH$_2$) gives the triazole of formula B-10. During this step, the R$^{12}$ substituent of the amine should be represented by the same moiety as is desired in the final product, Formula II, or a protected variation thereof.

Method C

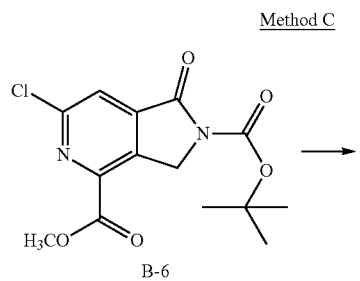

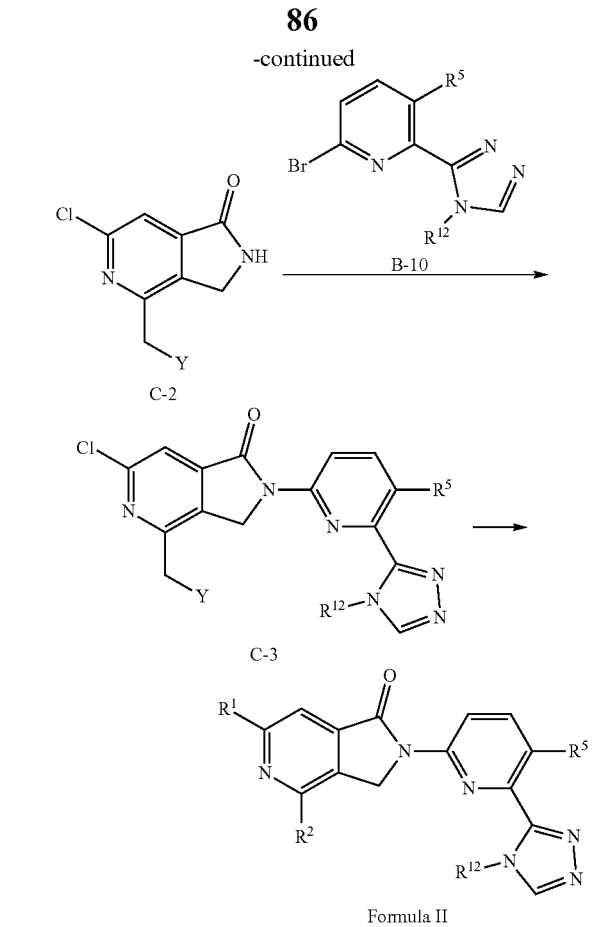

Formula II

Method C refers to another synthetic sequence for the preparation of compounds of Formula II, as depicted above. Referring to Method C, in a first step, a reduction of the ester functionality of the compound of formula B-6 provides the alcohol compound of formula C-1. Next, activation of the alcohol functionality of formula C-1 as a mesylate (C-2, Y=OSO$_2$CH$_3$) was followed by either:

i) azidation (C-2, Y=N$_3$) and reduction of the azide functionality under standard conditions to provide primary amines (formula C-2, Y=NH$_2$); or ii) direct displacement of the mesylate (formula C-2, Y=OSO$_2$CH$_3$) with primary amines to give the corresponding secondary amines (formula C-2, Y=N(R$^8$)(R$^9$), R$^8$ and R$^9$=H and/or alkyl) to yield a compound of formula C-2.

Protection of the amino functionality as the corresponding tert-butyl carbamate yields C-2 (Y=N(R$^8$) Boc, R$^8$=H or alkyl) is followed by coupling with the bromo pyridine of formula B-10 under palladium or copper catalysis to provide protected pyrrolo[3,4-c]pyridin-1-ones of formula C-3 (R$^2$=CH$_2$N(R$^8$) Boc, R$^8$=H or alkyl). During this step, the R$^5$ and R$^{12}$ substituents of formula B-10 should be represented by the same moiety as is desired in the final product, Formula II, or a protected variation thereof. Next, palladium or copper-mediated cross-coupling of formula C-3 with either amines, protected amines or alkyl trifluoroborates/boronic acids/boronates/zincates or alkenyl boronic esters followed by reduction or cyclopropanation and subsequent deprotection of the carbamate protecting group gives the pyrrolo[3,4-c]pyridin-1-ones Formula II (R$^2$=CH$_2$N(R$^8$)(R$^9$), R$^8$ and R$^9$=H and/or alkyl, R$^1$ substituent should be represented by the same moiety as is desired in the final product, Formula II, or a protected variation thereof).

Method D

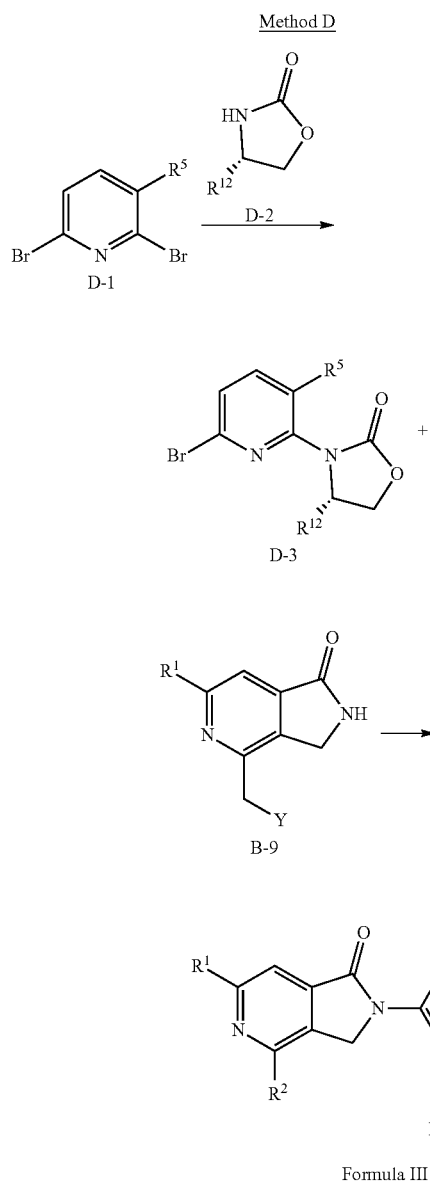

Formula III

Method E

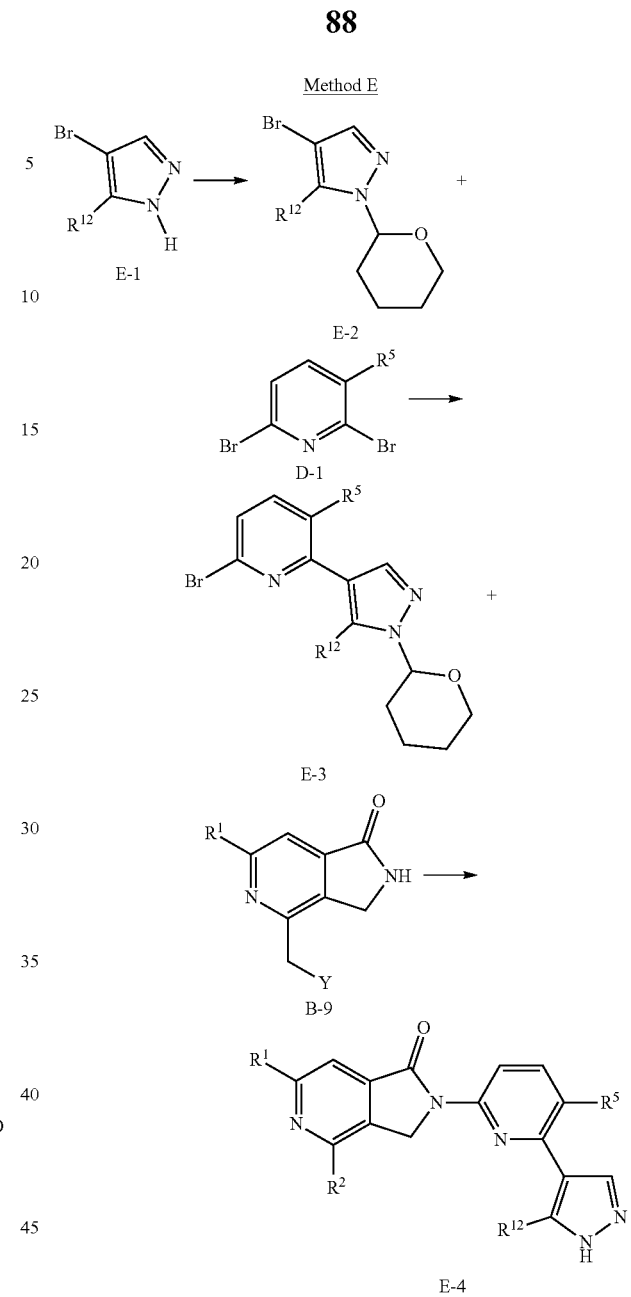

E-4

Method D refers to a synthetic sequence for the preparation of compounds of Formula III, as depicted above. Referring to Method D, in a first step, a coupling of 2,6-dibromopyridine of formula D-1 with the oxazolidinone of formula D-2 under palladium catalysis gives the bromopyridine of formula D-3. During this step, the $R^5$ substituent of formula D-1 and the $R^{12}$ substituent of formula D-2 should be represented by the same moiety as is desired in the final product, Formula III, or a protected variation thereof. Next, coupling of the compound of formula D-3 with the compound of formula B-9 (Y=N($R^8$) Boc, $R^8$=H or alkyl) under palladium or copper catalysis provides protected pyrrolo[3,4-c]pyridin-1-ones ($R^2$=CH$_2$N($R^8$) Boc, $R^8$=H or alkyl, $R^1$ substituent should be represented by the same moiety as is desired in the final product, Formula III, or a protected variation thereof). In a next step, deprotection of the carbamate protecting group under standard conditions yields pyrrolo[3,4-c]pyridin-1-ones of formula Formula III ($R^2$=CH$_2$N($R^8$)($R^9$) Boc, $R^8$ and $R^9$=H and/or alkyl).

Method E refers to a synthetic sequence for the preparation of compounds of Formula E-4, as depicted above. Referring to Method E, in a first step, protection of the compound of formula E-1 (e.g. 4-bromo-5-isopropyl-1H-pyrazole), with a tetrahydropyranyl (THP) group yields the pyrazole of formula E-2. During this step, the $R^{12}$ substituent of formula E-1 should be represented by the same moiety as is desired in the final product, Formula E-4, or a protected variation thereof. Next the formula of E-2 is coupled with a 2,6-dibromopyridine of formula D-1 (e.g., $R^5$=H or F) to give the bromopyridine of formula E-3. During this step, the $R^5$ substituent of formula D-1 should be represented by the same moiety as is desired in the final product, formula E-4, or a protected variation thereof. In a next step, coupling of the formula E-3 with the compound of formula B-9 (Y=N ($R^8$) Boc, $R^8$=H or alkyl) under palladium or copper catalysis provides the protected pyrrolo[3,4-c]pyridin-1-ones of the formula E-4 ($R^2$=CH$_2$N($R^8$) Boc, $R^8$=H or alkyl). During this step, the R¹ substituent of formula B-9 and the R⁵ substituent of formula E-3 should be represented by the same moiety as is desired in the final product, Formula E-4, or a protected variation thereof. Next, deprotection of the protected pyrrolo[3,4-c]pyridin-1-one under standard conditions yields pyrrolo[3,4-c]pyridin-1-ones of Formula E-4 ($R^2=CH_2N(R^8)(R^9)$, $R^8$ and $R^9=H$ and/or alkyl).

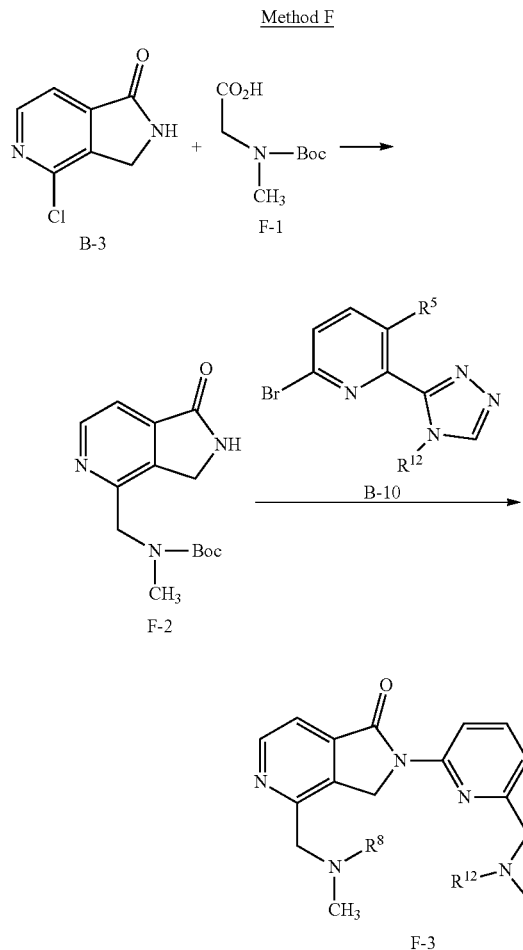

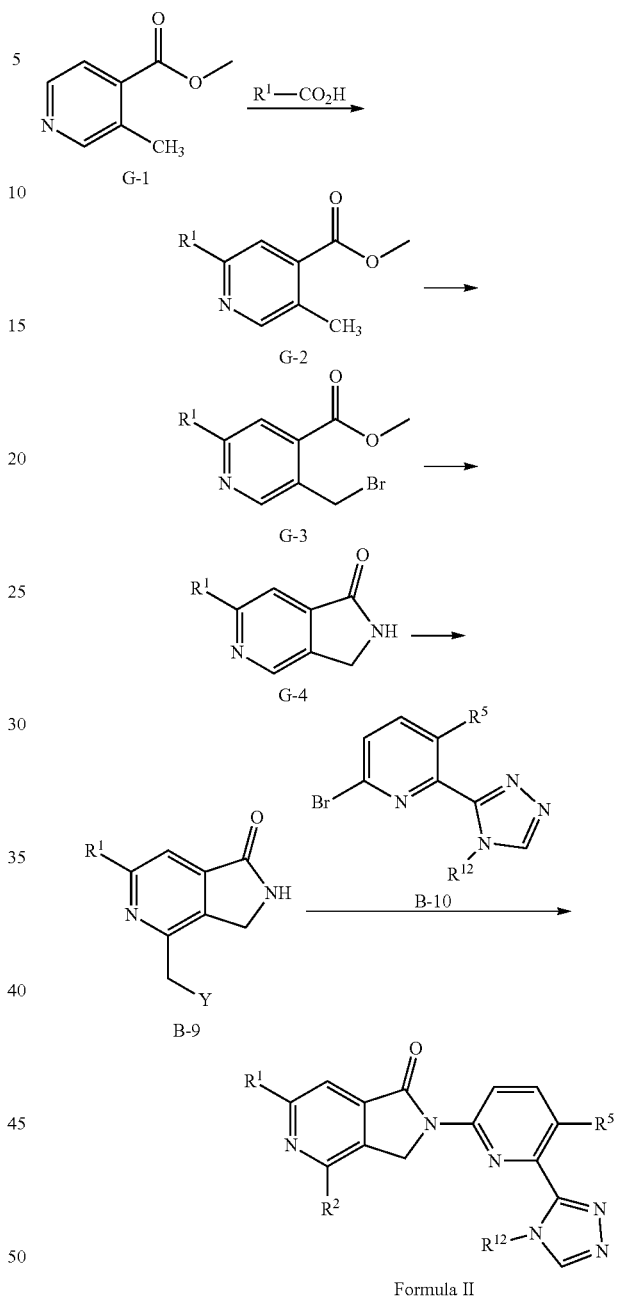

Method F refers to a synthetic sequence for the preparation of compounds of Formula F-3, as depicted above. Referring to Method F, in a first step, a coupling of the compound of formula B-3 under photoredox catalysis conditions (Zuo, et al., "Merging photoredox with nickel catalysis: Coupling of α-carboxyl sp³-carbons with aryl halides", Science 2014, 345, 437-440) using sarcosine (F-1) as a source of the aminoalkyl radical provides the pyrrolo[3,4-c]pyridin-1-one of formula F-2. Next, a coupling of the compound of formula F-2 with the bromo pyridine compound of formula B-10 under palladium or copper catalysis provides a protected pyrrolo[3,4-c]pyridin-1-one of the formula F-3 ($R^8$=Boc). During this step, the $R^5$ and $R^{12}$ substituents of formula B-10 should be represented by the same moiety as is desired in the final product, Formula F-3, or a protected variation thereof. In a next step, a deprotection of the carbamate protecting group under standard conditions yields pyrrolo[3,4-c]pyridin-1-one of formula F-3 wherein the $R^8$=H.

Method G refers to another synthetic sequence for the preparation of compounds of Formula II, as depicted above. Referring to Method G, in a first step, a nucleophilic radical substitution reaction of the compound of formula G-1 (e.g., methyl 3-methylisonicotinate) with a carboxylic acid (e.g., $R^1CO_2H$) under oxidative decarboxylation conditions with silver nitrate and an oxidizing agent (ammonium persulfate) provides the ester of formula G-2. During this step, the R¹ substituent of the carboxylic acid should be represented by the same moiety as is desired in the final product, Formula II, or a protected variation thereof. Next, a bromination using N-bromosuccinimide gives the bromide of formula G-3. In the next step, ammonolysis of the bromide of formula G-3 with ammonia yields the 2,3-dihydro-1H- pyrrolo[3,4-c]pyridin-1-one of formula G-4. Next, a decarboxylative radical substitution with an N-Boc protected amino acid under oxidative conditions yields the benzylic amine of formula B-9 (Y=N(R$^8$) Boc, R$^8$=H or alkyl). In the next step, a coupling with the bromo pyridine of formula B-10 under palladium or copper catalysis provides a protected pyrrolo[3,4-c]pyridin-1-ones of Formula II (R$^2$=CH$_2$N(R$^8$) Boc, R$^8$=H or alkyl). Next, a deprotection of the carbamate protecting group under standard conditions yields pyrrolo[3,4-c]pyridin-1-ones Formula II (R$^2$=CH$_2$N (R$^8$)(R$^9$), R$^8$ and R$^9$=H and/or alkyl).

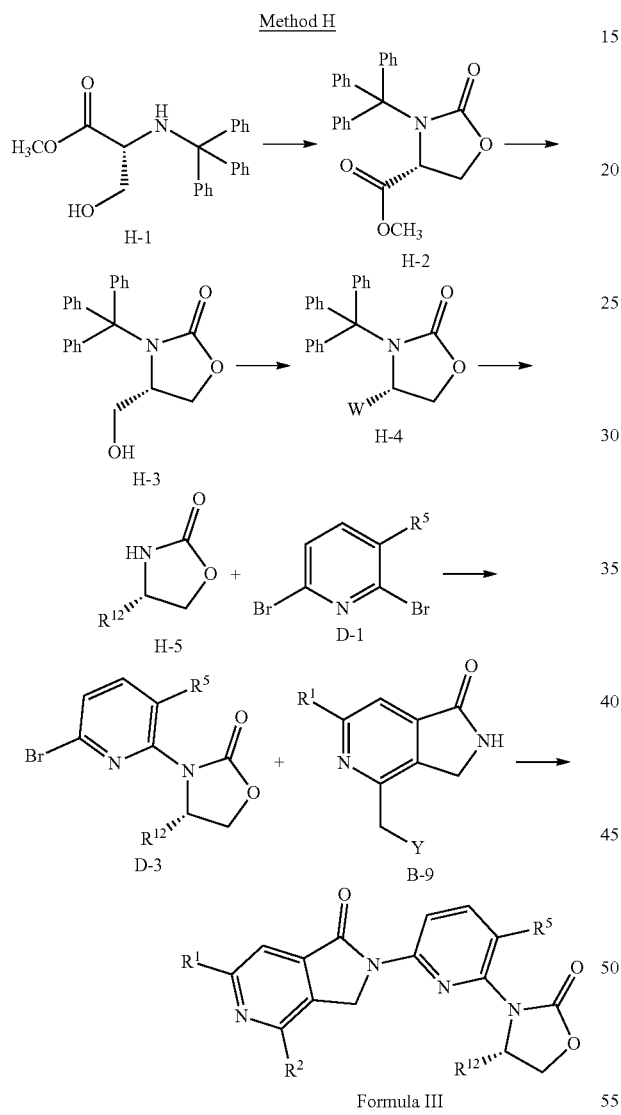

Method H

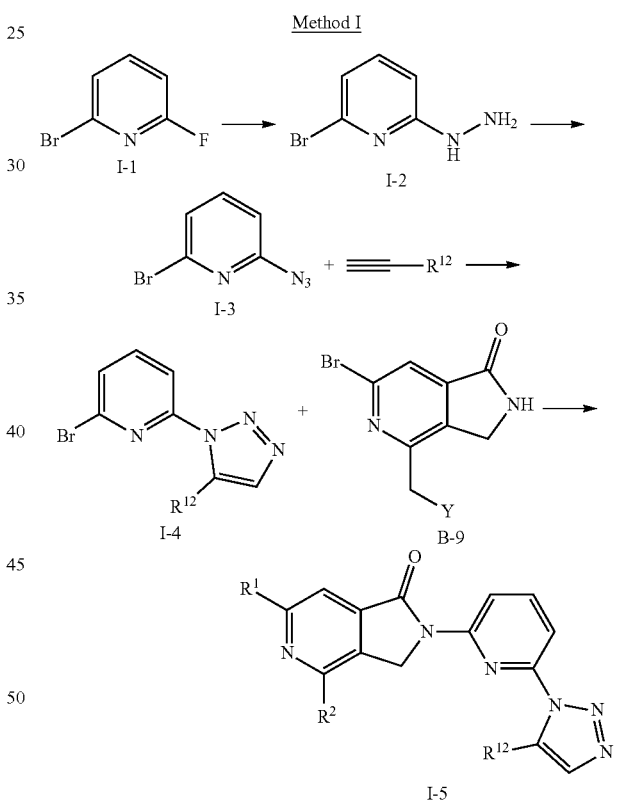

Method I

Method H refers to a synthetic sequence for the preparation of compounds of Formula III, as depicted above. Referring to Method H, in a first step, the oxazolidinone of formula H-2 is prepared via a cyclization of methyl trityl-D-serinate of formula H-1 using triphosgene. Next, a reduction of the ester of formula H-2 provides the alcohol of formula H-3. In the next step either (i) deoxyfluorination of the compound of formula H-3 yields the compound of formula H-4 (W=flouroalkyl, e.g., CH$_2$F), or (ii) oxidation of the alcohol of formula H-3 to the aldehyde of formula H-4 (W=CHO) followed by difluoromethylation provides the compound of formula H-4 (W=CHF$_2$).

Next, a deprotection of the N-trityl group of formula H-4 followed by coupling of the corresponding oxazolidinone of formula H-5 to 2,6-dibromopyridine of formula D-1 provides the bromo pyridine of formula D-3. During this step, the R$^5$ substituent of formula D-1 where the R$^{12}$ substituent of formula H-5 should be represented by the same moiety as is desired in the final product, Formula III, or a protected variation thereof. Next, coupling of the compound of formula D-3 to the compound of formula B-9 (R$^1$ substituent should be represented by the same moiety as is desired in the final product, Formula III, or a protected variation thereof, Y=N(R$^8$) Boc, R$^8$=H or alkyl) under palladium or copper catalysis provides a protected pyrrolo[3,4-c]pyridin-1-one of Formula III (R$^2$=CH$_2$N(R$^8$) Boc, R$_8$=H or alkyl, R$^{12}$=CH$_2$F or CHF$_2$). In the final step, a deprotection of the carbamate protecting group under standard conditions yields pyrrolo[3,4-c]pyridin-1-one of Formula III (R$^2$=CH$_2$N(R$^8$) (R$^9$), R$^8$ and R$^9$=H and/or alkyl).

Method I refers to a synthetic sequence for the preparation of compounds of Formula I-5, as depicted above. Referring to Method I, in a first step, hydrazinolysis of 2-bromo-6-fluoropyridine of formula I-1 yields a compound of formula I-2. In a next step diazotization of the hydrazine of formula I-2 yields the azide of formula I-3. Next, cycloaddition of the azide of formula I-3 with an alkyne provides the 1,2,3-triazole of formula I-4. During this step, the R$^{12}$ substituent of the alkyne should be represented by the same moiety as is desired in the final product, Formula I-5, or a protected variation thereof. In a next step, coupling of the compound of formula I-4 with B-9 (Y=N(R$^8$) Boc, R$^8$=H or alkyl, R$^1$ substituent should be represented by the same moiety as is desired in the final product, Formula I-5, or a protected variation thereof) under palladium catalysis provides a protected pyrrolo[3,4-c]pyridin-1-one of Formula I-5. Next, deprotection of the carbamate protecting group under standard conditions yields the pyrrolo[3,4-c]pyridin-1-one of Formula I-5 ($R^2=CH_2N(R^8)(R^9)$, $R^8$ and $R^9$=H and/or alkyl).

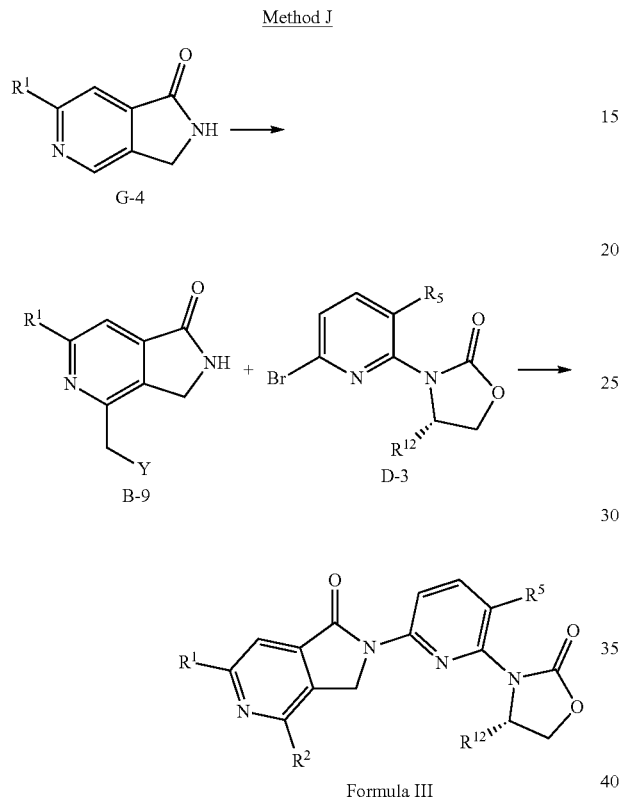

Method J

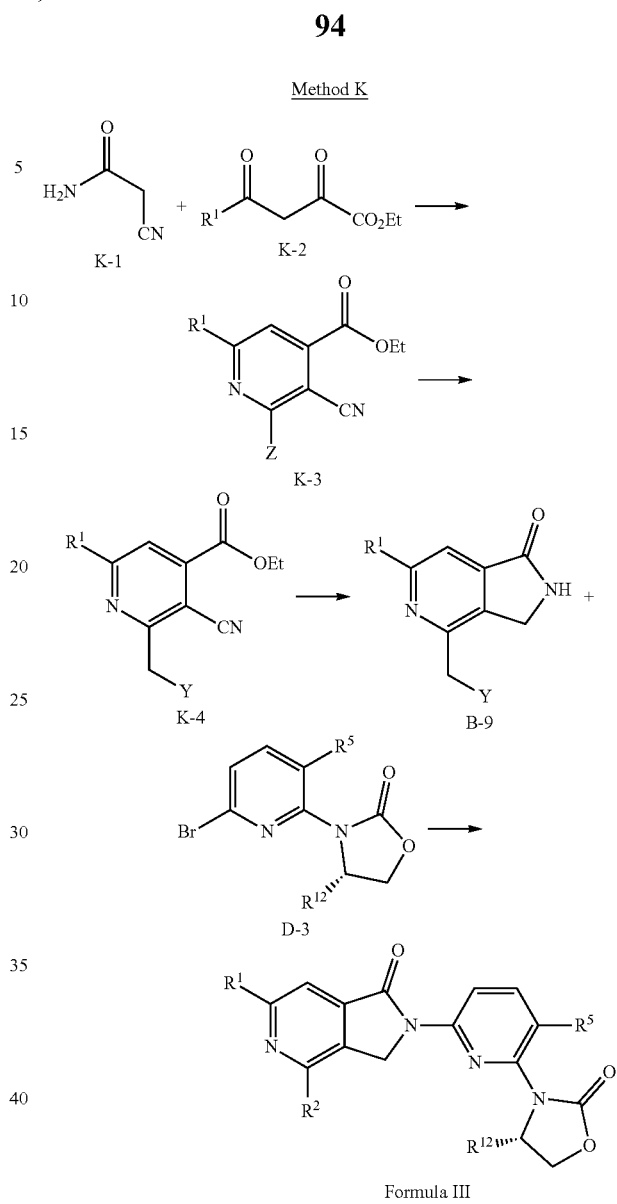

Method K

Method J refers to another synthetic sequence for the preparation of compounds of Formula III, as depicted above. Referring to Method J, in a first step, a radical mediated hydroxymethylation of a compound of formula G-4 using methanol and ammonium persulfate provides the compound of formula B-9 (Y=OH). During this step, the $R^1$ substituent of formula G-4 should be represented by the same moiety as is desired in the final product, Formula III, or a protected variation thereof. Next, activation of the alcohol functionality as a mesylate (B-9, $Y=OSO_2CH_3$) is followed by azidation (B-9, $Y=N_3$) and reduction of the azide functionality under standard conditions to provide primary amines (B-9, $Y=NH_2$). In a next step, protection of the amino functionality as the corresponding tert-butyl carbamate yields B-9 ($Y=N(R^8)$ Boc, $R^8$=H). Next, a coupling of the compound of formula D-3 with B-9 under palladium or copper catalysis provides a protected pyrrolo[3,4-c]pyridin-1-one of Formula III ($R^2=CH_2N(R^8)$ Boc, $R^8$=H, $R^{12}$ substituent should be represented by the same moiety as is desired in the final product, Formula III, or a protected variation thereof). In a final step, deprotection of the carbamate protecting group under standard conditions yields pyrrolo[3,4-c]pyridin-1-one of Formula III ($R^2=CH_2N(R^8)$ ($R^9$), $R^8$ and $R^9$=H).

Method K refers to another synthetic sequence for the preparation of compounds of Formula III, as depicted above. Referring to Method K, in a first step, condensation of 2-cyanoacetamide of formula K-1 with oxalate ester of formula K-2 yields the hydroxy pyridine of formula K-3 (Z=OH). During this step, the $R^1$ substituent of formula K-2 should be represented by the same moiety as is desired in the final product, Formula III, or a protected variation thereof. In a next step, chlorination under standard conditions ($POCl_3$) provides the chloropyridine of formula K-3 (Z=Cl). Next, coupling of the chloropyridine of formula K-3 (Z=Cl) under photoredox catalysis conditions (Zuo, et al., "Merging photoredox with nickel catalysis: Coupling of α-carboxyl $sp^3$-carbons with aryl halides", Science 2014, 345, 437-440) using sarcosine as a source of the aminoalkyl radical, provides the benzyl amine of formula K-4 Y=N($CH_3$) Boc)]. In the next step, reduction of the cyano group and concomitant cyclization yields the 2,3-dihydro-1H-pyrrolo[3,4-c]pyridin-1-one of formula B-9 (Y=N($CH_3$) Boc). Next, coupling of the compound of formula D-3 with B-9 (Y=N($CH_3$) Boc) under palladium or copper catalysis provides a protected pyrrolo[3,4-c]pyridin-1-one of Formula III ($R^2$=$CH_2N(CH_3)$ Boc, $R^5$ and $R^{12}$ substituents should be represented by the same moiety as is desired in the final product, Formula III, or a protected variation thereof). In a final step, deprotection of the carbamate protecting group under standard conditions yields pyrrolo[3,4-c]pyridin-1-one of Formula III ($R^2$=$CH_2N(CH_3)$H.

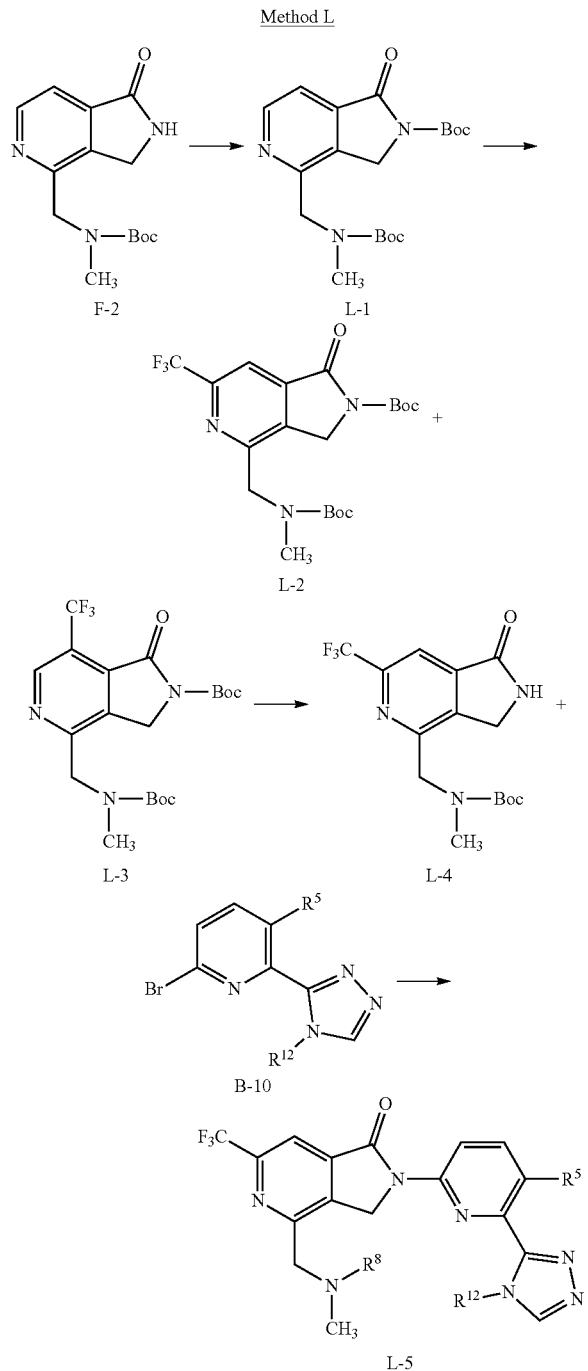

Method L

Method L refers to a synthetic sequence for the preparation of compounds of Formula L-5, as depicted above. Referring to Method L, in a first step, protection of the lactam of formula F-2 with a carbamate protecting group using di-tert-butyl dicarbonate and 4-dimethylaminopyridine yields a compound of formula L-1. Next, trifluoromethylation of the compound of formula L-1 using zinc trifluoromethanesulfinate and tert-butyl hydroperoxide yields a mixture of the 6-(trifluoromethyl)-1,3-dihydro-2H-pyrrolo[3,4-c]pyridine of formula L-2 and 7-(trifluoromethyl)-1,3-dihydro-2H-pyrrolo[3,4-c]pyridine of formula L-3. After separation by column chromatography, global deprotection of the carbamate protecting groups of formula L-2 under acidic conditions (TFA) followed by selective protection of the benzyl amine functionality with a carbamate protecting group, using di-tert-butyl dicarbonate and trimethylamine provides the trifluoromethyl lactam of formula L-4. In the next step, coupling of the compound of formula L-4 with the compound of formula B-10 under palladium catalysis provides a protected pyrrolo[3,4-c]pyridin-1-one of Formula L-5 ($R^8$=Boc). During this step, the $R^5$ and the $R^{12}$ substituents of formula B-10 should be represented by the same moiety as is desired in the final product, Formula L-5, or a protected variation thereof. In the final step, deprotection of the carbamate protecting group under standard conditions yields pyrrolo[3,4-c]pyridin-1-one of Formula L-5 ($R^8$=H).

Method M

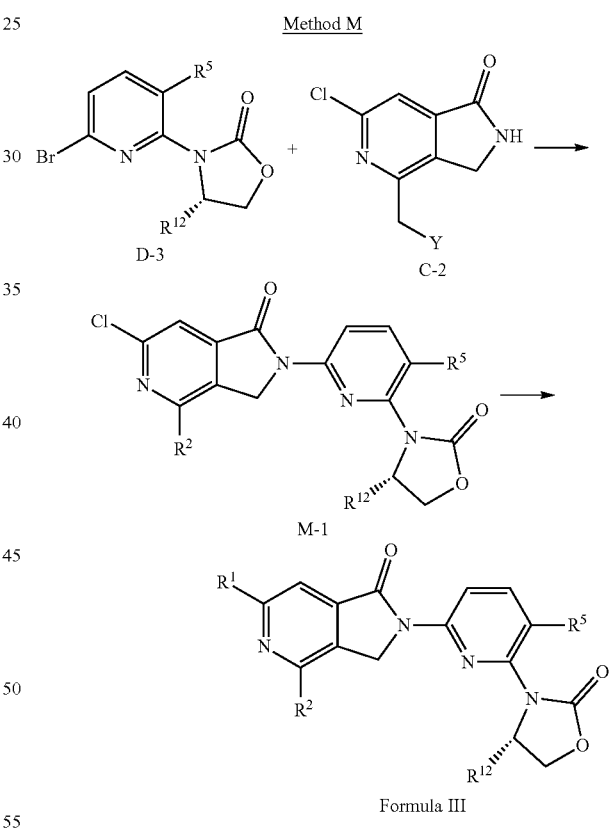

Method M refers to another synthetic sequence for the preparation of compounds of Formula III, as depicted above. Referring to Method M, in a first step, coupling of the compound of formula D-3 to the compound of formula C-2 (Y=N(R) Boc, $R^8$=H or alkyl) under palladium or copper catalysis provides a protected pyrrolo[3,4-c]pyridin-1-one of formula M-1 ($R^2$=$CH_2N(R^8)$ Boc, $R^8$=H or alkyl). During this step, the $R^5$ and the $R^{12}$ substituents of formula D-3 should be represented by the same moiety as is desired in the final product, Formula III or a protected variation thereof. Next, palladium or copper-mediated cross-coupling of formula M-1 with either amines, protected amines or alkyl trifluoroborates/boronic acids/boronates/zincates or alkenyl boronic esters followed by reduction or cyclopropanation and subsequent deprotection of the carbamate protecting group gives the pyrrolo[3,4-c]pyridin-1-one of Formula III where the $R^1$ substituent should be represented by the same moiety as is desired in the final product, Formula III, or a protected variation thereof ($R^2$=CH$_2$N($R^8$)($R^9$), $R^8$ and $R^9$=H and/or alkyl).

should be represented by the same moiety as is desired in the final product, Formula III, or a protected variation thereof.

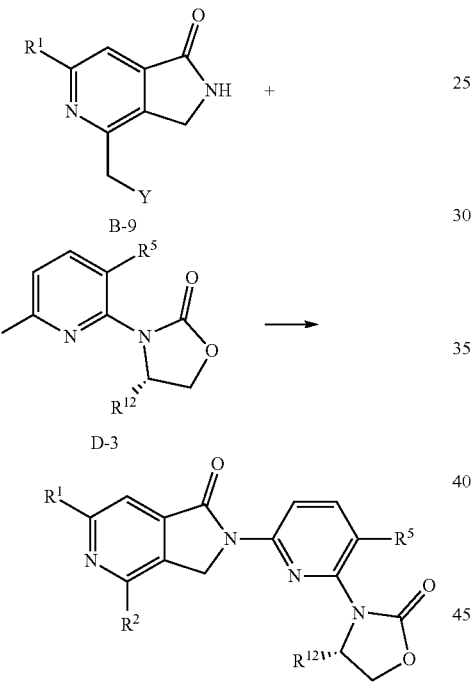

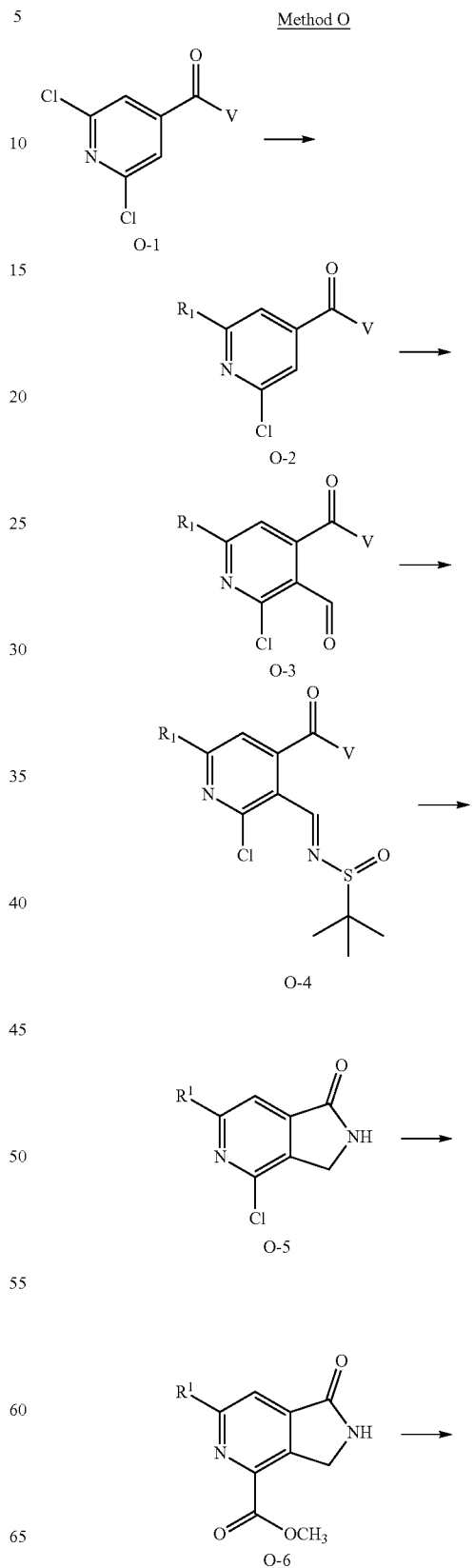

Method N refers to another synthetic sequence for the preparation of compounds of Formula III, as depicted above. Referring to Method N, in a first step, palladium or copper-mediated cross-coupling between a compound of formula C-2 (Y=N($R^8$) Boc, R=H or alkyl) and either amines, protected amines or alkyl trifluoroborates/boronic acids/boronates/zincates or alkenyl boronic esters followed by reduction or cyclopropanation provides a compound of formula B-9. During this step, the $R^1$ substituent of formula B-9 should be represented by the same moiety as is desired in the final product, Formula III, or a protected variation thereof. In a next step, coupling of formula D-3 to the compound of formula B-9 under palladium or copper catalysis followed by deprotection of the carbamate protecting group provides the pyrrolo[3,4-c]pyridin-1-one of Formula III ($R^2$=CH$_2$N($R^8$)($R^9$), $R^8$ and $R^9$=H and/or alkyl). During this step, the $R^5$ and the $R^{12}$ substituents of formula D-3

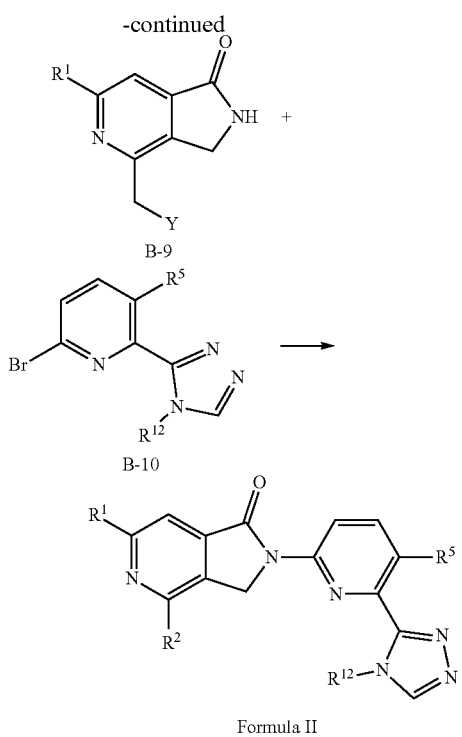

Method O refers to another synthetic sequence for the preparation of compounds of Formula II, as depicted above. Referring to Method O, in a first step, cross coupling or nucleophilic aromatic substitution between requisite coupling partner or amine (or protected version thereof) and the dichloropyridine of formula O-1 (V=N(CH$_3$)$_2$ or OH or piperidine or OMe) yields O-2 (R$^1$=NR$^6$R$^7$ or alkyl). Formylation of O-2 then provides aldehyde O-3. Subsequent condensation with Ellman's sulfinamide provides the compound of formula O-4. Subsequent reduction furnished the compound of formula O-5. Carbonylation of the chloride of the formula O-5 using carbon monoxide and methanol under palladium catalysis provides the ester of the formula O-6. Reduction of the ester of formula O-6 provides the benzylic alcohol B-9 (Y=OH). Activation of the alcohol functionality yields the mesylate (B-9, Y=OSO$_2$CH$_3$). In the next step either:

i) azidation (B-9, Y=N$_3$) and reduction of the azide functionality under standard conditions to provide primary amines (formula B-9, Y=NH$_2$); or ii) direct displacement of the mesylate (formula B-9, Y=OSO$_2$CH$_3$) with primary amines to give the corresponding secondary amines (formula B-9, Y=N(R$^8$) (R$^9$), R$^8$ and R$^9$=H and/or alkyl) to yield the compound of formula B-9.

Protection of the amino functionality as the corresponding tert-butyl carbamate, B-9 (Y=N(R$^8$) Boc), followed by coupling with the bromopyridine triazole B-10 under palladium or copper catalysis provides the protected pyrrolo[3,4-c]pyridin-1-ones of Formula II (R$^2$=CH$_2$N(R$^8$) Boc, R$^8$=H or alkyl, R$^1$=N(R$^6$)(R$^7$) or alkyl). In this step the R$^{12}$ substituent of formula B-10 should be represented by the same moiety as is desired in the final product, Formula II, or a protected variation thereof. Cleavage of the protecting group(s) under standard conditions yields pyrrolo[3,4-c]pyridin-1-ones of Formula II (R$^2$=CH$_2$N(R$^8$)(R$^9$), R$^1$=N(R$^6$)(R$^7$) or alkyl).

Method P

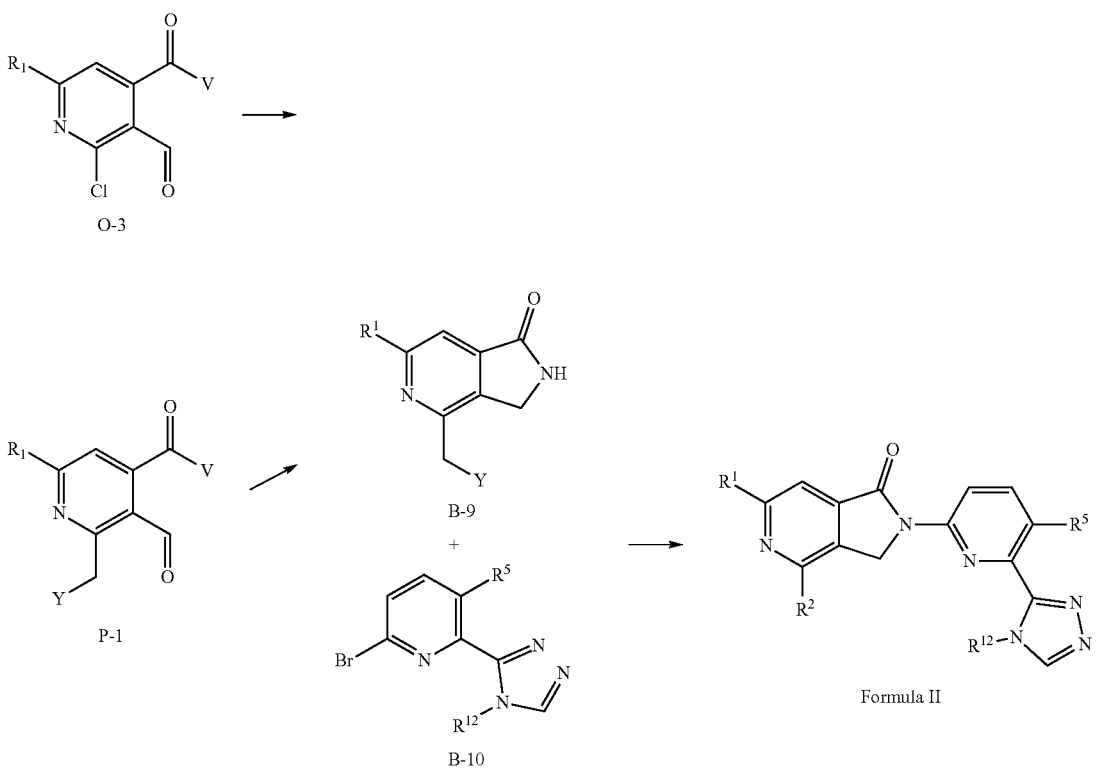

Method P refers to another synthetic sequence for the preparation of compounds of Formula II, as depicted above. n a first step, from the compound of formula O-3 (V=N (CH$_3$)$_2$ or OH or piperidine or OMe or OEt or OiPr) either i. Iridium-mediated decarboxylative photoredox coupling with the requisite carboxylic acid to provide the compound of formula P-1 (Y=N(R$^8$) Boc); or
ii. Negishi coupling with the requisite aminoalkylzincate to provide the compound of formula P-1 (Y=N(R$^8$) Boc); or
iii. Suzuki cross coupling with the requisite trifluoroborate salt, boronic acid or boronic ester to provide the compound of formula P-1 (Y=N(R$^8$) Boc)

Subsequent condensation with Ellman's sulfinamide and reduction furnishes the compound of formula B-9. Coupling with the bromopyridine triazole B-10 under palladium or copper catalysis provides the protected pyrrolo[3,4-c]pyridin-1-one of Formula II (R$^2$=CH$_2$N(R$^8$) Boc). In this step the R$^{12}$ substituent of formula B-10 should be represented by the same moiety as is desired in the final product, Formula II, or a protected variation thereof. Cleavage of the protecting group(s) under standard conditions yields the pyrrolo[3,4-c]pyridin-1-one of Formula II (R$^2$=CH$_2$N(R$^8$)(R$^9$)).

Method Q

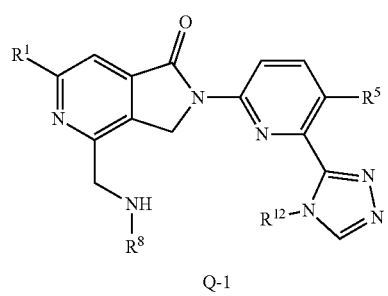

Q-1

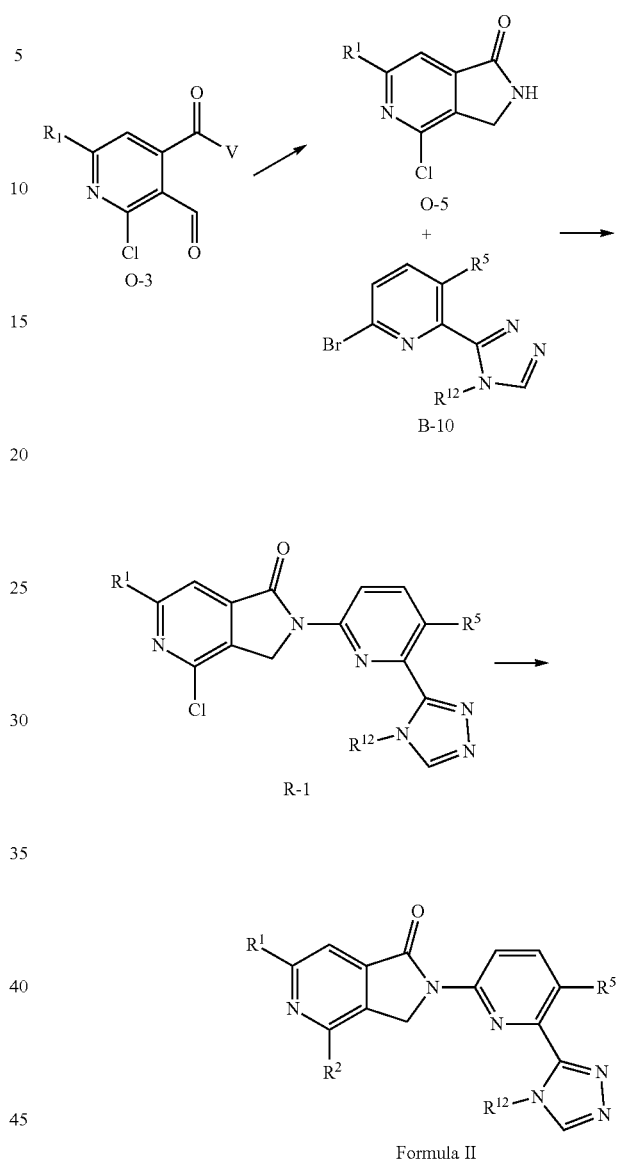

Formula II

Method Q refers to another synthetic sequence for the preparation of compounds of Formula II, as depicted above. In a first step, reductive amination or alkylation of the amine of formula Q-1 provides the pyrrolo[3,4-c]pyridin-1-one of Formula II (R$^2$=CH$_2$N(R$^8$)(R$^9$)). In this step the R$^5$, R$^{12}$ and R$^1$ substituents of formula Q-1 should be represented by the same moiety as is desired in the final product, Formula II.

Method R refers to another synthetic sequence for the preparation of compounds of Formula II, as depicted above. In a first step, reductive amination the compound of formula O-3 with an equivalent of ammonia or alternatively with Ellman's sulfinamide provides the compound of formula O-5. In this step, the R$^1$ substituent of formula O-3 should be represented by the same moiety as is desired in the final product, Formula II, or a protected variation thereof. Coupling with the bromopyridine triazole B-10 under palladium or copper catalysis provides the compound of formula R-1. In this step the R$^{12}$ substituent of formula B-10 should be represented by the same moiety as is desired in the final product, Formula II, or a protected variation thereof. Suzuki cross-coupling with the appropriate trifluoroborate followed by deprotection of the protecting group(s) under standard conditions yields the pyrrolo[3,4-c]pyridin-1-one of Formula II (R$^2$=CH$_2$N(R$^8$)(R$^9$)).

Method S

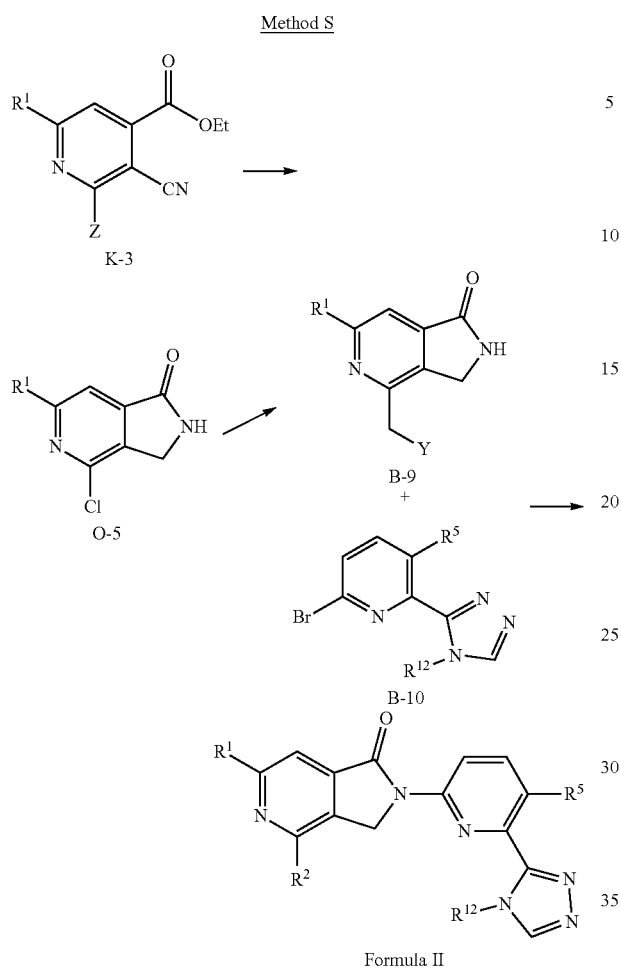

Formula II

Method S refers to another synthetic sequence for the preparation of compounds of Formula II, as depicted above. In a first step, nickel-mediated reduction of the nitrile of the compound of formula K-3 (Z=Cl) yields the compound of formula O-5. In this step, the $R^1$ substituent of formula K-3 should be represented by the same moiety as is desired in the final product, Formula II, or a protected variation thereof. In the next step either
  i) Nickel-mediated decarboxylative photoredox cross coupling of the compound of formula O-5 with the requisite acid provides the compound of formula B-9 (Y=N($R^8$) Boc); or
  ii) Carbonylation of the chloride for formula O-5 using carbon monoxide and methanol under palladium catalysis provides an ester which is then reduced (B-9, Y=OH) and activated as a mesylate (B-9, Y=OSO$_2$CH$_3$). In the next step either
    a. Direct displacement of the mesylate with primary amines provides the corresponding secondary amines of formula B-9 (Y=N($R^8$)($R^9$)); or
    b. Azidation (B-9, Y=N$_3$) and reduction of the azide functionality under standard conditions provides the primary amine of formula B-9 (Y=NH$_2$).
Coupling of the compound of the formula B-9 with the bromopyridine triazole B-10 under palladium or copper catalysis followed by cleavage of the protecting group(s) under standard conditions provides the pyrrolo[3,4-c]pyridin-1-one of the Formula II.

Method T

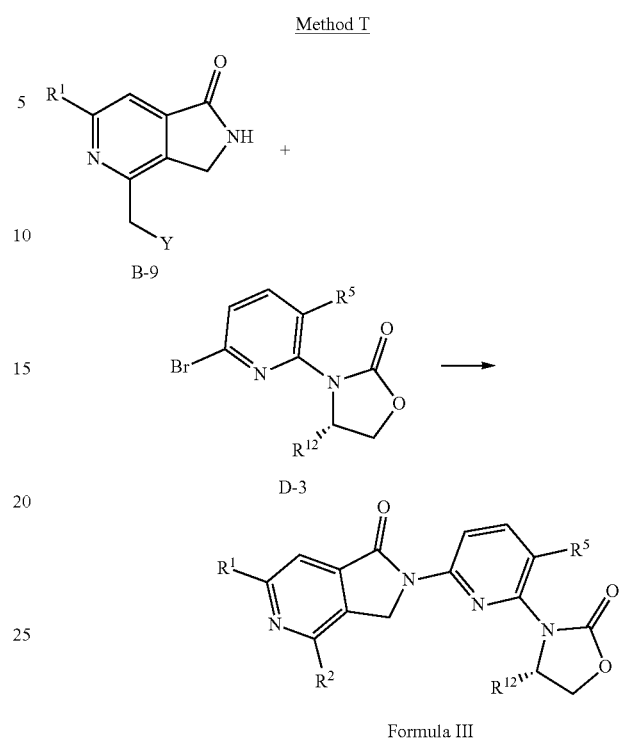

Formula III

Method T refers to another synthetic sequence for the preparation of compounds of Formula III, as depicted above. In a first step, the compound of the formula B-9 (Y=N($R^8$) Boc, $R^1$ is as represented in the compound of Formula III or a protected version thereof), undergoes coupling with the palladium of copper-mediated coupling with the compound of formula bromopyridine D-3 (prepared as described in method H) to provide pyrrolo[3,4-c]pyridin-1-one of Formula III ($R^2$=CH$_2$N($R^8$) Boc). Cleavage of the protecting group(s) under standard conditions yields the pyrrolo[3,4-c]pyridin-1-one of Formula III ($R^2$=CH$_2$N($R^8$)($R^9$)).

Method U

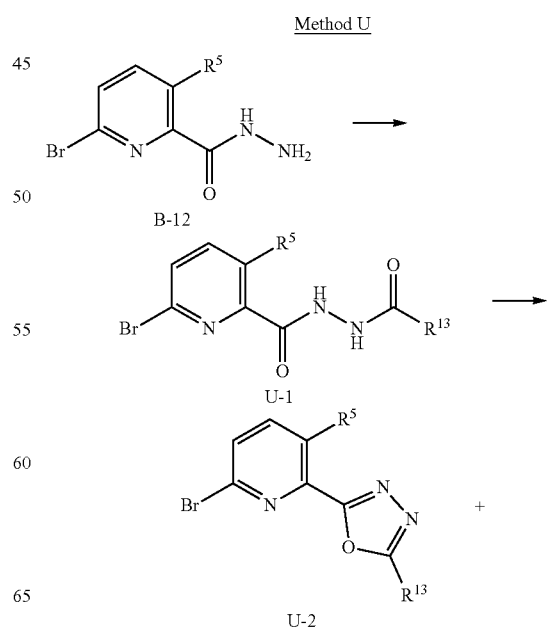

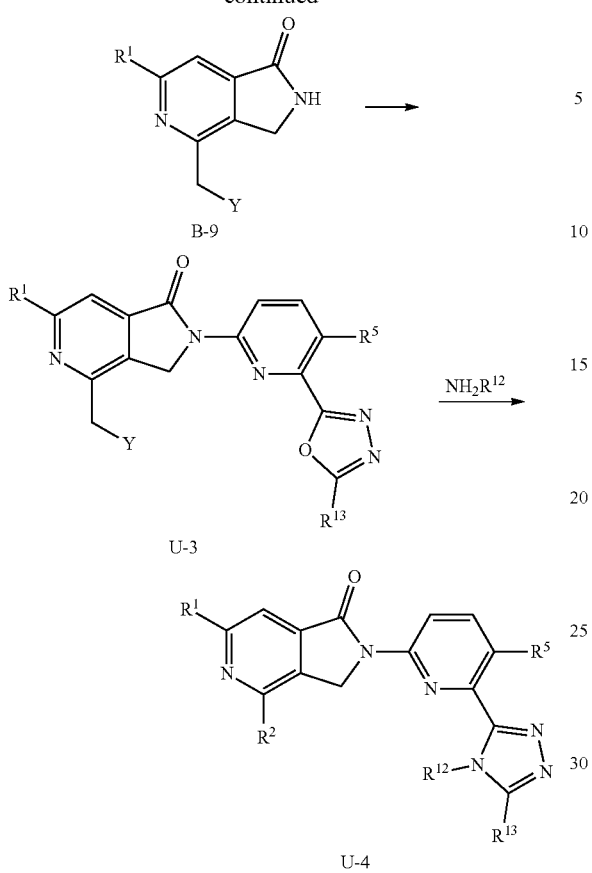

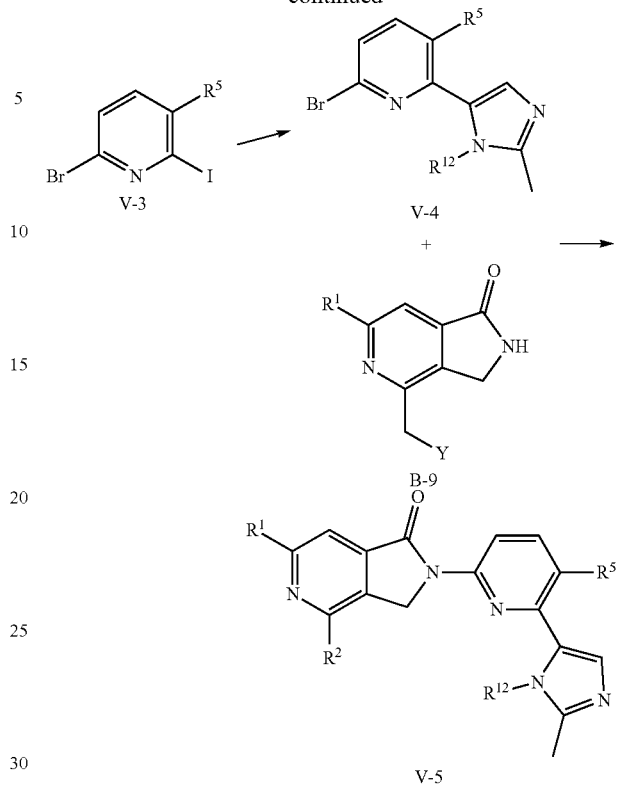

Method U refers to a synthetic sequence for the preparation of compounds of Formula U-4, as depicted above. In a first step, the compound of the formula B-12 undergoes reaction with the appropriate acyl chloride to provide the compound of the formula U-1. In this step, the $R^{13}$ substituent of the acyl chloride is as represented in the final product, Formula U-4, or a protected version thereof. Cyclization of the compound of the formula U-1 provides the compound of formula U-2. The bromopyridine of the formula U-2 (e.g. intermediate 4) undergoes coupling with the compound of the formula B-9 under palladium or copper catalysis to provide the compound of formula U-3 (Y=N($R^8$) Boc). In this step the $R^5$ substituent of U-2 and the $R^1$ substituent B-9 should be represented by the same moiety as is desired in the final product, Formula U-4, or a protected variation thereof. The compound of formula U-3 undergoes reaction with the requisite amine to provide the compound of the protected pyrrolo[3,4-c]pyridin-1-one of U-4. Cleavage of the protecting group(s) under standard conditions yields the pyrrolo[3,4-c]pyridin-1-one of Formula U-4 ($R^2$=CH$_2$N($R^8$)($R^9$)).

Method V refers to a synthetic sequence for the preparation of compounds of Formula V-5, as depicted above. In a first step, alkylation of the imidazole of the formula V-1 provides the compound of formula V-2 where the $R^{12}$ substituent should be represented by the same moiety as is desired in the final product, Formula V-5, or a protected variation thereof. Palladium-mediated coupling of the compound of formula V-2 with the compound of the formula V-3 provides the compound of the formula V-4. In this step the $R^5$ substituent of V-3 should be represented by the same moiety as is desired in the final product, Formula V-5, or a protected variation thereof. Coupling of the compound of formula V-4 with the compound of the formula B-9 under palladium or copper catalysis provides the protected pyrrolo[3,4-c]pyridin-1-one of Formula V-5 ($R^2$=CH$_2$N($R^8$) Boc). In this step, the $R^1$ substituent of B-9 should be represented by the same moiety as is desired in the final product, Formula V-5, or a protected variation thereof. Cleavage of the protecting group(s) under standard conditions yields the pyrrolo[3,4-c]pyridin-1-one of Formula V-5 ($R^2$=CH$_2$N($R^8$)($R^9$)).

Method V

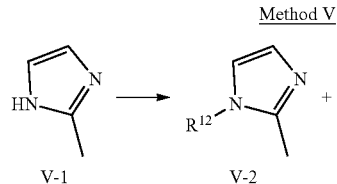

Method W

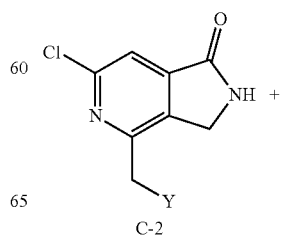

-continued

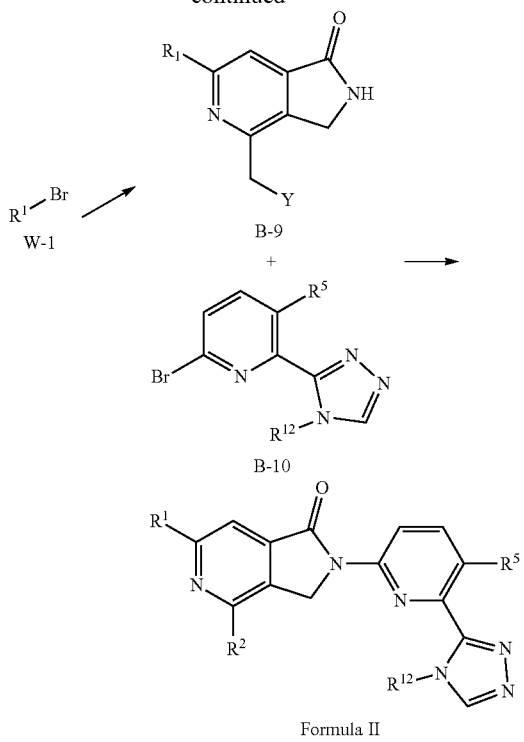

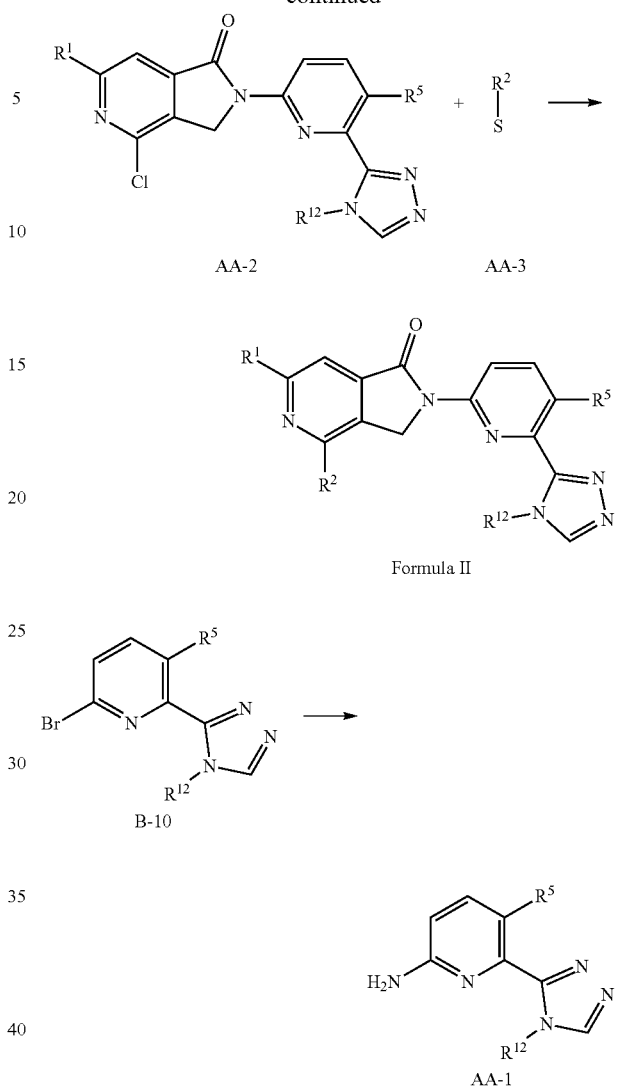

Method W refers to another synthetic sequence for the preparation of compounds of Formula II, as depicted above. In a first step, nickel-mediated photoredox cross coupling of the compound of the formula C-2 (Y=N(R$^8$)Boc) and W-1 provides the compound of formula B-9. In this step the R$^1$ substituent of W-1 should be represented by the same moiety as is desired in the final product, Formula II, or a protected variation thereof. The compound of the formula B-9 undergoes coupling with the compound of the formula B-10 under palladium or copper catalysis followed by cleavage of the protecting group(s) under standard conditions to yield the pyrrolo[3,4-c]pyridin-1-one of Formula II (R$^2$=CH$_2$N(R$^8$)(R$^9$)). In this step the R$^5$ and R$^{12}$ substituents of B-10 should be represented by the same moiety as is desired in the final product, Formula II, or a protected variation thereof.

Method AA

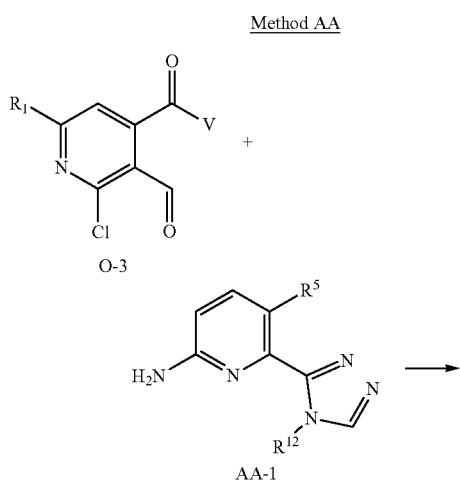

Method AA refers to another synthetic sequence for the preparation of compounds of Formula II, as depicted above. In a first step, the compound of the formula O-3 (V=piperidine, dimethylamine, OH, OMe, OEt, OiPr) undergoes reductive amination with the pyridine amine of the formula AA-1 to provide the compound of the formula AA-2. In this step the R$^1$ substituent of O-3 and the R$^5$ and R$^{12}$ substituents of formula AA-1 should be represented by the same moiety as is desired in the final product, Formula II, or a protected variation thereof. Next, palladium-mediated cross-coupling of formula AA-2 with trifluoroborates or zincates of the formula AA-3 followed by cleavage of the protecting group(s) under standard conditions provides the pyrrolo[3,4-c]pyridin-1-one of the Formula II. In this step the R$^2$ substituent should be represented by the same moiety as is desired in the final product, Formula II, or a protected variation thereof.

The compound of the formula B-10 undergoes coupling with tert-butyl carbamate under palladium catalysis followed by cleavage of the carbamate protecting group under standard conditions to yield the amino pyridine of the formula AA-1.

Method AB

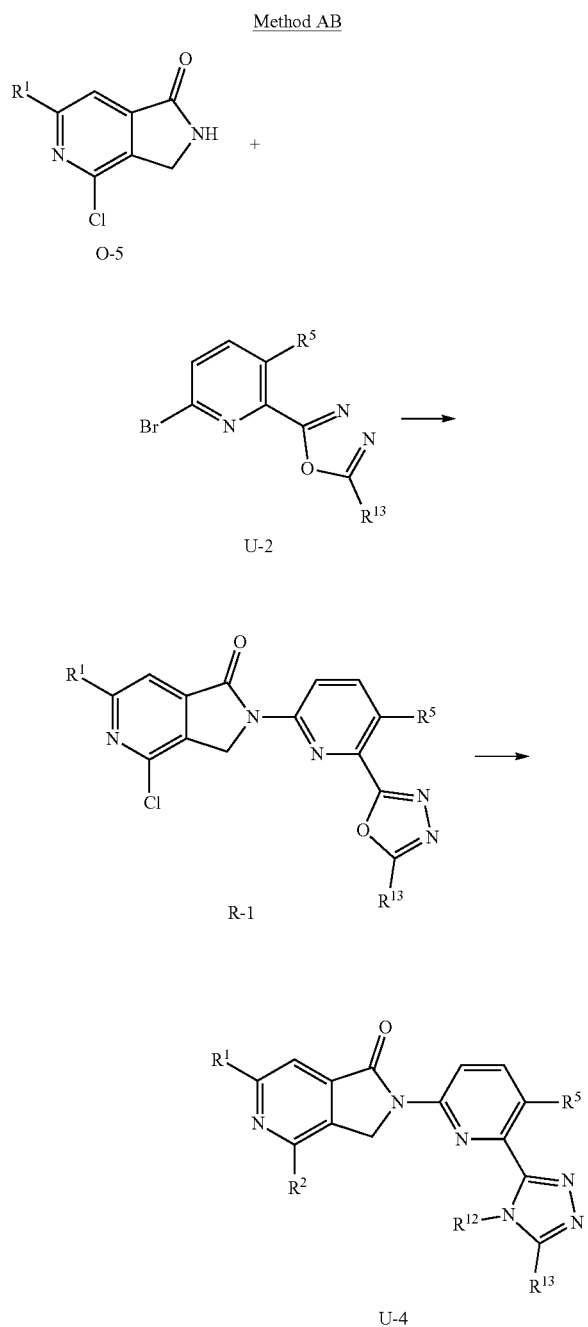

Method AC

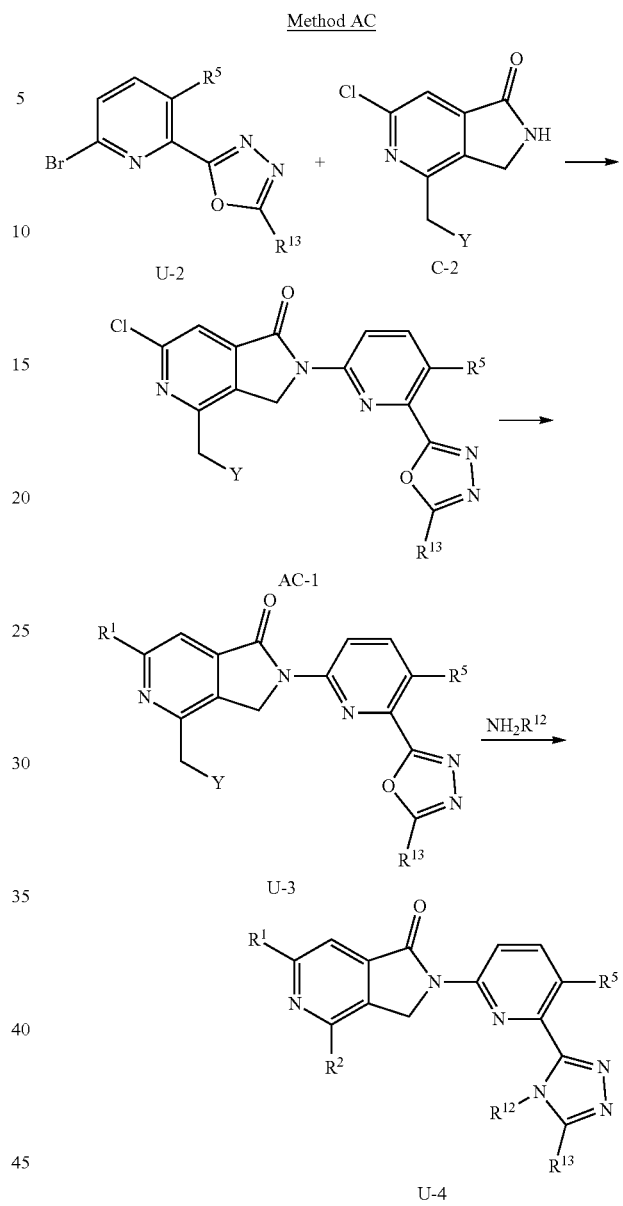

Method AB refers to another synthetic sequence for the preparation of compounds of Formula U-4, as depicted above. In a first step, coupling of the compound of formula O-5 with bromopyridine of the formula U-2 under palladium or copper catalysis provides the compound of formula R-1. In this step the $R^1$ substituent of formula O-5 and the $R^5$ and $R^{13}$ substituents of formula U-2 should be represented by the same moiety as is desired in the final product, Formula U-4, or a protected variation thereof. Suzuki cross-coupling with the appropriate trifluoroborate or Negishi cross coupling with the requisite aminoalkyl zincate followed by deprotection of the protecting group(s) under standard conditions yields the pyrrolo[3,4-c]pyridin-1-one of Formula U-4 ($R^2$=CH$_2$N(R$^8$)(R$^9$)).

Method AC refers to another synthetic sequence for the preparation of compounds of Formula U-4, as depicted above. In a first step, a bromopyridine of the formula U-2 (e.g. intermediate 4) undergoes coupling with the compound of the formula C-2 under palladium or copper catalysis to provide the compound of formula AC-1 (Y=N(R$^8$) Boc). In this step the $R^5$ and $R^{13}$ substituents of U-2 should be represented by the same moiety as is desired in the final product, Formula U-4, or a protected variation thereof. The compound of formula AC-1 undergoes palladium-mediated coupling with the requisite amine or boronic ester or boronic acid or tetrafluoroborate salt to provide the compound of the formula U-3. In this step, the $R^1$ substituent of U-3 should be represented by the same moiety as is desired in the final product, Formula U-4, or a protected variation thereof. Reaction of the compound of formula U-3 with the requisite amine provides the compound of the protected pyrrolo[3,4-c]pyridin-1-one of Formula U-4. Cleavage of the protecting group(s) under standard conditions yields the pyrrolo[3,4-c]pyridin-1-one of Formula U-4 ($R^2$=CH$_2$N(R$^8$)(R$^9$)).

Method AD

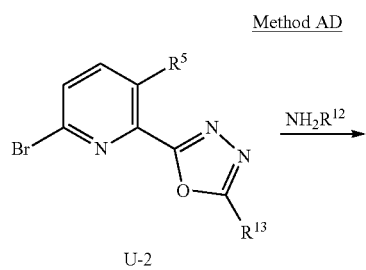

U-2

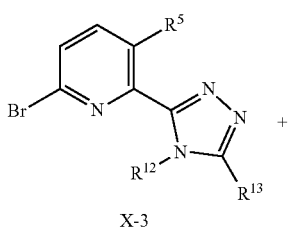

X-3

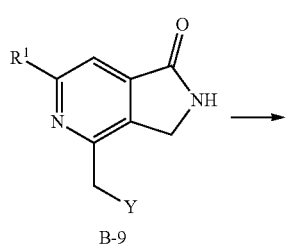

B-9

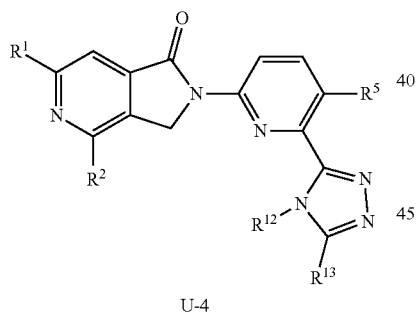

U-4

Method AD refers to another synthetic sequence for the preparation of compounds of Formula U-4, as depicted above. In a first step, a bromopyridine of the formula U-2 (e.g. intermediate 4) undergoes reaction with the requisite amine to provide the compound of the formula X-3. In this step the $R^5$ and $R^{12}$ substituents of U-2 should be represented by the same moiety as is desired in the final product, Formula U-4, or a protected variation thereof. Coupling with the compound of the formula X-3 with the compound of the formula B-9 under palladium or copper catalysis to provide the compound of Formula U-4 (Y=N($R^8$) Boc). In this step, the $R^1$ substituent of B-9 should be represented by the same moiety as is desired in the final product, Formula U-4, or a protected variation thereof. Cleavage of the protecting group(s) under standard conditions yields the pyrrolo[3,4-c]pyridin-1-one of Formula U-4 ($R^2$=$CH_2N(R^8)(R^9)$).

Method AE

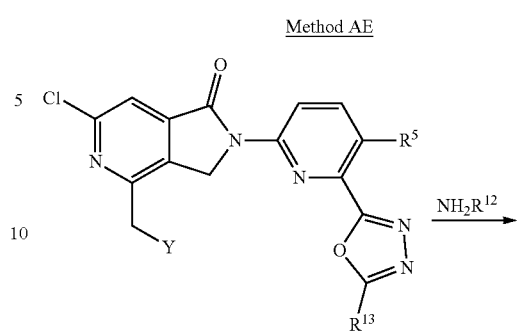

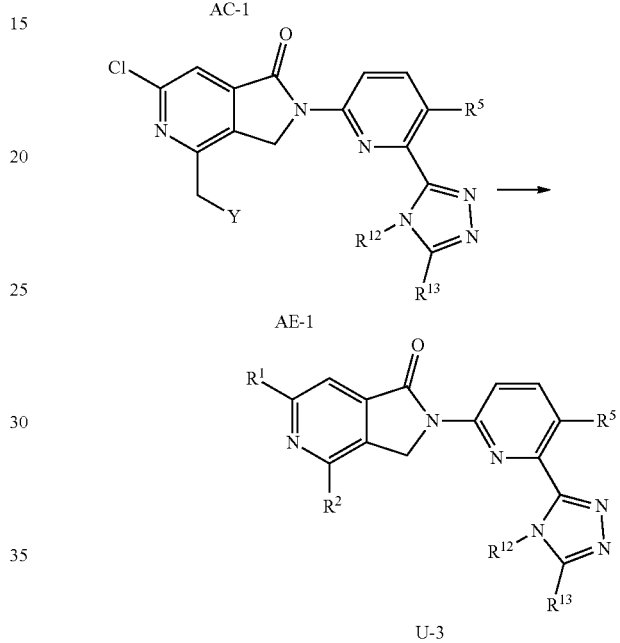

Method AE refers to another synthetic sequence for the preparation of compounds of Formula U-4, as depicted above. In a first step, reaction of the compound of formula AC-1 (Y=N($R^8$) Boc) with the requisite amine provides the compound of the formula AE-1. In this step, the $R^5$ and $R^{12}$ substituents should be represented by the same moiety as is desired in the final product, Formula U-4, or a protected variation thereof. The compound of formula AE-1 undergoes palladium-mediated coupling with the requisite amine or boronic ester or boronic acid or tetrafluoroborate salt to provide the compound of the protected pyrrolo[3,4-c]pyridin-1-one of Formula U-4. Cleavage of the protecting group(s) under standard conditions yields the pyrrolo[3,4-c]pyridin-1-one of Formula U-4 ($R^2$=$CH_2N(R^8)(R^9)$).

Method AF

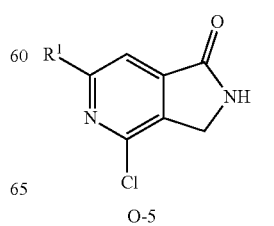

O-5

113

-continued

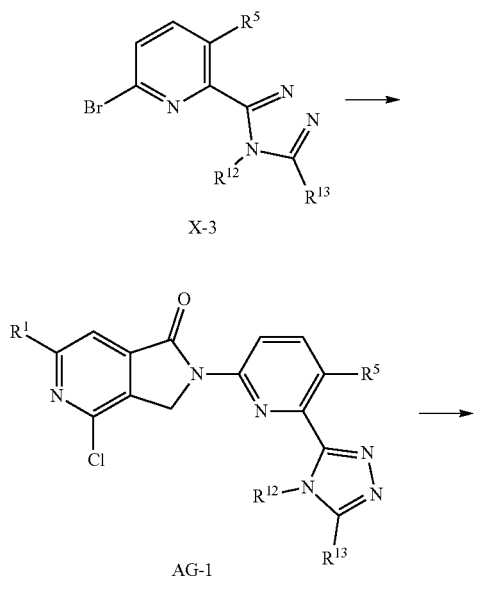

X-3

AG-1

U-3

Method AF refers to another synthetic sequence for the preparation of compounds of Formula U-4, as depicted above. In a first step, coupling of the compound of formula O-5 with bromopyridine X-3 under palladium or copper catalysis provides the compound of formula AF-1. In this step the R¹ substituent of formula O-5 and the R⁵, R¹² and R¹³ substituent(s) of formula X-3 should be represented by the same moiety as is desired in the final product, Formula U-4, or a protected variation thereof. Suzuki cross-coupling with the appropriate trifluoroborate or Negishi cross coupling with the appropriate aminoalkyl zincate followed by deprotection of the protecting group(s) under standard conditions yields the pyrrolo[3,4-c]pyridin-1-one of Formula U-4 (R²=CH₂N(R⁸)(R⁹)).

Method AG

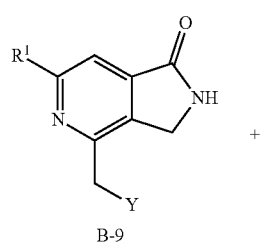

B-9

114

-continued

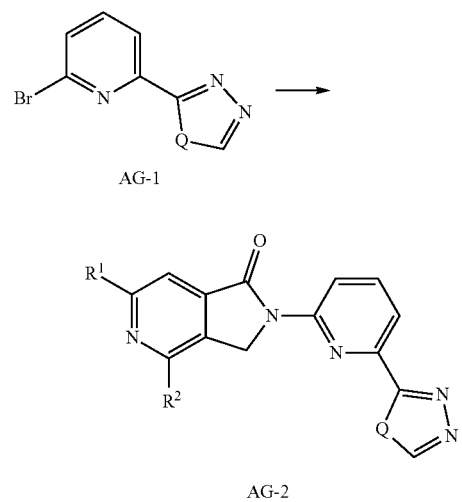

AG-1

AG-2

Method AG refers to a synthetic sequence for the preparation of compounds of Formula AG-2, as depicted above. In a first step, coupling of the compound of formula B-9 with bromopyridine AG-1 (ex. Q=O, Intermediate 5 or Q=S, Intermediate 6) under palladium or copper catalysis provides the compound of formula AH-2. In this step the R¹ substituent of formula B-9 should be represented by the same moiety as is desired in the final product, Formula AG-2, or a protected variation thereof. Cleavage of the protecting group(s) under standard conditions yields the pyrrolo[3,4-c]pyridin-1-one of Formula AG-2 (R²=CH₂N(R⁸)(R⁹)).

Method AH

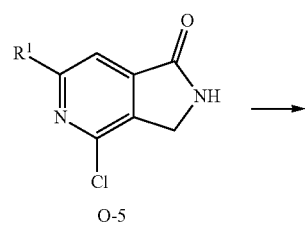

O-5

B-9

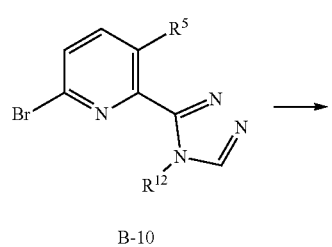

B-10

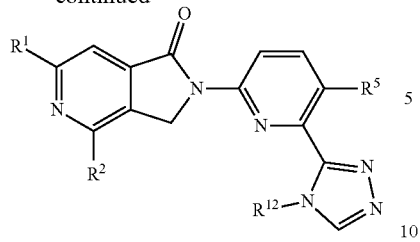

Formula II

Method AH refers to another synthetic sequence for the preparation of compounds of Formula II, as depicted above. In a first step, where the $R^1$ substituent of formula O-5 should be represented by the same moiety as is desired in the final product, Formula II, or a protected variation thereof either
  i. Nickel-mediated decarboxylative cross coupling of the compound of formula O-5 with the requisite acid provides the compound of formula B-9 (Y=N($R^8$) Boc); or
  ii. Suzuki or Molander cross coupling with the requisite boronic acid, boronic ester, or trifluoroborate salt provides the compound of formula B-9 (Y=N($R^8$) Boc); or
  iii. Negishi cross coupling with the requisite aminoalkyl zincate provides the compound of formula B-9 (Y=N ($R^8$) Boc); or
  iv. Carbonylation of the chloride for formula O-5 using carbon monoxide and methanol under palladium catalysis provides an ester which is then reduced (B-9, Y=OH) and activated as a mesylate (B-9, Y=OSO$_2$CH$_3$). In a subsequent step either
    a. Direct displacement of the mesylate with the requisite primary amine to provide the corresponding secondary amine of formula B-9, (Y=N($R^8$)($R^9$)); or
    b. Azidation (B-9, Y=N3) and reduction of the azide functionality under standard conditions to provide primary amine of the formula B-9 (Y=NH2).

Coupling of the compound of the formula B-9 with the bromopyridine triazole B-10 under palladium or copper catalysis followed by cleavage of the protecting group(s) under standard conditions provides the pyrrolo[3,4-c]pyridin-1-one of the Formula II.

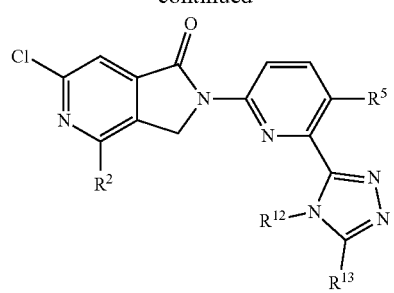

AI-1

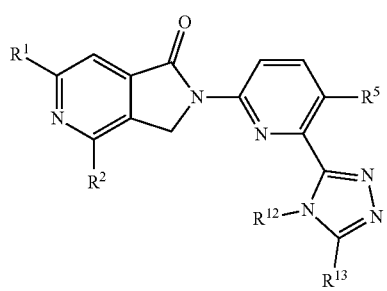

U-4

Method AI refers to another synthetic sequence for the preparation of compounds of Formula U-4, as depicted above. In a first step, a bromopyridine of the formula X-3 undergoes coupling with the compound of the formula C-2 (Y=N($R^8$) Boc) under palladium or copper catalysis. In this step, the $R^5$, $R^{12}$ and $R^{13}$ substituents of X-3 should be represented by the same moiety as is desired in the final product, Formula U-4, or a protected variation thereof. The compound of formula AI-1 undergoes palladium-mediated coupling with the requisite amine or boronic ester or tetrafluoroborate salt to provide the compound of the Formula U-4. In this step, the $R^1$ substituent should be represented by the same moiety as is desired in the final product, Formula U-4, or a protected variation thereof. Cleavage of the protecting group(s) under standard conditions yields the pyrrolo[3,4-c]pyridin-1-one of Formula U-4 ($R^2$=CH$_2$N($R^8$) ($R^9$)).

Method AI

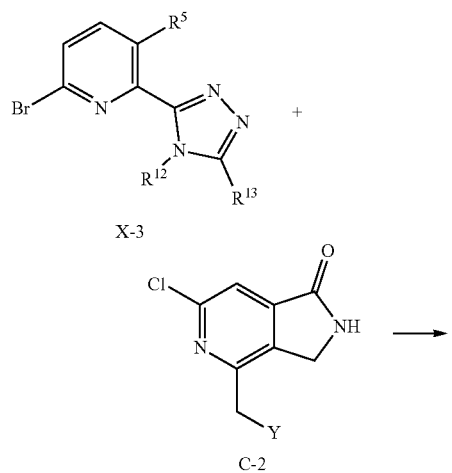

Method AJ

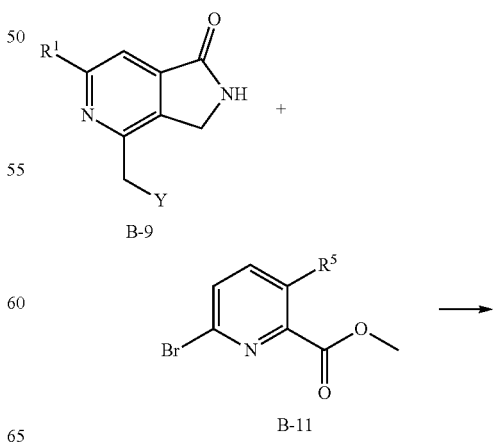

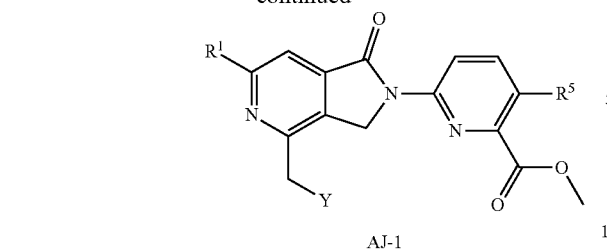

AJ-1

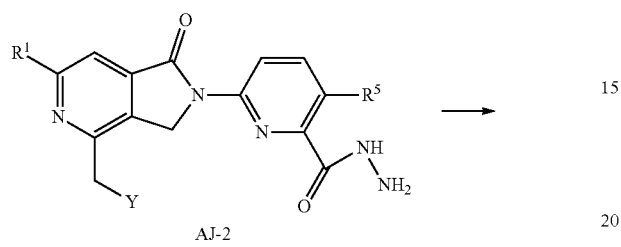

AJ-2

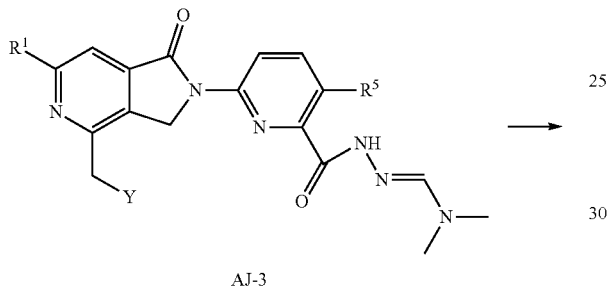

AJ-3

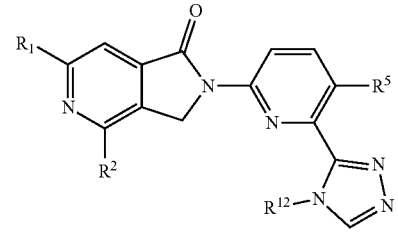

Formula II

Method AJ refers to another synthetic sequence for the preparation of compounds of Formula II, as depicted above. In a first step, the compound of formula B-9 undergoes coupling with the bromopyridine of the formula B-11 under palladium or copper catalysis to provide the compound of formula AJ-1. In this step the $R^1$ substituent of B-9 and the $R^5$ substituent of B-11 should be represented by the same moiety as is desired in the final product, Formula II, or a protected variation thereof. Hydrazinolysis of the compound of formula AJ-1 provides the compound of formula AJ-2. Next, the hydrazine of formula AJ-2 undergoes reaction with dimethylformamide dimethyl acetal to provide the compound of formula AJ-3. Condensation of the compound of formula AJ-3 with the appropriate amine (e.g., $R^{12}$—$NH_2$) followed by cleavage of the protecting group(s) under standard conditions yields the pyrrolo[3,4-c]pyridin-1-one of Formula U-3 ($R^2$=$CH_2N(R^8)(R^9)$). During this step, the $R^{12}$ substituent of the amine should be represented by the same moiety as is desired in the final product, Formula II, or a protected variation thereof.

Method AK

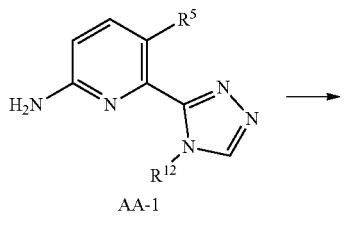

P-1

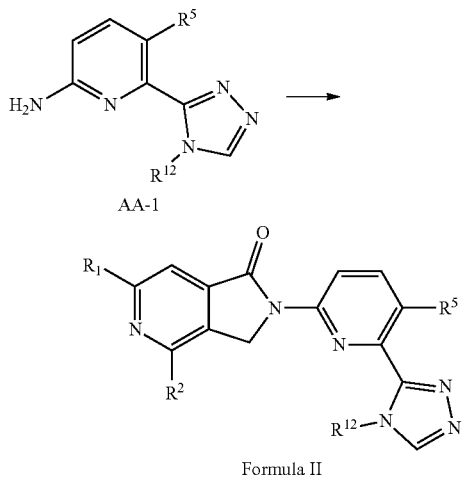

AA-1

Formula II

Method AK refers to another synthetic sequence for the preparation of compounds of Formula II, as depicted above. In Method AK, the compound of the formula P-1 undergoes reductive amination with the pyridine amine of the formula AA-1 followed by cleavage of the protecting groups to provide the compound of the Formula II. In this step the $R^1$ substituent of P-1 and the $R^5$ and $R^{12}$ substituents of formula AA-1 should be represented by the same moiety as is desired in the final product, Formula II, or a protected variation thereof.

REPRESENTATIVE EXAMPLES

Example 1: 6-(dimethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

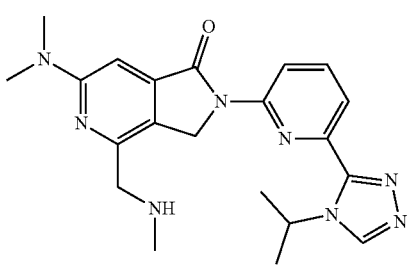

Ex-1

Step 1: tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate

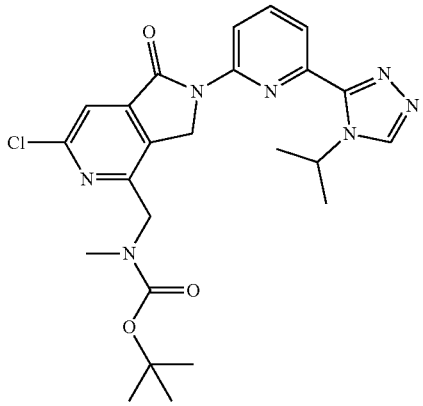 [SMILES: CC(C)n1cnnc1-c1cccc(N2Cc3c(cc(Cl)nc3CN(C)C(=O)OC(C)(C)C)C2=O)n1]

A microwave vial was charged with tert-butyl [(6-chloro-1-oxo-2,3-dihydro-1H-pyrrolo[3,4-c]pyridin-4-yl)methyl]methylcarbamate (224 mg, 0.72 mmol), 2-bromo-6-[4-(propan-2-yl)-4H-1,2,4-triazol-3-yl]pyridine (192 mg, 0.72 mmol), potassium carbonate (218 mg, 1.6 mmol), 2-(dimethylamino)ethylamine (0.04 mL, 0.36 mmol), copper iodide (34 mg, 0.18 mmol) and acetonitrile (3 mL, 0.2 M). The reaction was sealed and heated in the microwave at 120° C. for 90 minutes. The mixture was quenched with water and extracted with DCM. The organic layer was dried over anhydrous sodium sulfate, filtered and concentrated. The resulting residue was purified using flash chromatography (0-10% methanol in 1:1 DCM/ethyl acetate) to give the title compound as an off-white solid (210 mg, 59%). $^1$H NMR (400 MHz, CDCl$_3$) δ 8.74 (d, J=8.44 Hz, 1H) 8.63-8.72 (m, 1H) 8.19 (s, 1H) 8.01 (t, J=8.01 Hz, 1H) 7.80 (s, 1H) 5.65-5.86 (m, 1H) 5.26 (br.s., 2H) 4.63 (br. s., 2H) 3.04 (s, 3H) 1.72 (d, J=5.26 Hz, 6H) 1.40 (br. s., 9H). m/z (APCI+) for (C$_{24}$H$_{28}$ClN$_7$O$_3$) 497.9 (M+H)+.

Step 2: tert-butyl {[6-(dimethylamino)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate

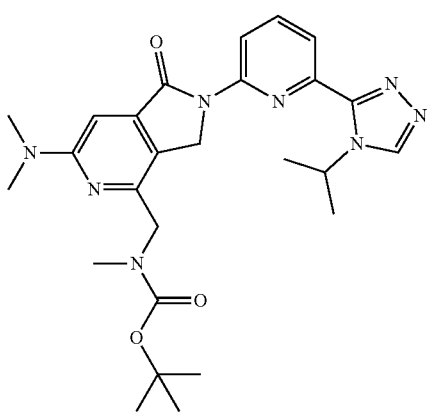 [SMILES: CC(C)n1cnnc1-c1cccc(N2Cc3c(cc(N(C)C)nc3CN(C)C(=O)OC(C)(C)C)C2=O)n1]

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (50 mg, 0.10 mmol), cesium carbonate (98.1 mg, 0.30 mmol), 2 M dimethylamine in THF (0.11 mL, 0.21 mmol), 1,4-dioxane (3 mL) and (2-dicyclohexylphosphino-2',6'-diisopropoxy-1,1'-biphenyl)[2-(2'-amino-1,1'-biphenyl)]palladium(II) methanesulfonate (8.4 mg, 0.01 mmol). The reaction was heated to 100° C. under nitrogen atmosphere and allowed to stir for 16 hours. The crude mixture was combined with another crude batch of this reaction (210 mg scale). The combined material was filtered and washed with 1:10 methanol/DCM (30 mL). The filtrate was concentrated to provide a brown solid, which was purified using column chromatography (20:1 DCM/methanol) to provide the title compound as a yellow solid (160 mg, average yield 61%). $^1$H NMR (400 MHz, CDCl$_3$) δ 8.72 (d, J=8.3 Hz, 1H), 8.40 (s, 1H), 8.09 (br s, 1H), 7.98-7.90 (m, 1H), 6.89 (s, 1H), 5.81-5.41 (m, 1H), 5.14-4.90 (m, 2H), 4.49 (s, 2H), 3.16 (s, 6H), 3.02 (s, 3H), 1.72-1.62 (m, 6H), 1.46-1.29 (m, 9H) m/z (APCI+) for (C$_{26}$H$_{34}$N$_8$O$_3$) 507.3 (M+H)+.

Step 3: 6-(dimethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

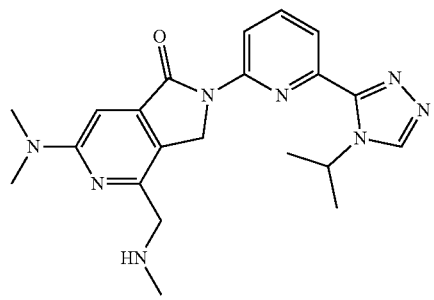 [SMILES: CNCc1nc(N(C)C)cc2c1CN(c1cccc(-c3nncn3C(C)C)n1)C2=O]

A flask was charged with tert-butyl {[6-(dimethylamino)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate (43 mg, 0.09 mmol) and ethyl acetate (2 mL). The solution was cooled to 5° C. and a 4 M solution of HCl in ethyl acetate (5 mL) was added. The reaction was allowed to warm to 20° C. and stir for 1 hour at which point the reaction mixture became a suspension. The suspension was filtered and the solids were collected to provide the title compound as a yellow solid (35 mg, 93%). $^1$H NMR (400 MHz, DMSO-d$_6$) δ 9.27 (br s, 2H), 9.20 (s, 1H), 8.66 (d, J=8.3 Hz, 1H), 8.15 (t, J=8.0 Hz, 1H), 7.96 (d, J=7.5 Hz, 1H), 6.95 (s, 1H), 5.48 (quin, J=6.8 Hz, 1H), 5.17 (s, 2H), 4.32 (br t, J=5.6 Hz, 2H), 3.18 (s, 6H), 2.73 (t, J=5.4 Hz, 3H), 1.61 (d, J=6.8 Hz, 6H). m/z (APCI+) for (C$_{21}$H$_{26}$N$_8$O) 429.1 (M+Na)+.

Example 2: 6-(azetidin-1-yl)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

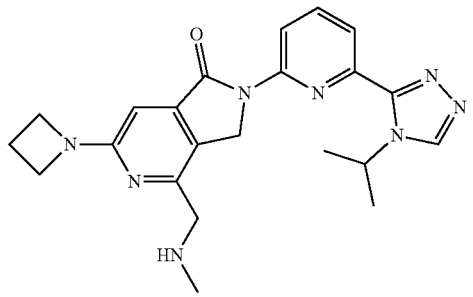
Ex-2

Step 1: tert-butyl {[6-(azetidin-1-yl)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate

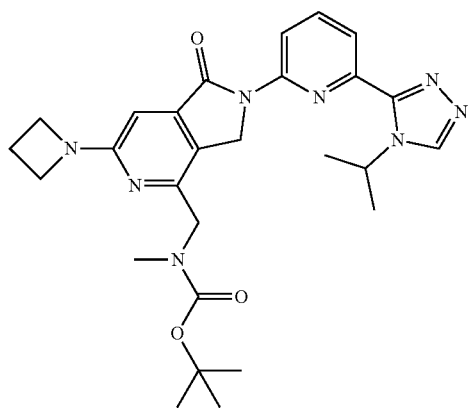 [SMILES: CC(C)n1cnnc1-c1cccc(N2Cc3c(cc(N4CCC4)nc3CN(C)C(=O)OC(C)(C)C)C2=O)n1]

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (70.0 mg, 0.14 mmol), azetidine hydrochloride (39 mg, 0.42 mmol), cesium carbonate (210 mg, 0.65 mmol), (2-dicyclohexylphosphino-2',6'-diisopropoxy-1,1'-biphenyl)[2-(2'-amino-1,1'-biphenyl)]palladium(II) methanesulfonate (11.8 mg, 0.014 mmol) and 1,4-dioxane (2.8 mL, 0.05 M). The reaction was heated at 100° C. for 18 hours at which point more azetidine (39 mg, 0.42 mmol) and (2-dicyclohexylphosphino-2',6'-diisopropoxy-1,1'-biphenyl)[2-(2'-amino-1,1'-biphenyl)]palladium(II) methanesulfonate (11.8 mg, 0.014 mmol) were added and the reaction was heated for 24 hours at 110° C. The reaction mixture was concentrated in vacuo and purified using column chromatography (0-10% methanol in 1:1 DCM/ethyl acetate) to give the title compound as an off-white solid (45 mg, 62%). m/z (APCI+) for ($C_{27}H_{34}N_8O_3$) 519.95 (M+H)+.

Step 2: 6-(azetidin-1-yl)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

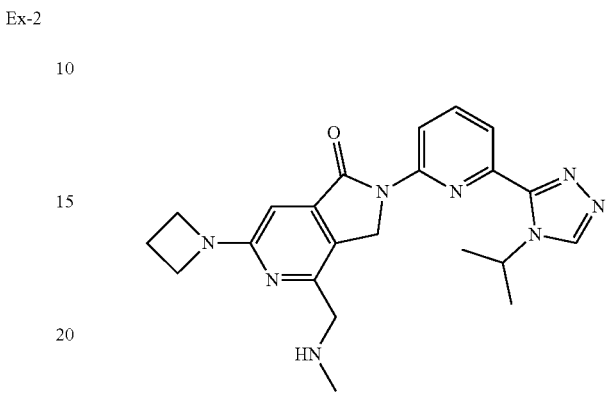

A flask was charged with tert-butyl {[6-(azetidin-1-yl)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate (45 mg, 0.09 mmol) and DCM (3 mL, 0.03 M). Trifluoroacetic acid (0.8 mL, 10 mmol) was added and the reaction was allowed to stir at room temperature for 2 hours. The reaction was azeotroped with toluene (2×) and the resulting residue was purified by SFC (HA-Morpholine 60 Å 5 μm, 150×21.2 mm column at 40° C., eluted with a gradient of 12-30% MeOH in $CO_2$ ramping over 7 min. Pressure held at 120 bar with flow rate of 85 mL/min, monitored by UV 224 nm) to provide the title compound (17 mg, 48%). $^1$H NMR (400 MHz, DMSO-$d_6$) δ 8.83-8.93 (m, 1H) 8.50-8.62 (m, 1H) 7.97-8.08 (m, 1H) 7.83-7.93 (m, 1H) 6.36-6.55 (m, 1H) 5.51 (dt, J=13.42, 6.68 Hz, 1H), 5.06-5.18 (m, 2H) 3.87-3.98 (m, 4H) 3.66-3.81 (m, 2H) 2.24-2.32 (m, 5H) 1.51 (d, J=6.60 Hz, 6H). m/z (APCI+) for ($C_{22}H_{26}N_8O$) 420.0 (M+H)$^+$.

Example 3: 6-[(2R,4R)-2,4-dimethylazetidin-1-yl]-4-[(methyl amino)methyl]-2-{6-[4-(propan-2-yl)-4H-1,2,4-triazol-3-yl]pyridin-2-yl}-2,3-dihydro-1H-pyrrolo[3,4-c]pyridin-1-one

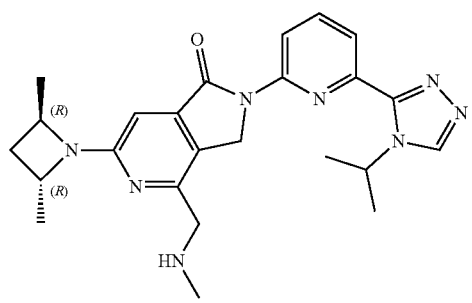
Ex-3

Step 1: tert-butyl [(6-[(2R,4R)-2,4-dimethylazetidin-1-yl]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate

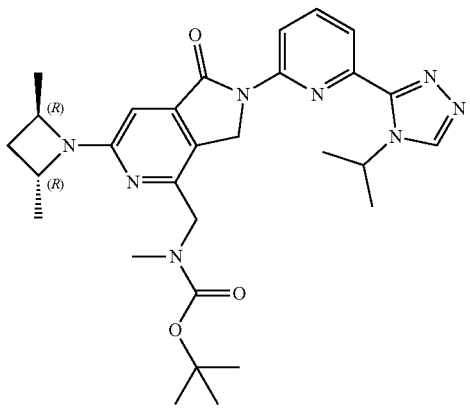

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (100 mg, 0.20 mmol), (2R,4R)-2,4-dimethylazetidine hydrochloride (45.6 mg, 0.40 mmol) and 1,4-dioxane (4 mL, 0.05 M). Cesium carbonate (196 mg, 0.60 mmol) was added followed by (2-dicyclohexylphosphino-2',6'-diisopropoxy-1,1'-biphenyl)[2-(2'-amino-1,1'-biphenyl)]palladium(II) methanesulfonate (16.8 mg, 0.02 mmol). The reaction was heated for 16 hours at 100° C. under nitrogen atmosphere. The mixture was diluted with ethyl acetate (50 mL) and was washed with brine (3×30 mL). The organic layer was dried over anhydrous sodium sulfate, filtered and concentrated in vacuo to provide a residue that was purified using preparative TLC (silica gel, 1:4 petroleum ether/ethyl acetate, twice) to provide the title compound as an off-white solid (40 mg, 36%). TLC $R_f$=0.3 (EtOAc, UV visualization). $^1$H NMR (400 MHz, DMSO-$d_6$) δ 8.95 (s, 1H), 8.60 (d, J=8.31 Hz, 1H), 8.05-8.15 (m, 1H), 7.88-7.97 (m, 1H), 6.53 (s, 1H), 5.51 (br s, 1H), 5.06 (br d, J=19.32 Hz, 2H), 4.32-4.53 (m, 4H), 3.57 (s, 1H), 2.94 (s, 3H), 2.08 (brt, J=6.36 Hz, 2H), 1.56-1.70 (m, 6H), 1.37 (br s, 11H), 1.09-1.28 (m, 6H). m/z for ($C_{29}H_{38}N_8O_3$) 569.4 (M+Na)+.

Step 2: 6-[(2R,4R)-2,4-dimethylazetidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

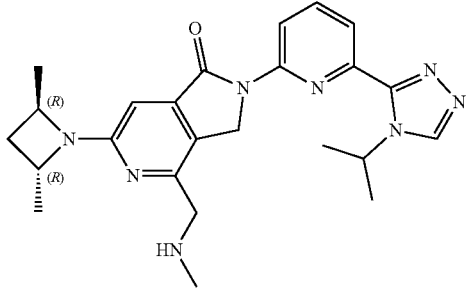

A flask was charged with tert-butyl [(6-[(2R,4R)-2,4-dimethylazetidin-1-yl]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (40 mg, 0.07 mmol) and DCM (3 mL, 0.02) and cooled to below 10° C. Trifluoroacetic acid (0.06 mL, 0.73 mmol) was added dropwise and the reaction was allowed to warm to room temperature. After 2 hours of stirring the reaction was added to ice-water (20 mL). Solid sodium bicarbonate was added until the solution was at pH=9. The aqueous layer was extracted with DCM (3×20 mL). The combined organic layer was dried over sodium sulfate, filtered and concentrated in vacuo. The resulting residue was purified using chromatography (0-10% methanol in DCM) to give the title compound as a yellow solid (20 mg, 61%). $^1$H NMR (400 MHz, DMSO-$d_6$) δ 8.83-8.93 (m, 1H) 8.50-8.62 (m, 1H) 7.97-8.08 (m, 1H) 7.83-7.93 (m, 1H) 6.36-6.55 (m, 1H) 5.51 (dt, J=13.42, 6.68 Hz, 1H) 5.06-5.18 (m, 2H) 3.87-3.98 (m, 4H) 3.66-3.81 (m, 2H) 2.24-2.32 (m, 6H) 1.51 (d, J=6.60 Hz, 6H). m/z (APCI+) for ($C_{24}H_{30}N_8O$) 447.2 (M+H)$^+$.

Example 4: 6-(diethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

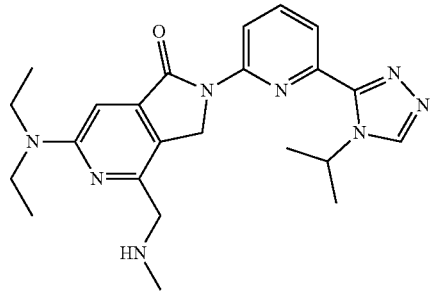 [SMILES: CCN(CC)c1cc2c(c(CNC)n1)CN(c1cccc(-c3nncn3C(C)C)n1)C2=O]

Ex-4

Step 1: tert-butyl {[6-(diethylamino)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate

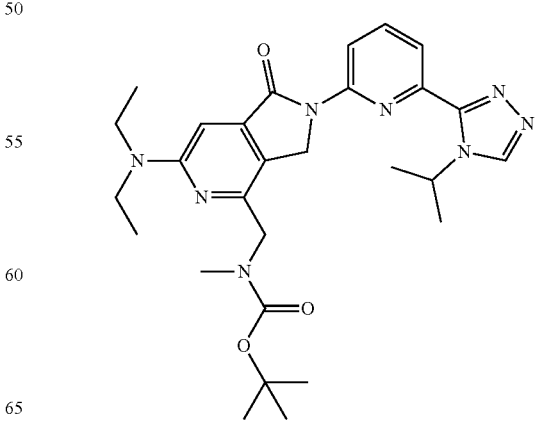

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (100 mg, 0.20 mmol), diethyl amine (0.04 mL, 0.40 mmol), cesium carbonate (229 mg, 0.70 mmol) and 1,4-dioxane (4 mL, 0.05 M). (2-dicyclohexylphosphino-2',6'-diisopropoxy-1,1'-biphenyl)[2-(2'-amino-1,1'-biphenyl)]palladium(II) methanesulfonate (16.8 mg, 0.02 mmol) was added. The reaction was degassed with nitrogen gas (three times) and was heated for 16 hours at 100° C. at which point diethyl amine (0.04 mL, 0.40 mmol) and (2-dicyclohexylphosphino-2',6'-diisopropoxy-1,1'-biphenyl)[2-(2'-amino-1,1'-biphenyl)]palladium(II) methanesulfonate (16.8 mg, 0.02 mmol) were added. The reaction was degassed with nitrogen gas (three times) and was heated for 16 hours at 100° C. The mixture was added to water (15 mL) and extracted with ethyl acetate (2×10 mL). The combined organic layers were washed with brine (15 mL), dried over sodium sulfate, filtered and concentrated in vacuo to provide the crude compound as a yellow gum (100 mg). The crude material was purified using preparative TLC (20:1 ethyl acetate/methanol, Rf=0.5 in ethyl acetate, UV visualization) to provide a yellow solid (60 mg). The compound was further purified using preparative HPLC using water (0.04% NH$_3$H$_2$O+10 mM NH$_4$HCO$_3$) as the mobile phase on a Waters Xbridge Prep PBD C18 150*30 10 µm column. This provided the title compound as a yellow solid (40 mg, 37%). $^1$H NMR (400 MHz, CDCl$_3$) δ 8.74 (d, J=7.8 Hz, 1H), 8.42 (s, 1H), 8.15-8.06 (m, 1H), 7.98-7.93 (m, 1H), 6.85 (s, 1H), 5.78-5.45 (m, 1H), 5.09 (br s, 2H), 4.48 (s, 2H), 3.60 (q, J=7.1 Hz, 4H), 3.08-3.02 (m, 3H), 1.74-1.66 (m, 6H), 1.46-1.30 (m, 9H), 1.23 (t, J=7.0 Hz, 6H). m/z (APCI+) for (C$_{28}$H$_{38}$N$_8$O$_3$) 535.4 (M+H)$^+$.

Step 2: 6-(diethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

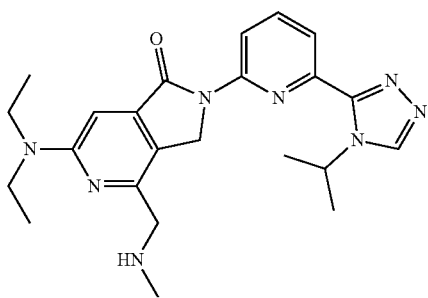

A flask was charged with tert-butyl {[6-(diethylamino)-1-oxo-2-{6-[4-(propan-2-yl)-4H-1,2,4-triazol-3-yl]pyridin-2-yl}-2,3-dihydro-1H-pyrrolo[3,4-c]pyridin-4-yl]methyl}methylcarbamate (40 mg, 0.075 mmol) and ethyl acetate (5 mL, 0.02 M) and was cooled to 0° C. A solution of 4 M hydrochloric acid in ethyl acetate (5 mL, 20 mmol) was added dropwise. The solution was allowed to warm to room temperature and stirred for 1 hour. Methanol (3 mL) was added and the reaction was stirred for 1 hour and the mixture was concentrated in vacuo. The resulting residue was lyophilized for 16 hours to provide the title compound as a yellow solid (28 mg, 79%). $^1$H NMR (400 MHz, DMSO-d$_6$) δ 9.76 (br s, 1H), 9.60 (br s, 2H), 8.69 (br d, J=8.2 Hz, 1H), 8.18 (br t, J=7.6 Hz, 1H), 7.98 (br d, J=7.2 Hz, 1H), 6.85 (s, 1H), 5.65-5.48 (m, 1H), 5.22 (br s, 2H), 4.25 (br s, 2H), 3.63 (br d, J=6.6 Hz, 4H), 2.77-2.58 (m, 3H), 1.65 (br d, J=6.1 Hz, 6H), 1.15 (br t, J=6.5 Hz, 6H)].m/z (APCI+) for (C$_{23}$H$_{30}$N$_8$O) 435.3 (M+H)$^+$.

Example 5: 6-cyclopropyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one Ex-5

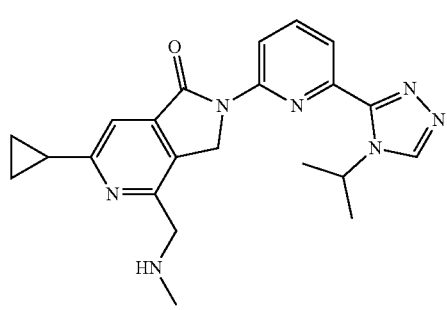

Step 1: tert-butyl [(6-cyclopropyl-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate

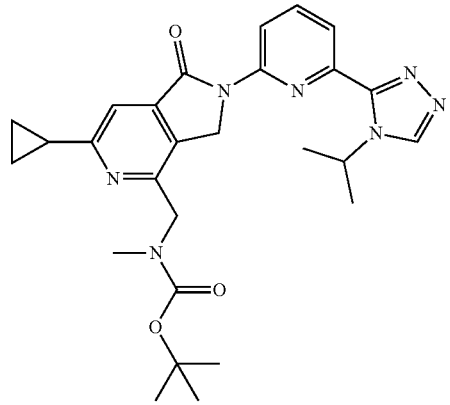 [SMILES: CC(C)n1cnnc1-c1cccc(N2Cc3c(cc(C4CC4)nc3CN(C)C(=O)OC(C)(C)C)C2=O)n1]

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (100 mg, 0.20 mmol), potassium cyclopropyltrifluoroborate (59.4 mg, 0.40 mmol), palladium acetate (9.0 mg, 0.04 mmol), di(1-adamantyl)-n-butylphosphine (21.6 mg, 0.06 mmol), cesium carbonate (196 mg, 0.60 mmol), water (0.25 mL) and toluene (2.5 mL, 0.08 M). The reaction was heated for 20 hours at 110° C. at which point the reaction was diluted with ethyl acetate (50 mL). The solution was washed with brine (3×30 mL), dried over sodium sulfate, filtered and concentrated. The resulting residue was purified using column chromatography (0-5% methanol in DCM) to provide the title compound as an off-white solid (80 mg, 79%). $^1$H NMR (400 MHz, DMSO-d$_6$) δ 8.95 (s, 1H), 8.62 (d, J=7.95 Hz, 1H), 8.12 (t, J=8.07 Hz, 1H), 7.95 (d, J=7.46 Hz, 1H), 7.67 (s, 1H), 5.50 (br s, 1H), 5.20 (br s, 2H), 4.55 (s, 2H), 2.90 (s, 3H), 2.26-2.35 (m, 1H), 1.58 (br s, 6H), 1.18-1.45 (m, 9H), 0.93-1.05 (m, 4H)). m/z (APCI+) for ($C_{27}H_{33}N_7O_3$) 404.2 (M+H)+.

Step 2: 6-cyclopropyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

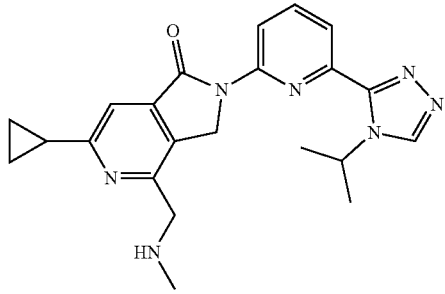 [SMILES: CNCc1nc(C2CC2)cc2c1CN(c1cccc(-c3nncn3C(C)C)n1)C2=O]

A flask was charged with tert-butyl [(6-cyclopropyl-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (80 mg, 0.16 mmol) and DCM (3 mL, 0.5 M). The solution was cooled to below 10° C. and TFA (0.12 mL, 1.6 mmol) was added dropwise. The reaction was allowed to warm to room temperature and stir for 2 hours. The solution was diluted with ice-water (20 mL) and solid sodium bicarbonate was added until the aqueous layer reached pH 9. The layers were separated and the aqueous layer was extracted with DCM (3×20 mL). The combined organic layer was washed with brine, dried over anhydrous sodium sulfate, filtered and concentrated in vacuo to provide a crude residue. This material was purified using column chromatography (0-10% methanol in DCM) to provide the title compound as an off-white solid (30 mg, 47%). $^1$H NMR (400 MHz, DMSO-$d_6$) δ 8.96 (s, 1H), 8.63 (d, J=8.31 Hz, 1H), 8.11 (t, J=8.01 Hz, 1H), 7.94-8.00 (m, 1H), 7.60 (s, 1H), 5.58 (quin, J=6.76 Hz, 1H), 5.28 (s, 2H), 3.93 (s, 2H), 2.35 (s, 3H), 2.25-2.32 (m, 1H), 1.59 (d, J=6.72 Hz, 6H), 0.97-1.04 (m, 4H). m/z (APCI+) for ($C_{22}H_{25}N_7O$) 404.2 (M+H)+.

Example 6: 4-[(methylamino)methyl]-6-[methyl(propan-2-yl)amino]-2-{6-[4-(propan-2-yl)-4H-1,2,4-triazol-3-yl]pyridin-2-yl}-2,3-dihydro-1H-pyrrolo[3,4-c]pyridin-1-one Ex-6

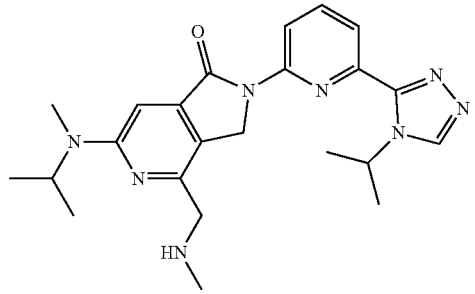

Step 1: tert-butyl methyl[(6-[methyl(propan-2-yl)amino]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]carbamate

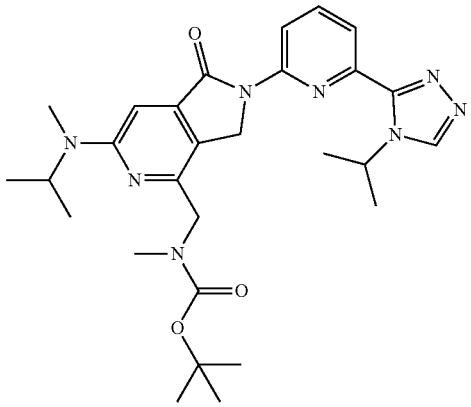 [SMILES: CC(C)N(C)c1cc2c(c(CN(C)C(=O)OC(C)(C)C)n1)CN(c1cccc(-c3nncn3C(C)C)n1)C2=O]

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (96 mg, 0.19 mmol), N-methylisopropylamine (0.1 mL, 0.96 mmol), cesium carbonate (188 mg, 0.58 mmol), (2-dicyclohexylphosphino-2',6'-diisopropoxy-1,1'-biphenyl)[2-(2'-amino-1,1'-biphenyl)]palladium(II) methanesulfonate (16 mg, 0.019 mmol), and 1,4-dioxane (3.9 mL). The reaction was heated for 18 hours at 100° C. The mixture was cooled to room temperature and filtered through a pad of Celite® and washed with 10% methanol in DCM. The filtrate was concentrated in vacuo and the resulting material was purified using column chromatography (0-10% methanol in 1:1 DCM/ethyl acetate) to provide the title compound as a white solid (60 mg, 58%). m/z (APCI+) for ($C_{28}H_{38}N_8O_3$) 535.3 (M+H)+.

Step 2: 4-[(methylamino)methyl]-6-[methyl(propan-2-yl)amino]-2-{6-[4-(propan-2-yl)-4H-1,2,4-triazol-3-yl]pyridin-2-yl}-2,3-dihydro-1H-pyrrolo[3,4-c]pyridin-1-one

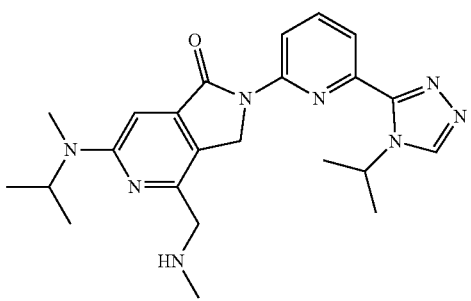 [SMILES: CNCc1nc(N(C)C(C)C)cc2c1CN(c1cccc(-c3nncn3C(C)C)n1)C2=O]

A flask was charged with tert-butyl methyl[(6-[methyl(propan-2-yl)amino]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]carbamate (60 mg, 0.11 mmol) and DCM (6 mL). A 4 N solution of hydrogen chloride in 1,4-dioxane (2 mL, 8.0 mmol) was added and the solution was allowed to stir at room temperature for 1 hour. The solution was partially concentrated in vacuo and then azeotroped with toluene (2×). The resulting material was purified using SFC (DCPak SFC-B 150×21.2 mm, 5 μm column at 40° C., eluted with a gradient of 15-35% methanol in carbon dioxide ramping over 7 min, pressure held at 120 bar with flow rate of 85 mL/min) to provide the title compound as a solid (28.9 mg, 59%). $^1$H NMR (400 MHz, DMSO-d$_6$) δ 8.95 (s, 1H) 8.63 (d, J=7.95 Hz, 1H) 8.10 (t, J=8.01 Hz, 1H) 7.95 (d, J=7.21 Hz, 1H) 6.81 (s, 1H) 5.54 (dt, J=13.36, 6.71 Hz, 1H) 5.15 (s, 2H) 4.89-5.05 (m, 1H) 3.98 (s, 2H) 2.89 (s, 3H) 2.48 (s, 3H) 1.59 (d, J=6.72 Hz, 6H) 1.16 (d, J=6.72 Hz, 6H). m/z (APCI+) for (C$_{23}$H$_{30}$N$_8$O) 435.0 (M+H)$^+$ Example 7: 4-[(methylamino)methyl]-6-(1-methylcyclopropyl)-2-{6-[4-(propan-2-yl)-4H-1,2,4-triazol-3-yl]pyridin-2-yl}-2,3-dihydro-1H-pyrrolo[3,4-c]pyridin-1-one Ex-7

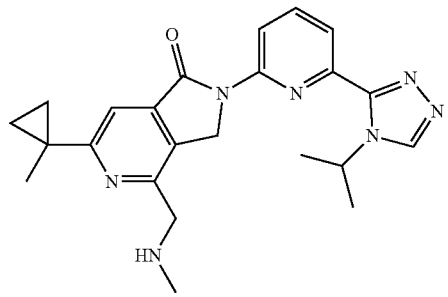 [SMILES: CNCc1nc(C2(C)CC2)cc2c1CN(c1cccc(-c3nncn3C(C)C)n1)C2=O]

Step 1: 4-[(methylamino)methyl]-6-(1-methylcyclopropyl)-2-{6-[4-(propan-2-yl)-4H-1,2,4-triazol-3-yl]pyridin-2-yl}-2,3-dihydro-1H-pyrrolo[3,4-c]pyridin-1-one

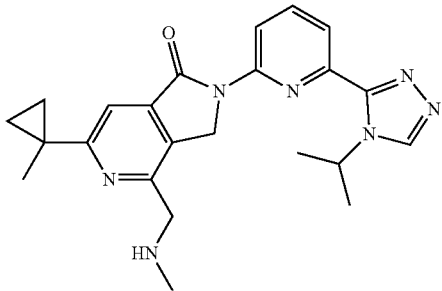

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (88 mg, 0.18 mmol), 4,4,5,5-tetramethyl-2-(1-methylcyclopropyl)-1,3,2-dioxaborolane (43 mg, 0.26 mmol), palladium acetate (7.9 mg, 0.035 mmol), di(1-adamantyl)-n-butylphosphine (19 mg, 0.053 mmol), cesium carbonate (172 mg, 0.53 mmol), toluene (4 mL) and water (0.4 mL). The mixture was degassed with nitrogen for 8 minutes, then heated for 4 hours at 110° C. The reaction mixture was filtered through a pad of Celite® and concentrated in vacuo. The resulting material was purified using column chromatography (0-80% ethyl acetate in heptane) to provide a light yellow solid (96 mg), which was carried on to the next step directly. A flask was charged with the isolated solid, DCM (2 mL), and trifluoroacetic acid (0.4 mL). The reaction was allowed to stir at room temperature for 2 hours. The mixture was concentrated and purified using reversed-phase HPLC (5-100% mobile phase B in mobile phase A, Mobile phase A: 0.05% TFA in water (v/v), Mobile phase B: 0.05% TFA in acetonitrile (v/v), Waters Sunfire C18 19×100, 5 μm column, flow rate: 25 mL/min) to provide the title compound as a solid (94 mg, 90% over 2 steps). $^1$H NMR (600 MHz, DMSO-d$_6$) δ 8.95 (s, 1H) 8.63 (d, J=8.44 Hz, 1H) 8.14 (t, J=7.98 Hz, 1H) 7.95 (d, J=7.70 Hz, 1H) 7.71 (s, 1H) 5.43 (quin, J=6.60 Hz, 1H) 5.23 (s, 2H) 4.48 (s, 2H) 2.77 (s, 3H) 1.57-1.62 (m, 9H) 1.42-1.47 (m, 2H) 0.92-0.97 (m, 2H). m/z (APCI+) for (C$_{23}$H$_{27}$N$_7$O) 418.2 (M+H)$^+$.

Example 8: 6-[(2R,5R)-2,5-dimethylpyrrolidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one Ex-8

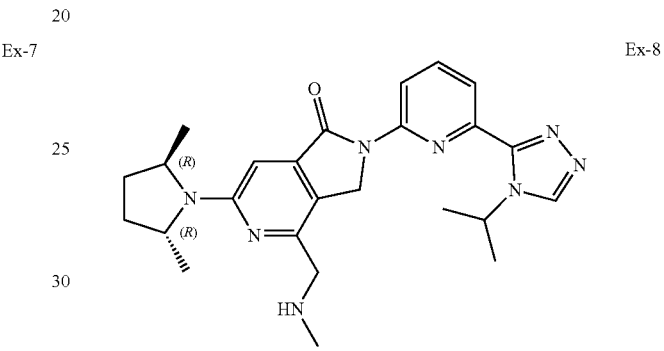

Step 1: tert-butyl [(6-[(2R,5R)-2,5-dimethylpyrrolidin-1-yl]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate

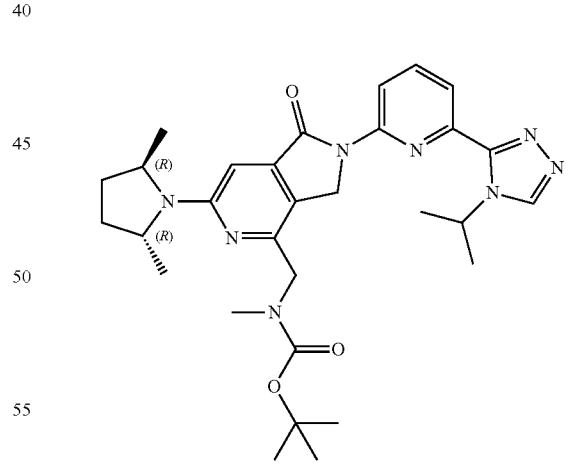

A flask was charged with tert-butyl [(6-chloro-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (100 mg, 0.20 mmol), (2R,5R)-2,5-dimethylpyrrolidine HCl salt (55 mg, 0.40 mmol), cesium carbonate (196 mg, 0.60 mmol), 1,4-dioxane (3 mL) and (2-dicyclohexylphosphino-2',6'-diisopropoxy-1,1'-biphenyl)[2-(2'-amino-1,1'-biphenyl)]palladium(II) methanesulfonate (17 mg, 0.02 mmol). The atmosphere was exchanged for nitrogen gas and the reaction was heated for 40 hours at 100° C. The mixture was cooled to room temperature and diluted with DCM (50 mL). The solution was washed with brine (30 mL), dried over anhydrous sodium sulfate, filtered and concentrated to provide a yellow gum. The crude material was purified using preparative TLC (1:4 petroleum ether/ ethyl acetate) to provide the title compound as a light green solid (10 mg, 9%). $^1$H NMR (400 MHz, CDCl$_3$) δ 8.73 (d, J=8.2 Hz, 1H), 8.43 (s, 1H), 8.11 (br s, 1H), 8.00-7.90 (m, 1H), 6.76 (s, 1H), 5.82-5.47 (m, 1H), 5.15-4.93 (m, 2H), 4.63-4.40 (m, 2H), 3.05 (br s, 3H), 2.30 (br s, 2H), 1.73-1.66 (m, 8H), 1.45-1.30 (m, 11H), 1.21 (d, J=6.1 Hz, 6H). m/z (APCI+) for (C$_{30}$H$_{40}$N$_8$O$_3$) 561.4 (M+H)$^+$.

Step 2: 6-[(2R,5R)-2,5-dimethylpyrrolidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one

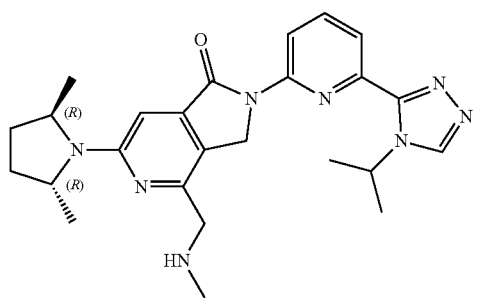

A flask was charged with tert-butyl [(6-[(2R,5R)-2,5-dimethylpyrrolidin-1-yl]-1-oxo-2-{6-[4-(propan-2-yl)-4H-1,2,4-triazol-3-yl]pyridin-2-yl}-2,3-dihydro-1H-pyrrolo[3,4-c]pyridin-4-yl)methyl]methylcarbamate (10 mg, 0.018 mmol) and DCM (3 mL) and cooled to 0° C. Trifluoroacetic acid (0.2 mL) was added in a dropwise fashion. The solution was allowed to warm to 25° C. and stir for 3 hours. The mixture was diluted with ice-water (10 mL) and the pH was adjusted to pH=9 though addition of solid sodium carbonate. The layers were separated with the aqueous layer was extracted with DCM (3×20 mL). The combined organic layer was washed with brine (2×30 mL), dried over anhydrous sodium sulfate, filtered and concentrated to provide the title compound as a yellow solid (8 mg, 97%). $^1$H NMR (400 MHz, DMSO-d$_6$) δ 8.96 (s, 1H), 8.62 (d, J=7.9 Hz, 1H), 8.14-8.06 (m, 1H), 7.95 (d, J=7.1 Hz, 1H), 6.64 (s, 1H), 5.55 (td, J=6.7, 13.3 Hz, 1H), 5.21-5.08 (m, 2H), 4.27 (br s, 1H), 3.95-3.85 (m, 2H), 2.43 (s, 3H), 2.23 (br s, 2H), 1.65 (br d, J=5.5 Hz, 2H), 1.58 (d, J=6.7 Hz, 6H), 1.36-1.28 (m, 2H), 1.17-1.07 (m, 6H). m/z (APCI+) for (C$_{25}$H$_{32}$N$_8$O) 483.3 (M+Na)$^+$.

Example 9: 6-(diethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one

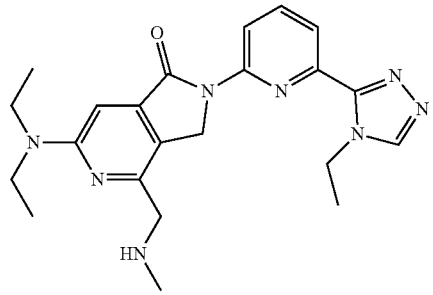

Step 1: 2-bromo-6-(4-ethyl-4H-1,2,4-triazol-3-yl)pyridine

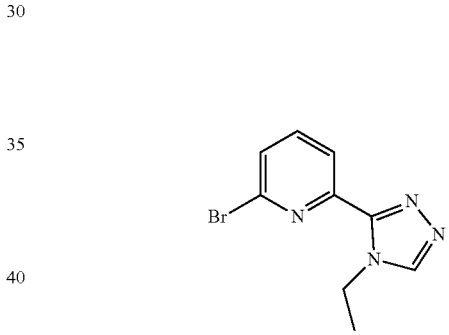

A flask was charged with N'-[(6-bromopyridin-2-yl)carbonyl]-N,N-dimethylhydrazonoformamide (2.0 g, 7.4 mmol), ethylamine (0.5 mL, 333 mg, 7.4 mmol), acetic acid (3 mL) and acetonitrile (15 mL, 0.5 M). The solution was heated for 16 hours at 95° C. The reaction was diluted with ethyl acetate (10 mL) and water (10 mL). Solid potassium carbonate was added until the pH of the aqueous layer was pH 8. The layers were separated and the aqueous layer was extracted with ethyl acetate (3×30 mL). The combined organic layer was washed with brine (30 mL), dried over sodium sulfate, filtered and concentrated to provide the crude product (1.8 g) as a yellow solid. The crude material was diluted with ethyl acetate (0.3 mL) and petroleum ether (3 mL), which was stirred for 5 minutes and filtered. This provided the title compound as a pale yellow solid (1.5 g, 80%). $^1$H NMR (400 MHz, CDCl$_3$) δ 8.32 (d, J=7.8 Hz, 1H), 8.24 (s, 1H), 7.70 (t, J=7.8 Hz, 1H), 7.54 (d, J=7.8 Hz, 1H), 4.59 (q, J=7.3 Hz, 2H), 1.52 (t, J=7.2 Hz, 3H). m/z (APCI+) for (C$_9$H$_9$BrN$_4$), 252.7 (M+H)$^+$.

Step 2: tert-butyl ({6-chloro-2-[6-(4-ethyl-4H-1,2,4-triazol-3-yl)pyridin-2-yl]-1-oxo-2,3-dihydro-1H-pyrrolo[3,4-c]pyridin-4-yl}methyl)methylcarbamate

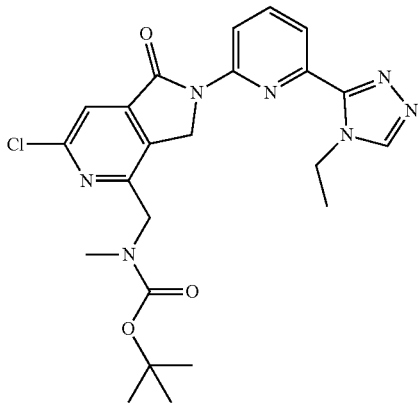 [SMILES: CCn1cnnc1-c1cccc(N2Cc3c(cc(Cl)nc3CN(C)C(=O)OC(C)(C)C)C2=O)n1]

A flask was charged with tert-butyl ((6-chloro-1-oxo-2,3-dihydro-1H-pyrrolo[3,4-c]pyridin-4-yl)methyl)(methyl)carbamate (100 mg, 0.32 mmol), 2-bromo-6-(4-ethyl-4H-1,2,4-triazol-3-yl)pyridine (97.4 mg, 0.39 mmol), copper iodide (15.3 mg, 0.08 mmol), potassium carbonate (97.5 mg, 0.71 mmol) and acetonitrile (5 mL, 0.06 M). The solution was bubbled with nitrogen gas for 5 minutes, sealed, and heated for 1.5 hours at 120° C. The reaction was cooled to room temperature and diluted with DCM (100 mL). The solution was washed with brine (20 mL), dried over anhydrous sodium sulfate, filtered and concentrated to provide a yellow gum (200 mg). The crude material was purified using column chromatography (10:1 DCM/MeOH) to provide the title compound as a white solid (120 mg, 77%). $^1$H NMR (400 MHz, CDCl$_3$) δ 8.69 (d, J=8.5 Hz, 1H), 8.28 (s, 1H), 8.17 (br d, J=6.8 Hz, 1H), 7.97 (t, J=8.0 Hz, 1H), 7.79 (s, 1H), 5.24 (br s, 2H), 4.72 (br s, 2H), 4.68-4.63 (m, 2H), 2.98 (s, 3H), 1.47-1.28 (m, 12H). m/z (APCI+) for (C$_{23}$H$_{26}$ClN$_7$O) 484.1 (M+H)$^+$.

Step 3: tert-butyl ({6-(diethylamino)-2-[6-(4-ethyl-4H-1,2,4-triazol-3-yl)pyridin-2-yl]-1-oxo-2,3-dihydro-1H-pyrrolo[3,4-c]pyridin-4-yl}methyl)methylcarbamate

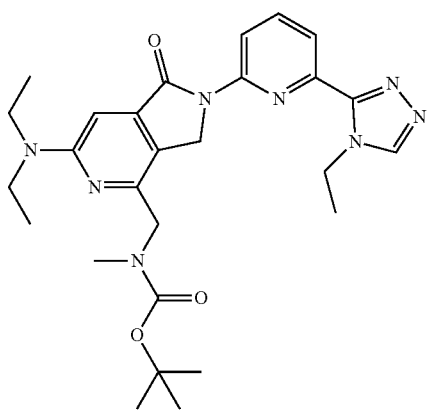 [SMILES: CCN(CC)c1cc2c(c(CN(C)C(=O)OC(C)(C)C)n1)CN(c1cccc(-c3nncn3CC)n1)C2=O]

A flask was charged with tert-butyl ({6-chloro-2-[6-(4-ethyl-4H-1,2,4-triazol-3-yl)pyridin-2-yl]-1-oxo-2,3-dihydro-1H-pyrrolo[3,4-c]pyridin-4-yl}methyl)methylcarbamate (120 mg, 0.25 mmol), cesium carbonate (242 mg, 0.74 mmol), diethylamine (0.05 mL, 0.52 mmol) and 1,4-dioxane (4 mL, 0.06 M). (2-dicyclohexylphosphino-2',6'-diisopropoxy-1,1'-biphenyl)[2-(2'-amino-1,1'-biphenyl)]palladium(II) methanesulfonate (20.7 mg, 0.025 mmol) was added and the reaction mixture was heated for 16 hours at 100° C. under nitrogen atmosphere. The reaction mixture was diluted with ethyl acetate (50 mL) and was washed with brine (3×30 mL). The organic layer was dried over sodium sulfate, filtered and concentrated to provide a crude residue. The crude material was purified using column chromatography (10:1 DCM/methanol) to provide the title compound (60 mg, 46%). $^1$H NMR (400 MHz, CDCl$_3$) δ 8.78-8.69 (m, 1H), 8.27 (s, 1H), 8.17-8.08 (m, 1H), 7.93 (t, J=7.9 Hz, 1H), 6.83 (s, 1H), 5.10-4.92 (m, 2H), 4.72 (br s, 2H), 4.50 (br s, 2H), 3.59 (q, J=7.3 Hz, 4H), 2.99 (br s, 3H), 1.46-1.31 (m, 11H), 1.21 (t, J=7.0 Hz, 6H). m/z (APCI+) for (C$_{27}$H$_{36}$N$_8$O$_3$) 521.3 (M+H)$^+$.

Step 4: 6-(diethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one

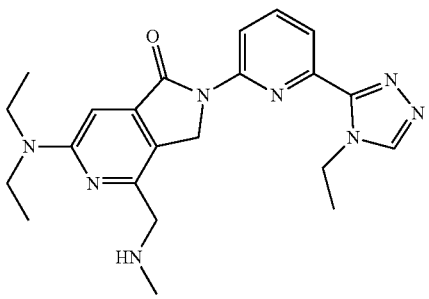 [SMILES: CCN(CC)c1cc2c(c(CNC)n1)CN(c1cccc(-c3nncn3CC)n1)C2=O]

A flask was charged with tert-butyl ({6-(diethylamino)-2-[6-(4-ethyl-4H-1,2,4-triazol-3-yl)pyridin-2-yl]-1-oxo-2,3-dihydro-1H-pyrrolo[3,4-c]pyridin-4-yl}methyl)methylcarbamate (60 mg, 0.12 mmol) and ethyl acetate (2 mL, 0.06 M) and the reaction was cooled to below 5° C. A solution of 4 M hydrochloric acid in ethyl acetate (5 mL, 20 mmol) was added and the reaction was allowed to warm to room temperature and stir for 1 hour. The reaction was concentrated to provide a yellow solid. The crude material was purified using preparative HPLC using water (0.05% HCl)/acetonitrile on a PhenomenexSynergi C18 150*30 mm*4 µm column to provide the tittle compound as a yellow solid (30 mg, 57%). $^1$H NMR (400 MHz, DMSO-d$_6$) δ 9.28 (br d, J=5.8 Hz, 2H), 9.10 (s, 1H), 8.66 (d, J=8.3 Hz, 1H), 8.15 (t, J=8.0 Hz, 1H), 8.02 (d, J=7.5 Hz, 1H), 6.87 (s, 1H), 5.17 (s, 2H), 4.67 (q, J=7.0 Hz, 2H), 4.32 (t, J=5.8 Hz, 2H), 3.65 (q, J=6.8 Hz, 4H), 2.73 (t, J=5.3 Hz, 3H), 1.52 (t, J=7.2 Hz, 3H), 1.16 (t, J=6.9 Hz, 6H). m/z (APCI+) for (C$_{22}$H$_{28}$N$_8$O) 442.9 (M+Na)$^+$.

Additional compounds of the invention were prepared by modifications of the methods exemplified herein. Except where otherwise indicated, all compounds having chiral centers were prepared and/or isolated as a single enantiomer having a known relative configuration. Compounds marked "absolute stereochemistry unknown" were typically prepared from racemic intermediates and resolved into single enantiomers by an appropriate chiral preparative SFC method before characterization and testing. Where the absolute stereochemistry is unknown for a pair of enantiomers, the stereochemistry represented in Table 1 is assigned based on the sign of the optical rotation ($[\alpha]_D^{20}$) and the relative biological activity, by analogy to compounds having known absolute configurations. Compounds marked "absolute stereochemistry known" were typically prepared from chiral intermediates having known stereochemistry.

Selected compounds and their corresponding characterization data are presented in Table 1 below, where the method used to make the compound is provided in parentheses below the example number:

TABLE 1

| Ex. No. | Structure/IUPAC name | LCMS [M + H]$^+$ | $^1$H NMR (ppm); $^{19}$F NMR (ppm); optical rotation; stereochem. notes |
|---|---|---|---|
| 1-9 | in methods text | | |
| 10 (D) | 6-(dimethylamino)-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one | 397.1 | $^1$H NMR (400 MHz, DMSO-d$_6$) δ 9.23 (br s, 2H), 8.23 (d, J = 8.0 Hz, 1H), 7.96 (t, J = 8.2 Hz, 1H), 7.82 (d, J = 8.0 Hz, 1H), 6.91 (s, 1H), 5.15-4.99 (m, 2H), 4.98-4.90 (m, 1H), 4.61 (t, J = 8.3 Hz, 1H), 4.40-4.30 (m, 2H), 4.17 (dd, J = 3.8, 8.5 Hz, 1H), 3.17 (s, 6H), 2.72 (t, J = 5.4 Hz, 3H), 1.49 (d, J = 6.3 Hz, 3H) absolute stereochemistry known |
| 11 (E) | 4-(aminomethyl)-6-(dimethylamino)-2-{6-[5-(propan-2-yl)-1H-pyrazol-4-yl]pyridin-2-yl}-2,3-dihydro-1H-pyrrolo[3,4-c]pyridin-1-one | [M + Na]$^+$ 392.1 | $^1$H NMR (400 MHz, DMSO-d$_6$) δ 8.48 (br s, 3H), 8.32 (d, J = 8.0 Hz, 1H), 8.16 (s, 1H), 7.89 (t, J = 7.9 Hz, 1H), 7.49 (d, J = 7.5 Hz, 1H), 6.89 (s, 1H), 5.14 (s, 2H), 4.24 (br d, J = 5.5 Hz, 2H), 3.96-3.95 (m, 1H), 3.17 (s, 6H), 1.38 (d, J = 7.0 Hz, 6H) |
| 12 (B) | 4-(aminomethyl)-6-(dimethylamino)-2-{6-[4-(propan-2-yl)-4H-1,2,4-triazol-3-yl]pyridin-2-yl}-2,3-dihydro-1H-pyrrolo[3,4-c]pyridin-1-one | 393.3 | $^1$H NMR (400 MHz, DMSO-d$_6$) δ 9.07 (s, 1H), 8.65 (d, J = 7.8 Hz, 1H), 8.38 (br s, 3H), 8.14 (t, J = 8.0 Hz, 1H), 7.95 (dd, J = 0.6, 7.6 Hz, 1H), 6.91 (s, 1H), 5.54-5.41 |

TABLE 1-continued

| Ex. No. | Structure/IUPAC name | LCMS [M + H]+ | ¹H NMR (ppm); ¹⁹F NMR (ppm); optical rotation; stereochem. notes |
|---|---|---|---|
| 13 (B) | 4-(aminomethyl)-6-(dimethylamino)-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one | [M + Na]+ 429 | ¹H NMR (400 MHz, DMSO-d₆) δ 9.27 (br s, 2H), 9.20 (s, 1H), 8.66 (d, J = 8.3 Hz, 1H), 8.15 (t, J = 8.0 Hz, 1H), 7.96 (d, J = 7.5 Hz, 1H), 6.95 (s, 1H), 5.48 (quin, J = 6.8 Hz, 1H), 5.17 (s, 2H), 4.32 (br t, J = 5.6 Hz, 2H), 3.18 (s, 6H), 2.73 (t, J = 5.4 Hz, 3H), 1.61 (d, J = 6.8 Hz, 6H) absolute stereochemistry known |
| 14 (B) | 2-(6-{4-[(2S)-butan-2-yl]-4H-1,2,4-triazol-3-yl}pyridin-2-yl)-6-(dimethylamino)-4-[(methylamino)methyl]-2,3-dihydro-1H-pyrrolo[3,4-c]pyridin-1-one | [M + Na]+ 443 | ¹H NMR (400 MHz, DMSO-d₆) δ 9.33 (br s, 2H), 9.22 (s, 1H), 8.67 (br d, J = 8.5 Hz, 1H), 8.15 (br t, J = 8.2 Hz, 1H), 7.96 (br d, J = 7.5 Hz, 1H), 6.94 (s, 1H), 5.34 (br d, J = 6.3 Hz, 1H), 5.16 (s, 2H), 4.29 (br s, 2H), 3.18 (s, 6H), 2.78-2.68 (m, 3H), 2.06-1.86 (m, 2H), 1.60 (br d, J = 6.5 Hz, 3H), 0.83 (br t, J = 7.2 Hz, 3H) absolute stereochemistry known |
| 15 (B) | 4-[(methylamino)methyl]-6-(pyrrolidin-1-yl)-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one | 500.2 | ¹H NMR (400 MHz, DMSO-d₆) δ 9.10 (s, 1 H) 8.65 (d, J = 8.31 Hz, 1 H) 8.12 (t, J = 8.01 Hz, 1 H) 7.96 (d, J = 7.46 Hz, 1 H) 6.65 (s, 1 H) 5.87-6.12 (m, 1 H) 5.13 (d, J = 11.13 Hz, 2 H) 3.92 (s, 2 H) 3.48 (br. s., 4 H) 2.44 (s, 3 H) 1.94-2.07 (m, 4 H) 1.91 (s, 2 H) 1.68 (d, J = 6.72 Hz, 3 H) absolute stereochemistry known |
| 16 (B) | 4-(aminomethyl)-2-{6-[4-(cyclopropylmethyl)-4H-1,2,4-triazol-3-yl]pyridin-2-yl}-6-(dimethylamino)-2,3-dihydro-1H-pyrrolo[3,4-c]pyridin-1-one | 405.2 | ¹H NMR (400 MHz, DMSO-d₆) δ 9.04 (s, 1H), 8.65 (d, J = 7.5 Hz, 1H), 8.55 (br s, 3H), 8.18-8.11 (m, 1H), 8.08-8.03 (m, 1H), 6.91 (s, 1H), 5.21 (s, 2H), 4.50 (d, J = 7.0 Hz, 2H), 4.23 (br d, J = 5.8 Hz, 2H), 3.18 (s, 6H), 1.49 (br d, J = 7.5 Hz, 1H), 0.66-0.59 (m, 2H), 0.56-0.50 (m, 2H) |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 17 (B) | 6-(dimethylamino)-4-[(methylamino)methyl]-2-(6-{4-[(2S)-4,4,4-trifluorobutan-2-yl]-4H-1,2,4-triazol-3-yl}pyridin-2-yl)-2,3-dihydro-1H-pyrrolo[3,4-c]pyridin-1-one | 475.2 | 1H NMR (400 MHz, DMSO-d6) δ 9.37 (br s, 2H), 9.22 (s, 1H), 8.65 (d, J = 8.5 Hz, 1H), 8.15 (t, J = 8.0 Hz, 1H), 7.95 (d, J = 7.5 Hz, 1H), 6.95 (s, 1H), 6.01-5.91 (m, 1H), 5.24-5.11 (m, 2H), 4.27 (br t, J = 5.9 Hz, 2H), 3.35-3.23 (m, 1H), 3.18 (s, 6H), 3.14-3.01 (m, 1H), 2.71 (t, J = 5.4 Hz, 3H), 1.71 (d, J = 6.8 Hz, 3H) absolute stereochemistry known |
| 18 (B) | 6-(dimethylamino)-4-[(methylamino)methyl]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 489.2 | 1H NMR (400 MHz, DMSO-d6) δ 9.33 (br s, 2H), 9.14 (s, 1H), 8.65 (d, J = 8.3 Hz, 1H), 8.14 (t, J = 8.0 Hz, 1H), 7.95 (d, J = 7.5 Hz, 1H), 6.95 (s, 1H), 5.99-5.87 (m, 1H), 5.21-5.08 (m, 2H), 4.25 (br t, J = 5.8 Hz, 2H), 3.31-3.20 (m, 1H), 3.18 (s, 6H), 3.13-2.98 (m, 1H), 2.72 (t, J = 5.4 Hz, 3H), 2.15-1.91 (m, 2H), 0.82 (t, J = 7.4 Hz, 3H) [α]20D = 3.8° (0.02 M, MeOH), >99% ee absolute stereochemistry unknown* |
| 19 (B) | 6-(dimethylamino)-4-[(methylamino)methyl]-2-(6-{4-[(3ξ)-1,1,1-trifluoropentan-3-yl]-4H-1,2,4-triazol-3-yl}pyridin-2-yl)-2,3-dihydro-1H pyrrolo[3,4-c]pyridin-1-one | [M + Na]+ 489.2 | 1H NMR (400 MHz, DMSO-d6) δ 9.32 (br s, 2H), 9.13 (s, 1H), 8.65 (d, J = 8.5 Hz, 1H), 8.14 (t, J = 8.0 Hz, 1H), 7.95 (d, J = 7.8 Hz, 1H), 6.95 (s, 1H), 5.98-5.87 (m, 1H), 5.21-5.08 (m, 2H), 4.26 (br t, J = 5.8 Hz, 2H), 3.30-3.20 (m, 1H), 3.18 (s, 6H), 3.12-2.99 (m, 1H), 2.72 (t, J = 5.3 Hz, 3H), 2.14-1.93 (m, 2H), 0.82 (t, J = 7.4 Hz, 3H) [α]20D = 20.2° (0.02 M, MeOH), 99% ee absolute stereochemistry unknown* |
| 20 (B) | 6-(dimethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 392.9 | 1H NMR (400 MHz, DMSO-d6) δ 9.33 (br d, J = 5.5 Hz, 2H), 9.08 (s, 1H), 8.66 (d, J = 8.3 Hz, 1H), 8.14 (t, J = 8.0 Hz, 1H), 8.01 (d, J = 7.5 Hz, 1H), 6.93 (s, 1H), 5.17 (s, 2H), 4.67 (q, J = 7.0 Hz, 2H), 4.34 (br t, J = 5.6 Hz, 2H), 3.17 (s, 6H), 2.72 (t, J = 5.3 Hz, 3H), 1.51 (t, J = 7.2 Hz, 3H) |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 21 (B) | 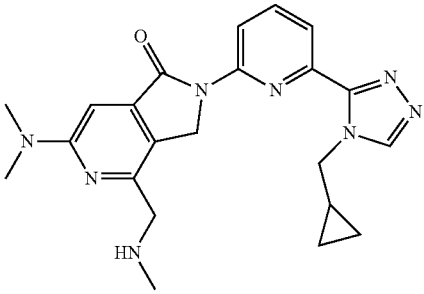 [SMILES: CNCc1nc(N(C)C)cc2c1CN(c1cccc(-c3nncn3CC3CC3)n1)C2=O]<br>2-{6-[4-(cyclopropylmethyl)-4H-1,2,4-triazol-3-yl]pyridin-2-yl}-6-(dimethylamino)-4-[(methylamino)methyl]-2,3-dihydro-1H-pyrrolo[3,4-c]pyridin-1-one | [M + Na]+ 441 | 1H NMR (400 MHz, DMSO-$d_6$) δ 9.33 (br s, 2H), 9.01 (s, 1H), 8.65 (d, J = 8.3 Hz, 1H), 8.17-8.11 (m, 1H), 8.05 (d, J = 7.3 Hz, 1H), 6.94 (s, 1H), 5.20 (s, 2H), 4.49 (d, J = 7.3 Hz, 2H), 4.32 (br t, J = 5.8 Hz, 2H), 3.18 (s, 6H), 2.73 (t, J = 5.4 Hz, 3H), 1.46 (br d, J = 7.3 Hz, 1H), 0.65-0.58 (m, 2H), 0.55-0.48 (m, 2H) |
| 22 (E) | 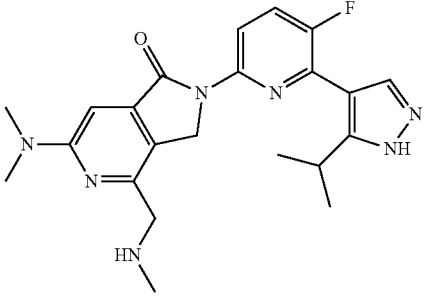 [SMILES: CNCc1nc(N(C)C)cc2c1CN(c1ccc(F)c(-c3cn[nH]c3C(C)C)n1)C2=O]<br>6-(dimethylamino)-2-{5-fluoro-6-[5-(propan-2-yl)-1H-pyrazol-4-yl]pyridin-2-yl}-4-[(methylamino)methyl]-2,3-dihydro-1H-pyrrolo[3,4-c]pyridin-1-one | 424.2 | 1H NMR (400 MHz, DMSO-$d_6$) δ 9.12 (br d, J = 3.8 Hz, 2H), 8.38 (dd, J = 3.3, 9.0 Hz, 1H), 8.02-7.96 (m, 1H), 7.89 (t, J = 9.7 Hz, 1H), 6.92 (s, 1H), 5.10 (s, 2H), 4.32 (br t, J = 5.6 Hz, 2H), 3.87-3.77(m, 1H), 3.17 (s, 6H), 2.79-2.70 (m, 3H), 1.37 (d, J = 7.0 Hz, 6H) |
| 23 (F) | 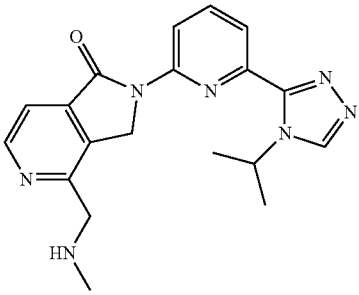 [SMILES: CNCc1nccc2c1CN(c1cccc(-c3nncn3C(C)C)n1)C2=O]<br>4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 363.9 | 1H NMR (400 MHz, Methanol-$d_4$) δ 1.79-1.86 (d, J = 6.7 Hz, 6H), 2.93-2.98 (s, 3H), 4.65-4.70 (s, 2H), 5.38-5.43 (s, 2H), 5.77-5.91 (p, J = 6.7 Hz, 1H), 7.89-7.95 (d, J = 5.0 Hz, 1H), 8.03-8.10 (dd, J = 7.6, 0.8 Hz, 1H), 8.19-8.28 (dd, J = 8.6, 7.6 Hz, 1H), 8.83-8.98 (m, 2H), 10.11- (s, 1H). |
| 24 (C) | 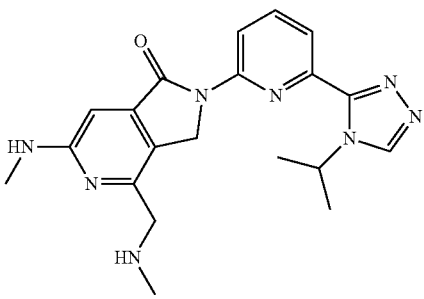 [SMILES: CNCc1nc(NC)cc2c1CN(c1cccc(-c3nncn3C(C)C)n1)C2=O]<br>4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 393.0 | 1H NMR (600 MHz, DMSO-$d_6$) δ 8.93 (s, 1 H) 8.61 (dd, J = 8.25, 2.38 Hz, 1 H) 8.07 (td, J = 7.84, 2.48 Hz, 1 H) 7.95 (d, J = 7.52 Hz, 1 H) 6.72 (br. s., 1 H) 6.64 (br. s., 1 H) 5.55-5.62 (m, 1 H) 5.14 (br. s., 2 H) 3.79 (s, 2 H) 2.83 (d, J = 3.67 Hz, 3 H) 2.35 (s, 3 H) 1.59 (d, J = 6.60 Hz, 6 H) |

TABLE 1-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 25 (C) | 6-[(1s,4s)-7-azabicyclo[2.2.1]hept-7-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 459.2 | ¹H NMR (600 MHz, DMSO-d₆) δ 8.86 (d, J = 1.47 Hz, 1 H) 8.53 (d, J = 8.25 Hz, 1 H) 8.02 (t, J = 7.98 Hz, 1 H) 7.88 (dd, J = 7.52, 0.73 Hz, 1 H) 7.01 (s, 1 H) 5.46 (dq, J = 12.75, 6.45 Hz, 1 H) 5.10 (s, 2 H) 4.56 (br. s., 2 H) 3.85 (br. s., 2 H) 2.36 (br. s., 3 H) 1.60 (d, J = 7.70 Hz, 4 H) 1.51 (d, J = 6.60 Hz, 6 H) 1.37-1.40 (m, 4 H) |
| 26 (M) | 4-(aminomethyl)-6-cyclopropyl-2-{6-[(4S)-4-methyl-2-oxo-1,3-oxazolidin-3-yl]pyridin-2-yl}-2,3-dihydro-1H-pyrrolo[3,4-c]pyridin-1-one | 380.1 | ¹H NMR (400 MHz, DMSO-d₆) δ 8.23 (d, J = 7.83 Hz, 1 H) 7.96 (t, J = 8.07 Hz, 1 H) 7.83 (d, J = 7.83 Hz, 1 H) 7.71 (s, 1 H) 6.58 (br. s., 1 H) 5.19-5.27 (m, 1 H) 5.07-5.15 (m, 1 H) 4.91-4.98 (m, 1 H) 4.60 (t, J = 8.19 Hz, 1 H) 4.29-4.39 (m, 2 H) 4.16 (dd, J = 8.44, 3.79 Hz, 1 H) 3.51 (s, 1 H) 2.28-2.37 (m, 1 H) 1.49 (d, J = 6.36 Hz, 3 H) 1.11-1.22 (m, 2 H) 1.03 (dd, J = 7.83, 3.18 Hz, 2 H) absolute stereochemistry known |
| 27 (C) | 6-[(2R,5S)-2,5-dimethylpyrrolidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 461.2 | ¹H NMR (400 MHz, DMSO-d₆) δ 8.94 (s, 1 H) 8.64 (d, J = 8.31 Hz, 1 H) 8.10 (t, J = 8.01 Hz, 1 H) 7.96 (d, J = 7.58 Hz, 1 H) 6.61 (s, 1 H) 5.59 (dquin, J = 13.31, 6.76, 6.76, 6.76, 6.76 Hz, 1 H) 5.17 (s, 2 H) 4.01-4.19 (m, 2 H) 3.83 (s, 2 H) 2.37 (s, 3 H) 2.02-2.14 (m, 2 H) 1.67-1.84 (m, 2 H) 1.59 (d, J = 6.60 Hz, 6 H) 1.31 (d, J = 5.99 Hz, 6 H) |
| 28 (C) | 6-[(2R,4R)-2,4-dimethylazetidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 447.2 | ¹H NMR (400 MHz, DMSO-d₆) δ 8.95 (s, 1H), 8.62 (d, J = 8.44 Hz, 1H), 8.06-8.15 (m, 1H), 7.95 (d, J = 7.58 Hz, 1H), 6.56 (s, 1H), 5.53 (td, J = 6.51, 13.39 Hz,1H), 5.09-5.22 (m, 2H), 4.43-4.55 (m, 2H), 3.96 (s, 2H), 2.47 (s, 3H), 2.10 (br t, J = 6.48 Hz, 2H), 1.58 (d, J = 6.60 Hz, 6H), 1.39 (d, J = 6.11 Hz, 6H) absolute stereochemistry known |

TABLE 1-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 29 (G) | 6-tert-butyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 420.0 | $^1$H NMR (600 MHz, DMSO-d$_6$) δ 8.95 (s, 1 H) 8.62 (d, J = 8.44 Hz, 1 H) 8.06-8.19 (m, 1 H) 7.97 (d, J = 7.52 Hz, 1 H) 7.63 (s, 1 H) 5.59 (dt, J = 13.34, 6.63 Hz, 1 H) 5.30 (s, 2 H) 3.99 (s, 2 H) 2.38 (s, 3 H) 1.60 (d, J = 6.79 Hz, 6 H) 1.39 (s, 9 H) |
| 30 (C) | 4-[(methylamino)methyl]-6-(propan-2-yl)-2-{6-[4-(propan-2-yl)-4H-1,2,4-triazol-3-yl]pyridin-2-yl}-2,3-dihydro-1H-pyrrolo[3,4-c]pyridin-1-one | 406.0 | $^1$H NMR (600 MHz, DMSO-d$_6$) δ 8.94 (s, 1 H) 8.61 (d, J = 8.25 Hz, 1 H) 8.09 (t, J = 7.98 Hz, 1 H) 7.97 (d, J = 7.52 Hz, 1 H) 7.54 (s, 1 H) 5.59 (dt, J = 13.20, 6.60 Hz, 1 H) 5.30 (s, 2 H) 3.98 (s, 2 H) 3.17 (dt, J = 13.62, 6.85 Hz, 2 H) 2.37 (s, 3 H) 1.60 (d, J = 6.60 Hz, 6 H) 1.30 (d, J = 6.79 Hz, 6 H) |
| 31 (C) | 4-(aminomethyl)-6-cyclopropyl-2-{6-[4-(propan-2-yl)-4H-1,2,4-triazol-3-yl]pyridin-2-yl}-2,3-dihydro-1H-pyrrolo[3,4-c]pyridin-1-one | 390.1 | $^1$H NMR (600 MHz, DMSO-d$_6$) δ ppm 8.89-8.97 (m, 1 H) 8.56-8.64 (m, 1 H) 8.05-8.14 (m, 1 H) 7.90-7.97 (m, 1 H) 7.52-7.62 (m, 1 H) 5.52 (dt, J = 13.34, 6.63 Hz, 1 H) 5.28 (br. s., 2 H) 4.08 (br. s., 2 H) 3.17 (s, 2 H) 2.30 (br. s., 1 H) 1.52-1.61 (m, 6 H) 1.03-1.09 (m, 2 H) 0.94-1.03 (m, 2 H) |
| 32 (D) | 4-(aminomethyl)-6-(dimethylamino)-2-{6-[(4S)-4-methyl-2-oxo-1,3-oxazolidin-3-yl]pyridin-2-yl}-2,3-dihydro-1H-pyrrolo[3,4-c]pyridin-1-one | 382.9 | $^1$H NMR (400 MHz, DMSO-d$_6$) δ 8.43 (br s, 3H), 8.23 (d, J = 8.0 Hz, 1H), 7.96 (t, J = 8.2 Hz, 1H), 7.82 (d, J = 8.0 Hz, 1H), 6.89 (s, 1H), 5.17-4.99 (m, 2H), 4.99-4.90 (m, 1H), 4.60 (t, J = 8.3 Hz, 1H), 4.30-4.20 (m, 2H), 4.16 (dd, J = 3.6, 8.4 Hz, 1H), 3.17 (s, 6H), 1.49 (d, J = 6.3 Hz, 3H) absolute stereochemistry known |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 33 (M) | 6-(azetidin-1-yl)-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one | [M + Na]+ 431.2 | 1H NMR (400 MHz, DMSO-d6) δ 8.20 (d, J = 8.03 Hz, 1H), 7.92 (t, J = 8.03 Hz, 1H), 7.79 (d, J = 8.28 Hz, 1H), 6.52 (s, 1H), 4.96-5.16 (m, 2H), 4.82-4.92 (m,1H), 4.59 (t, J = 8.28 Hz, 1H), 4.15 (dd, J = 3.76, 8.53 Hz, 1H), 4.00 (t, J = 7.40 Hz, 4H), 3.86 (d, J = 1.25 Hz, 2H), 2.40 (s, 3H), 2.29-2.37 (m, 2H), 1.49 (d, J = 6.27 Hz, 3H) absolute stereochemistry known |
| 34 (C) | 4-(aminomethyl)-6-[(2R,4S)-2,4-dimethylazetidin-1-yl]-2-{6-[4-(propan-2-yl)-4H-1,2,4-triazol-3-yl]pyridin-2-yl}-2,3-dihydro-1H-pyrrolo[3,4-c]pyridin-1-one | 433.2 | 1H NMR (700 MHz, DMSO-d6) δ 8.90-8.96 (m, 1 H) 8.60 (d, J = 7.96 Hz, 1 H), 8.08 ( J = 7.53 Hz, 1 H) 7.91-7.97 (m, 1 H) 6.49 (s, 1 H) 5.54 (quin, J = 6.67 Hz, 1 H) 5.19 (br. s., 2 H) 4.06-4.14 (m, 2 H) 3.86 (br. s., 2 H) 1.57 (d, J = 6.45 Hz, 6 H) 1.49 (d, J = 6.24 Hz, 6 H) 1.33 (s, 4 H) |
| 35 (I) | 4-(aminomethyl)-6-(dimethylamino)-2-{6-[5-(propan-2-yl)-1H-1,2,3-triazol-1-yl]pyridin-2-yl}-2,3-dihydro-1H-pyrrolo[3,4-c]pyridin-1-one | 393.2 | 1H NMR (400 MHz, DMSO-d6) δ 8.67 (d, J = 8.59 Hz, 1 H) 8.32 (br. s., 3 H) 8.23 (t, J = 8.00 Hz, 1 H) 7.84 (s, 1 H) 7.72 (d, J = 7.41 Hz, 1 H) 6.90 (s, 1 H) 5.07 (s, 2 H) 4.27 (s, 2 H) 3.66-3.78 (m, 1 H) 3.16 (s, 6 H) 2.54 (s, 1 H) 1.30 (d, J = 6.63 Hz, 6 H) |
| 36 (J) | 4-(aminomethyl)-6-tert-butyl-2-{6-[(4S)-4-methyl-2-oxo-1,3-oxazolidin-3-yl]pyridin-2-yl}-2,3-dihydro-1H-pyrrolo[3,4-c]pyridin-1-one | 396.4 | 1H NMR (400 MHz, DMSO-d6) δ 8.16 (d, J = 7.95 Hz, 1 H) 7.88 (t, J = 8.13 Hz, 1 H) 7.74 (d, J = 8.07 Hz, 1 H) 7.53 (s, 1 H) 5.69 (s, 1 H) 5.05-5.34 (m, 2 H) 4.75-5.00 (m, 1 H) 4.52 (t, J = 8.31 Hz, 1 H) 4.07 (dd, J = 8.38, 3.85 Hz, 1 H) 3.95 (br s, 2 H) 1.42 (d, J = 6.11 Hz, 3 H) 1.32 (s, 9 H) absolute stereochemistry known |

TABLE 1-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 37 (H) | 2-{6-[(4R)-4-(difluoromethyl)-2-oxo-1,3-oxazolidin-3-yl]pyridin-2-yl}-6-(dimethylamino)-4-[(methylamino)methyl]-2,3-dihydro-1H-pyrrolo[3,4-c]pyridin-1-one | 433.5 | $^1$H NMR (600 MHz, DMSO-$d_6$) δ 8.96 (s, 1H), 8.28 (d, J = 8.0 Hz, 1H), 8.01 (t, J = 8.1 Hz, 1H), 7.87 (d, J = 8.1 Hz, 1H), 6.92 (s, 1H), 6.78 (t, J = 54 Hz, 1H), 5.36-5.25 (m, 1H), 5.07 (q, J = 17.0 Hz, 2H), 4.70-4.60 (m, 2H), 4.36 (s, 2H), 3.17 (s, 6H), 2.55 (s, 3H) absolute stereochemistry known |
| 38 (C) | 4-(aminomethyl)-6-(diethylamino)-2-{6-[4-(propan-2-yl)-4H-1,2,4-triazol-3-yl]pyridin-2-yl}-2,3-dihydro-1H-pyrrolo[3,4-c]pyridin-1-one | [M + Na]⁺ 442.9 | $^1$H NMR (400 MHz, DMSO-$d_6$) δ 9.28 (br d, J = 5.8 Hz, 2H), 9.10 (s, 1H), 8.66 (d, J = 8.3 Hz, 1H), 8.15 (t, J = 8.0 Hz, 1H), 8.02 (d, J = 7.5 Hz, 1H), 6.87 (s, 1H), 5.17 (s, 2H), 4.67 (q, J = 7.0 Hz, 2H), 4.32 (t, J = 5.8 Hz, 2H), 3.65 (q, J = 6.8 Hz, 4H), 2.73 (t, J = 5.3 Hz, 3H), 1.52 (t, J = 7.2 Hz, 3H), 1.16 (t, J = 6.9 Hz, 6H) |
| 39 (K) | 6-tert-butyl-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one | 410.0 | $^1$H NMR (600 MHz, DMSO-$d_6$) δ ppm 8.14 (d, J = 8.07 Hz, 1 H) 7.86 (t, J = 8.07 Hz, 1 H) 7.74 (d, J = 8.25 Hz, 1 H) 7.54 (s, 1 H) 5.03-5.27 (m, 2 H) 4.73-4.93 (m, 1 H) 4.53 (t, J = 8.25 Hz, 1 H) 4.08 (dd, J = 8.44, 3.85 Hz, 1 H) 3.90 (s, 2 H) 2.32 (s, 3 H) 1.44 (d, J = 6.24 Hz, 3 H) 1.31 (s, 9 H) absolute stereochemistry known |
| 40 (M) | 6-cyclopropyl-4-[(methylamino)methyl]-2-{6-[(4S)-4-methyl-2-oxo-1,3-oxazolidin-3-yl]pyridin-2-yl}-2,3-dihydro-1H-pyrrolo[3,4-c]pyridin-1-one | 394.2 | $^1$H NMR (400 MHz, DMSO-$d_6$) δ 8.22 (d, J = 7.95 Hz, 1H), 7.94 (t, J = 8.13 Hz, 1H), 7.81 (d, J = 8.07 Hz, 1H), 7.56 (s, 1H), 5.07-5.28 (m, 2H), 4.84-4.97 (m,1H), 4.59 (t, J = 8.31 Hz, 1H), 4.15 (dd, J = 3.79, 8.44 Hz, 1H), 3.85-3.95 (m, 2H), 2.35 (s, 3H), 2.25-2.31 (m, 1H), 1.50 (d, J = 6.24 Hz, 3H), 0.95-1.05 (m, 4H) absolute stereochemistry known |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 41 (N) | 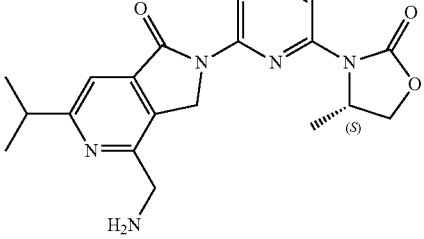<br>4-(aminomethyl)-2-{6-[(4S)-4-methyl-2-oxo-1,3-oxazolidin-3-yl]pyridin-2-yl}-6-(propan-2-yl)-2,3-dihydro-1H-pyrrolo[3,4-c]pyridin-1-one | 382.1 | 1H NMR (400 MHz, DMSO-d6) δ 8.66 (br s, 3H), 8.23 (d, J = 7.9 Hz, 1H), 7.96 (br t, J = 8.1 Hz, 1H), 7.83 (d, J = 8.1 Hz, 1H), 7.68 (s, 1H), 5.30 (br d, J = 18.3 Hz, 1H), 5.19 (br d, J = 18.3 Hz, 1H), 4.98 (br s, 1H), 4.60 (br t, J = 8.1 Hz, 1H), 4.45-4.31 (m, 2H), 4.16 (br dd, J = 3.2, 7.9 Hz, 1H), 3.30-3.14 (m, 1H), 1.49 (br d, J = 6.0 Hz, 3H), 1.34 (d, J = 6.8 Hz, 6H) absolute stereochemistry known |
| 42 (M) | 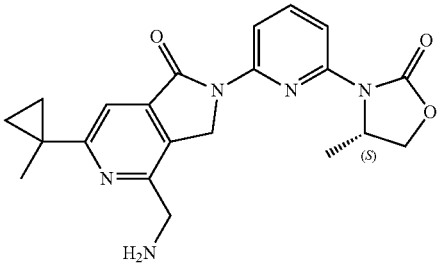<br>4-(aminomethyl)-6-(1-methylcyclopropyl)-2-{6-[(4S)-4-methyl-2-oxo-1,3-oxazolidin-3-yl]pyridin-2-yl}-2,3-dihydro-1H-pyrrolo[3,4-c]pyridin-1-one | 394.4 | 1H NMR (600 MHz, DMSO-d6) δ 8.31 (s., 2H), 8.23 (d, J = 8.1 Hz, 1H), 7.97 (t, J = 8.1 Hz, 1H), 7.83 (d, J = 8.3 Hz, 1H), 7.66 (s, 1H), 5.28-5.09 (m, 2H), 5.00-4.92 (m, 1H), 4.60 (t, J = 8.3 Hz, 1H), 4.44-4.34 (m, 2H), 4.17 (dd, J = 3.9, 8.4 Hz, 1H), 1.59 (s, 3H), 1.50 (d, J = 6.2 Hz, 3H), 1.48-1.43 (m, 2H), 0.91 (d, J = 2.9 Hz, 2H) absolute stereochemistry known |
| 43 (M) | 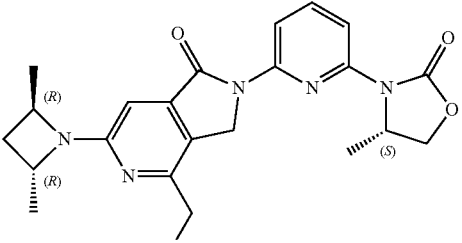<br>4-(aminomethyl)-6-[(2R,4R)-2,4-dimethylazetidin-1-yl]-2-{6-[(4S)-4-methyl-2-oxo-1,3-oxazolidin-3-yl]pyridin-2-yl}-2,3-dihydro-1H-pyrrolo[3,4-c]pyridin-1-one | [M + Na]+ 444.8 | 1H NMR (400 MHz, DMSO-d6) δ 8.21 (d, J = 8.1 Hz, 1H), 7.93 (t, J = 8.1 Hz, 1H), 7.80 (d, J = 8.1 Hz, 1H), 6.48 (s, 1H), 5.16-5.01 (m, 2H), 4.98-4.88 (m, 1H), 4.59 (t, J = 8.3 Hz, 1H), 4.52-4.42 (m, 2H), 4.14 (dd, J = 3.8, 8.4 Hz, 1H), 3.84 (s, 2H), 2.09 (t, J = 6.5 Hz, 2H), 1.48 (d, J = 6.2 Hz, 3H), 1.38 (d, J = 6.1 Hz, 6H) absolute stereochemistry known |
| 44 (M) | 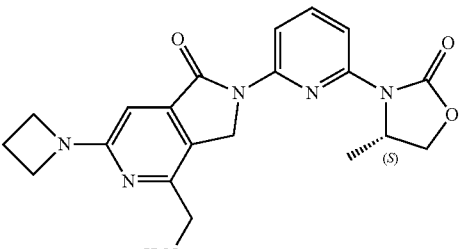<br>4-(aminomethyl)-6-(azetidin-1-yl)-2-{6-[(4S)-4-methyl-2-oxo-1,3-oxazolidin-3-yl]pyridin-2-yl}-2,3-dihydro-1H-pyrrolo[3,4-c]pyridin-1-one | 394.9 | 1H NMR (400 MHz, DMSO-d6) δ 8.22 (d, J = 7.7 Hz, 1H), 7.93 (t, J = 8.1 Hz, 1H), 7.80 (d, J = 7.7 Hz, 1H), 6.54 (s, 1H), 5.20-5.02 (m, 2H), 4.93 (ddd, J = 3.8, 6.2, 8.1 Hz, 1H), 4.59 (t, J = 8.3 Hz, 1H), 4.14 (dd, J = 3.8, 8.4 Hz, 1H), 4.02 (t, J = 7.3 Hz, 4H), 3.90 (s, 2H), 2.40-2.34 (m, 2H), 1.48 (d, J = 6.1 Hz, 3H) absolute stereochemistry known |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 45 (H) | 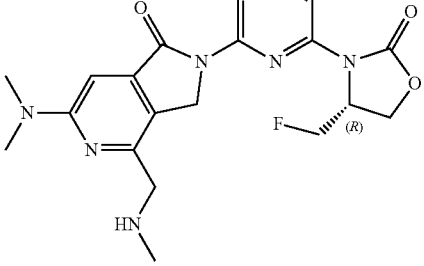<br>6-(dimethylamino)-2-{6-[(4R)-4-(fluoromethyl)-2-oxo-1,3-oxazolidin-3-yl]pyridin-2-yl}-4-[(methylamino)methyl]-2,3-dihydro-1H-pyrrolo[3,4-c]pyridin-1-one | 415.3 | 1H NMR (400 MHz, DMSO-d6) δ 8.25 (d, J = 8.0 Hz, 1H), 7.98 (t, J = 8.1 Hz, 1H), 7.89 (d, J = 8.2 Hz, 1H), 6.85 1H), 5.06 (dt, J = 25.4, 13.9 Hz, 4H), 4.80 (dd, J = 45.7, 10.1 Hz, 1H), 4.65 (t, J = 8.9 Hz, 1H), 4.53 (s, 1H), 4.12 (s, 2H), 3.14 (s, 6H), 2.58 (s, 3H).<br>absolute stereochemistry known |
| 46 (C) | 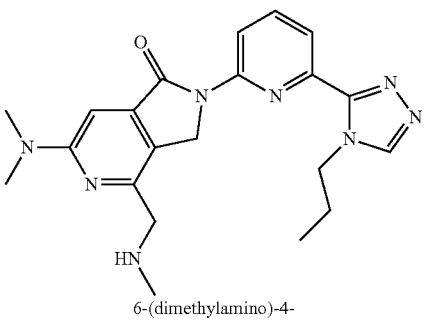<br>6-(dimethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 406.9 | 1H NMR (400 MHz, DMSO-d6) δ 8.75 (s, 1H), 8.63 (d, J = 8.3 Hz, 1H), 8.12-8.06 (m, 1H), 8.03-7.99 (m, 1H), 6.81 (s, 1H), 5.15 (s, 2H), 4.58 (t, J = 7.2 Hz, 2H), 3.89 (s, 2H), 3.12 (s, 6H), 2.41 (s, 3H), 1.94-1.83 (m, 2H), 0.94 (t, J = 7.4 Hz, 3H) |
| 47 (C) | 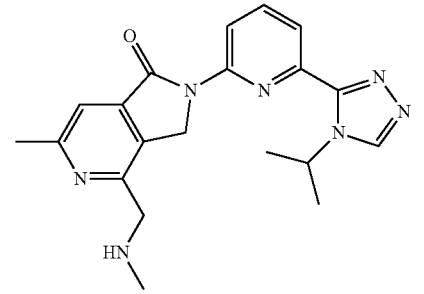 [SMILES: CNCc1nc(C)cc2c1CN(c1cccc(-c3nncn3C(C)C)n1)C2=O]<br>6-methyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | [M + Na]+ 400.2 | 1H NMR (400 MHz, DMSO-d6) δ 9.56 (br s, 2H), 9.41 (s, 1H), 8.68 (d, J = 7.82 Hz, 1H), 8.18 (t, J = 8.07 Hz, 1H), 7.99 (d, J = 7.09 Hz, 1H), 7.79 (s, 1H), 5.51(td, J = 6.71, 13.36 Hz, 1H), 5.39 (s, 2H), 4.43 (br s, 2H), 2.63-2.76 (m, 6H), 1.64 (d, J = 6.72 Hz, 6H) |
| 48 (C) | 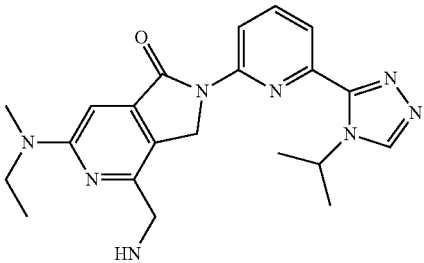<br>6-[ethyl(methyl)amino]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 421.2 | 1H NMR (400 MHz, DMSO-d6) δ 8.95 (s, 1 H) 8.63 (d, J = 8.31, 1 H) 8.09 (t, J = 8.01 Hz, 1 H) 7.96 (d, J = 7.34 Hz, 1 H) 6.75 (s, 1 H) 5.59 (quin, J = 6.76 Hz, 1 H) 5.17 (s, 2 H) 3.82 (s, 2 H) 3.55-3.70 (m, 2 H) 3.05 (s, 3 H) 2.36 (s, 3 H) 1.59 (d, J = 6.72 Hz, 6 H) 1.10 (t, J = 6.97 Hz, 3 H) |

TABLE 1-continued

| Ex. No. | Structure/IUPAC name | LCMS [M + H]+ | ¹H NMR (ppm); ¹⁹F NMR (ppm); optical rotation; stereochem. notes |
|---|---|---|---|
| 49 (M) | 4-[(methylamino)methyl]-6-(1-methylcyclopropyl)-2-{6-[(4S)-4-methyl-2-oxo-1,3-oxazolidin-3-yl]pyridin-2-yl}-2,3-dihydro-1H-pyrrolo[3,4-c]pyridin-1-one | 408.6 | ¹H NMR (600 MHz, DMSO-d₆) δ 8.89 (s, 1H), 8.24 (d, J = 8.1 Hz, 1H), 7.98 (t, J = 8.1 Hz, 1H), 7.84 (d, J = 8.1 Hz, 1H), 7.69 (s, 1H), 5.25-5.07 (m, 2H), 4.99-4.89 (m, 1H), 4.61 (t, J = 8.3 Hz, 1H), 4.51 (br. s., 2H), 4.17 (dd, J = 3.9, 8.3 Hz, 1H), 2.57 (s, 3H), 1.59 (s, 3H), 1.50 (d, J = 6.2 Hz, 3H), 1.43 (d, J = 3.9 Hz, 2H), 0.93 (d, J = 2.8 Hz, 2H) absolute stereochemistry known |
| 50 (C) | 6-amino-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 379.1 | ¹H NMR (600 MHz, DMSO-d₆) δ 8.40-8.49 (m, 1 H) 8.05-8.16 (m, 1 H) 7.57-7.67 (m, 1 H) 7.42-7.49 (m, 1 H) 6.79 (br. s., 1 H) 6.71 (br. s., 1 H) 6.62 (br. s., 1 H) 6.40 (s, 1 H) 4.89-4.99 (m, 1 H) 4.51-4.67 (m, 2 H) 3.77 (s, 2 H) 2.24 (s, 3 H) 1.04-1.15 (m, 6 H) |
| 51 (G) | 6-tert-butyl-4-[(methylamino)methyl]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 502.3 | ¹H NMR (400 MHz, Methanol-d₄) δ 8.89 (s, 1H), 8.70 (dd, J = 0.67, 8.50 Hz, 1H), 8.00 (dd, J = 7.70, 8.44 Hz, 1H), 7.85 (dd, J = 0.79, 7.64 Hz, 1H), 7.69 (s, 1H), 5.84-6.03 (m, 1H), 5.07-5.29 (m, 2H), 3.95 (s, 2H), 2.95-3.11 (m, 1H), 2.71-2.93 (m, 1H), 2.47 (s, 3H), 1.86-2.17 (m, 2H), 1.36 (s, 9H), 0.80-0.90 (m, 3H) [α]D22 = 6.6°, (0.2 M, MeOH), >99% ee absolute stereochemistry unknown* |
| 52 (L) | 4-[(methylamino)methyl]-2-{6-[4-(propan-2-yl)-4H-1,2,4-triazol-3-yl]pyridin-2-yl}-6-(trifluoromethyl)-2,3-dihydro-1H-pyrrolo[3,4-c]pyridin-1-one | 432.2 | ¹H NMR (400 MHz, DMSO-d₆) δ 9.22 (br s, 2 H) 8.96 (s, 1 H) 8.63 (dd, J = 8.31, 0.73 Hz, 1 H) 8.36 (s, 1 H) 8.18 (dd, J = 8.31, 7.58 Hz, 1 H) |

TABLE 1-continued

| Ex. No. | Structure/IUPAC name | LCMS [M + H]+ | 1H NMR (ppm); 19F NMR (ppm); optical rotation; stereochem. notes |
|---|---|---|---|
| 53 (C) | 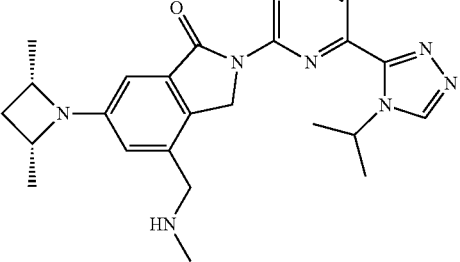<br>6-[(2R,4S)-2,4-dimethylazetidin-1-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 447 | 1H NMR (400 MHz, DMSO-d6) δ 8.95 (s, 1 H) 8.56-8.70 (m, 1 H) 8.06-8.15 (m, 1 H) 7.92-8.00 (m, 1 H) 6.53 (s, 1 H) 5.49-5.70 (m, 1 H) 5.19 (s, 2 H) 4.01-4.18 (m, 2 H) 3.82 (s, 2 H) 2.61-2.68 (m, 1 H) 2.35 (s, 3 H) 1.61-1.70 (m, 1 H) 1.59 (d, J = 6.72 Hz, 6 H) 1.50 (d, J = 6.11 Hz, 6 H) |

*Use of orl in a structure and ξ within the name identify a chiral center that has been resolved into the two separate enantiomers, but the specific enantiomer has not been confirmed; a solid or dashed wedge is drawn in the structure but the actual enantiomer may be the other enantiomer.

Example 46: 6-(dimethylamino)-4-[(methylamino) methyl]-2-[6-(4-propyl-4H-1,2,4-triazol-3-yl)pyridin-2-yl]-2,3-dihydro-1H-pyrrolo[3,4-c]pyridin-1-one

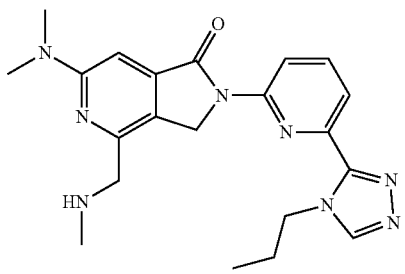

Ex-46

Step 1: tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl) methylcarbamate

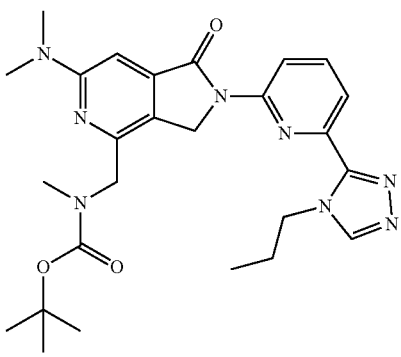 [SMILES: CCCn1cnnc1-c1cccc(N2Cc3c(cc(N(C)C)nc3CN(C)C(=O)OC(C)(C)C)C2=O)n1]

A mixture of Intermediate 3 (1.33 g, 4.15 mmol), Intermediate 13 (1.16 g, 4.36 mmol), Pd2(dba)3 (380 mg, 0.415 mmol), Xantphos (480 g, 0.830 mmol), and K3PO4 (2.64 g, 12.5 mmoL) in 1,4-dioxane (46 mL) was degassed with N2 for 5 min and the stirred at 85° C. for 16 h. The reaction was analyzed by LCMS, which showed consumption of the starting material. The mixture was cooled to room temperature, filtered through a pad of Celite®, and concentrated under vacuum. The residue was slurried with EtOAc (15 mL) for 10 min and the solids were collected by filtration. The filter cake was washed with EtOAc (4×) and then dried under vacuum. The residue was purified by flash chromatography (40 g SiO2, 0-100% EtOAc/heptane then 10% MeOH/EtOAc) to provide a light-yellow solid. The material was dissolved in 1:9 EtOH/DCM and treated with Ultra-pure Si-Thio SiO2 (1.59 g). The mixture was stirred for 2 h and the filtered. The filter cake was washed with 1:9 EtOH/DCM and the combined filtrate was concentrated under vacuum. The residue was dissolved in 1:9 EtOH/DCM and treated with Ultra-pure Si-Thio SiO2 (1.32 g). The mixture was stirred for 3 h and then filtered. The filter cake was washed with 1:9 EtOH/DCM and the combined filtrate was concentrated. The residue was dissolved in 1:9 EtOH and treated with Ultra-pure Si-Thio SiO2 (1.22 g). The mixture was stirred for 16 h and then filtered. The filter cake was washed with 1:9 EtOH/DCM. The combined filtrate was concentrated to dryness provide tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl) methylcarbamate (2.08 g, 95% yield) as a light-yellow solid. 1H NMR (400 MHz, DMSO-d6) δ 8.74 (s, 1H), 8.61 (d, J=8.4 Hz, 1H), 8.09 (t, J=8.0 Hz, 1H), 7.97 (d, J=7.6 Hz, 1H), 6.82 (s, 1H), 5.05 (d, J=11.7 Hz, 2H), 4.56 (s, 2H), 4.52-4.46 (m, 2H), 3.09 (s, 6H), 2.92 (s, 3H), 1.88-1.76 (m, 2H), 1.40-1.19 (m, 9H), 0.87 (t, J=7.4 Hz, 3H); LCMS m/z (ESI+) for (C26H34N8O3), 507.4 (M+H)+.

Alternative Step 1: tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate To a solution of tert-butyl {[6-(dimethylamino)-4-(dimethylcarbamoyl)-3-formylpyridin-2-yl] methyl}methylcarbamate (3e) (500 mg, 1.37 mmol) and 6-(4-propyl-4H-1,2,4-triazol-3-yl)pyridin-2-amine (Intermediate 16) (293 mg, 1.44 mmol) in MeOH (9.1 mL) was added decaborane (62.0 mg, 0.508 mmol). The mixture was stirred at room temperature for 16 h and then a solution of NaOMe (25% in MeOH, 5.02 mL, 22.0 mmol) was added. The mixture was stirred at 65° C. for 2 h, providing a yellow suspension. Additional NaOMe (0.5 M in MeOH, 13.7 mL, 6.86 mmol) was added and the mixture was stirred at 65° C. for 3 h. The reaction was cooled to room temperature and the yellow solids were collected by filtration. The filter cake was washed with H₂O (2×3 mL) and dried under vacuum to provide tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (518 mg, 75% yield) as a light yellow solid. LCMS m/z (ESI+) for ($C_{26}H_{34}N_8O_3$), 507.5 (M+H)⁺.

Step 2: 6-(dimethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one

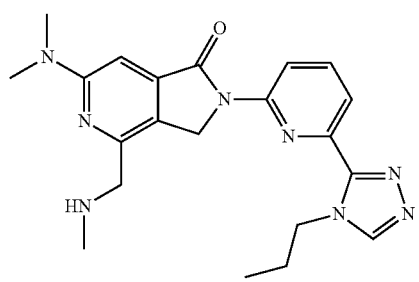 [SMILES: CCCn1cnnc1-c1cccc(N2Cc3c(cc(N(C)C)nc3CNC)C2=O)n1]

To a suspension of tert-butyl ({6-(dimethylamino)-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (1.96 g, 3.87 mmol) in MeOH (20 mL) was added a solution of HCl (4.0 M in 1,4-dioxane, 19.3 mL, 77.4 mmoL) slowly at 0° C. The mixture was stirred for 3 h at 0° C. and then allowed to warm slowly to room temperature. The mixture was stirred at room temperature for 16 h. The reaction was concentrated to dryness. The solids were dissolved in 1:9 MeOH/DCM (80 mL), cooled to 0° C., and then stirred with saturated aqueous Na₂CO₃ (25 mL) for 20 min. The mixture was separated. The aqueous layer was extracted with 1:19 MeOH/DCM (3×50 mL). The combined organic layers were washed with H₂O (2×30 mL), dried over Na₂SO₄, filtered, and concentrated. The solids were slurried in EtOAc at 40° C. for 40 min. The solids were collected by filtration. The filter cake was washed with EtOAc and then dried for 16 h in a vacuum oven at 30° C. to provide 6-(dimethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one (1.42 g, 90% yield) as a yellow solid. ¹H NMR (400 MHz, DMSO-d₆) δ 8.73 (s, 1H), 8.62 (dd, J=8.4, 1.0 Hz, 1H), 8.11-8.04 (m, 1H), 8.00 (dd, J=7.7, 1.0 Hz, 1H), 6.78 (s, 1H), 5.14 (s, 2H), 4.57 (dd, J=7.9, 6.5 Hz, 2H), 3.80 (s, 2H), 3.09 (s, 6H), 2.35 (s, 3H), 1.88 (h, J=7.4 Hz, 2H), 0.93 (t, J=7.4 Hz, 3H); LCMS m/z (ESI+) for ($C_{21}H_{26}N_8O$), 407.3 (M+H)⁺.

Example 55: 4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one Ex-55

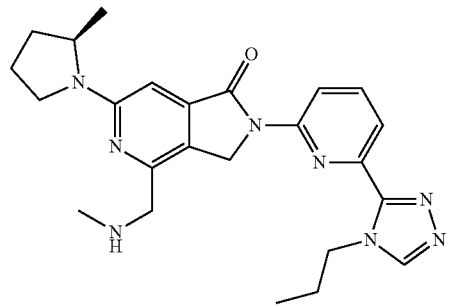

Step 1: tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate

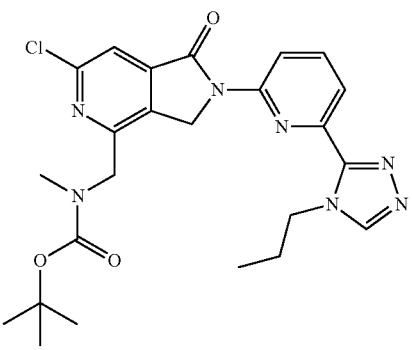 [SMILES: CCCn1cnnc1-c1cccc(N2Cc3c(cc(Cl)nc3CN(C)C(=O)OC(C)(C)C)C2=O)n1]

To a solution of Intermediate 2 (430 mg, 1.38 mmol), Intermediate 13 (368 mg, 1.38 mmol), K₂CO₃ (419 mg, 3.03 mmol), and N,N-dimethylethylenediamine (60.7 mg, 0.690 mmol) in MeCN (10.0 mL) was added CuI (65.7 mg, 0.345 mmol). The mixture was sparged with N₂ for 5 min and then stirred at 120° C. for 1.5 h under microwave irradiation. LCMS analysis showed consumption of the starting material. The reaction was cooled to room temperature and H₂O (10 mL) was added. The mixture was stirred for 15 min and then filtered. The filter cake was washed with H₂O (3×3 mL) and dried under vacuum. The residue was purified by flash chromatography (12 g SiO₂, EtOAc) to provide tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (430 mg, 63% yield) as a yellow glass. ¹H NMR (400 MHz, Chloroform-d) δ 8.68 (d, J=8.4 Hz, 1H), 8.25 (s, 1H), 8.14 (s, 1H), 8.02-7.92 (m, 1H), 7.78 (s, 1H), 5.14 (s, 2H), 4.76-4.50 (m, 4H), 2.97 (s, 3H), 1.97-1.80 (m, 2H), 1.37 (s, 9H), 0.94 (s, 3H); m/z (ESI+) for ($C_{24}H_{28}ClN_7O_3$), 498.2 (M+H)⁺.

Step 2: tert-butyl methyl({6-[(2R)-2-methylpyrrolidin-1-yl]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate

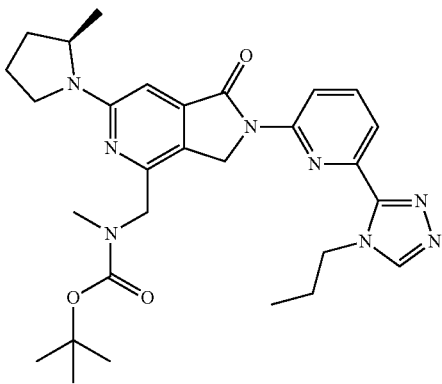 [SMILES: CCCn1cnnc1-c1cccc(N2Cc3c(cc(N4CCC[C@H]4C)nc3CN(C)C(=O)OC(C)(C)C)C2=O)n1]

A solution of tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (200 mg, 0.402 mmol) and $Cs_2CO_3$ (720 mg, 2.21 mmol) in 1,4-dioxane (5.0 mL) was sparged with argon for 3 min and RuPhos Pd G3 (33.6 mg, 0.0402 mmol) was added. The mixture was sparged with argon for 3 min and (2R)-2-methylpyrrolidine (171 mg, 2.01 mmol) was added. The mixture was stirred at 100° C. for 18 h. LCMS analysis showed consumption of the starting material. The mixture was filtered and the filter cake was washed with DCM (2×10 mL). The combined filtrate was concentrated to dryness. The residue was purified by flash chromatography (8 g $SiO_2$, EtOAc) to provide tert-butyl methyl({6-[(2R)-2-methylpyrrolidin-1-yl]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (210 mg, 96% yield) as a yellow solid. $^1$H NMR (400 MHz, $CDCl_3$) δ 8.82-8.62 (m, 1H), 8.25 (s, 1H), 8.17-8.09 (m, 1H), 7.97-7.89 (m, 1H), 6.74 (s, 1H), 5.13-4.85 (m, 2H), 4.76-4.58 (m, 2H), 4.64-4.42 (m, 2H), 4.35-4.19 (m, 1H), 3.84-3.73 (m, 2H), 3.67-3.57 (m, 1H), 3.46-3.31 (m, 1H), 3.01 (br. s, 3H), 2.19-2.08 (m, 2H), 1.99-1.90 (m, 1H), 1.81-1.74 (m, 1H), 1.48-1.31 (m, 9H), 1.27 (d, J=6.1 Hz, 3H), 0.98 (t, J=6.3 Hz, 3H); m/z (ESI+) for ($C_{29}H_{38}N_8O_3$), 547.4 (M+H)$^+$.

Step 3: 4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one hydrochloride-salt

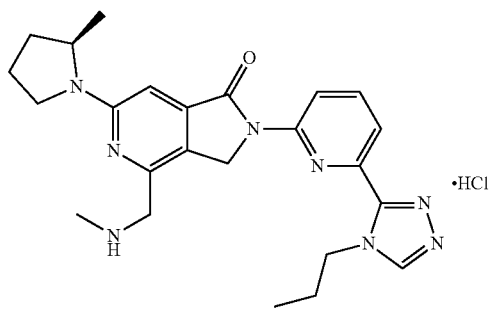 [SMILES: CCCn1cnnc1-c1cccc(N2Cc3c(cc(N4CCC[C@H]4C)nc3CNC)C2=O)n1 ; Cl]

To a solution of tert-butyl methyl({6-[(2R)-2-methylpyrrolidin-1-yl]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (210 mg, 0.384 mmol) in DCM (5.0 mL) at 0° C. was added a solution of HCl (1.0 M in EtOAc, 5.0 mL). The mixture was stirred at 20° C. for 4 h to provide a suspension. LCMS analysis showed consumption of the starting material. The suspension was filtered. The filter cake was washed with DCM (5 mL) and dried under vacuum. The material was dissolved in $H_2O$ (30 mL) and dried by lyophilization to provide 4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one, isolated as a hydrochloride (170 mg, 92% yield) as a yellow solid. $^1$H NMR (600 MHz, DMSO-$d_6$) δ 8.68 (s, 1H), 8.53 (dt, J=6.2, 2.9 Hz, 1H), 8.04-7.98 (m, 1H), 7.94 (dd, J=8.0, 2.8 Hz, 1H), 6.53 (s, 1H), 5.06-4.98 (m, 2H), 4.56-4.48 (m, 2H), 3.84 (2H obscured by solvent peak), 3.28 (d, J=9.3 Hz, 1H), 2.46-2.34 (m, 3H), 2.09-1.96 (m, 2H), 1.96-1.89 (m, 1H), 1.88-1.74 (m, 4H), 1.74-1.63 (m, 1H), 1.15 (d, J=6.1 Hz, 3H), 0.90 (t, J=7.4 Hz, 3H); m/z (ESI+) for ($C_{24}H_{30}N_8O$), 447.1 (M+H)$^+$.

Example 56: 4-(aminomethyl)-6-[ethyl(methyl)amino]-2-[6-(4-propyl-4H-1,2,4-triazol-3-yl)pyridin-2-yl]-2,3-dihydro-1H-pyrrolo[3,4-c]pyridin-1-one hydrochloride

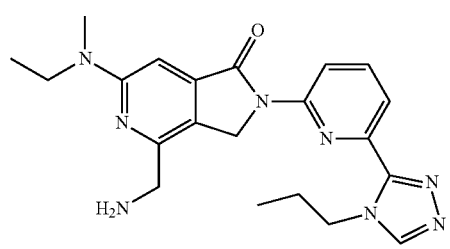

Ex-56

Step 1: tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate

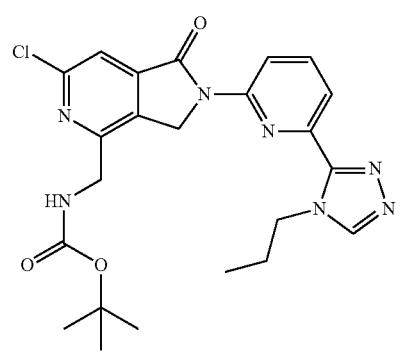 [SMILES: CCCn1cnnc1-c1cccc(N2Cc3c(cc(Cl)nc3CNC(=O)OC(C)(C)C)C2=O)n1]

To a solution of Intermediate 7 (300 mg, 1.01 mmol), Intermediate 13 (306 mg, 2.22 mmol), N,N-dimethylethylenediamine (44.4 mg, 0.504 mmol), and $K_2CO_3$ (306 mg, 2.22 mmol) in MeCN (10.0 mL) was added CuI (48.0 mg, 0.252 mmol) and the mixture was sparged with argon for 5 min. The mixture was stirred at 120° C. for 1.5 h with microwave irradiation. TLC analysis indicated consumption of the starting material. The reaction was cooled to room temperature and H$_2$O (80 mL) was added. The mixture was filtered and the filter cake was washed with H$_2$O (3×5 mL) and dried under vacuum to provide tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (290 mg, 60% yield) as a brown solid. $^1$H NMR (400 MHz, DMSO-d$_6$) δ 8.78 (s, 1H), 8.59 (d, J=8.3 Hz, 1H), 8.18-8.07 (m, 1H), 8.01 (d, J=7.6 Hz, 1H), 7.84 (s, 1H), 7.55 (t, J=5.9 Hz, 1H), 5.26 (s, 2H), 4.58 (t, J=7.1 Hz, 2H), 4.39 (d, J=5.9 Hz, 2H), 1.83 (q, J=7.4 Hz, 2H), 1.35 (s, 9H), 0.86 (t, J=7.3 Hz, 3H); m/z (ESI+) for (C$_{23}$H$_{26}$ClN$_7$O$_3$), 484.2 (M+H)$^+$.

Step 2: tert-butyl ({6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate

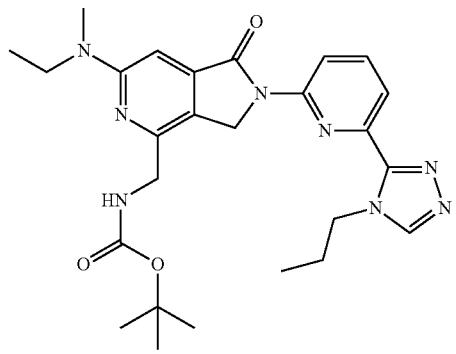 [SMILES: CCCn1cnnc1-c1cccc(N2Cc3c(cc(N(C)CC)nc3CNC(=O)OC(C)(C)C)C2=O)n1]

A solution of tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (290 mg, 0.599 mmol) and Cs$_2$CO$_3$ (586 mg, 1.8 mmol) in 1,4-dioxane (10.0 mL) was sparged with argon for 3 min and RuPhos Pd G3 (50.1, 0.0599 mmol) was added. The mixture was sparged with argon for 3 min and N-methylethanamine (70.8 mg, 1.2 mmol) was added. The mixture was stirred at 100° C. for 18 h under Ar. LCMS analysis showed consumption of the starting material. The reaction was concentrated to dryness and the residue was purified by preparative TLC (SiO$_2$, 1:20 MeOH/EtOAc) to provide tert-butyl ({6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (90 mg, 30% yield) as a yellow solid. m/z (ESI+) for (C$_{26}$H$_{34}$N$_8$O$_3$), 507.3 (M+H)$^+$.

Step 3: 4-(aminomethyl)-6-[ethyl(methyl)amino]-2-[6-(4-propyl-4H-1,2,4-triazol-3-yl)pyridin-2-yl]-2,3-dihydro-1H-pyrrolo[3,4-c]pyridin-1-one hydrochloride

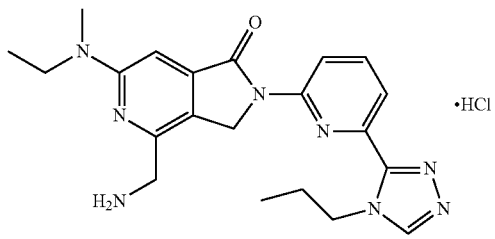 [SMILES: CCCn1cnnc1-c1cccc(N2Cc3c(cc(N(C)CC)nc3CN)C2=O)n1 ; Cl]

To a solution of tert-butyl ({6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (90 mg, 0.18 mmol) in EtOAc (5.0 mL) was added a solution of HCl (4.0 M in EtOAc, 3.0 mL) at 0° C. The mixture was stirred at 15° C. for 20 h. LCMS analysis showed consumption of the starting material. The reaction was concentrated to dryness. The residue was purified by preparative HPLC with a YMC-Actus Triart C-18 column (150×30 mm, 5 μm particle size), which was eluted with 11-51% MeCN/H$_2$O (+0.05% HCl) with a flow rate of 30 mL/min to provide 4-(aminomethyl)-6-[ethyl(methyl)amino]-2-[6-(4-propyl-4H-1,2,4-triazol-3-yl)pyridin-2-yl]-2,3-dihydro-1H-pyrrolo[3,4-c]pyridin-1-one, isolated as a hydrochloride (37 mg, 47% yield) as a yellow solid. $^1$H NMR (400 MHz, DMSO-d$_6$) δ 8.97 (s, 1H), 8.65 (d, J=8.4 Hz, 1H), 8.48 (s, 3H), 8.16-8.09 (m, 1H), 8.02 (d, J=7.6 Hz, 1H), 6.88 (s, 1H), 5.14 (s, 2H), 4.59 (t, J=7.3 Hz, 2H), 4.22 (d, J=6.1 Hz, 2H), 3.71 (q, J=7.1 Hz, 2H), 3.11 (s, 3H), 1.89 (q, J=7.3 Hz, 2H), 1.11 (t, J=6.9 Hz, 3H), 0.94 (t, J=7.4 Hz, 3H); m/z (ESI+) for (C$_{21}$H$_{26}$N$_8$O), 407.3 (M+H)$^+$.

Example 57: 4-[(methylamino)methyl]-6-(1-methylcyclopropyl)-2-{6-[4-(pentan-3-yl)-4H-1,2,4-triazol-3-yl]pyridin-2-yl}-2,3-dihydro-1H-pyrrolo[3,4-c]pyridin-1-one Ex-57

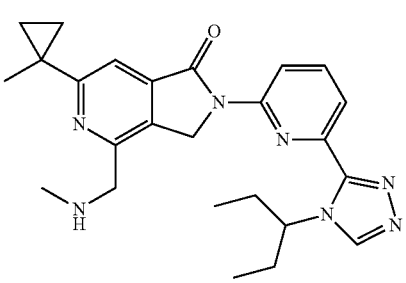

Step 1: tert-butyl methyl{[6-(1-methylcyclopropyl)-1-oxo-2-{6-[4-(pentan-3-yl)-4H-1,2,4-triazol-3-yl]pyridin-2-yl}-2,3-dihydro-1H-pyrrolo[3,4-c]pyridin-4-yl]methyl}carbamate

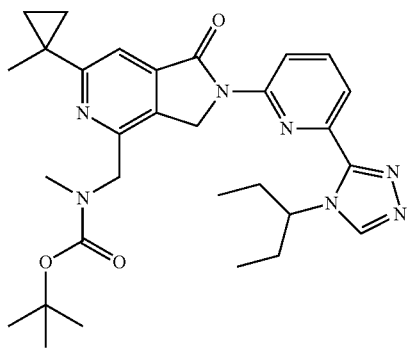 [SMILES: CCC(CC)n1cnnc1-c1cccc(N2Cc3c(cc(C4(C)CC4)nc3CN(C)C(=O)OC(C)(C)C)C2=O)n1]

To a mixture of Intermediate 8 (100 mg, 0.302 mmol), Intermediate 14 (89.1 mg, 0.302 mmol), and K₃PO₄ (192 mg, 0.905 mmol) in 1,4-dioxane (5.0 mL) under an atmosphere of N₂ was added Pd₂(dba)₃ (27.6 mg, 0.0302 mmol) and Xantphos (34.9 mg, 0.0603 mmol). The mixture was sparged with N₂ for two minutes. The mixture was stirred at 85° C. for 18 h. LCMS analysis showed consumption of the starting material. The reaction was diluted with H₂O (1.5 mL) and extracted with EtOAc (2×10 mL). The combined organics were dried over Na₂SO₄, filtered, and concentrated. The residue was purified by preparative TLC (SiO₂, 1:30 MeOH/EtOAc) to provide tert-butyl methyl{[6-(1-methylcyclopropyl)-1-oxo-2-{6-[4-(pentan-3-yl)-4H-1,2,4-triazol-3-yl]pyridin-2-yl}-2,3-dihydro-1H-pyrrolo[3,4-c]pyridin-4-yl]methyl}carbamate (100 mg, 61% yield) as a light-yellow solid. $^1$H NMR (400 MHz, DMSO-d$_6$) δ 8.92 (s, 1H), 8.61 (d, J=8.4 Hz, 1H), 8.14-8.06 (m, 1H), 7.93 (d, J=7.6 Hz, 1H), 7.58 (s, 1H), 5.17 (d, J=23.7 Hz, 2H), 4.53 (s, 2H), 2.92 (s, 3H), 1.99-1.83 (m, 1H), 1.54 (s, 3H), 1.38 (s, 5H), 1.23 (s, 4H), 1.18 (s, 4H), 0.91-0.82 (m, 4H), 0.78 (t, J=7.4 Hz, 6H); m/z (ESI+) for (C$_{30}$H$_{39}$N$_7$O$_3$), 546.5 (M+H)$^+$.

Step 2: 4-[(methylamino)methyl]-6-(1-methylcyclopropyl)-2-{6-[4-(pentan-3-yl)-4H-1,2,4-triazol-3-yl]pyridin-2-yl}-2,3-dihydro-1H-pyrrolo[3,4-c]pyridin-1-one

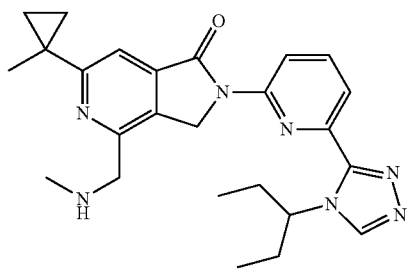 [SMILES: CCC(CC)n1cnnc1-c1cccc(N2Cc3c(cc(C4(C)CC4)nc3CNC)C2=O)n1]

A solution of tert-butyl methyl{[6-(1-methylcyclopropyl)-1-oxo-2-{6-[4-(pentan-3-yl)-4H-1,2,4-triazol-3-yl]pyridin-2-yl}-2,3-dihydro-1H-pyrrolo[3,4-c]pyridin-4-yl]methyl}carbamate (100 mg, 0.183 mmol) in DCM (3.0 mL) was cooled to 0° C. and TFA (1.0 mL) was added dropwise. The mixture was stirred at room temperature for 4 h. LCMS analysis showed consumption of the starting material. The mixture was concentrated. The residue was dissolved in DCM (50 mL) and washed with saturated aqueous NaHCO₃ (20 mL) and brine (20 mL). The organic layer was dried over Na₂SO₄, filtered, and concentrated. The solids were dried by lyophilization to provide 4-[(methylamino)methyl]-6-(1-methylcyclopropyl)-2-{6-[4-(pentan-3-yl)-4H-1,2,4-triazol-3-yl]pyridin-2-yl}-2,3-dihydro-1H-pyrrolo[3,4-c]pyridin-1-one (33 mg, 40% yield) as an off-white solid. $^1$H NMR (400 MHz, DMSO-d$_6$) δ 8.93 (s, 1H), 8.65 (d, J=8.4 Hz, 1H), 8.14-8.06 (m, 1H), 7.96 (d, J=7.6 Hz, 1H), 7.57 (s, 1H), 5.43 (td, J=8.7, 4.3 Hz, 1H), 5.26 (s, 2H), 3.91 (s, 2H), 2.34 (s, 4H), 1.99-1.86 (m, J=6.7 Hz, 4H), 1.56 (s, 3H), 1.25 (p, J=3.5 Hz, 2H), 0.87 (q, J=3.6 Hz, 2H), 0.83 (s, 6H); m/z (ESI+) for (C$_{25}$H$_{31}$N$_7$O), 446.5 (M+H)$^+$.

Example 58: 2-(6-{4-[(2S)-butan-2-yl]-4H-1,2,4-triazol-3-yl}pyridin-2-yl)-4-[(methylamino)methyl]-6-(1-methylcyclopropyl)-2,3-dihydro-1H-pyrrolo[3,4-c]pyridin-1-one

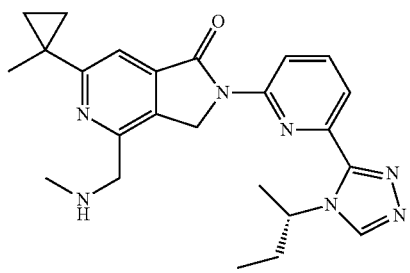

Ex-58

A mixture of Intermediate 8 (68.4 mg, 0.206 mmol), Intermediate 15 (58.0 mg, 0.210 mmol), K₂CO₃ (71.3 mg, 0.516 mmol), N,N-dimethylethylenediamine (8.61 mg, 0.0977 mmol), and CuI (9.3 mg, 0.0488 mmol) was stirred at 120° C. for 90 min under microwave irradiation. LCMS analysis showed consumption of the starting material. The mixture was cooled to room temperature and filtered through Celite®. The filter cake was washed with 10% MeOH/DCM and the combined filtrate was concentrated to dryness. The residue was dissolved in DCM (2.0 mL) and TFA (1.0 mL) was added. The mixture was stirred at room temperature for 2 h. The reaction was concentrated to dryness. The residue was purified by preparative SFC with a ZymorSPHERE HADP column (4.6×150 mm, 5 μm particle size), which was eluted with 5-50% MeOH/CO₂ with a flow rate of 4.0 mL/min to provide (57.6 mg, 65% yield) as a solid. $^1$H NMR (600 MHz, DMSO-d$_6$) b 8.92 (s, 1H), 8.61 (d, J=8.0 Hz, 1H), 8.15-8.07 (m, 1H), 7.93 (d, J=7.2 Hz, 1H), 7.66 (s, 1H), 5.31 (p, J=7.2 Hz, 1H), 5.25-5.17 (m, 2H), 4.35 (s, 2H), 2.68 (s, 3H), 1.92 (ddp, J=36.2, 14.6, 7.4 Hz, 2H), 1.57 (s, 3H), 1.42-1.37 (m, 2H), 0.91 (d, J=5.4 Hz, 2H), 0.82 (t, J=7.3 Hz, 3H); m/z (ESI+) for (C$_{24}$H$_{29}$N$_7$O), 432.2 (M+H)$^+$.

Example 59: 6-[ethyl(methyl)amino]-4-[(methylamino)methyl]-2-[6-(4-propyl-4H-1,2,4-triazol-3-yl)pyridin-2-yl]-2,3-dihydro-1H-pyrrolo[3,4-c]pyridin-1-one

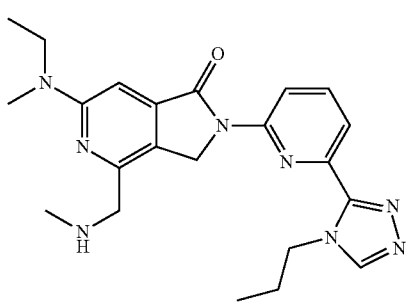

Ex-59

Step 1: tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate

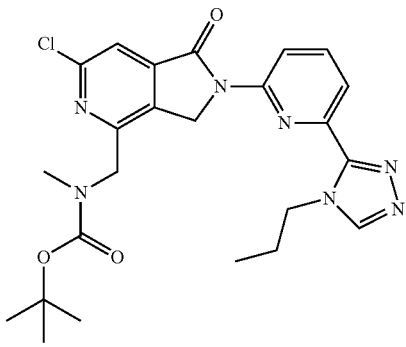 [SMILES: CCCn1cnnc1-c1cccc(N2Cc3c(cc(Cl)nc3CN(C)C(=O)OC(C)(C)C)C2=O)n1]

To a solution of Intermediate 2 (200 mg, 0.642 mmol), Intermediate 13 (180 mg, 0.674 mmol), $K_2CO_3$ (195 mg, 1.41 mmol), and N,N-dimethylethylenediamine (28.3 mg, 0.321 mmol) in MeCN (7.0 mL) was added CuI (30.5 mg, 0.160 mmol). The mixture was sparged with argon for 5 min and then stirred at 120° C. for 1.5 h under microwave irradiation. LCMS analysis showed consumption of the starting material. The mixture was diluted with $H_2O$ (30 mL). The resultant precipitate was collected by filtration. The filter cake was stirred in EtOAc (100 mL) and filtered to remove undissolved solids. The filtrate was concentrated to dryness to provide tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (270 mg, 85% yield) as a grey solid. $^1$H NMR (400 MHz, DMSO-$d_6$) δ 8.78 (s, 1H), 8.60 (d, J=8.3 Hz, 1H), 8.17-8.10 (m, 1H), 8.00 (d, J=7.6 Hz, 1H), 7.87 (s, 1H), 5.21 (s, 2H), 4.66 (s, 2H), 4.60-4.54 (m, 2H), 2.93 (s, 3H), 1.81 (s, 2H), 1.37 (s, 5H), 1.24 (s, 4H), 0.86 (t, J=7.3 Hz, 3H); m/z (ESI+) for ($C_{24}H_{28}ClN_7O_3$), 498.2 (M+H)$^+$.

Step 2: tert-butyl ({6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate

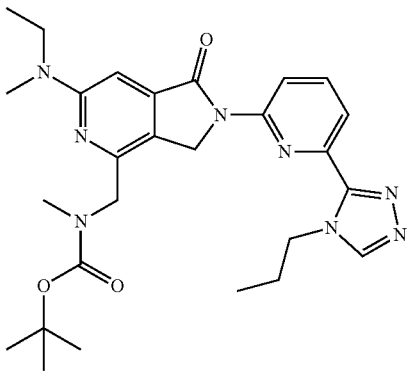 [SMILES: CCCn1cnnc1-c1cccc(N2Cc3c(cc(N(C)CC)nc3CN(C)C(=O)OC(C)(C)C)C2=O)n1]

A mixture of tert-butyl ({6-chloro-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (270 mg, 0.542 mmol), N-methylethanamine (64.1 mg, 1.08 mmol), and $Cs_2CO_3$ (530 mg, 1.63 mmol) in 1,4-dioxane (8.0 mL) was sparged with argon for 3 min and RuPhos Pd G3 (45.4 mg, 0.542 mmol) was added. The mixture was sparged with argon for an additional 3 min and then stirred at 100° C. for 18 h. LCMS analysis showed consumption of the starting material. The mixture was diluted with $H_2O$ (50 mL) and extracted with EtOAc (2×50 mL). The combined organic layers were washed with brine, dried over $Na_2SO_4$, filtered, and concentrated. The residue was purified by preparative TLC (1:20 MeOH/EtOAc) to provide tert-butyl ({6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)methylcarbamate (99 mg, 35% yield) as a brown solid. $^1$H NMR (400 MHz, DMSO-$d_6$) δ 8.76 (s, 1H), 8.62 (d, J=8.4 Hz, 1H), 8.12-8.06 (m, 1H), 7.98 (d, J=7.6 Hz, 1H), 6.78 (s, 1H), 5.09-5.00 (m, 2H), 4.57 (s, 2H), 4.49 (s, 2H), 3.68-3.60 (m, 2H), 3.05 (s, 3H), 2.94 (s, 3H), 1.90-1.77 (m, 2H), 1.38 (s, 4H), 1.23 (s, 5H), 1.07 (d, J=7.9 Hz, 3H), 0.89 (t, J=7.5 Hz, 3H); m/z (ESI+) for ($C_{27}H_{36}N_8O_3$), 521.4 (M+H)$^+$.

Step 3: 6-[ethyl(methyl)amino]-4-[(methylamino)methyl]-2-[6-(4-propyl-4H-1,2,4-triazol-3-yl)pyridin-2-yl]-2,3-dihydro-1H-pyrrolo[3,4-c]pyridin-1-one, hydrochloride

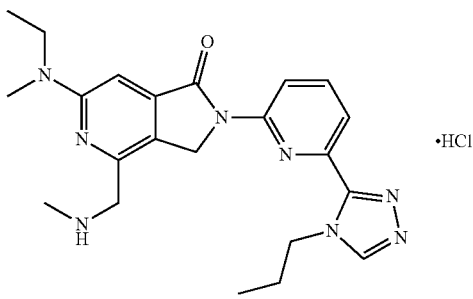 [SMILES: CCCn1cnnc1-c1cccc(N2Cc3c(cc(N(C)CC)nc3CNC)C2=O)n1 ; Cl]

A solution of tert-butyl (\{6-[ethyl(methyl)amino]-1-oxo-2-[6-(4-propyl-4H-1,2,4-triazol-3-yl)pyridin-2-yl]-2,3-dihydro-1H-pyrrolo[3,4-c]pyridin-4-yl\}methyl)methylcarbamate (99 mg, 0.19 mmol) in DCM (20 mL) was cooled to 0° C. and treated dropwise with a solution of HCl (4.0 M in EtOAc, 5.0 mL). The reaction was stirred at room temperature for 2 d. LCMS showed consumption of the starting material. The mixture was concentrated to dryness. The residue was purified by preparative HPLC with a YMC-Actus Triart C18 column (150×30 mm, 5 μm particle size), which was eluted with 12-52% MeCN/$H_2O$ (+0.05% HCl) with a flow rate of 30 mL/min to provide 6-[ethyl(methyl)amino]-4-[(methylamino)methyl]-2-[6-(4-propyl-4H-1,2,4-triazol-3-yl)pyridin-2-yl]-2,3-dihydro-1H-pyrrolo[3,4-c]pyridin-1-one, isolated as a hydrochloride (62.2 mg, 72% yield) as a yellow solid. $^1$H NMR (400 MHz, DMSO-$d_6$) δ 9.15 (d, J=8.2 Hz, 2H), 8.85 (s, 1H), 8.65 (d, J=8.2 Hz, 1H), 8.16-8.10 (m, 1H), 8.04-7.98 (m, 1H), 6.92 (s, 1H), 5.13 (s, 2H), 4.58 (t, J=7.2 Hz, 2H), 4.33 (t, J=5.9 Hz, 2H), 3.72 (q, J=7.0 Hz, 2H), 3.12 (s, 3H), 2.73 (t, J=5.4 Hz, 3H), 1.87 (h, J=7.4 Hz, 2H), 1.12 (t, J=7.0 Hz, 3H), 0.93 (t, J=7.4 Hz, 3H); m/z (ESI+) for ($C_{22}H_{28}N_8O$), 421.2 (M+H)$^+$.

Example 60: 4-(aminomethyl)-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one Ex-60

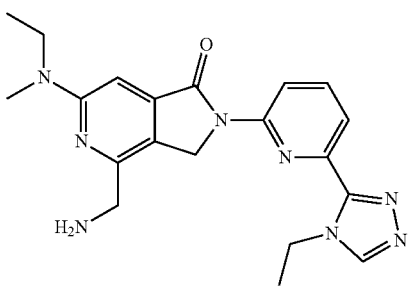

Step 1: 4-chloro-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one

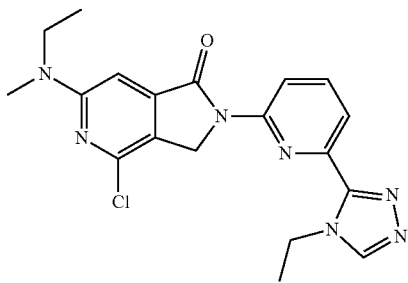 [SMILES: CCN(C)c1cc2c(c(Cl)n1)CN(c1cccc(-c3nncn3CC)n1)C2=O]

A mixture of 4-chloro-6-[ethyl(methyl)amino]-2,3-dihydro-1H-pyrrolo[3,4-c]pyridin-1-one (Intermediate 9) (123 mg, 0.487 mmol), Intermediate 12 (110 mg, 0.487 mmol), $K_2CO_3$ (196 mg, 1.42 mmol), N,N-dimethylethylenediamine (28.4 mg, 0.322 mmol), and CuI (30.7 mg, 0.161 mmol) in MeCN (4.0 mL) was stirred at 120° C. for 90 min under microwave irradiation. LCMS analysis showed consumption of the starting material. The mixture was filtered through Celite®. The filter cake was washed with 10% MeOH/DCM and the combined filtrate was concentrated to dryness. The residue was purified by flash chromatography (12 g $SiO_2$, 0-10% MeOH/DCM) to provide 4-chloro-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one (173 mg, 89% yield) as a yellow solid. m/z (APCI+) for ($C_{19}H_{20}ClN_7O$), 398.2 (M+H)$^+$.

Step 2: 4-(aminomethyl)-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one

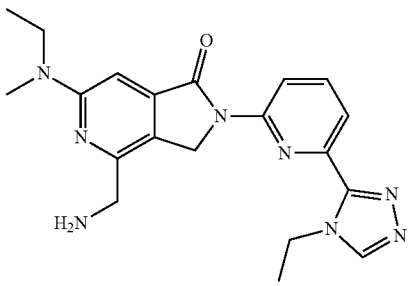 [SMILES: CCN(C)c1cc2c(c(CN)n1)CN(c1cccc(-c3nncn3CC)n1)C2=O]

A mixture of 4-chloro-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one (172 mg, 0.432 mmol), potassium N-Boc-aminomethyltrifluoroborate (205 mg, 0.865 mmol), $K_2CO_3$ (299 mg, 2.16 mmol), cataCXium A (31.0 mg, 0.0865 mmol), Pd(OAc)$_2$ (19.4 mg, 0.0865 mmol), and tetraethylammonium tetrafluoroborate (93.8 mg, 0.432 mmol) in t-AmOH (4.0 mL) and $H_2O$ (0.4 mL) was stirred at 110° C. for 20 h under an atmosphere of $N_2$. LCMS analysis showed consumption of the starting material. The mixture was cooled to room temperature, diluted with $H_2O$ (10 mL), and extracted with DCM (2×10 mL). The combined organic layers were dried over $Na_2SO_4$, filtered, and concentrated. The residue was taken up in DCM (2.0 mL) and treated with TFA (1.0 mL). The mixture was stirred for 2 h and then concentrated to dryness. The residue was purified by preparative SFC with a Princeton SFC HA-Morpholine column (150×4.6 mm, 5 μm particle size), which was eluted with 5-50% MeOH/$CO_2$ with a flow rate of 4.0 mL/min to provide 4-(aminomethyl)-6-[ethyl(methyl)amino]-2-[6-(4-ethyl-4H-1,2,4-triazol-3-yl)pyridin-2-yl]-2,3-dihydro-1H-pyrrolo[3,4-c]pyridin-1-one (114.4 mg, 67% yield) as a solid. $^1$H NMR (600 MHz, DMSO-$d_6$) δ 8.75 (s, 1H), 8.60 (d, J=8.4 Hz, 1H), 8.32 (s, 3H), 8.12-8.06 (m, 1H), 7.98 (d, J=7.6 Hz, 1H), 6.87 (s, 1H), 5.11 (s, 2H), 4.61 (q, J=7.2 Hz, 2H), 4.26 (s, 2H), 3.70 (q, J=7.0 Hz, 2H), 3.11 (s, 3H), 1.47 (t, J=7.1 Hz, 3H), 1.12 (t, J=7.0 Hz, 3H); m/z (APCI+) for ($C_{20}H_{24}N_8O$), 393.0 (M+H)$^+$.

Example 61: 4-(aminomethyl)-2-[6-(4-ethyl-5-methyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one

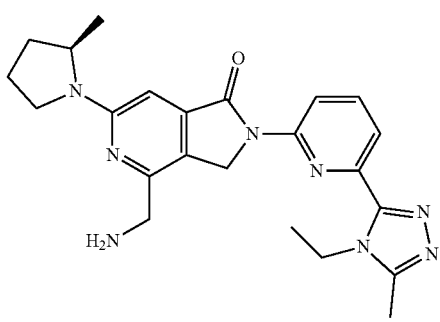

Ex-61

Step 1: 4-chloro-2-[6-(5-methyl-1,3,4-oxadiazol-2-yl)pyridin-2-yl]-6-[(2R)-2-methylpyrrolidin-1-yl]-2,3-dihydro-1H-pyrrolo[3,4-c]pyridin-1-one

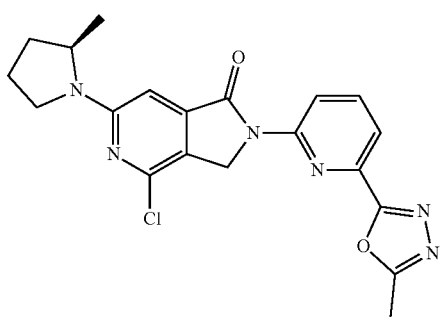 [SMILES: Cc1nnc(-c2cccc(N3Cc4c(cc(N5CCC[C@H]5C)nc4Cl)C3=O)n2)o1]

A mixture of Intermediate 10 (142 mg, 0.593 mmol), Intermediate 4 (120 mg, 0.477 mmol), $K_2CO_3$ (145 mg, 1.05 mmol), CuI (22.7 mg, 0.119 mmol), and N,N-dimethylethylenediamine (21.0 mg, 0.238 mmol) in MeCN (3.0 mL) was stirred at 120° C. for 90 min under microwave irradiation. LCMS analysis showed consumption of the starting material. The mixture was concentrated to dryness and the residue was purified by flash chromatography (SiO$_2$, 1:1 EtOAc/DCM) to provide 4-chloro-2-[6-(5-methyl-1,3,4-oxadiazol-2-yl)pyridin-2-yl]-6-[(2R)-2-methylpyrrolidin-1-yl]-2,3-dihydro-1H-pyrrolo[3,4-c]pyridin-1-one (162 mg, 83% yield) as a pale-yellow foam. $^1$H NMR (400 MHz, CDCl$_3$) δ 8.79 (d, J=8.07 Hz, 1H), 7.91-8.08 (m, 2H), 6.76 (s, 1H), 5.13 (s, 2H), 4.23 (quin, J=5.84 Hz, 1H), 3.59-3.70 (m, 1H), 3.36-3.50 (m, 1H), 2.73 (s, 3H), 2.10-2.29 (m, 2H) 1.97-2.09 (m, 1H), 1.74-1.86 (m, 1H) 1.28 (d, J=6.36 Hz, 3H); m/z (APCI+) for ($C_{20}H_{19}ClN_6O_2$), 411.0 (M+H)$^+$.

Step 2: tert-butyl ({2-[6-(5-methyl-1,3,4-oxadiazol-2-yl)pyridin-2-yl]-6-[(2R)-2-methylpyrrolidin-1-yl]-1-oxo-2,3-dihydro-1H-pyrrolo[3,4-c]pyridin-4-yl}methyl)carbamate

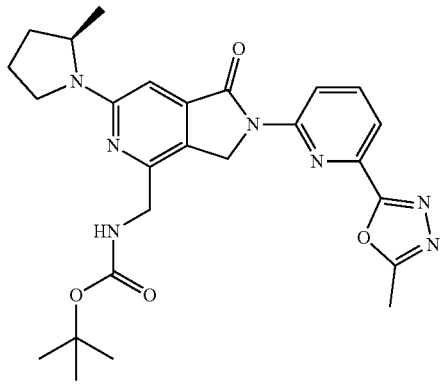 [SMILES: Cc1nnc(-c2cccc(N3Cc4c(cc(N5CCC[C@H]5C)nc4CNC(=O)OC(C)(C)C)C3=O)n2)o1]

A mixture of 4-chloro-2-[6-(5-methyl-1,3,4-oxadiazol-2-yl)pyridin-2-yl]-6-[(2R)-2-methylpyrrolidin-1-yl]-2,3-dihydro-1H-pyrrolo[3,4-c]pyridin-1-one (160 mg, 0.389 mmol), potassium N-Boc-aminomethyltrifluoroborate (369 mg, 1.56 mmol), cataCXium (27.9 mg, 0.0779 mmol), Pd(OAc)$_2$ (17.5 mg, 0.0779 mmol), and tetraethylammonium tetrafluoroborate (84.5 mg, 0.389 mmol) in t-BuOH (6.0 mL) and H$_2$O (0.6 mL) was stirred at 110° C. for 18 h. LCMS showed consumption of the starting material. The reaction was cooled to room temperature, diluted with H$_2$O (10 mL), and extracted with DCM (2×10 mL). The combined organic layers were dried over Na$_2$SO$_4$, filtered, and concentrated. The residue was purified by flash chromatography (12 g SiO$_2$, 30-100% EtOAc/heptane) to provide tert-butyl ({2-[6-(5-methyl-1,3,4-oxadiazol-2-yl)pyridin-2-yl]-6-[(2R)-2-methylpyrrolidin-1-yl]-1-oxo-2,3-dihydro-1H-pyrrolo[3,4-c]pyridin-4-yl}methyl)carbamate (182 mg, 92% yield) as a white solid. m/z (APCI+) for ($C_{26}H_{31}N_7O_4$), 506.2 (M+H)$^+$.

Step 3: 4-(aminomethyl)-2-[6-(4-ethyl-5-methyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one

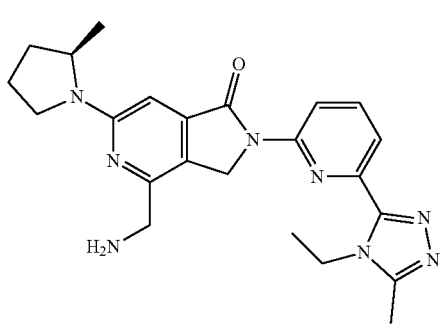 [SMILES: CCn1c(C)nnc1-c1cccc(N2Cc3c(cc(N4CCC[C@H]4C)nc3CN)C2=O)n1]

A mixture of tert-butyl ({2-[6-(5-methyl-1,3,4-oxadiazol-2-yl)pyridin-2-yl]-6-[(2R)-2-methylpyrrolidin-1-yl]-1-oxo-2,3-dihydro-1H-pyrrolo[3,4-c]pyridin-4-yl}methyl)carbamate (84 mg, 0.17 mmol), ethylamine hydrochloride (279 mg, 3.42 mmol), and TEA (353 mg, 3.49 mmol) in NMP (1.0 mL) was stirred at 140° C. for 18 h. LCMS analysis showed consumption of the starting material. The reaction was cooled to room temperature, diluted with H$_2$O (20 mL), and extracted with EtOAc (20 mL). The organic layer was dried over Na$_2$SO$_4$, filtered, and concentrated. The residue was purified by flash chromatography (0-10% MeOH/DCM). The desired fractions were concentrated to dryness. The residue was dissolved in DCM (5.0 mL) and treated with a solution of HCl (4.0 N in 1,4-dioxane, 1.0 mL). The mixture was stirred for 4 h and then concentrated to dryness. The residue was purified by preparative HPLC with a Phenemonex Gemini NX C18 column (150×21.2 mm, 5 μm particle size), which was eluted with 30-100% MeCN/H$_2$O (+10 mM NH$_4$OAc) with a flow rate of 40 mL/min to provide tert-butyl ({2-[6-(5-methyl-1,3,4-oxadiazol-2-yl)pyridin-2-yl]-6-[(2R)-2-methylpyrrolidin-1-yl]-1-oxo-2,3-dihydro-1H-pyrrolo[3,4-c]pyridin-4-yl}methyl)carbamate (24.0 mg, 33% yield) as a solid. $^1$H NMR (400 MHz, DMSO-d$_6$) δ 8.59 (dd, J=8.3, 0.9 Hz, 1H), 8.08-8.01 (m, 1H), 7.96 (dd, J=7.7, 1.0 Hz, 1H), 6.60 (s, 1H), 5.19 (s, 2H), 4.56 (q, J=7.1 Hz, 2H), 4.31-4.20 (m, 1H), 3.91 (s, 2H), 3.53-3.43 (4H obscured by solvent peak), 3.21 (s, 3H), 2.15-2.03 (m, 2H), 1.45 (t, J=7.1 Hz, 3H), 1.24 (d, J=6.2 Hz, 3H); m/z (APCI+) for (C$_{23}$H$_{28}$N$_8$O), 433.3 (M+H)$^+$.

Example 62: 4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one

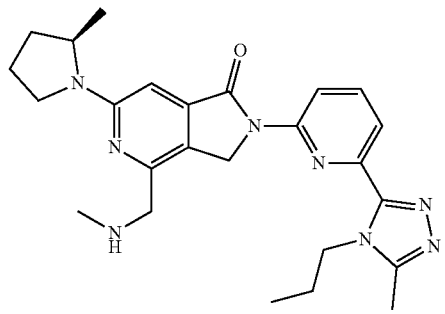

Ex-62

Step 1: tert-butyl ({6-chloro-2-[6-(5-methyl-1,3,4-oxadiazol-2-yl)pyridin-2-yl]-1-oxo-2,3-dihydro-1H-pyrrolo[3,4-c]pyridin-4-yl}methyl)methylcarbamate

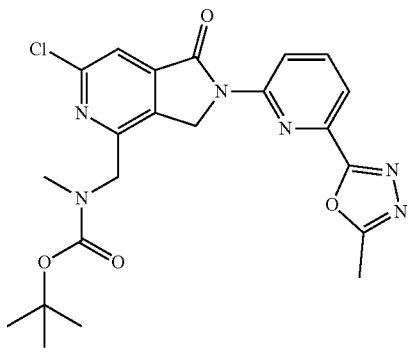 [SMILES: Cc1nnc(-c2cccc(N3Cc4c(cc(Cl)nc4CN(C)C(=O)OC(C)(C)C)C3=O)n2)o1]

A mixture of Intermediate 2 (200 mg, 0.642 mmol), Intermediate 4 (154 mg, 0.642 mmol), K$_2$CO$_3$ (195 mg, 1.41 mmol), CuI (30.5 mg, 0.160 mmol), and N,N-dimethylethylenediamine (28.3 mg, 0.321 mmol) in MeCN (2.0 mL) was sparged with N$_2$ for 5 min and then stirred at 120° C. for 100 min under microwave irradiation. LCMS analysis showed consumption of the starting material. The mixture was filtered through pad of Celite® and the filtrate was concentrated to dryness. The residue was purified by flash chromatography (SiO$_2$, 0-70% [8:1:1 EtOAc/MeOH/DCM]/heptane) to provide tert-butyl ({6-chloro-2-[6-(5-methyl-1,3,4-oxadiazol-2-yl)pyridin-2-yl]-1-oxo-2,3-dihydro-1H-pyrrolo[3,4-c]pyridin-4-yl}methyl)methylcarbamate (217 mg, 72% yield) as a white solid. $^1$H NMR (400 MHz, DMSO-d$_6$) b 8.68 (d, J=8.5 Hz, 1H), 8.22-8.14 (m, 1H), 8.00 (d, J=7.6 Hz, 1H), 7.87 (s, 1H), 5.21 (s, 2H), 4.71 (s, 2H), 3.29 (s, 3H), 2.64 (s, 3H), 1.43 (s, 4H), 1.36 (s, 5H); m/z (ESI+) for (C$_{22}$H$_{23}$ClN$_6$O$_4$), 471.3 (M+H)$^+$.

Step 2: tert-butyl ({6-chloro-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)methylcarbamate

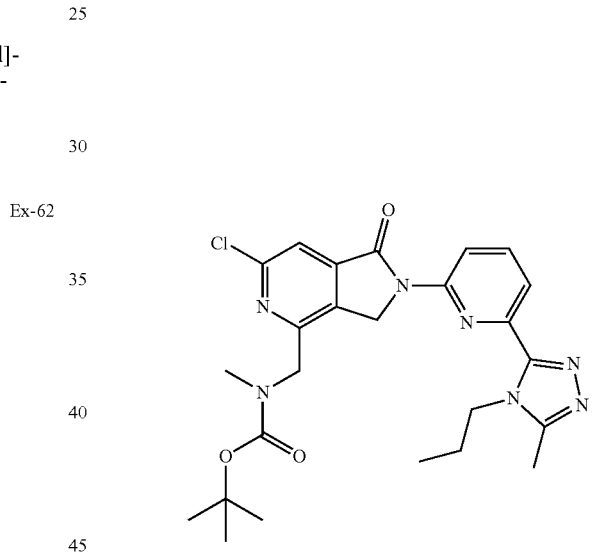

This reaction was carried out in two parallel batches. To a mixture of tert-butyl ({6-chloro-2-[6-(5-methyl-1,3,4-oxadiazol-2-yl)pyridin-2-yl]-1-oxo-2,3-dihydro-1H-pyrrolo[3,4-c]pyridin-4-yl}methyl)methylcarbamate (100 mg, 0.212 mmol) and acetic acid (31.9 mg, 0.531 mmol) in MeCN (2.5 mL) was added N-propylamine hydrochloride (203 mg, 2.12 mmol) and TEA (215 mg, 2.12 mmol). The reaction was stirred at 100° C. for 16 h. The mixture was concentrated to dryness. The combined crude reaction residues were purified by flash chromatography (12 g SiO$_2$, 40-100% EtOAc/heptane then 10% MeOH/EtOAc) to provide tert-butyl ({6-chloro-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)methylcarbamate (68.4 mg, 31% yield) as an off-white foam. $^1$H NMR (600 MHz, DMSO-d$_6$) δ 8.59 (d, J=8.4 Hz, 1H), 8.15-8.09 (m, 1H), 7.96 (d, J=7.6 Hz, 1H), 7.87 (s, 1H), 5.26-5.15 (m, 2H), 4.65 (s, 2H), 4.53-4.45 (m, 2H), 2.93 (s, 3H), 2.49 (s, 3H), 1.77-1.68 (m, 2H), 1.37 (s, 5H), 1.23 (s, 4H), 0.86 (t, J=7.4 Hz, 3H); m/z (ESI+) for ($C_{25}H_{30}ClN_7O_3$), 512.3 (M+H)+.

Step 3: 4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one, trifluoroacetate

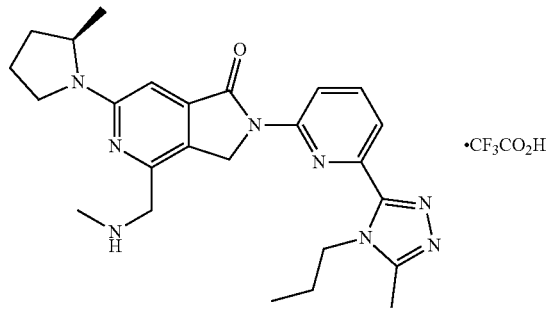 [SMILES: CCCn1c(C)nnc1-c1cccc(N2Cc3c(cc(N4CCC[C@H]4C)nc3CNC)C2=O)n1 ; "·CF3CO2H"]

·CF$_3$CO$_2$H

A mixture of tert-butyl ({6-chloro-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)methylcarbamate (50.0 mg, 0.098 mmol), (2R)-2-methylpyrrolidine (41.6 mg, 0.488 mmol), Cs$_2$CO$_3$ (95.5 mg, 0.293 mmol), and RuPhos-Pd G3 (12.3 mg, 0.0146 mmol) was sparged with N$_2$ for 5 min and then stirred at 100° C. for 18 h. The mixture was cooled to room temperature and filtered through Celite®. The filter cake was washed with 10% MeOH/EtOAc. The combined filtrate was concentrated to dryness. The residue was dissolved in DCM (1.5 mL) and TFA (0.6 mL) was added. The mixture was stirred for 30 min and then concentrated to dryness. The residue was purified by preparative HPLC with a Waters Sunfire C-18 column (19×100 mm, 5 µm particle size), which was eluted with 5-100% MeCN/H$_2$O (+0.05% TFA) with a flow rate of 25 mL/min to provide 4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one, isolated as a trifluoroacetate salt (38 mg, 68% yield) as a solid. $^1$H NMR (400 MHz, DMSO-d$_6$) δ 8.85 (s, 3H), 8.63 (d, J=8.4 Hz, 1H), 8.16-8.06 (m, 1H), 7.96 (d, J=7.6 Hz, 1H), 6.75 (s, 1H), 5.10 (s, 2H), 4.44 (dd, J=8.6, 6.6 Hz, 2H), 4.38-4.31 (m, 3H), 3.65 (t, J=9.0 Hz, 1H), 2.81-2.73 (m, 3H), 2.54 (s, 3H), 2.16-1.96 (m, 4H), 1.85-1.71 (m, 3H), 1.20 (d, J=6.2 Hz, 3H), 0.93 (t, J=7.4 Hz, 3H); m/z (ESI+) for (C$_{25}$H$_{32}$N$_8$O), 461.7 (M+H)+. [α]$^D_{22}$=−53.3° (c=0.5, MeOH).

Example 63: 4-[(methylamino)methyl]-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one

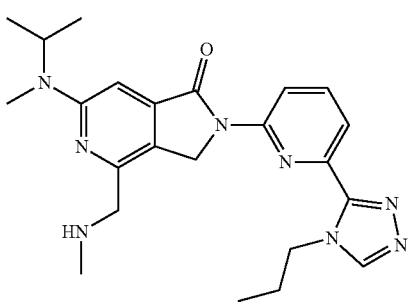

Ex-63

Step 1: methyl 6-[methyl(propan-2-yl)amino]-1-oxo-2,3-dihydro-1H-pyrrolo[3,4-c]pyridine-4-carboxylate

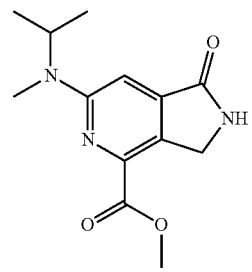 [SMILES: COC(=O)c1nc(N(C)C(C)C)cc2c1CNC2=O]

A mixture of Intermediate 11 (11.3 g, 47.1 mmol), PdCl$_2$(dppf) (2.16 g, 2.95 mmol), and TEA (14.3 g, 141 mmol) in MeOH (200 mL) was stirred at 80° C. for 40 h under an atmosphere of CO at 50 psi. TLC analysis (1:1 EtOAc/petroleum ether) showed consumption of the starting material. The reaction was concentrated to dryness. The residue was dissolved in H$_2$O (200 mL) and extracted with DCM (2×150 mL). The combined organic layers were washed with brine (200 mL), dried over Na$_2$SO$_4$, filtered, and concentrated. The residue was slurried in DCM (50 mL) for 30 min. The solids were collected by filtration. The filter cake was washed with petroleum ether (3×5 mL) and dried under vacuum. The filtrate was purified by flash chromatography (SiO$_2$, 40-70% EtOAc/DCM). The desired fractions were concentrated to dryness and combined with the above filter cake to provide methyl 6-[methyl(propan-2-yl)amino]-1-oxo-2,3-dihydro-1H-pyrrolo[3,4-c]pyridine-4-carboxylate (12.3 g, 99% yield) as a yellow solid. $^1$H NMR (400 MHz, CDCl$_3$) δ 7.12 (s, 1H), 6.79 (s, 1H), 4.89 (p, J=6.6 Hz, 1H), 4.68 (d, J=1.1 Hz, 2H), 3.97 (s, 3H), 2.96 (s, 3H), 1.21 (d, J=6.7 Hz, 6H); m/z (ESI+) for (C$_{13}$H$_{17}$N$_3$O$_3$), 263.9 (M+H)+.

Step 2: 4-(hydroxymethyl)-6-[methyl(propan-2-yl)amino]-2,3-dihydro-1H-pyrrolo[3,4-c]pyridin-1-one

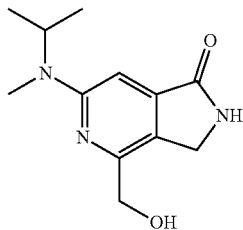 [SMILES: CC(C)N(C)c1cc2c(c(CO)n1)CNC2=O]

To a mixture of methyl 6-[methyl(propan-2-yl)amino]-1-oxo-2,3-dihydro-1H-pyrrolo[3,4-c]pyridine-4-carboxylate (1.0 g, 3.80 mmol) in THF (60 mL) was added a solution of LiAlH$_4$ (2.5 M in THF, 1.67 mL, 4.18 mmol) dropwise at 0° C. The mixture was stirred at 0° C. for 1 h and then at 20° C. for 16 h. TLC analysis (1:1 EtOAc/petroleum ether) showed consumption of the starting material. The mixture was quenched by addition of 20% aqueous NaOH (0.5 mL). To the mixture was added Na$_2$SO$_4$ (4 g). The mixture was stirred for 30 min and then filtered. The filtrate was concentrated to dryness to provide 4-(hydroxymethyl)-6-[methyl(propan-2-yl)amino]-2,3-dihydro-1H-pyrrolo[3,4-c]pyridin-1-one (890 mg, >99% yield) as a yellow solid. $^1$H NMR (400 MHz, CDCl$_3$) b 7.04 (s, 1H), 6.82 (s, 1H), 4.85 (p, J=6.6 Hz, 1H), 4.67 (d, J=4.7 Hz, 2H), 4.33 (s, 2H), 4.09 (t, J=4.6 Hz, 1H), 2.92 (s, 3H), 1.20 (d, J=6.7 Hz, 6H); m/z (ESI+) for (C$_{12}$H$_{17}$N$_3$O$_2$), 236.0 (M+H)$^+$.

Step 3: {6-[methyl(propan-2-yl)amino]-1-oxo-2,3-dihydro-1H-pyrrolo[3,4-c]pyridin-4-yl}methyl methanesulfonate

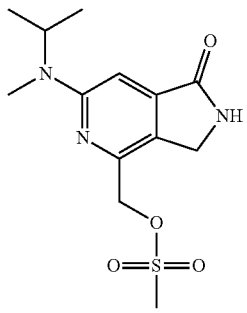 [SMILES: CC(C)N(C)c1cc2c(c(COS(C)(=O)=O)n1)CNC2=O]

To a mixture of 4-(hydroxymethyl)-6-[methyl(propan-2-yl)amino]-2,3-dihydro-1H-pyrrolo[3,4-c]pyridin-1-one (890 mg, 3.78 mmol) and TEA (957 mg, 9.46 mmol) in THF (20.0 mL) was added MsCl (953 mg, 8.23 mmol) dropwise at 0° C. under an atmosphere of N$_2$. The mixture was stirred at 0° C. LCMS analysis showed consumption of the starting material. The reaction was diluted with saturated aqueous Na$_2$CO$_3$ (30 mL) and extracted with EtOAc (2×20 mL). The combined organic layers were washed with brine (30 mL), dried over Na$_2$SO$_4$, filtered, and concentrated to provide {6-[methyl(propan-2-yl)amino]-1-oxo-2,3-dihydro-1H-pyrrolo[3,4-c]pyridin-4-yl}methyl methanesulfonate (1.2 g, >99% yield) as a yellow solid, which was taken on without further purification. m/z (ESI+) for (C$_{13}$H$_{19}$N$_3$O$_4$S), 314.0 (M+H)$^+$.

Step 4: 4-[(methylamino)methyl]-6-[methyl(propan-2-yl)amino]-2,3-dihydro-1H-pyrrolo[3,4-c]pyridin-1-one

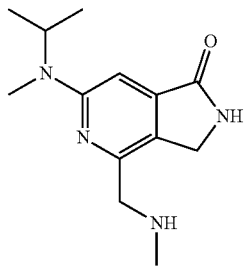 [SMILES: CNCc1nc(N(C)C(C)C)cc2c1CNC2=O]

To a mixture of {6-[methyl(propan-2-yl)amino]-1-oxo-2,3-dihydro-1H-pyrrolo[3,4-c]pyridin-4-yl}methyl methanesulfonate (1.18 g, 3.78 mmol) in THF (20.0 mL) was added a solution of methylamine (2.0 M in THF, 37.8 mL, 75.6 mmol). The mixture was stirred for 1 h. LCMS analysis indicated consumption of the starting material. The mixture was concentrated to dryness to provide 4-[(methylamino)methyl]-6-[methyl(propan-2-yl)amino]-2,3-dihydro-1H-pyrrolo[3,4-c]pyridin-1-one (940 mg, >99% yield) as a brown solid, which was taken on without further purification. m/z (ESI+) for (C$_{13}$H$_{20}$N$_4$O), 249.0 (M+H)$^+$.

Step 5: tert-butyl methyl({6-[methyl(propan-2-yl)amino]-1-oxo-2,3-dihydro-1H-pyrrolo[3,4-c]pyridin-4-yl}methyl)carbamate

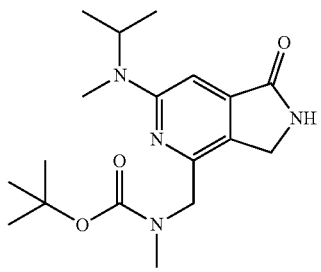 [SMILES: CC(C)N(C)c1cc2c(c(CN(C)C(=O)OC(C)(C)C)n1)CNC2=O]

To a solution of 4-[(methylamino)methyl]-6-[methyl(propan-2-yl)amino]-2,3-dihydro-1H-pyrrolo[3,4-c]pyridin-1-one (940 mg, 11.4 mmol) and TEA (1.15 g, 11.4 mmol) in DCM (20.0 mL) was added Boc$_2$O (1.65 mg, 7.57 mmol). The mixture was stirred for 30 min. LCMS analysis showed consumption of the starting material. The reaction was concentrated to dryness. The residue was purified by flash chromatography (SiO$_2$, EtOAc) to provide tert-butyl methyl ({6-[methyl(propan-2-yl)amino]-1-oxo-2,3-dihydro-1H-pyrrolo[3,4-c]pyridin-4-yl}methyl)carbamate (600 mg, 46% yield) as a yellow solid. $^1$H NMR (400 MHz, CDCl$_3$) δ 6.81 (s, 1H), 6.57-6.42 (m, 1H), 4.91 (p, J=6.6 Hz, 1H), 4.48 (s, 2H), 4.35 (d, J=12.4 Hz, 2H), 2.92 (s, 3H), 2.88 (s, 3H), 1.48 (s, 5H), 1.41 (s, 4H), 1.17 (d, J=6.7 Hz, 6H); m/z (ESI+) for (C$_{18}$H$_{28}$N$_4$O$_3$), 349.2 (M+H)$^+$.

Step 6: tert-butyl methyl({6-[methyl(propan-2-yl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate

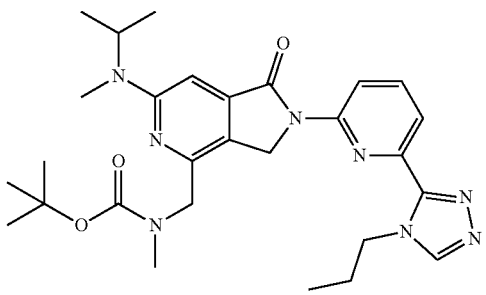 [SMILES: CCCn1cnnc1-c1cccc(N2Cc3c(cc(N(C)C(C)C)nc3CN(C)C(=O)OC(C)(C)C)C2=O)n1]

To a mixture of tert-butyl methyl({6-[methyl(propan-2-yl)amino]-1-oxo-2,3-dihydro-1H-pyrrolo[3,4-c]pyridin-4-yl}methyl)carbamate (80 mg, 0.23 mmol), Intermediate 13 (64.4 mg, 0.24 mmol), and $K_3PO_4$ (146 mg, 0.69 mmol) in 1,4-dioxane (3.0 mL) was added $Pd_2(dba)_3$ (21.0 mg, 0.023 mmol) and Xantphos (26.6 mg, 0.046 mmol). The mixture was sparged with $N_2$ for 2 min and then stirred at 85° C. for 18 h. LCMS analysis indicated consumption of the starting material. The reaction was concentrated to dryness. The residue was purified by flash chromatography ($SiO_2$, 1:10 MeOH/EtOAc) to provide tert-butyl methyl({6-[methyl(propan-2-yl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (90 mg, 73% yield) as a brown solid. $^1H$ NMR (400 MHz, $CDCl_3$) δ 8.71 (d, J=8.4 Hz, 1H), 8.23 (s, 1H), 8.14-8.06 (m, 1H), 7.96-7.87 (m, 1H), 6.86 (s, 1H), 5.04 (s, 1H), 5.00-4.90 (m, 2H), 4.68-4.57 (m, 2H), 4.51 (s, 2H), 3.03-2.93 (m, 3H), 2.92 (s, 3H), 1.90 (s, 2H), 1.41 (s, 5H), 1.33 (s, 4H), 1.20 (d, J=6.7 Hz, 6H), 0.98-0.91 (m, 3H); m/z (ESI+) for ($C_{28}H_{38}N_8O_3$), 535.4 (M+H)$^+$.

Step 7: 4-[(methylamino)methyl]-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one, hydrochloride

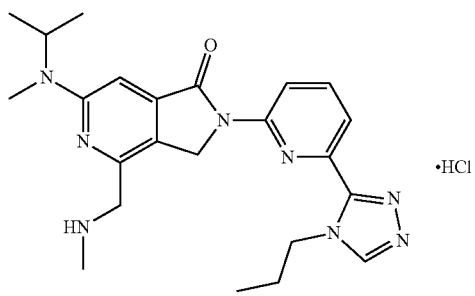 [SMILES: CCCn1cnnc1-c1cccc(N2Cc3c(cc(N(C)C(C)C)nc3CNC)C2=O)n1 ; Cl]

To a solution of tert-butyl methyl({6-[methyl(propan-2-yl)amino]-1-oxo-2-[6-(4-propyl-4H-1,2,4-triazol-3-yl)pyridin-2-yl]-2,3-dihydro-1H-pyrrolo[3,4-c]pyridin-4-yl}methyl)carbamate (90 mg, 0.17 mmol) in EtOAc (5.0 mL) was added a solution of HCl (4.0 M in EtOAc, 2.0 mL) at 0° C. The mixture was stirred at room temperature for 4 h. LCMS analysis showed consumption of the starting material. The reaction was concentrated under vacuum and then dried by lyophilization to provide 4-[(methylamino)methyl]-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one, isolated as a hydrochloride (62.9 mg, 79% yield) as a yellow solid. $^1H$ NMR (400 MHz, DMSO-$d_6$) δ 9.21 (s, 1H), 8.65 (dd, J=8.4, 0.9 Hz, 1H), 8.17-8.10 (m, 1H), 7.99 (dd, J=7.6, 0.9 Hz, 1H), 6.88 (s, 1H), 5.10 (s, 2H), 5.05-4.92 (m, 1H), 4.60 (dd, J=8.1, 6.4 Hz, 2H), 4.31 (s, 2H), 2.90 (s, 3H), 2.71 (s, 3H), 1.88 (h, J=7.3 Hz, 2H), 1.14 (d, J=6.6 Hz, 6H), 0.92 (t, J=7.4 Hz, 3H); m/z (ESI+) for ($C_{23}H_{30}N_8O$), 435.3 (M+H)$^+$.

Example 64: 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one

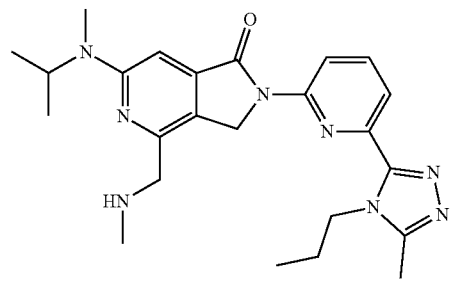

Step 1: tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate

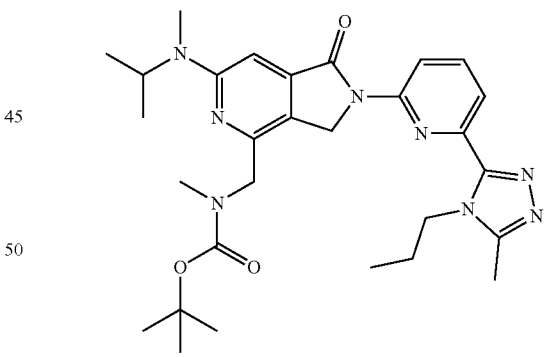

To a mixture of tert-butyl methyl({6-[methyl(propan-2-yl)amino]-1-oxo-2,3-dihydro-1H-pyrrolo[3,4-c]pyridin-4-yl}methyl)carbamate (see synthesis in Example 63) (200 mg, 0.574 mmol), Intermediate 17 (169 mg, 0.603 mmol), and $K_3PO_4$ (366 mg, 1.72 mmol) in 1,4-dioxane (10.0 mL) under an atmosphere of $N_2$ were added $Pd_2(dba)_3$ (52.6 mg, 0.0574 mmol) and Xantphos (66.4 mg, 0.115 mmol). The mixture was sealed and stirred at 85° C. for 18 h. TLC analysis (EtOAc) showed consumption of the starting material. The reaction was concentrated to dryness and the residue was purified by flash chromatography ($SiO_2$, 1:20 MeOH/EtOAc). The following steps were done five consecutive times: The residue was dissolved in 1:10 MeOH/EtOAc (30 mL) and Ultra-pure Si-Thio SiO₂ (1 g) was added. The mixture was stirred at 50° C. for 30 min. The mixture was filtered and the filter cake was washed with 1:10 MeOH/EtOAc (3×30 mL). The filtrate was concentrated to dryness. The resultant residue was purified by flash chromatography (SiO₂, 1:10 MeOH/EtOAc) to provide tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate (250 mg, 79% yield) as a yellow solid. ¹H NMR (400 MHz, CDCl₃) δ 8.68 (d, J=9.4 Hz, 1H), 8.04 (d, J=7.7 Hz, 1H), 7.94-7.85 (m, 1H), 6.86 (s, 1H), 5.02 (s, 1H), 4.94 (d, J=9.4 Hz, 2H), 4.53 (s, 3H), 3.01-2.94 (m, 4H), 2.92 (s, 3H), 2.55 (s, 3H), 1.75 (s, 2H), 1.47-1.27 (m, 9H), 1.20 (d, J=6.7 Hz, 6H), 0.90 (t, J=7.3 Hz, 3H); LCMS m/z (ESI+) for (C₂₉H₄₀N₈O₃), 549.6 (M+H)⁺.

Step 2: 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one, hydrochloride

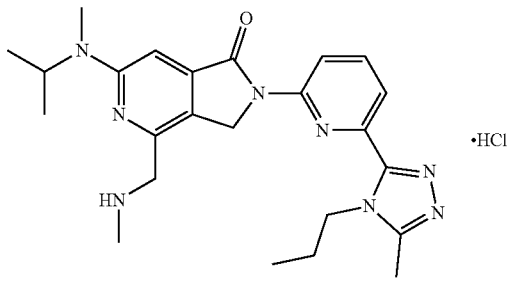 [SMILES: CCCn1c(C)nnc1-c1cccc(N2Cc3c(cc(N(C)C(C)C)nc3CNC)C2=O)n1 ; Cl]

A solution of tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate (250 mg, 0.456 mmol) in EtOAc (5.0 mL) was cooled to 0° C. and treated with a solution of HCl (4.0 N in EtOAc, 3.0 mL). The mixture was stirred at 25° C. for 1 h. LCMS showed consumption of the starting material. The mixture was concentrated to dryness. The residue was purified by preparative HPLC with a Phenomenex Gemini-NX column (150×30 mm, 5 μm particle size), which was eluted with 19-39% MeCN/H₂O (+0.05% HCl) with a flow rate of 30 mL/min to provide 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one, isolated as a hydrochloric acid salt (140 mg, 63% yield) as a yellow solid. ¹H NMR (400 MHz, DMSO-d₆) δ 9.30 (s, 2H), 8.71 (d, J=8.5 Hz, 1H), 8.21-8.14 (m, 1H), 7.98 (d, J=7.6 Hz, 1H), 6.92 (s, 1H), 5.15 (s, 2H), 5.11-4.98 (m, 1H), 4.58-4.48 (m, 2H), 4.30 (t, J=5.8 Hz, 2H), 2.93 (s, 3H), 2.71 (t, J=5.4 Hz, 3H), 2.67 (s, 3H), 1.87 (p, J=7.5 Hz, 2H), 1.17 (d, J=6.6 Hz, 6H), 0.97 (t, J=7.4 Hz, 3H); LCMS m/z (ESI+) for (C₂₄H₃₂N₈O), 449.2 (M+H)⁺.

Alternatively, Example 64 was also prepared as follows:

Step 1: tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate To a mixture of tert-butyl methyl({6-[methyl(propan-2-yl)amino]-1-oxo-2,3-dihydro-1H-pyrrolo[3,4-c]pyridin-4-yl}methyl)carbamate (see synthesis in Example 63) (7000 mg, 20.09 mmol), Intermediate 17 (5650, 20.1 mmol), and K₃PO₄ (12800 mg, 60.3 mmol) in 1,4-dioxane (70 mL) under an atmosphere of N₂ were added Pd₂(dba)₃ (1840 mg, 2.01 mmol) and Xantphos (2320 mg, 4.02 mmol). The mixture was sealed and stirred at 85° C. for 18 h. TLC analysis (EtOAc) showed consumption of the starting material. The reaction mixture was filtered through a pad of Celite® and the filter cake was washed with EtOAc (250 mL). The filtrate was concentrated to a residue which was triturated with 35 mL of a 60:40 mixture of EtOAc:H₂O. The suspension was then filtered and filter cake was dried under vacuum to yield tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate (10400 mg, 94% yield) as a yellow solid. ¹H NMR (400 MHz, CDCl₃) δ 8.68 (d, J=9.4 Hz, 1H), 8.04 (d, J=7.7 Hz, 1H), 7.94-7.85 (m, 1H), 6.86 (s, 1H), 5.02 (s, 1H), 4.94 (d, J=9.4 Hz, 2H), 4.53 (s, 3H), 3.01-2.94 (m, 4H), 2.92 (s, 3H), 2.55 (s, 3H), 1.75 (s, 2H), 1.47-1.27 (m, 9H), 1.20 (d, J=6.7 Hz, 6H), 0.90 (t, J=7.3 Hz, 3H); LCMS m/z (ESI+) for (C₂₉H₄₀N₈O₃), 549.3 (M+H)⁺.

Step 2: 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one A solution of tert-butyl methyl({6-[methyl(propan-2-yl)amino]-2-[6-(5-methyl-4-propyl-4H-1,2,4-triazol-3-yl)pyridin-2-yl]-1-oxo-2,3-dihydro-1H-pyrrolo[3,4-c]pyridin-4-yl}methyl)carbamate (10400 mg, 18.95 mmol) in EtOAc (15.0 mL) and MeOH (5 mL) was cooled to 0° C. and treated with a solution of HCl (4.0 N in EtOAc, 100 mL). The mixture was stirred at 25° C. for 4 h. TLC (EtOAc, 254 nM, UV) showed consumption of the starting material. The reaction mixture was filtered and concentrated to a residue which was dissolved in water (200 mL) and extracted with EtOAc (150 mL). To the aqueous layer was added DCM (250 mL) and solid NaHCO₃ was then added until the pH of the mixture was ~8. The layers were separated, and the aqueous layer was extracted with DCM (2×100 mL). The combined organic layers were washed with brine (150 mL), dried over sodium sulfate, filtered and concentrated to a residue. The residue was triturated with 22 mL of a 10:1 mixture of EtOAc:MeCN and the suspension was filtered, the filter cake was vacuum dried to give 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one (5.59 g, 66% yield) as a yellow solid. ¹H NMR (400 MHz, CDCl₃) δ 8.73 (d, J=8.5 Hz, 1H), 8.13 (d, J=7.8 Hz, 1H), 7.92 (t, J=8.0 Hz, 1H), 6.88 (s, 1H), 5.05 (s, 2H), 4.98-4.92 (m, 1H), 4.53-4.45 (m, 2H), 3.88 (s, 2H), 2.95 (s, 3H), 2.58 (s, 3H), 2.55 (s, 3H), 1.91-1.85 (m, 2H), 1.23 (d, J=6.8 Hz, 6H), 1.04 (t, J=7.4 Hz, 3H); LCMS m/z (ESI+) for (C₂₄H₃₂N₈O), 449.2 (M+H)⁺.

Example 65: 2-[6-(4-cyclobutyl-4H-1,2,4-triazol-3-yl)pyridin-2-yl]-4-[(methylamino)methyl]-6-(1-methylcyclopropyl)-2,3-dihydro-1H-pyrrolo[3,4-c]pyridin-1-one

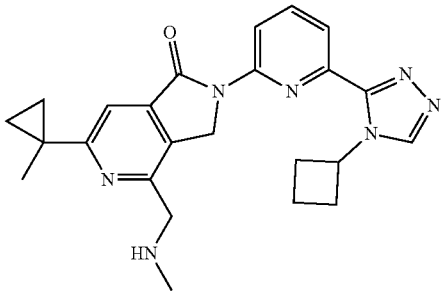

Ex-65

Step 1: methyl 6-[4-{[(tert-butoxycarbonyl)(methyl)amino]methyl}-6-(1-methylcyclopropyl)-1-oxo-1,3-dihydro-2H-pyrrolo[3,4-c]pyridin-2-yl]pyridine-2-carboxylate

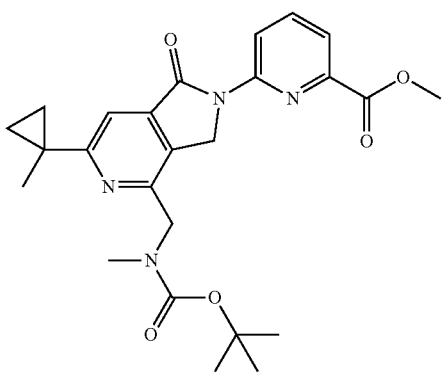 [SMILES: COC(=O)c1cccc(N2Cc3c(cc(C4(C)CC4)nc3CN(C)C(=O)OC(C)(C)C)C2=O)n1]

To a mixture of Intermediate 8 (1.50 g, 4.53 mmol), methyl 6-bromopyridine-2-carboxylate (1.17 g, 5.43 mmol) and K$_3$PO$_4$ (2.88 g, 13.6 mmol) in 1,4-dioxane (50.0 mL) under N$_2$ were added Pd$_2$(dba)$_3$ (414 mg, 0.453 mmol) and Xantphos (524 mg, 0.905 mmol). The mixture was sparged with N$_2$ for 2 min and then sealed and stirred at 85° C. for 5 h. LCMS analysis showed consumption of the starting material. The reaction was diluted with H$_2$O (50 mL) and extracted with EtOAc (3×50 mL). The combined organic layers were washed with brine (50 mL), dried over Na$_2$SO$_4$, filtered, and concentrated. The residue was purified by flash chromatography (SiO$_2$, 1:3 EtOAc/petroleum ether) to provide methyl 6-[4-{[(tert-butoxycarbonyl)(methyl)amino]methyl}-6-(1-methylcyclopropyl)-1-oxo-1,3-dihydro-2H-pyrrolo[3,4-c]pyridin-2-yl]pyridine-2-carboxylate (1.89 g, 89% yield) as a brown solid. $^1$H NMR (400 MHz, CDCl$_3$) δ 8.95-8.61 (m, 1H), 7.96-7.83 (m, 2H), 7.78-7.62 (m, 1H), 5.18 (s, 2H), 4.64 (d, J=10.3 Hz, 2H), 3.99 (s, 3H), 2.96 (s, 3H), 1.58 (s, 3H), 1.53-1.41 (m, 9H), 1.33 (q, J=3.7 Hz, 2H), 0.95-0.77 (m, 2H); LCMS m/z (ESI+) for (C$_{25}$H$_{30}$N$_4$O$_5$), 467.4 (M+H)$^+$.

Step 2: tert-butyl ({2-[6-(hydrazinecarbonyl)pyridin-2-yl]-6-(1-methylcyclopropyl)-1-oxo-2,3-dihydro-1H-pyrrolo[3,4-c]pyridin-4-yl}methyl)methylcarbamate

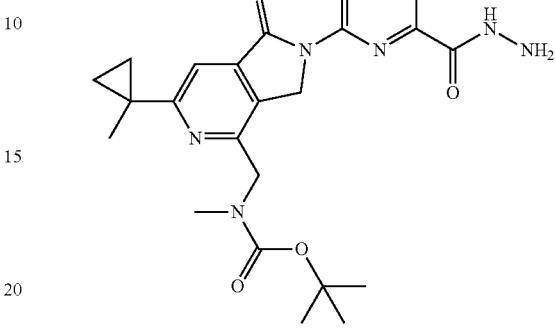

To a suspension of methyl 6-[4-{[(tert-butoxycarbonyl)(methyl)amino]methyl}-6-(1-methylcyclopropyl)-1-oxo-1,3-dihydro-2H-pyrrolo[3,4-c]pyridin-2-yl]pyridine-2-carboxylate (1.89 g, 4.05 mmol) in MeOH (50.0 mL) was added hydrazine monohydrate (715 mg, 12.1 mmol). The mixture was stirred for 3 h. TLC analysis (1:3 EtOAc/petroleum ether) showed consumption of the starting material. The reaction was concentrated to dryness to provide tert-butyl ({2-[6-(hydrazinecarbonyl)pyridin-2-yl]-6-(1-methylcyclopropyl)-1-oxo-2,3-dihydro-1H-pyrrolo[3,4-c]pyridin-4-yl}methyl)methylcarbamate (1.74 g, 92% yield) as a yellow solid, which was taken on without further purification. $^1$H NMR (400 MHz, DMSO-d$_6$) δ 10.09-9.54 (m, 1H), 8.73-8.52 (m, 1H), 8.17-7.98 (m, 1H), 7.82 (d, J=7.4 Hz, 1H), 7.56 (s, 1H), 5.29 (d, J=8.3 Hz, 2H), 4.81-4.07 (m, 4H), 2.93 (s, 3H), 1.55 (s, 3H), 1.44 (br. s, 4H), 1.28-1.15 (m, 7H), 0.94-0.70 (m, 2H); LCMS m/z (ESI+) for (C$_{24}$H$_{30}$N$_6$O$_4$), 467.3 (M+H)$^+$.

Step 3: tert-butyl {[2-(6-{(2E)-2-[(dimethylamino)methylidene]hydrazinecarbonyl}pyridin-2-yl)-6-(1-methylcyclopropyl)-1-oxo-2,3-dihydro-1H-pyrrolo[3,4-c]pyridin-4-yl]methyl}methylcarbamate

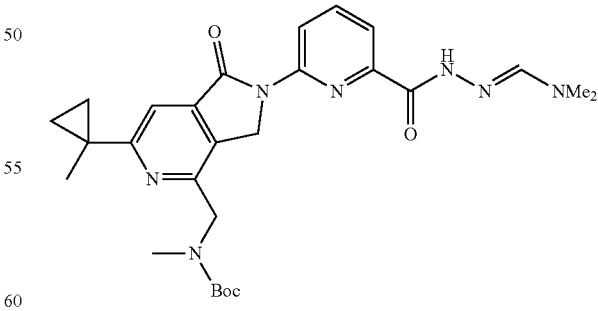

A solution of tert-butyl ({2-[6-(hydrazinecarbonyl)pyridin-2-yl]-6-(1-methylcyclopropyl)-1-oxo-2,3-dihydro-1H-pyrrolo[3,4-c]pyridin-4-yl}methyl)methylcarbamate (1.74 g, 3.84 mmol) in N,N-dimethyldimethoxymethylamine (40.0 mL) was stirred at 80° C. for 6 h. TLC analysis (1:10 MeOH/EtOAc) showed consumption of the starting material. The mixture was concentrated to dryness. The residue was slurried with TBME (40 mL) for 20 min. The solids were collected by filtration and dried under vacuum to provide tert-butyl {[2-(6-{(2E)-2-[(dimethylamino)methylidene]hydrazinecarbonyl}pyridin-2-yl)-6-(1-methylcyclopropyl)-1-oxo-2,3-dihydro-1H-pyrrolo[3,4-c]pyridin-4-yl]methyl}methylcarbamate (1.76 g, 88% yield) as a white solid. $^1$H NMR (400 MHz, DMSO-d$_6$) δ 10.77-10.44 (m, 1H), 8.82-8.34 (m, 1H), 8.25-7.98 (m, 2H), 7.82 (d, J=7.5 Hz, 1H), 7.58 (s, 1H), 5.30 (br. d, J=11.0 Hz, 2H), 4.66 (s, 2H), 2.92 (s, 3H), 2.91 (s, 6H), 1.56 (s, 3H), 1.43 (s, 4H), 1.25 (d, J=6.9 Hz, 5H), 1.11 (s, 2H), 0.93-0.73 (m, 2H); LCMS m/z (ESI+) for (C$_{27}$H$_{35}$N$_7$O$_4$), 522.4 (M+H)$^+$.

Step 4: tert-butyl ({2-[6-(4-cyclobutyl-4H-1,2,4-triazol-3-yl)pyridin-2-yl]-6-(1-methylcyclopropyl)-1-oxo-2,3-dihydro-1H-pyrrolo[3,4-c]pyridin-4-yl}methyl)methylcarbamate

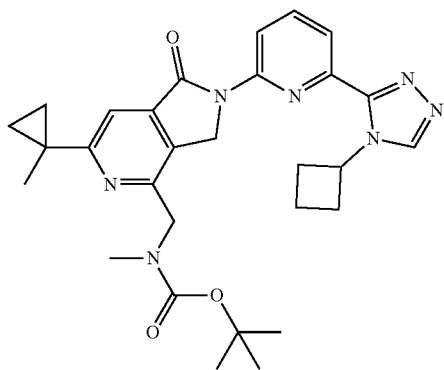 [SMILES: CN(Cc1nc(C2(C)CC2)cc2c1CN(c1cccc(-c3nncn3C3CCC3)n1)C2=O)C(=O)OC(C)(C)C]

To a suspension of tert-butyl {[2-(6-{(2E)-2-[(dimethylamino)methylidene]hydrazinecarbonyl}pyridin-2-yl)-6-(1-methylcyclopropyl)-1-oxo-2,3-dihydro-1H-pyrrolo[3,4-c]pyridin-4-yl]methyl}methylcarbamate (180 mg, 0.345 mmol) in MeCN (2.0 mL) were added cyclobutanamine (61.4 mg, 0.863 mmol) and acetic acid (0.4 mL). The mixture was stirred at 95° C. for 3 h. TLC analysis (1:10 MeOH/EtOAc) showed consumption of the starting material. The solution was concentrated to dryness. The residue was dissolved in H$_2$O (20 mL) and extracted with EtOAc (3×20 mL). The combined organic layers were washed with brine (30 mL), dried over Na$_2$SO$_4$, filtered, and concentrated. The residue was purified by flash chromatography (SiO$_2$, 1:10 MeOH/EtOAc) to provide tert-butyl ({2-[6-(4-cyclobutyl-4H-1,2,4-triazol-3-yl)pyridin-2-yl]-6-(1-methylcyclopropyl)-1-oxo-2,3-dihydro-1H-pyrrolo[3,4-c]pyridin-4-yl}methyl)methylcarbamate (104 mg, 57% yield) as a white glass. $^1$H NMR (400 MHz, DMSO-d$_6$) δ 9.05 (br. s, 1H), 8.62 (br. d, J=8.3 Hz, 1H), 8.19-8.01 (m, 1H), 7.91 (br. s, J=7.5 Hz, 1H), 7.61 (s, 1H), 5.74-5.55 (m, 1H), 5.25 (s, 2H), 4.61 (s, 2H), 2.97-2.88 (m, 3H), 1.93-1.75 (m, 2H), 1.57 (s, 3H), 1.47-1.10 (m, 15H), 0.94-0.73 (m, 2H); LCMS m/z (ESI+) for (C$_{29}$H$_{35}$N$_7$O$_3$), 530.3 (M+H)$^+$.

Step 5: 2-[6-(4-cyclobutyl-4H-1,2,4-triazol-3-yl)pyridin-2-yl]-4-[(methylamino)methyl]-6-(1-methylcyclopropyl)-2,3-dihydro-1H-pyrrolo[3,4-c]pyridin-1-one

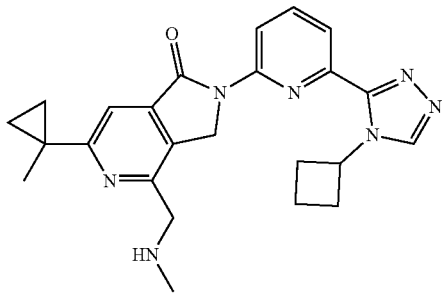 [SMILES: CNCc1nc(C2(C)CC2)cc2c1CN(c1cccc(-c3nncn3C3CCC3)n1)C2=O]

A solution of tert-butyl ({2-[6-(4-cyclobutyl-4H-1,2,4-triazol-3-yl)pyridin-2-yl]-6-(1-methylcyclopropyl)-1-oxo-2,3-dihydro-1H-pyrrolo[3,4-c]pyridin-4-yl}methyl)methylcarbamate (104 mg, 0.196 mmol) in DCM (5.0 mL) was cooled to 0° C. and treated with TFA (3.0 mL). The mixture was stirred at 15° C. for 2 h. LCMS analysis showed consumption of the starting material. The mixture was concentrated to dryness. The residue was dissolved in H$_2$O (20 mL) and basified with saturated aqueous Na$_2$CO$_3$ (~3 mL) to pH~9. The mixture was extracted with DCM (2×20 mL). The combined organic layers were washed with brine (2×15 mL), dried over Na$_2$SO$_4$, filtered, and concentrated. The residue was purified by preparative HPLC with an Agela DuraShell C18 column (150×25 mm, 5 μm particle size), which was eluted with 33-63% MeCN/H$_2$O (+0.04% NH$_4$OH, +10 mM NH$_4$HCO$_3$) with a flow rate of 2 mL/min. The desired fractions were re-purified by preparative HPLC with a Phenomenex Gemini NX column (150×30 mm, 5 μm particle size), which was eluted with 36-76% MeCN/H$_2$O (+0.05% NH$_4$OH) with a flow rate of 30 mL/min to provide Example 65 (15.4 mg, 18% yield) as a white solid. $^1$H NMR (400 MHz, DMSO-d$_6$) δ 9.09 (s, 1H), 8.64 (d, J=8.3 Hz, 1H), 8.24-8.01 (m, 1H), 7.94 (d, J=7.6 Hz, 1H), 7.57 (s, 1H), 5.74 (p, J=8.6 Hz, 1H), 5.35 (s, 2H), 3.94 (s, 2H), 2.61-2.54 (m, 2H), 2.48-2.42 (m, 2H), 2.35 (s, 3H), 1.98-1.78 (m, 2H), 1.56 (s, 3H), 1.38-1.09 (m, 2H), 1.06-0.66 (m, 2H); LCMS m/z (ESI+) for (C$_{24}$H$_{27}$N$_7$O), 430.2 (M+H)$^+$.

Example 66: 2-[6-(4,5-diethyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one Ex-66

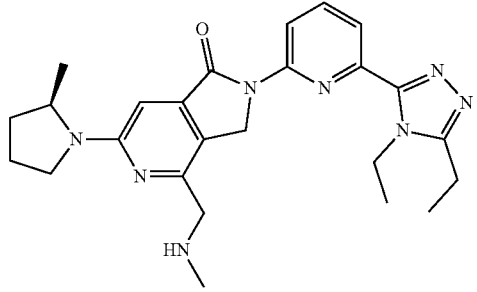

Step 1: tert-butyl ({2-[6-(4,5-diethyl-4H-1,2,4-tri-azol-3-yl)pyridin-2-yl]-6-[(2R)-2-methylpyrrolidin-1-yl]-1-oxo-2,3-dihydro-1H-pyrrolo[3,4-c]pyridin-4-yl}methyl)methylcarbamate

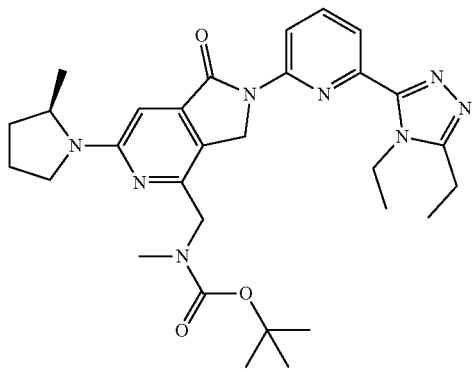 [SMILES: CCc1nnc(-c2cccc(N3Cc4c(cc(N5CCC[C@H]5C)nc4CN(C)C(=O)OC(C)(C)C)C3=O)n2)n1CC]

To a solution of Intermediate 19 (80.0 mg, 0.222 mmol), Intermediate 18 (93.6 mg, 0.333 mmol), and K$_3$PO$_4$ (141 mg, 0.666 mmol) in 1,4-dioxane (5.0 mL) under an atmosphere of N$_2$ were added Pd$_2$(dba)$_3$ (20.3 mg, 0.0223 mmol) and Xantphos (25.7 mg, 0.0444 mmol). The mixture was sparged with N$_2$ for 2 min and then sealed and stirred at 85° C. for 18 h. TLC analysis (EtOAc) showed consumption of the starting material. The mixture was concentrated to dryness. The residue was purified by flash chromatography (SiO$_2$, 1:10 MeOH/EtOAc) to provide tert-butyl ({2-[6-(4,5-diethyl-4H-1,2,4-triazol-3-yl)pyridin-2-yl]-6-[(2R)-2-methylpyrrolidin-1-yl]-1-oxo-2,3-dihydro-1H-pyrrolo[3,4-c]pyridin-4-yl}methyl)methylcarbamate (120 mg, >99% yield) as a yellow solid. $^1$H NMR (400 MHz, CDCl$_3$) δ 8.69 (br. d, J=8.3 Hz, 1H), 8.09 (br. d, J=7.5 Hz, 1H), 7.97-7.73 (m, 1H), 6.72 (s, 1H), 5.14-4.90 (m, 2H), 4.73-4.43 (m, 5H), 4.31-4.16 (m, 1H), 3.70-3.52 (m, 2H), 3.44-3.29 (m, 2H), 2.99 (br. s, 3H), 2.92-2.77 (m, 2H), 2.20-1.96 (m, 3H), 1.80-1.70 (m, 1H), 1.62 (s, 9H), 1.43-1.38 (m, 3H), 1.32-1.11 (m, 3H). LCMS m/z (ESI+) for (C$_{30}$H$_{40}$N$_8$O$_3$), 561.4 (M+H)$^+$.

Step 2: 2-[6-(4,5-diethyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one, hydrochloride

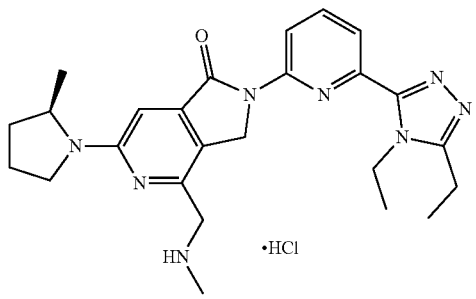 [SMILES: CCc1nnc(-c2cccc(N3Cc4c(cc(N5CCC[C@H]5C)nc4CNC)C3=O)n2)n1CC ; Cl]

A suspension of tert-butyl ({2-[6-(4,5-diethyl-4H-1,2,4-triazol-3-yl)pyridin-2-yl]-6-[(2R)-2R)-2-methylpyrrolidin-1-yl]-1-oxo-2,3-dihydro-1H-pyrrolo[3,4-c]pyridin-4-yl}methyl)methylcarbamate (120 mg, 0.222 mmol) in EtOAc (10.0 mL) was cooled to 0° C. and treated with a solution of HCl (4.0 N in EtOAc, 5.0 mL). The mixture was stirred for 2 h. LCMS analysis showed consumption of the starting material. The mixture was concentrated to dryness. The residue was purified by preparative HPLC with a Phenomenex Gemini-NX column (150×30 mm, 5 μm particle size), which was eluted with 12-42% MeCN/H$_2$O (+0.05% HCl) with a flow rate of 30 mL/min to provide 2-[6-(4,5-diethyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one, isolated as a hydrochloric acid salt (72.0 mg, 66% yield) as a yellow solid. $^1$H NMR (400 MHz, DMSO-d$_6$) δ 9.65-9.29 (m, 2H), 8.73 (d, J=8.4 Hz, 1H), 8.33-8.13 (m, 1H), 8.02 (d, J=7.6 Hz, 1H), 6.75 (s, 1H), 5.21 (s, 2H), 4.66 (q, J=7.1 Hz, 2H), 4.42-4.28 (m, 3H), 3.65 (t, J=8.7 Hz, 1H), 3.50-3.30 (m, 1H), 3.10 (q, J=7.5 Hz, 2H), 2.72 (t, J=5.3 Hz, 3H), 2.21-1.93 (m, 3H), 1.81-1.64 (m, 1H), 1.51 (t, J=7.1 Hz, 3H), 1.43 (t, J=7.5 Hz, 3H), 1.21 (d, J=6.2 Hz, 3H); LCMS m/z (ESI+) for (C$_{25}$H$_{32}$N$_8$O), 461.3 (M+H)$^+$.

Example 67: 2-[6-(4,5-diethyl-4H-1,2,4-triazol-3-yl)pyridin-2-yl]-4-[(methylamino)methyl]-6-[methyl(propan-2-yl)amino]-2,3-dihydro-1H-pyrrolo[3,4-c]pyridin-1-one

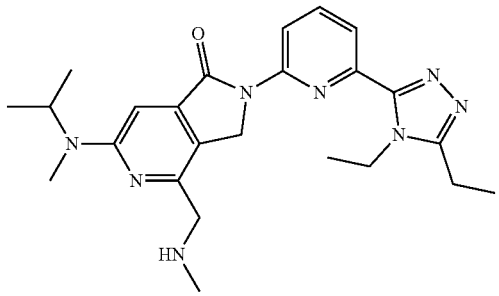

Ex-67

Step 1: tert-butyl ({2-[6-(4,5-diethyl-4H-1,2,4-triazol-3-yl)pyridin-2-yl]-6-[methyl(propan-2-yl)amino]-1-oxo-2,3-dihydro-1H-pyrrolo[3,4-c]pyridin-4-yl}methyl)methylcarbamate

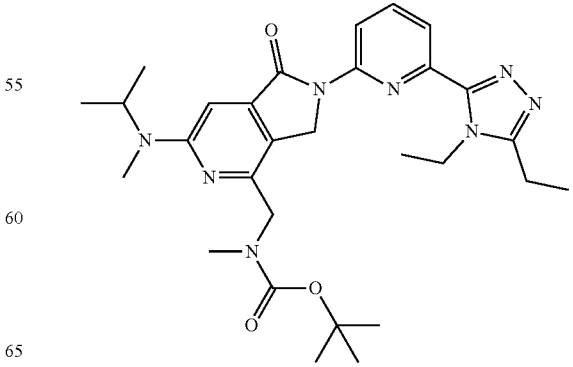

To a solution of tert-butyl methyl({6-[methyl(propan-2-yl)amino]-1-oxo-2,3-dihydro-1H-pyrrolo[3,4-c]pyridin-4-yl}methyl)carbamate (see synthesis in Example 63) (100 mg, 0.287 mmol), Intermediate 18 (80.7 mg, 0.287 mmol), and K$_3$PO$_4$ (183 mg, 0.861 mmol) in 1,4-dioxane (5.0 mL) under an atmosphere of N$_2$ were added Pd$_2$(dba)$_3$ (26.3 mg, 0.0287 mmol) and Xantphos (33.2 mg, 0.0574 mmol). The mixture was sparged with N$_2$ for 2 min, sealed, and stirred at 85° C. for 18 h. LCMS analysis showed consumption of the starting material. The mixture was filtered through Celite®. The filter cake was washed with EtOAc (100 mL). The combined filtrate was concentrated to dryness and purified by preparative TLC (EtOAc) to provide tert-butyl ({2-[6-(4,5-diethyl-4H-1,2,4-triazol-3-yl)pyridin-2-yl]-6-[methyl(propan-2-yl)amino]-1-oxo-2,3-dihydro-1H-pyrrolo[3,4-c]pyridin-4-yl}methyl)methylcarbamate (120 mg, 76% yield) as a yellow solid. $^1$H NMR (400 MHz, CDCl$_3$) δ 8.70 (d, J=8.2 Hz, 1H), 8.10 (d, J=7.6 Hz, 1H), 7.99-7.80 (m, 1H), 6.89 (s, 1H), 5.12-5.01 (m, 1H), 4.98-4.84 (m, 2H), 4.71-4.62 (m, 2H), 4.58-4.26 (m, 2H), 3.04-2.96 (m, 3H), 2.94 (s, 3H), 2.89 (q, J=7.5 Hz, 2H), 1.51 (t, J=7.5 Hz, 3H), 1.45-1.34 (m, 12H), 1.23 (s, 3H), 1.21 (s, 3H). LCMS m/z (ESI+) for (C$_{29}$H$_{40}$N$_8$O$_3$), 549.2 (M+H)$^+$.

Step 2: 2-[6-(4,5-diethyl-4H-1,2,4-triazol-3-yl)pyridin-2-yl]-4-[(methylamino)methyl]-6-[methyl(propan-2-yl)amino]-2,3-dihydro-1H-pyrrolo[3,4-c]pyridin-1-one, hydrochloride

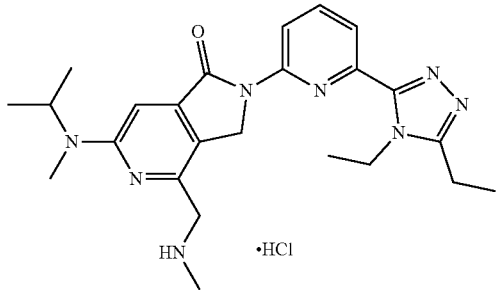 [SMILES: CCc1nnc(-c2cccc(N3Cc4c(cc(N(C)C(C)C)nc4CNC)C3=O)n2)n1CC ; Cl]

A solution of tert-butyl ({2-[6-(4,5-diethyl-4H-1,2,4-triazol-3-yl)pyridin-2-yl]-6-[methyl(propan-2-yl)amino]-1-oxo-2,3-dihydro-1H-pyrrolo[3,4-c]pyridin-4-yl}methyl)methylcarbamate (120 mg, 0.219 mmol) in EtOAc (1.0 mL) was cooled to 0° C. and treated dropwise with a solution of HCl (4.0 N in EtOAc, 5.0 mL). The mixture was stirred for 2 h at room temperature. LCMS analysis showed consumption of the starting material. The resultant solids were collected by filtration. The filter cake was dried under vacuum to provide 2-[6-(4,5-diethyl-4H-1,2,4-triazol-3-yl)pyridin-2-yl]-4-[(methylamino)methyl]-6-[methyl(propan-2-yl)amino]-2,3-dihydro-1H-pyrrolo[3,4-c]pyridin-1-one, isolated as a hydrochloric acid salt (95 mg, 90% yield) as a yellow solid. $^1$H NMR (400 MHz, DMSO-d$_6$) δ 9.23 (br. s, 2H), 8.67 (d, J=8.4 Hz, 1H), 8.19-8.09 (m, 1H), 7.99 (d, J=7.7 Hz, 1H), 6.92 (s, 1H), 5.16 (s, 2H), 5.11-4.97 (m, 1H), 4.57 (q, J=6.4 Hz, 2H), 4.33 (t, J=6.0 Hz, 2H), 3.01-2.88 (m, 5H), 2.72 (t, J=5.4 Hz, 3H), 1.45 (t, J=7.1 Hz, 3H), 1.39 (t, J=7.5 Hz, 3H), 1.18 (s, 3H), 1.16 (s, 3H); LCMS m/z (ESI+) for (C$_{24}$H$_{32}$N$_8$O), 449.2 (M+H)$^+$.

Example 68: 4-(aminomethyl)-2-{6-[(4R)-4-(fluoromethyl)-2-oxo-1,3-oxazolidin-3-yl]pyridin-2-yl}-6-[(2R)-2-methylpyrrolidin-1-yl]-2,3-dihydro-1H-pyrrolo[3,4-c]pyridin-1-one

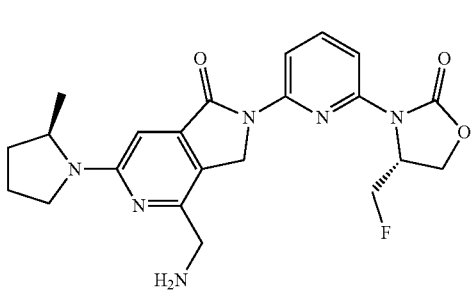

Ex-68

Step 1: tert-butyl [(6-chloro-2-{6-[(4R)-4-(fluoromethyl)-2-oxo-1,3-oxazolidin-3-yl]pyridin-2-yl}-1-oxo-2,3-dihydro-1H-pyrrolo[3,4-c]pyridin-4-yl)methyl]carbamate

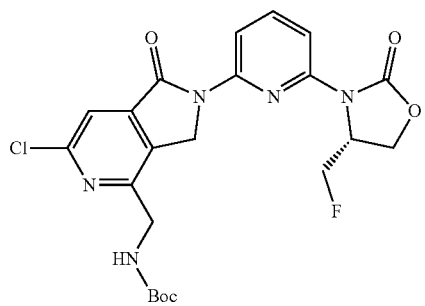 [SMILES: CC(C)(C)OC(=O)NCc1nc(Cl)cc2c1CN(c1cccc(N3C(=O)OC[C@@H]3CF)n1)C2=O]

To a solution of Intermediate 20 (462 mg, 1.68 mmol), Intermediate 7 (500 mg, 1.68 mmol), K$_2$CO$_3$ (511 mg, 3.69 mmol), and N,N-dimethylethylenediamine (74.0 mg, 0.840 mmol) was added CuI (80.0 mg, 0.420 mmol). The mixture was sparged with N$_2$ for 5 min and then stirred at 120° C. for 1.5 with microwave irradiation. LCMS analysis showed consumption of the starting material. The mixture was diluted with H$_2$O (8 mL) and MeCN (1 mL) and the resultant solids were collected by filtration. The filter cake was washed with H$_2$O (3×2 mL) and MeCN (4×1 mL) and dried under vacuum to provide tert-butyl [(6-chloro-2-{6-[(4R)-4-(fluoromethyl)-2-oxo-1,3-oxazolidin-3-yl]pyridin-2-yl}-1-oxo-2,3-dihydro-1H-pyrrolo[3,4-c]pyridin-4-yl)methyl] carbamate (595 mg, 72% yield) as a white solid. $^1$H NMR (400 MHz, DMSO-d$_6$) δ 8.22 (d, J=7.9 Hz, 1H), 8.03-7.97 (m, 1H), 7.92 (d, J=8.1 Hz, 1H), 7.80 (s, 1H), 7.54 (t, J=6.2 Hz, 1H), 5.31-5.00 (m, 4H), 4.87-4.71 (m, 1H), 4.65 (t, J=8.9 Hz, 1H), 4.59-4.50 (m, 1H), 4.41 (d, J=6.0 Hz, 2H), 1.39 (s, 9H); $^{19}$F NMR (376 MHz, DMSO-d$_6$) 5-238.40 (s, 1F); m/z (ESI+) for (C$_{22}$H$_{23}$ClFN$_5$O$_5$), 436.1 (M-tBu+H)$^+$.

Step 2: tert-butyl [(2-{6-[(4R)-4-(fluoromethyl)-2-oxo-1,3-oxazolidin-3-yl]pyridin-2-yl}-6-[(2R)-2-methylpyrrolidin-1-yl]-1-oxo-2,3-dihydro-1H-pyrrolo[3,4-c]pyridin-4-yl)methyl]carbamate Step 3: 4-(aminomethyl)-2-{6-[(4R)-4-(fluoromethyl)-2-oxo-1,3-oxazolidin-3-yl]pyridin-2-yl}-6-[(2R)-2-methylpyrrolidin-1-yl]-2,3-dihydro-1H-pyrrolo[3,4-c]pyridin-1-one, hydrochloride

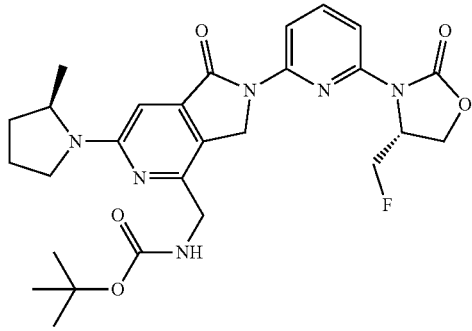 [SMILES: C[C@@H]1CCCN1c1cc2c(c(CNC(=O)OC(C)(C)C)n1)CN(c1cccc(N3C(=O)OC[C@@H]3CF)n1)C2=O]

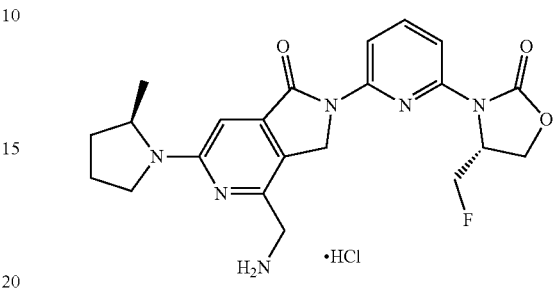

A solution of tert-butyl [(6-chloro-2-{6-[(4R)-4-(fluoromethyl)-2-oxo-1,3-oxazolidin-3-yl]pyridin-2-yl}-1-oxo-2,3-dihydro-1H-pyrrolo[3,4-c]pyridin-4-yl)methyl]carbamate (595 mg, 1.21 mmol), (2R)-2-methylpyrrolidine (294 mg, 2.42 mmol), and $Cs_2CO_3$ (2.36 g, 7.26 mmol) in 1,4-dioxane was sparged with argon for 3 min and RuPhos Pd G3 (101 mg, 0.121 mmol) was added. The mixture was sparged with argon for 3 min, sealed, and stirred at 100° C. for 16 h. LCMS analysis showed consumption of the starting material. The mixture was filtered and the filter cake was washed with EtOAc (2×10 mL). The combined filtrate was concentrated to dryness. The crude material was purified by flash chromatography (8 g $SiO_2$, 1:1 EtOAc/petroleum ether). The desired fractions were concentrated to dryness. The residue was slurried with EtOAc/petroleum ether (2:1, 10 mL) for 5 min at room temperature and the solids were collected by filtration. The filter cake was washed with EtOAc/petroleum ether (2:1, 3×10 mL) and dried under vacuum. The solids were dissolved in MeOH/EtOAc (1:10, 30 mL). Ultra-pure Si-Thio $SiO_2$ (1 g) was added and the mixture was stirred at 50° C. for 30 min. The mixture was filtered and the filter cake was washed with MeOH/EtOAc (1:10, 3×30 mL). The filtrate was concentrated to dryness. Treatment with Ultra-pure Si-Thio $SiO_2$ was repeated in identical fashion (4×). The crude material was purified by flash chromatography ($SiO_2$, 1:10 MeOH/EtOAc) to provide tert-butyl [(2-{6-[(4R)-4-(fluoromethyl)-2-oxo-1,3-oxazolidin-3-yl]pyridin-2-yl}-6-[(2R)-2-methylpyrrolid in-1-yl]-1-oxo-2,3-dihydro-1H-pyrrolo[3,4-c]pyridin-4-yl)methyl]carbamate (330 mg, 51% yield) as a yellow solid. $^1$H NMR (400 MHz, DMSO-$d_6$) δ 8.23 (d, J=8.0 Hz, 1H), 8.01-7.91 (m, 1H), 7.87 (d, J=8.1 Hz, 1H), 7.25 (t, J=6.0 Hz, 1H), 6.56 (s, 1H), 5.20-4.90 (m, 4H), 4.79 (dd, J=45.8, 10.0 Hz, 1H), 4.64 (t, J=8.9 Hz, 1H), 4.57-4.48 (m, 1H), 4.26 (dd, J=6.0, 2.0 Hz, 2H), 4.21 (t, J=6.2 Hz, 1H), 3.58-3.50 (m, 1H), 3.33-3.29 (m, 1H), 2.10-2.01 (m, 2H), 1.97-1.87 (m, 1H), 1.73-1.58 (m, 1H), 1.39 (s, 9H), 1.20 (d, J=5.4 Hz, 3H); $^{19}$F NMR (377 MHz, DMSO-$d_6$) δ −238.33 (s, 1F); m/z (ESI+) for ($C_{27}H_{33}FN_6O_5$), 541.3 (M+H)$^+$.

A solution of tert-butyl [(2-{6-[(4R)-4-(fluoromethyl)-2-oxo-1,3-oxazolidin-3-yl]pyridin-2-yl}-6-[(2R)-2-methylpyrrolidin-1-yl]-1-oxo-2,3-dihydro-1H-pyrrolo[3,4-c]pyridin-4-yl)methyl]carbamate (300 mg, 0.610 mmol) in EtOAc (5.0 mL) and MeOH (10.0 mL) was cooled to 0° C. and treated with a solution of HCl (4.0 N in EtOAc, 5.0 mL). The reaction was stirred at room temperature for 9 h. LCMS analysis showed consumption of the starting material. The mixture was concentrated to dryness. The solids were dissolved in $H_2O$ (25 mL) and washed with EtOAc (20 mL). The aqueous layer was concentrated to dryness. The residue was purified by preparative HPLC with a Phenomenex Gemini-NX column (150×30 mm, 5 μm particle size), which was eluted with 24-44% MeCN/$H_2O$ (+0.05% HCl) with a flow rate of 30 mL/min to provide 4-(aminomethyl)-2-{6-[(4R)-4-(fluoromethyl)-2-oxo-1,3-oxazolidin-3-yl]pyridin-2-yl}-6-[(2R)-2-methylpyrrolidin-1-yl]-2,3-dihydro-1H-pyrrolo[3,4-c]pyridin-1-one, isolated as the hydrochloric acid salt (200 mg, 69% yield) as a yellow solid. $^1$H NMR (400 MHz, DMSO-$d_6$) δ 8.53 (br. s, 3H), 8.24 (d, J=8.0 Hz, 1H), 8.08-7.94 (m, 1H), 7.89 (d, J=8.0 Hz, 1H), 6.69 (s, 1H), 5.21-4.99 (m, 4H), 4.74 (br. d, J=9.8 Hz, 1H), 4.64 (t, J=8.9 Hz, 1H), 4.52 (dd, J=3.3, 8.5 Hz, 1H), 4.39-4.29 (m, 1H), 4.25-4.15 (m, 2H), 3.63 (br. t, J=8.7 Hz, 1H), 3.47-3.34 (m, 1H), 2.14-1.94 (m, 3H), 1.77-1.68 (m, 1H), 1.20 (d, J=6.0 Hz, 3H); $^{19}$F NMR (377 MHz, DMSO-$d_6$) δ −238.09 (s, 1F); m/z (ESI+) for ($C_{22}H_{25}FN_6O_3$), 441.3 (M+H)$^+$.

Additional compounds of the invention in Tables 1A and 1B were prepared by modifications of the methods exemplified herein. Use of or 1 in a structure and ξ within the name identify a chiral center that has been resolved into the two separate enantiomers, but the specific enantiomer has not been confirmed; a solid or dashed wedge is drawn in the structure but the actual enantiomer may be the other enantiomer. These are labeled as "absolute stereochemistry unknown" and include optical rotation. Compounds marked "absolute stereochemistry known" were typically prepared from intermediates having known stereochemistry.

Compounds and their corresponding characterization data are presented in Table 1A below, where the method used to make the compound is provided in parentheses below the example number:

TABLE 1A

| Ex. No. | Structure/IUPAC name | LCMS [M + H]⁺ | ¹H NMR (ppm); ¹⁹F NMR (ppm); optical rotation; stereochem. notes |
|---|---|---|---|
| 69 (C) | 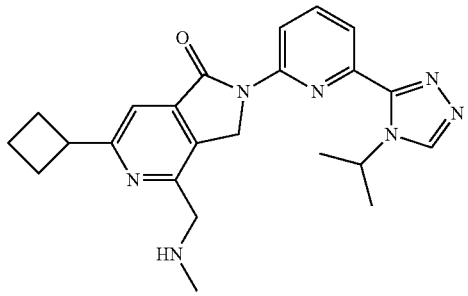<br>6-cyclobutyl-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 418.3 | ¹H NMR (400 MHz, DMSO-d₆) δ 9.17-9.10 (m, 2H), 8.97 (s, 1H), 8.66-8.58 (m, 1H), 8.18-8.09 (m, 1H), 7.98-7.91 (m, 1H), 7.71 (s, 1H), 5.42 (hept, J = 6.7 Hz, 1H), 5.25 (s, 2H), 4.52 (t, J = 5.7 Hz, 2H), 3.88 (q, J = 8.6 Hz, 1H), 2.78 (t, J = 5.1 Hz, 3H), 2.53 (s, 1H), 2.50-2.38 (m, 2H), 2.42-2.32 (m, 1H), 2.36-2.27 (m, 1H), 2.14-1.97 (m, 1H), 1.98-1.84 (m, 1H), 1.59 (d, J = 6.7 Hz, 6H). |
| 70 (P) | 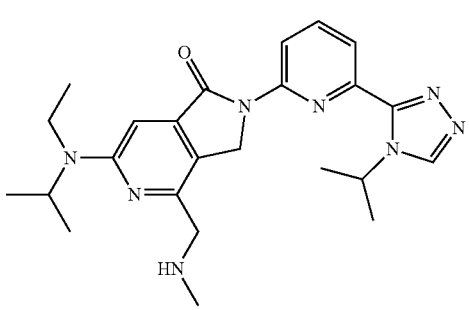 [SMILES: CCN(c1cc2c(c(CNC)n1)CN(c1cccc(-c3nncn3C(C)C)n1)C2=O)C(C)C]<br>6-[ethyl(propan-2-yl)amino]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 449.0 | ¹H NMR (600 MHz, DMSO-d₆) δ 8.93 (s, 1H) 8.61 (d, J = 8.44 Hz, 1H) 8.07-8.13 (m, 1H) 7.93 (d, J = 7.52 Hz, 1H) 6.77 (s, 1H) 5.49 (dt, J = 13.25, 6.67 Hz, 1H) 5.12 (s, 2H) 4.84-4.93 (m, 1H) 4.06 (s, 2H) 3.14-3.20 (m, 2H) 2.53-2.58 (m, 3H) 1.58 (d, J = 6.60 Hz, 6H) 1.15-1.21 (m, 9H) |
| 71 (O) | 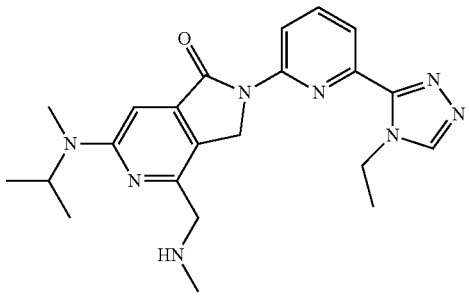 [SMILES: CCn1cnnc1-c1cccc(N2Cc3c(cc(N(C)C(C)C)nc3CNC)C2=O)n1]<br>2-[6-(4-ethyl-4H-1,2,4-triazol-3-yl)pyridin-2-yl]-4-[(methylamino)methyl]-6-[methyl(propan-2-yl)amino]-2,3-dihydro-1H-pyrrolo[3,4-c]pyridin-1-one | 421.0 | ¹H NMR (400 MHz, DMSO-d₆) δ 8.64 8.74 (m, 1H) 8.60 (br. s, 1H) 8.04-8.12 (m, 1H) 7.98-8.02 (m, 1H) 6.78 (s, 1H) 5.18 (s, 2H) 4.90 (dt, J = 13.05, 6.37 Hz, 1H) 4.60-4.75 (m, 2H) 3.85 (br. s, 2H) 2.91 (s, 3H) 2.41 (s, 3H) 1.52 (t, J = 7.09 Hz, 3H) 1.19 (d, J = 6.48 Hz, 6H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 72 (O) | 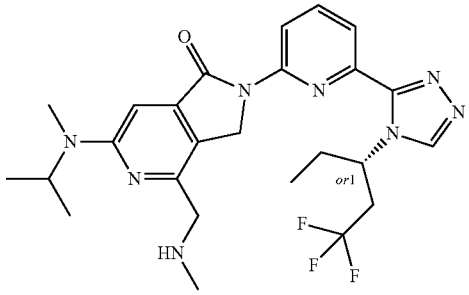 [SMILES: CC[C@@H](CC(F)(F)F)n1cnnc1-c1cccc(N2Cc3c(cc(N(C)C(C)C)nc3CNC)C2=O)n1]<br>4-[(methylamino)methyl]-6-[methyl(propan-2-yl)amino]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 517.3 | 1H NMR (600 MHz, DMSO-$d_6$) δ 9.06 (s, 1H), 8.65 (d, J = 8.44 Hz, 1H), 8.10 (t, J = 7.98 Hz, 1H), 7.97 (d, J = 7.52 Hz, 1H), 6.79 (s, 1H), 5.94-6.15 (m, 1H), 5.05-5.22 (m, 2H), 4.81-5.01 (m, 1H), 3.86 (br. s, 2H), 3.14-3.20 (m, 1H), 2.94-3.05 (m, 1H), 2.89 (s, 3H), 1.90-2.14 (m, 2H), 1.34 (s, 3H), 1.15 (d, J = 6.42 Hz, 6H), 0.84 (t, J = 7.34 Hz, 3H). absolute stereochemistry unknown* |
| 73 (O) | 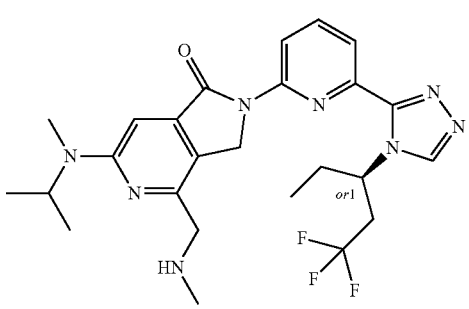 [SMILES: CC[C@H](CC(F)(F)F)n1cnnc1-c1cccc(N2Cc3c(cc(N(C)C(C)C)nc3CNC)C2=O)n1]<br>4-[(methylamino)methyl]-6-[methyl(propan-2-yl)amino]-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 517.3 | 1H NMR (600 MHz, DMSO-$d_6$) δ 9.06 (s, 1H), 8.64 (d, J = 8.44 Hz, 1H), 8.10 (t, J = 8.07 Hz, 1H), 7.97 (d, J = 7.52 Hz, 1H), 6.78 (s, 1H), 6.05 (d, J = 4.03 Hz, 1H), 5.04-5.20 (m, 2H), 4.83-5.01 (m, 1H), 3.85 (br. s, 2H), 3.10-3.21 (m, 1H), 2.95-3.06 (m, 1H), 2.88 (s, 3H), 1.92-2.17 (m, 2H), 1.34 (s, 3H), 1.12-1.20 (m, 6H), 0.84 (t, J = 7.34 Hz, 3H). absolute stereochemistry unknown* |
| 74 (T) | 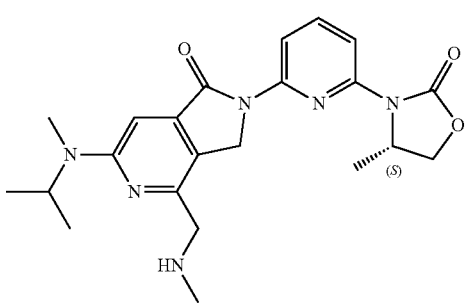<br>4-[(methylamino)methyl]-2-{6-[(4S)-4-methyl-2-oxo-1,3-oxazolidin-3-yl]pyridin-2-yl}-6-[methyl(propan-2-yl)amino]-2,3-dihydro-1H-pyrrolo[3,4-c]pyridin-1-one | [M + Na]+ 447.2 | 1H NMR (400 MHz, DMSO-$d_6$) δ 9.34-9.10 (m, 2H) 8.23 (d, J = 8.0 Hz, 1H) 7.95 (t, J = 8.2 Hz, 1H) 7.82 (d, J = 8.0 Hz, 1H) 6.88 (s, 1H) 5.12 (m, 1H) 5.01 (br. s, 2H) 4.98-4.90 (m, 1H) 4.61 (t, J = 8.3 Hz, 1H) 4.34 (br. d, J = 3.0 Hz, 2H) 4.17 (dd, J = 3.8, 8.3 Hz, 1H) 2.93 (s, 3H) 2.72 (br. t, J = 5.3 Hz, 3H) 1.49 (d, J = 6.0 Hz, 3H) 1.17 (d, J = 6.5 Hz, 6H). absolute stereochemistry known |
| 75 (O) | 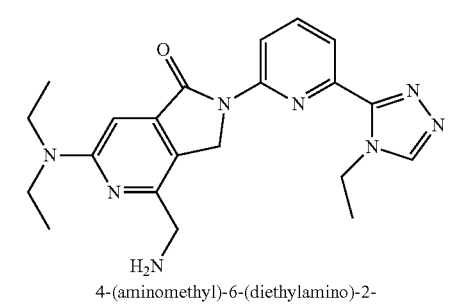<br>4-(aminomethyl)-6-(diethylamino)-2-[6-(4-ethyl-4H-1,2,4-triazol-3-yl)pyridin-2-yl]-2,3-dihydro-1H-pyrrolo[3,4-c]pyridin-1-one | [M + Na]+ 429.2 | 1H NMR (400 MHz, DMSO-$d_6$) δ 9.08 (s, 1H) 8.66 (d, J = 8.3 Hz, 1H) 8.44 (br. s, 3H) 8.15 (t, J = 8.0 Hz, 1H) 8.02 (d, J = 7.5 Hz, 1H) 6.85 (s, 1H) 5.16 (s, 2H) 4.67 (q, J = 7.2 Hz, 2H) 4.24 (q, J = 5.0 Hz, 2H) 1.51 (t, J = 7.2 Hz, 3H) 1.16 (t, J = 6.9 Hz, 6H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 76 (O) | 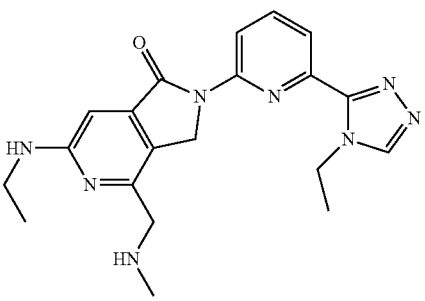 [SMILES: CCNc1cc2c(c(CNC)n1)CN(c1cccc(-c3nncn3CC)n1)C2=O]<br>6-(ethylamino)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 393.3 | 1H NMR (400 MHz, DMSO-d6) δ 9.33 (br. s, 2H) 9.19 (s, 1H) 8.66 (d, J = 8.3 Hz, 1H) 8.15 (t, J = 8.1 Hz, 1H) 8.02 (d, J = 7.6 Hz, 1H) 6.87 (s, 1H) 5.17 (s,2H) 4.68 (q, J = 7.2 Hz, 3H) 4.28 (br. t, J = 5.6 Hz, 2H) 3.45 (q, J = 7.1 Hz, 2H) 2.76-2.66 (m, 3H) 1.52 (t, J = 7.2 Hz, 3H) 1.19 (t, J = 7.2 Hz, 3H). |
| 77 (O) | 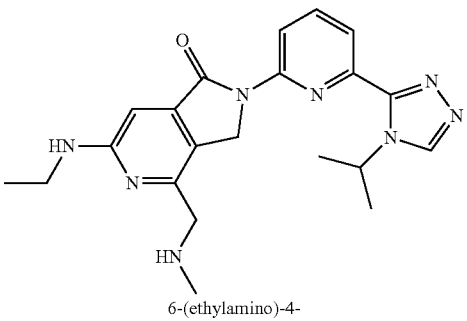<br>6-(ethylamino)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 406.9 | 1H NMR (400 MHz, DMSO-d6) δ 9.23 (s, 3H) 8.65 (d, J = 8.3 Hz, 1H) 8.15 (t, J = 8.0 Hz, 1H) 7.96 (d, J = 7.5 Hz, 1H) 6.86 (s, 1H) 5.57-5.40 (m, 1H) 5.16(s, 2H) 4.25 (br. s, 2H) 3.45 (q, J = 7.0 Hz, 2H) 2.72 (br. t, J = 5.1 Hz, 3H) 1.61 (d, J = 6.5 Hz, 6H) 1.19 (t, J = 7.2 Hz, 3H). |
| 78 (C) | 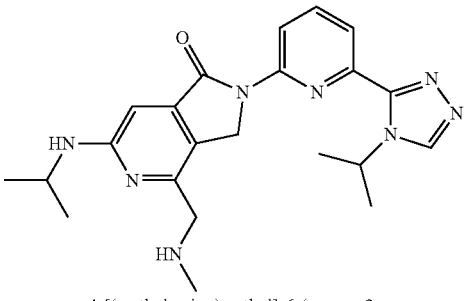<br>4-[(methylamino)methyl]-6-(propan-2-ylamino)-2-{6-[4-(propan-2-yl)-4H-1,2,4-triazol-3-yl]pyridin-2-yl}-2,3-dihydro-1H-pyrrolo[3,4-c]pyridin-1-one | 421.2 | 1H NMR (500 MHz, DMSO-d6) δ 8.88 (s, 1H) 8.55 (d, J = 7.78 Hz, 1H) 8.01 (t, J = 8.01 Hz, 1H) 7.88 (d, J = 7.48 Hz, 1H) 6.60 (s, 1H) 6.55 (d, J = 7.73 Hz, 1H) 5.51 (quin, J = 6.68 Hz, 1H) 5.07 (s, 2H) 3.96 (dq, J = 13.41, 6.57 Hz, 1H) 3.71 (s, 2H) 2.28 (s, 3H) 1.51 (d, J = 6.71 Hz, 6H) 1.11 (d, J = 6.41 Hz, 6H). |
| 79 (O) | 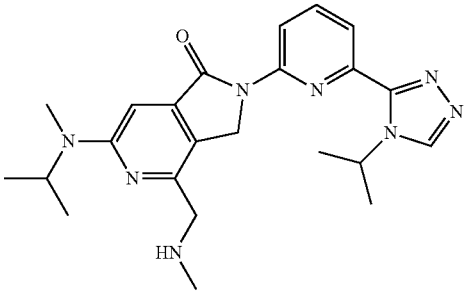 [SMILES: CNCc1nc(N(C)C(C)C)cc2c1CN(c1cccc(-c3nncn3C(C)C)n1)C2=O]<br>4-(aminomethyl)-6-[methyl(propan-2-yl)amino]-2-{6-[4-(propan-2-yl)-4H-1,2,4-triazol-3-yl]pyridin-2-yl}-2,3-dihydro-1H-pyrrolo[3,4-c]pyridin-1-one | [M + Na]+ 443.1 | 1H NMR (400 MHz, DMSO-d6) δ 9.49 (s, 1H) 8.69 (d, J = 8.3 Hz, 1H) 8.56 (br. s, 3H) 8.17 (t, J = 8.0 Hz, 1H) 7.98 (d, J = 7.5 Hz, 1H) 6.89 (s, 1H) 5.58-5.47 (m, 1H) 5.19 (s, 2H) 5.13-4.95 (m, 1H) 4.21 (br. d, J = 5.5 Hz, 2H) 2.94 (s, 3H) 1.63 (d, J = 6.8 Hz, 6H) 1.17 (d, J = 6.8 Hz, 6H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 80 (O) | 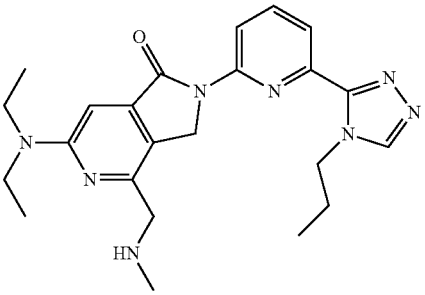 [SMILES: CCCn1cnnc1-c1cccc(N2Cc3c(cc(N(CC)CC)nc3CNC)C2=O)n1]<br>6-(diethylamino)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 435.0 | 1H NMR (600 MHz, DMSO-d6) δ 8.73 (s, 1H), 8.61 (d, J = 8.25 Hz, 1H), 8.04-8.15 (m, 1H), 8.00 (d, J = 7.52 Hz, 1H), 6.76 (s, 1H), 5.11 (s, 2H), 4.52-4.62 (m, 2H), 3.96 (s, 2H), 3.59 (q, J = 6.97 Hz, 3H), 2.49 (s, 3H), 1.81-1.94 (m, 2H), 1.34 (s, 1H), 1.15 (t, J = 6.97 Hz, 6H), 0.94 (t, J = 7.34 Hz, 3H). |
| 81 | 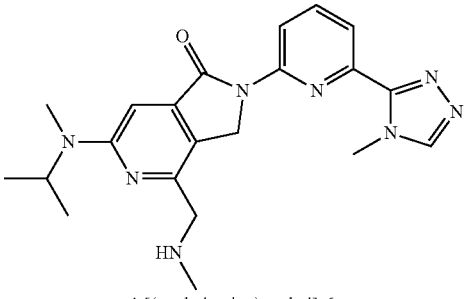<br>4-[(methylamino)methyl]-6-[methyl(propan-2-yl)amino]-2-[6-(4-methyl-4H-1,2,4-triazol-3-yl)pyridin-2-yl]-2,3-dihydro-1H-pyrrolo[3,4-c]pyridin-1-one | 406.9 | 1H NMR (400 MHz, DMSO-d6) δ 9.43-9.30 (m, 2H) 9.21 (s, 1H) 8.67 (d, J = 8.5 Hz, 1H) 8.16 (t, J = 8.0 Hz, 1H) 8.02 (d, J = 7.5 Hz, 1H) 6.91 (s, 1H) 5.21 (s, 2H) 5.14-4.93 (m, 1H) 4.36 (br. t, J = 5.6 Hz, 2H) 4.20 (s, 3H) 2.93 (s, 3H) 2.74-2.68 (m, 3H) 1.17 (d, J = 6.5 Hz, 6H). |
| 82 (O) | 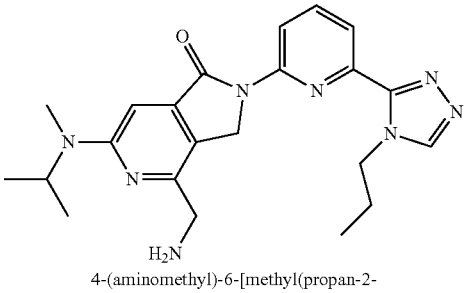<br>4-(aminomethyl)-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one | 421.3 | 1H NMR (400 MHz, DMSO-d6) δ 9.08 (s, 1H) 8.67 (d, J = 8.3 Hz, 1H) 8.51 (br. s, 3H) 8.14 (t, J = 7.9 Hz, 1H) 8.03 (d, J = 7.5 Hz, 1H) 6.89 (s, 1H) 5.15 (s, 2H) 5.10-4.98 (m, 1H) 4.61 (br. t, J = 7.2 Hz, 2H) 4.27-4.18 (m, 2H) 2.94 (s, 3H) 1.95-1.86 (m, 2H) 1.17 (d, J = 6.8 Hz, 6H) 0.96 (t, J = 7.3 Hz, 3H). |
| 83 (C) | 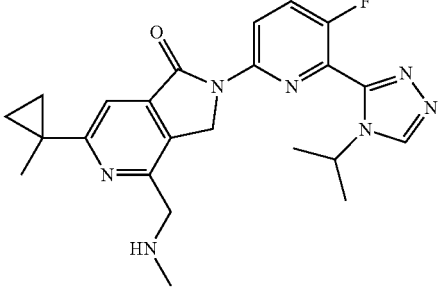<br>2-{5-fluoro-6-[4-(propan-2-yl)-4H-1,2,4-triazol-3-yl]pyridin-2-yl}-4-[(methylamino)methyl]-6-(1-methylcyclopropyl)-2,3-dihydro-1H-pyrrolo[3,4-c]pyridin-1-one | 436.1 | 1H NMR (400 MHz, DMSO-d6) δ 9.01-9.05 (m, 1H) 8.66-8.76 (m, 1H) 8.09-8.16 (m, 1H) 7.53-7.59 (m, 1H) 5.21-5.27 (m, 2H) 4.95-5.04 (m, 1H) 3.84-3.90 (m, 2H) 2.30-2.34 (m, 3H) 1.61-1.65 (m, 4H) 1.54 (d, J = 6.85 Hz, 6H) 1.24 (br. d, J = 2.69 Hz, 2H) 0.85-0.87 (m, 2H). |

TABLE 1A-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 84 (C) | 6-[ethyl(propan-2-yl)amino]-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 435.1 | $^1$H NMR (600 MHz, DMSO-$d_6$) δ 8.73 (s, 1H) 8.53-8.63 (m, 1H) 8.03-8.09 (m, 1H) 7.96-8.01 (m, 1H) 6.71 (s, 1H) 5.13 (s, 2H) 4.80-4.86 (m, 1H) 4.62 (q, J = 7.15 Hz, 2H) 3.86 (s, 2H) 3.18-3.35 (m, 2H) 2.40 (s, 3H) 1.49 (t, J = 7.15 Hz, 3H) 1.13-1.19 (m, 9H) |
| 85 (M) | 4-(aminomethyl)-2-{6-[(4R)-4-(fluoromethyl)-2-oxo-1,3-oxazolidin-3-yl]pyridin-2-yl}-6-(1-methylcyclopropyl)-2,3-dihydro-1H-pyrrolo[3,4-c]pyridin-1-one | 412.5 | $^1$H NMR (600 MHz, DMSO-$d_6$) δ 8.33-8.16 (m, 4H), 7.98 (t, J = 8.1 Hz, 1H), 7.89 (d, J = 8.1 Hz, 1H), 7.65 (s, 1H), 5.25-4.96 (m, 4H), 4.74 (s, 1H), 4.64 (t, J = 8.8 Hz, 1H), 4.51 (dd, J = 8.7, 3.3 Hz, 1H), 4.35 (d, J = 9.1 Hz, 2H), 1.57 (s, 3H), 1.50-1.37 (m, 2H), 0.89 (d, J = 2.7 Hz, 2H). absolute stereochemistry known |
| 86 (M) | 4-(aminomethyl)-6-cyclopropyl-2-{6-[(4R)-4-(fluoromethyl)-2-oxo-1,3-oxazolidin-3-yl]pyridin-2-yl}-2,3-dihydro-1H-pyrrolo[3,4-c]pyridin-1-one | 398.5 | $^1$H NMR (600 MHz, DMSO-$d_6$) δ 8.28-8.17 (m, 4H), 7.97 (t, J = 8.1 Hz, 1H), 7.89 (d, J = 8.0 Hz, 1H), 7.71 (s, 1H), 5.20-4.97 (m, 4H), 4.77 (ddd, J = 45.6, 10.1, 1.8 Hz, 1H), 4.63 (t, J = 8.9 Hz, 1H), 4.51 (dd, J = 8.6, 3.3 Hz, 1H), 4.38-4.27 (m, 2H), 2.33 (ddd, J = 8.1, 4.8, 3.4 Hz, 1H), 1.21-1.12 (m, 2H), 1.03 (dd, J = 8.1, 3.1 Hz, 2H). absolute stereochemistry known |
| 87 (M) | 6-cyclopropyl-2-{6-[(4R)-4-(fluoromethyl)-2-oxo-1,3-oxazolidin-3-yl]pyridin-2-yl}-4-[(methylamino)methyl]-2,3-dihydro-1H-pyrrolo[3,4-c]pyridin-1-one | 412.3 | $^1$H NMR (400 MHz, DMSO-$d_6$) δ 8.95 (s, 2H), 8.25 (dd, J = 8.0, 0.7 Hz, 1H), 7.99 (t, J = 8.1 Hz, 1H), 7.91 (dd, J = 8.2, 0.8 Hz, 1H), 7.76 (s, 1H), 5.23-4.96 (m, 4H), 4.77-4.61 (m, 2H), 4.57-4.38 (m, 3H), 2.54 (s, 2H), 2.41-2.31 (m, 1H), 1.17 (dq, J = 5.2, 3.1 Hz, 2H), 1.06 (dt, J = 8.2, 3.1 Hz, 2H). absolute stereochemistry known |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 88 (Q) | 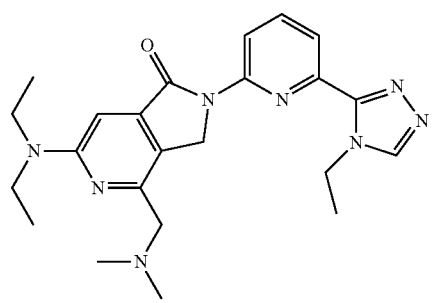 [SMILES: CCN(CC)c1cc2c(c(CN(C)C)n1)CN(c1cccc(-c3nncn3CC)n1)C2=O]<br>6-(diethylamino)-4-[(dimethylamino)methyl]-2-[6-(4-ethyl-4H-1,2,4-triazol-3-yl)pyridin-2-yl]-2,3-dihydro-1H-pyrrolo[3,4-c]pyridin-1-one | 435.4 | 1H NMR (600 MHz, DMSO-d6) δ 8.73 (s, 1H), 8.62 (d, J = 8.25 Hz, 1H), 8.05-8.16 (m, 1H), 8.01 (d, J = 7.52 Hz, 1H), 6.73 (s, 1H), 5.14 (s, 2H), 4.65 (q, J = 7.21 Hz, 2H), 3.60 (s, 2H), 3.54-3.58 (m, 4H), 2.23 (s, 6H), 1.52 (t, J = 7.15 Hz, 3H), 1.14 (t, J = 6.97 Hz, 6H). |
| 89 (R) | 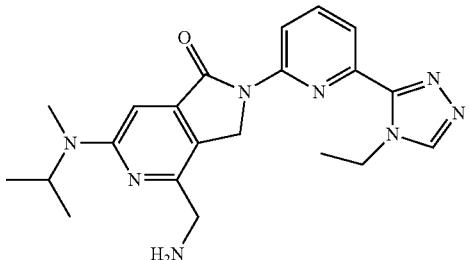<br>4-(aminomethyl)-2-[6-(4-ethyl-4H-1,2,4-triazol-3-yl)pyridin-2-yl]-6-[methyl(propan-2-yl)amino]-2,3-dihydro-1H-pyrrolo[3,4-c]pyridin-1-one | 407.3 | 1H NMR (400 MHz, DMSO-d6) δ 8.75 (s, 1 H) 8.63 (dd, J = 8.38, 0.67 Hz, 1 H) 8.06-8.16 (m, 1 H) 7.93-8.04 (m, 1 H) 6.75 (s, 1 H) 5.21 (s, 2 H) 4.88-5.05 (m, 1 H) 4.64 (q, J = 7.25 Hz, 2 H) 3.88 (s, 2 H) 2.89 (s, 3 H) 1.50 (t, J = 7.09 Hz, 3 H) 1.16 (d, J = 6.72 Hz, 6 H). |
| 90 (O) | 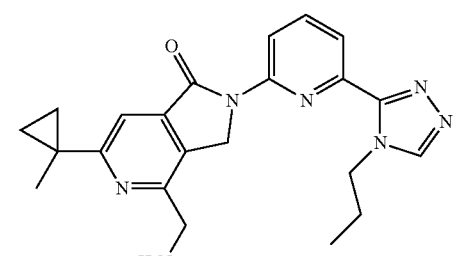<br>4-(aminomethyl)-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one | 404.3 | 1H NMR (400 MHz, DMSO-d6) δ 8.75 (s, 1H), 8.63 (d, J = 8.3 Hz, 1H), 8.11 (t, J = 7.9 Hz, 1H) 8.03 (d, J = 7.5 Hz, 1H) 7.55 (s, 1H) 5.29 (s, 2H) 4.58 (br. t, J = 7.3 Hz, 2H) 3.96 (s, 2H) 1.95-1.81 (m, 2H) 1.56 (s, 3H) 1.36-1.15 (m, 2H) 0.94 (t, J = 7.3 Hz, 3H) 0.89-0.84 (m, 2H). |
| 91 (M) | 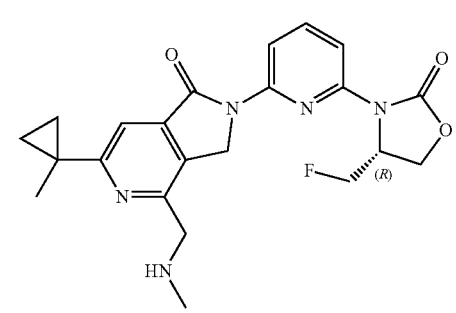<br>2-{6-[(4R)-4-(fluoromethyl)-2-oxo-1,3-oxazolidin-3-yl]pyridin-2-yl}-4-[(methylamino)methyl]-6-(1-methylcyclopropyl)-2,3-dihydro-1H-pyrrolo[3,4-c]pyridin-1-one | 426.2 | 1H NMR (600 MHz, DMSO-d6) δ 8.27-8.12 (m, 2H), 7.96 (t, J = 8.1 Hz, 1H), 7.86 (d, J = 8.1 Hz, 1H), 7.54 (s, 1H), 5.20-4.98 (m, 4H), 4.78 (ddd, J = 45.6, 10.0, 1.7 Hz, 1H), 4.62 (t, J = 8.8 Hz, 1H), 4.48 (dd, J = 8.6, 3.3 Hz, 1H), 3.94 (d, J = 1.6 Hz, 2H), 2.38 (s, 3H), 1.54 (s, 3H), 1.26 (q, J = 2.9 Hz, 2H), 0.85 (t, J = 3.2 Hz, 2H). absolute stereochemistry known |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 92 (O) | 6-(azetidin-1-yl)-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 404.9 | 1H NMR (400 MHz, DMSO-d6) δ 8.75 (s, 1H) 8.61 (d, J = 8.3 Hz, 1H) 8.07 (d, J = 8.0 Hz, 1H) 8.04-7.98 (m, 1H) 6.54 (s, 1H) 5.18 (s, 2H) 4.63 (d, J = 7.0 Hz, 2H) 4.00 (t, J = 7.4 Hz, 4H) 3.82 (s, 2H) 2.37-2.33 (m, 5H) 1.51 (t, J = 7.2 Hz, 3H). |
| 93 (O) | 6-(azetidin-1-yl)-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 418.9 | 1H NMR (400 MHz, DMSO-d6) δ 8.74 (s, 1H) 8.62 (d, J = 7.8 Hz, 1H) 8.07 (d, J = 8.0 Hz, 1H) 8.04-7.99 (m, 1H) 6.55 (s, 1H) 5.16 (s, 2H) 4.58 (t, J = 7.2 Hz, 2H) 4.00 (t, J = 7.4 Hz, 4H) 3.80 (s, 2H) 2.37-2.32 (m, 5H) 1.88 (br. d, J = 7.3 Hz, 2H) 0.94 (t, J = 7.4 Hz, 3H). |
| 94 (S) | 4-[(methylamino)methyl]-6-(1-methylcyclopropyl)-2-[6-(4-propyl-4H-1,2,4-triazol-3-yl)pyridin-2-yl]-2,3-dihydro-1H-pyrrolo[3,4-c]pyridin-1-one | 418.2 | 1H NMR (400 MHz, DMSO-d6) δ 8.75 (s, 1H) 8.63 (d, J = 8.0 Hz, 1H) 8.16-8.07 (m, 1H) 8.07-8.00 (m, 1H) 7.57 (s, 1H) 5.26 (s, 2H) 4.58 (t, J = 7.2 Hz, 2H) 3.93 (s, 2H) 2.36 (s, 3H) 1.89 (sxt, J = 7.1 Hz, 2H) 1.56 (s, 3H) 1.27 (br. d, J = 2.3 Hz, 2H) 0.95 (t, J = 7.4 Hz, 3H) 0.89-0.86 (m, 2H). |
| 95 (S) | 2-[6-(4-ethyl-4H-1,2,4-triazol-3-yl)pyridin-2-yl]-4-[(methylamino)methyl]-6-(1-methylcyclopropyl)-2,3-dihydro-1H-pyrrolo[3,4-c]pyridin-1-one | 404.2 | 1H NMR (400 MHz, DMSO-d6) δ 8.76 (s, 1H) 8.64 (d, J = 8.3 Hz, 1H) 8.16-8.08 (m, 1H) 8.07-7.99 (m, 1H) 7.58 (s, 1H) 5.29 (s, 2H) 4.64 (q, J = 6.8 Hz, 2H) 3.97 (s, 2H) 2.37 (s, 3H) 1.62-1.48 (m, 6H) 1.26 (br. s, 2H) 0.88 (br. d, J = 2.3 Hz, 2H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 96 (V) | 6-(diethylamino)-2-[6-(1-ethyl-2-methyl-1H-imidazol-5-yl)pyridin-2-yl]-4-[(methylamino)methyl]-2,3-dihydro-1H-pyrrolo[3,4-c]pyridin-1-one | 434.5 | 1H NMR (600 MHz, DMSO-d6) δ 8.87 (s, 2H), 8.53 (d, J = 8.5 Hz, 1H), 8.5 (t, J = 8.1 Hz, 2H), 7.65 (d, J = 7.7 Hz, 1H), 6.85 (s, 1H), 5.07 (s, 2H), 4.59 (q, J = 7.1 Hz, 2H), 4.32 (t, J = 5.4 Hz, 2H), 3.63 (q, J = 7.0 Hz, 4H), 2.74 (m, 3H), 2.64 (s, 3H), 1.41 (t, J = 7.1 Hz, 3H), 1.14 (t, J = 7.0 Hz, 6H). |
| 97 (U) | 6-(diethylamino)-2-[6-(4-ethyl-5-methyl-4H-1,2,4-triazol-3-yl)pyridin-2-yl]-4-[(methylamino)methyl]-2,3-dihydro-1H-pyrrolo[3,4-c]pyridin-1-one | 435.3 | 1H NMR (400 MHz, DMSO-d6) δ 8.60 (d, J = 8.4 Hz, 1H), 8.05 (t, J = 7.9 Hz, 1H), 7.96 (d, J = 7.4 Hz, 1H), 6.71 (s, 1H), 5.15 (s, 2H), 4.53 (d, J = 7.0 Hz, 2H), 3.80 (s, 2H), 3.56 (q, J = 6.8 Hz, 4H), 2.52 (s, 3H), 2.36 (s, 3H), 1.46 (t, J = 7.0 Hz, 3H), 1.13 (t, J = 7.0 Hz, 6H). |
| 98 (T) | 6-[ethyl(propan-2-yl)amino]-2-{6-[(4R)-4-(fluoromethyl)-2-oxo-1,3-oxazolidin-3-yl]pyridin-2-yl}-4-[(methylamino)methyl]-2,3-dihydro-1H-pyrrolo[3,4-c]pyridin-1-one | 457.0 | 1H NMR (700 MHz, DMSO-d6) δ 8.18-8.26 (m, 1H) 7.94 (t, J = 8.07 Hz, 1H) 7.85 (d, J = 8.17 Hz, 1H) 6.69 (s, 1H) 4.94-5.13 (m, 4H) 4.72-4.87 (m, 2H) 4.62 (t, J = 8.82 Hz, 1H) 4.44-4.52 (m, 1H) 3.78-3.85 (m, 2H) 3.35-3.39 (m, 3H) 2.40 (s, 3H) 1.10-1.20 (m, 9H). |
| 99 (O) | 6-[ethyl(propan-2-yl)amino]-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 449.0 | 1H NMR (600 MHz, DMSO-d6) δ 8.72 (s, 1H) 8.59-8.63 (m, 1H) 8.05-8.10 (m, 1H) 7.99 (dd, J = 7.70, 0.73 Hz, 1H) 6.71 (s, 1H) 5.12 (s, 2H) 4.78-4.84 (m, 1H) 4.57 (t, J = 7.15 Hz, 2H) 3.79 (s, 2H) 3.33-3.36 (m, 2H) 2.33-2.38 (m, 3H) 1.87 (sxt, J = 7.30 Hz, 2H) 1.14-1.20 (m, 9H) 0.93 (t, J = 7.43 Hz, 3H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 100 (T) | 4-(aminomethyl)-2-{6-[(4S)-4-methyl-2-oxo-1,3-oxazolidin-3-yl]pyridin-2-yl}-6-[methyl(propan-2-yl)amino]-2,3-dihydro-1H-pyrrolo[3,4-c]pyridin-1-one | 411.3 | 1H NMR (400 MHz, DMSO-d6) δ 8.59-8.40 (m, 3H) 8.23 (d, J = 8.0 Hz, 1H) 7.95 (t, J = 8.0 Hz, 1H) 7.82 (d, J = 8.3 Hz, 1H) 6.86 (s, 1H) 5.17-5.08 (m,1H) 5.08-4.91 (m, 3H) 4.60 (br. t, J = 8.2 Hz, 1H) 4.29-4.20 (m, 2H) 4.17-4.14 (m,1H) 2.93 (s, 3H) 1.49 (br. d, J = 6.0 Hz, 3H) 1.16 (br. d,J = 6.3 Hz, 6H). absolute stereochemistry known |
| 101 (W) | 6-cyclobutyl-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 404.3 | 1H NMR (400 MHz, DMSO-d6) δ 8.76 (s, 1H) 8.63 (d, J = 8.3 Hz, 1H) 8.15-8.07 (m, 1H) 8.06-8.00 (m, 1H) 7.53 (s, 1H) 5.32 (s, 2H) 4.65 (q, J = 7.2 Hz,2H) 4.00 (s, 2H) 3.79 (quin, J = 8.7 Hz, 1H) 2.37 (s, 3H) 2.35-2.29 (m, 4H) 2.10-1.98 (m, 1H) 1.94-1.81 (m, 1H) 1.53 (t, J = 7.2 Hz, 3H). |
| 102 (C) | 6-{bis[(pentadeuterio)ethyl]amino}-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 431.2 | 1H NMR (400 MHz, DMSO-d6) δ 9.23 (br. s, 2H) 9.00 (br. s, 1H) 8.65 (d, J = 8.3 Hz, 1H) 8.15 (t, J = 8.0 Hz, 1H) 8.02 (d, J = 7.5 Hz, 1H) 6.87 (s, 1H) 5.16(s, 2H) 4.66 (q, J = 7.2 Hz, 2H) 4.33 (br. d, J = 5.5 Hz, 2H) 2.73 (t, J = 5.3 Hz, 3H) 1.51 (t, J = 7.2 Hz, 3H). |
| 103 (W) | 6-cyclobutyl-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 418.3 | 1H NMR (400 MHz, DMSO-d6) δ 8.75 (s, 1H) 8.63 (d, J = 8.3 Hz, 1H) 8.15-8.07 (m, 1H) 8.06-8.01 (m, 1H) 7.54 (s, 1H) 5.30 (s, 2H) 4.59 (t, J = 7.2 Hz,2H) 4.00 (s, 2H) 3.80 (quin, J = 8.7 Hz, 1H) 2.38 (s, 3H) 2.35-2.27 (m, 4H) 2.10-1.98 (m, 1H) 1.95-1.81 (m, 3H) 0.95 (t, J = 7.4 Hz, 3H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 104 (C) | 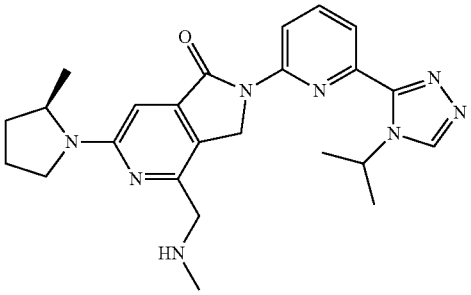 [SMILES: CNCc1nc(N2CCC[C@H]2C)cc2c1CN(c1cccc(-c3nncn3C(C)C)n1)C2=O]<br>4-[(methylamino)methyl]-6-[(2R)-2-methylpyrrolidin-1-yl]-2-{6-[4-(propan-2-yl)-4H-1,2,4-triazol-3-yl]pyridin-2-yl}-2,3-dihydro-1H-pyrrolo[3,4-c]pyridin-1-one | 447.3 | 1H NMR (600 MHz, DMSO-d6) δ 8.91 (d, J = 2.0 Hz, 1H), 8.77 (s, 1H), 8.59 (d, J = 8.7 Hz, 1H), 8.08 (t, J = 8.0 Hz, 1H), 7.90 (d, J = 7.8 Hz, 1H), 6.71 (s, 1H), 5.44-5.32 (m, 1H), 5.06 (s, 2H), 4.29 (s, 2H), 3.60 (m, 1H), 3.33-3.23 (m, 2H), 2.95 (d, J = 2.1 Hz, 3H), 2.09-1.93 (m, 3H), 1.66-1.72 (m, 1H), 1.54 (dd, J = 6.8, 2.1 Hz, 6H), 1.16 (dd, J = 6.4, 2.1 Hz, 3H). |
| 105 (C) | 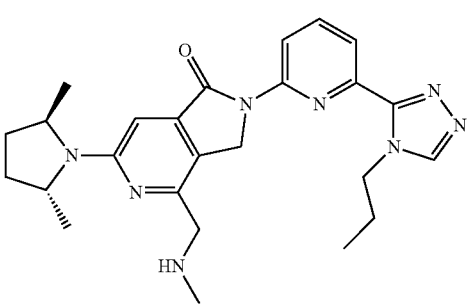 [SMILES: CCCn1cnnc1-c1cccc(N2Cc3c(cc(N4[C@H](C)CC[C@H]4C)nc3CNC)C2=O)n1]<br>6-[(2R,5R)-2,5-dimethylpyrrolidin-1-yl]-4-[(methylamino)methyl]-2-[6-(4-propyl-4H-1,2,4-triazol-3-yl)pyridin-2-yl]-2,3-dihydro-1H-pyrrolo[3,4-c]pyridin-1-one | 461.7 | 1H NMR (600 MHz, DMSO-d6) δ 8.74 (s, 2H), 8.61 (dd, J = 8.4, 0.8 Hz, 1H), 8.10 (t, J = 8.0 Hz, 1H), 8.05-7.94 (m, 1H), 6.75 (s, 1H), 5.15-5.01 (m, 2H), 4.53 (t, J = 7.3 Hz, 2H), 4.31 (m, 4H), 2.74 (t, J = 5.3 Hz, 3H), 2.23 (s, 2H), 1.83 (q, J = 7.3 Hz, 2H), 1.74-1.58 (m, 2H), 1.11 (d, J = 6.2 Hz, 6H), 0.89 (t, J = 7.4 Hz, 3H).<br>absolute stereochemistry known |
| 106 (C) | 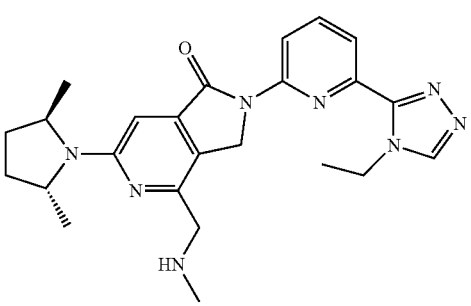 [SMILES: CCn1cnnc1-c1cccc(N2Cc3c(cc(N4[C@H](C)CC[C@H]4C)nc3CNC)C2=O)n1]<br>6-[(2R,5R)-2,5-dimethylpyrrolidin-1-yl]-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 447.6 | 1H NMR (400 MHz, DMSO-d6) δ 8.77 (s, 2H), 8.63 (d, J = 8.2 Hz, 1H), 8.13 (t, J = 8.0 Hz, 1H), 8.01 (d, J = 7.5 Hz, 1H), 6.78 (s, 1H), 5.18-5.03 (m, 2H), 4.62 (q, J = 7.1 Hz, 2H), 4.37 (m, 4H), 2.78 (t, J = 5.4 Hz, 3H), 2.26 (s, 2H), 1.69 (d, J = 5.8 Hz, 2H), 1.48 (t, J = 7.2 Hz, 3H), 1.14 (d, J = 6.1 Hz, 6H).<br>absolute stereochemistry known |
| 107 (AA) | 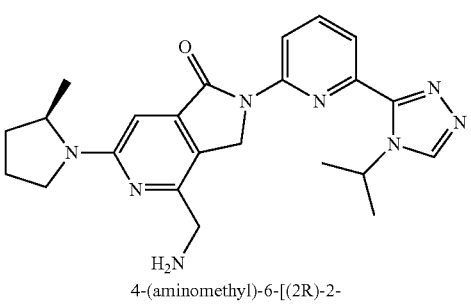<br>4-(aminomethyl)-6-[(2R)-2-methylpyrrolidin-1-yl]-2-{6-[4-(propan-2-yl)-4H-1,2,4-triazol-3-yl]pyridin-2-yl}-2,3-dihydro-1H-pyrrolo[3,4-c]pyridin-1-one | 433.2 | 1H NMR (600 MHz, DMSO-d6) δ 8.92-8.94 (m, 1H) 8.57-8.63 (m, 1H) 8.04-8.11 (m, 1H) 7.91-7.96 (m, 1H) 6.55-6.57 (m, 1H) 5.50-5.57 (m, 1H) 5.14-5.17 (m, 2H) 4.15-4.26 (m, 2H) 3.80-3.88 (m, 2H) 3.31-3.35 (m, 3H) 2.04-2.07 (m, 2H) 1.92-1.98 (m, 2H) 1.56-1.59 (m, 6H) 1.19 (br. d, J = 6.05 Hz, 3H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 108 (P) | 6-[ethyl(propan-2-yl)amino]-4-[(methylamino)methyl]-2-[6-(4-methyl-4H-1,2,4-triazol-3-yl)pyridin-2-yl]-2,3-dihydro-1H-pyrrolo[3,4-c]pyridin-1-one | 421.1 | 1H NMR (600 MHz, DMSO-d6) δ 8.64-8.66 (m, 1H) 8.58 (d, J = 8.44 Hz, 1H) 8.04-8.10 (m, 1H) 7.96 (d, J = 7.52 Hz, 1H) 6.72-6.74 (m, 1H) 5.13-5.16 (m, 2H) 4.79-4.89 (m, 1H) 4.10-4.12 (m, 3H) 3.88-3.98 (m, 2H) 3.41-3.46 (m, 5H) 1.15-1.19 (m, 9H). |
| 109 (C) | 6-(2,2-dimethylpyrrolidin-1-yl)-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 461.0 | 1H NMR (400 MHz, DMSO-d6) δ 8.92-8.96 (m, 1H) 8.60-8.66 (m, 1H) 8.08 (t, J = 8.01 Hz, 1H) 7.93-8.02 (m, 1H) 6.55 (s, 1H) 5.57 (dt, J = 13.33, 6.54 Hz, 1H) 5.15 (s, 2H) 4.09 (q, J = 5.09 Hz, 1H) 3.86 (s, 2H) 3.40-3.48 (m, 2H) 2.37-2.40 (m, 3H) 1.89-1.95 (m, 4H) 1.58 (d, J = 6.72 Hz, 6H) 1.53 (s, 6H). |
| 110 (C) | 4-(aminomethyl)-6-[(2R,5R)-2,5-dimethylpyrrolidin-1-yl]-2-[6-(4-ethyl-4H-1,2,4-triazol-3-yl)pyridin-2-yl]-2,3-dihydro-1H-pyrrolo[3,4-c]pyridin-1-one | 433.2 | 1H NMR (600 MHz, DMSO-d6) δ 8.52 (d, J = 1.5 Hz, 1H), 8.37 (d, J = 8.4 Hz, 1H), 7.97 (s, 3H), 7.87 (t, J = 8.1 Hz, 1H), 7.75 (d, J = 7.6 Hz, 1H), 6.49 (s, 1H), 4.94-4.82 (m, 2H), 4.37 (q, J = 7.2 Hz, 2H), 4.28-3.92 (m, 4H), 2.08-1.94 (m, 2H), 1.43 (d, J = 5.5 Hz, 2H), 1.28-1.19 (m, 3H), 0.90 (d, J = 6.1 Hz, 6H). |
| 111 (U) | 6-[(2R,5R)-2,5-dimethylpyrrolidin-1-yl]-2-[6-(4-ethyl-5-methyl-4H-1,2,4-triazol-3-yl)pyridin-2-yl]-4-[(methylamino)methyl]-2,3-dihydro-1H-pyrrolo[3,4-c]pyridin-1-one | 461.3 | 1H NMR (600 MHz, DMSO-d6) δ 8.53 (d, J = 8.25 Hz, 1H) 7.93-8.04 (m, 1H) 7.90 (d, J = 7.70 Hz, 1H) 6.65 (s, 1H) 5.31 (s, 2H) 4.48 (q, J = 6.97 Hz, 2H) 3.54-3.58 (m, 2H) 3.52 (br, s, 3H, assumed; partially obscured by water peak) 2.98 (s, 3H) 2.42 (s, 3H) 1.35-1.43 (m, 9H) 1.03 (t, J = 6.97 Hz, 3H). |

| Ex. No. | Structure/IUPAC name | LCMS [M + H]⁺ | ¹H NMR (ppm); ¹⁹F NMR (ppm); optical rotation; stereochem. notes |
|---|---|---|---|
| 112 (C) | 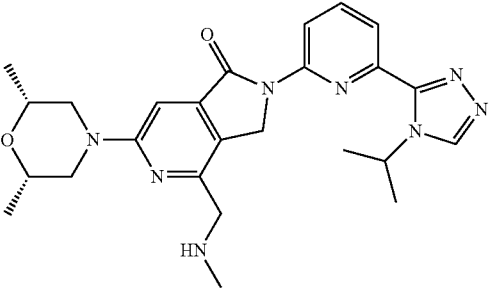 [SMILES: CNCc1nc(N2C[C@@H](C)O[C@@H](C)C2)cc2c1CN(c1cccc(-c3nncn3C(C)C)n1)C2=O]<br>6-[2,6-dimethylmorpholin-4-yl]-4-[(methylamino)methyl]-2-{6-[4-(propan-2-yl)-4H-1,2,4-triazol-3-yl]pyridin-2-yl}-2,3-dihydro-1H-pyrrolo[3,4-c]pyridin-1-one | 477.0 | ¹H NMR (600 MHz, DMSO-d₆) δ 8.83-8.89 (m, 1H) 8.54 (d, J = 8.44 Hz, 1H) 8.01-8.06 (m, 1H) 7.86-7.89 (m, 1H) 6.99-7.02 (m, 1H) 6.46-6.53 (m, 2H) 5.41-5.47 (m, 1H) 5.05-5.09 (m, 2H) 3.93-4.04 (m, 2H) 3.67-3.73 (m, 4H) 2.35-2.43 (m, 3H) 1.48-1.54 (m, 6H) 1.13 (br. d, J = 6.05 Hz, 6H). |
| 113 (C) | 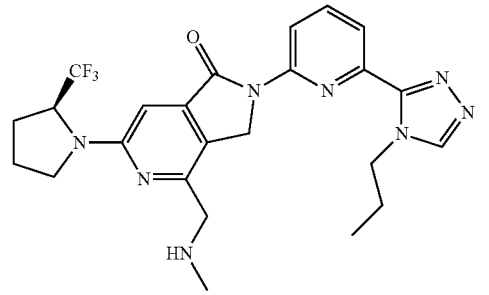 [SMILES: CCCn1cnnc1-c1cccc(N2Cc3c(cc(N4CCC[C@H]4C(F)(F)F)nc3CNC)C2=O)n1]<br>4-[(methylamino)methyl]-2-[6-(4-propyl-4H-1,2,4-triazol-3-yl)pyridin-2-yl]-6-[(2S)-2-(trifluoromethyl)pyrrolidin-1-yl]-2,3-dihydro-1H-pyrrolo[3,4-c]pyridin-1-one | 501.1 | ¹H NMR (400 MHz, DMSO-d₆) δ 8.75 (s, 1H) 8.64 (d, J = 8.0 Hz, 1H) 8.15-8.07 (m, 1H) 8.05-7.99 (m, 1H) 6.92 (s, 1H) 5.23-5.11 (m, 3H) 4.58 (t, J = 7.3 Hz, 2H) 3.87 (s, 2H) 3.82-3.72 (m, 1H) 3.52-3.38 (m, 1H) 2.37 (s, 3H) 2.14 (br. s, 4H) 1.89 (sxt, J = 7.2 Hz, 2H) 0.95 (t, J = 7.3 Hz, 3H). |
| 114 (C) | 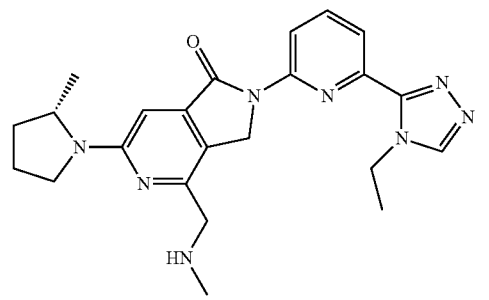 [SMILES: CCn1cnnc1-c1cccc(N2Cc3c(cc(N4CCC[C@@H]4C)nc3CNC)C2=O)n1]<br>2-[6-(4-ethyl-4H-1,2,4-triazol-3-yl)pyridin-2-yl]-4-[(methylamino)methyl]-6-[(2S)-2-methylpyrrolidin-1-yl]-2,3-dihydro-1H-pyrrolo[3,4-c]pyridin-1-one | 433.2 | ¹H NMR (600 MHz, DMSO-d₆) δ 8.71-8.73 (m, 1H) 8.51-8.59 (m, 1H) 8.03-8.09 (m, 1H) 7.93-7.98 (m, 1H) 6.60-6.65 (m, 1H) 5.04-5.10 (m, 2H) 4.54-4.62 (m, 2H) 4.17-4.25 (m, 1H) 4.06-4.11 (m, 2H) 3.53-3.58 (m, 2H) 3.29-3.37 (m, 1H) 2.58-2.62 (m, 3H) 1.99-2.08 (m, 2H) 1.92-1.98 (m, 1H) 1.66-1.73 (m, 1H) 1.45-1.49 (m, 3H) 1.14-1.21 (m, 3H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 115 (C) | 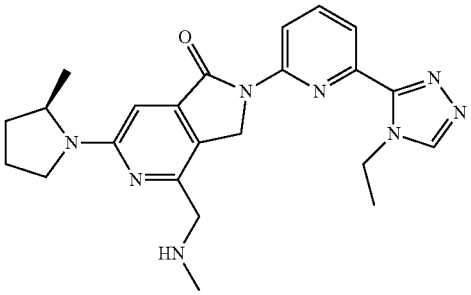 [SMILES: CCn1cnnc1-c1cccc(N2Cc3c(cc(N4CCC[C@H]4C)nc3CNC)C2=O)n1]<br>2-[6-(4-ethyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one | 433.2 | 1H NMR (600 MHz, DMSO-d6) δ 8.69-8.74 (m, 1H) 8.53-8.60 (m, 1H) 8.06-8.10 (m, 1H) 7.94-8.00 (m, 1H) 6.60-6.65 (m, 1H) 5.07-5.14 (m, 2H) 4.55-4.65 (m, 2H) 4.20-4.24 (m, 1H) 3.97-4.04 (m, 4H) 3.30-3.35 (m, 1H) 2.52-2.54 (m, 3H) 2.01-2.09 (m, 2H) 1.92-1.98 (m, 1H) 1.66-1.74 (m, 1H) 1.43-1.50 (m, 3H) 1.12-1.19 (m, 3H). |
| 116 (U) | 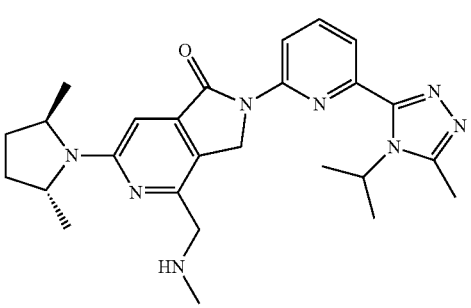 [SMILES: CNCc1nc(N2[C@H](C)CC[C@H]2C)cc2c1CN(c1cccc(-c3nnc(C)n3C(C)C)n1)C2=O]<br>6-[(2R,5R)-2,5-dimethylpyrrolidin-1-yl]-4-[(methylamino)methyl]-2-{6-[5-methyl-4-(propan-2-yl)-4H-1,2,4-triazol-3-yl]pyridin-2-yl}-2,3-dihydro-1H-pyrrolo[3,4-c]pyridin-1-one | 475.3 | 1H NMR (600 MHz, DMSO-d6) δ 8.5-8.6 (m, 1H), 8.0-8.1 (m, 1H), 7.78 (d, J = 7.0 Hz, 1H), 6.59 (s, 1H), 5.4-5.6 (m, 1H), 5.0-5.2 (m, 2H), 4.22 (br. s, 2H), 3.75 (dd, J = 2.5, 3.9 Hz, 2H), 2.58 (s, 3H), 2.2-2.3 (m, 2H), 1.6-1.6 (m, 2H), 1.55 (d, J = 7.0 Hz, 6H), 1.12 (d, J = 5.5 Hz, 6H). |
| 117 (AA) | 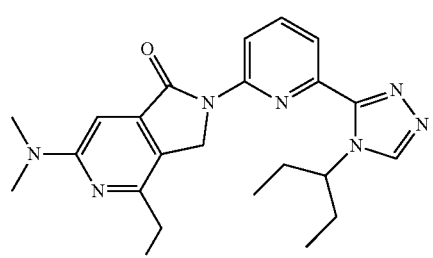<br>4-(aminomethyl)-6-(dimethylamino)-2-{6-[4-(pentan-3-yl)-4H-1,2,4-triazol-3-yl]pyridin-2-yl}-2,3-dihydro-1H-pyrrolo[3,4-c]pyridin-1-one | 421.2 | 1H NMR (400 MHz, DMSO-d6) δ 8.90 (s, 1H) 8.63 (dd, J = 8.31, 0.73 Hz, 1H) 8.04-8.13 (m, 1H) 7.93 (dd, J = 7.58, 0.73 Hz, 1H) 6.77 (s, 1H) 5.33-5.44 (m, 1H) 5.17 (s, 2H) 3.86 (br. d, J = 11.49 Hz, 2H) 3.11 (s, 7H) 1.85-1.99 (m, 4H) 0.78 (t, J = 7.34 Hz, 6H). |
| 118 (M) | 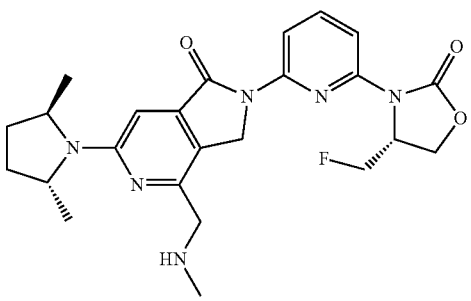 [SMILES: CNCc1nc(N2[C@H](C)CC[C@H]2C)cc2c1CN(c1cccc(N3C(=O)OC[C@@H]3CF)n1)C2=O]<br>6-[(2R,5R)-2,5-dimethylpyrrolidin-1-yl]-2-{6-[(4R)-4-(fluoromethyl)-2-oxo-1,3-oxazolidin-3-yl]pyridin-2-yl}-4-[(methylamino)methyl]-2,3-dihydro-1H-pyrrolo[3,4-c]pyridin-1-one | 469.3 | 1H NMR (400 MHz, DMSO-d6) δ 8.24 (d, J = 8.0 Hz, 1H) 8.00-7.92 (m, 1H) 7.86 (d, J = 8.1 Hz, 1H) 6.59 (s, 1H) 5.13 (br. d, J = 7.4 Hz, 1H) 5.10-4.96 (m, 3H) 4.88-4.70 (m, 1H) 4.68-4.60 (m, 1H) 4.50 (dd, J = 3.1, 8.6 Hz, 1H) 4.25 (br. s, 2H) 3.82-3.71 (m, 2H) 2.37 (s, 3H) 2.23 (br. s, 2H) 1.64 (br. d, J = 5.5 Hz, 2H) 1.13 (d, J = 6.1 Hz, 6H). 19F NMR (377 MHz, DMSO-d6) δ-237.98 (s, 1F). absolute stereochemistry known |

| Ex. No. | Structure/IUPAC name | LCMS [M + H]⁺ | ¹H NMR (ppm); ¹⁹F NMR (ppm); optical rotation; stereochem. notes |
|---|---|---|---|
| 119 (R) | 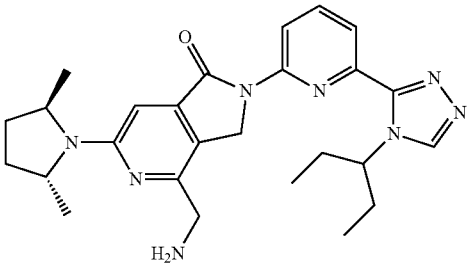 [SMILES: CCC(CC)n1cnnc1-c1cccc(N2Cc3c(cc(N4[C@H](C)CC[C@H]4C)nc3CN)C2=O)n1]<br>4-(aminomethyl)-6-[(2R,5R)-2,5-dimethylpyrrolidin-1-yl]-2-{6-[4-(pentan-3-yl)-4H-1,2,4-triazol-3-yl]pyridin-2-yl}-2,3-dihydro-1H-pyrrolo[3,4-c]pyridin-1-one | 475.3 | ¹H NMR (400 MHz, DMSO-$d_6$) δ 8.78 (s, 1H), 8.6-8.6 (m, 1H), 8.07 (t, J = 8.0 Hz, 1H), 7.9-8.0 (m, 1H), 6.61 (s, 1H), 5.3-5.5 (m, 1H), 5.15 (d, J = 1.2 Hz, 2H), 4.29 (quin, J = 6.3 Hz, 2H), 3.89 (br. s, 2H), 2.27 (dt, J = 2.2, 7.5 Hz, 2H), 1.9-2.0 (m, 4H), 1.6-1.7 (m, 2H), 1.17 (d, J = 6.2 Hz, 6H), 0.8-0.9 (m, 6H). |
| 120 (C) | 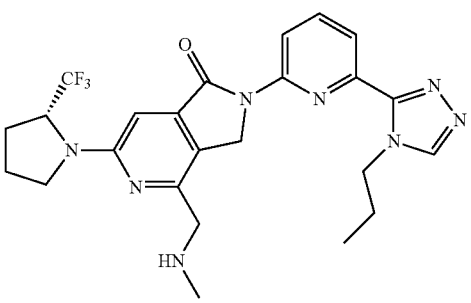 [SMILES: CCCn1cnnc1-c1cccc(N2Cc3c(cc(N4CCC[C@@H]4C(F)(F)F)nc3CNC)C2=O)n1]<br>4-[(methylamino)methyl]-2-[6-(4-propyl-4H-1,2,4-triazol-3-yl)pyridin-2-yl]-6-[(2R)-2-(trifluoromethyl)pyrrolidin-1-yl]-2,3-dihydro-1H-pyrrolo[3,4-c]pyridin-1-one | 501.2 | ¹H NMR (400 MHz, DMSO-$d_6$) δ 9.46 (br. s, 1H) 9.17 (br. s, 1H) 8.79 (s, 1H) 8.64 (d, J = 8.3 Hz, 1H) 8.12 (t, J = 8.0 Hz, 1H) 8.02 (d, J = 7.5 Hz, 1H) 7.07(s, 1H) 5.46 (br. s, 1H) 5.23-5.12 (m, 2H) 4.57 (br. t, J = 7.2 Hz, 2H) 4.37 (br. t, J = 5.1 Hz, 2H) 3.83 (br. d, J = 9.5 Hz, 1H) 3.59-3.47 (m, 1H) 2.77-2.68 (m, 3H) 2.22-2.07 (m, 4H) 1.86 (sxt, J = 7.2 Hz, 2H) 0.92 (t, J = 7.4 Hz, 3H). |
| 121 (AC) | 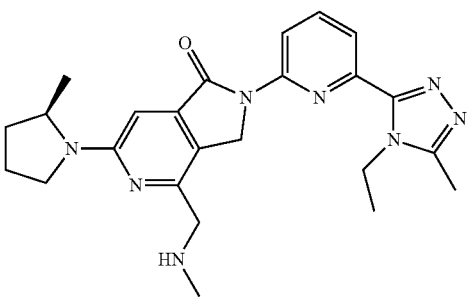 [SMILES: CCn1c(C)nnc1-c1cccc(N2Cc3c(cc(N4CCC[C@H]4C)nc3CNC)C2=O)n1]<br>2-[6-(4-ethyl-5-methyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one | 477.1 | ¹H NMR (700 MHz, DMSO-$d_6$) δ 8.52-8.59 (m, 1H) 8.04-8.09 (m, 1H) 7.90-7.95 (m, 1H) 6.67-6.72 (m, 1H) 5.01-5.10 (m, 2H) 4.46-4.53 (m, 2H) 4.28-4.33 (m, 2H) 3.56-3.62 (m, 3H) 3.34-3.40 (m, 1H) 2.73-2.79 (m, 3H) 2.45-2.49 (m, 3H) 2.01-2.11 (m, 2H) 1.94-1.98 (m, 1H) 1.67-1.76 (m, 1H) 1.38-1.45 (m, 3H) 1.16-1.22 (m, 3H). |
| 122 (AA) | 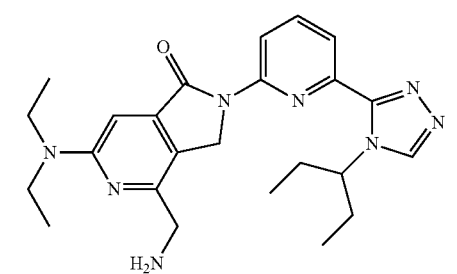 [SMILES: CCC(CC)n1cnnc1-c1cccc(N2Cc3c(cc(N(CC)CC)nc3CN)C2=O)n1]<br>4-(aminomethyl)-6-(diethylamino)-2-{6-[4-(pentan-3-yl)-4H-1,2,4-triazol-3-yl]pyridin-2-yl}-2,3-dihydro-1H-pyrrolo[3,4-c]pyridin-1-one | 449.1 | ¹H NMR (400 MHz, DMSO-$d_6$) δ 8.91 (s, 1H), 8.64 (d, J = 7.8 Hz, 1H), 8.10 (t, J = 8.0 Hz, 1H), 7.94 (d, J = 7.0 Hz, 1H), 6.71 (s, 1H), 5.3-5.5 (m, 1H), 5.16 (s, 2H), 3.85 (br. s, 2H), 3.5-3.6 (m, 4H), 1.8-2.0 (m, 4H), 1.15 (t, J = 6.9 Hz, 6H), 0.79 (t, J = 7.3 Hz, 6H). |

TABLE 1A-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 123 (T) | 4-(aminomethyl)-6-[ethyl(propan-2-yl)amino]-2-{6-[(4R)-4-(fluoromethyl)-2-oxo-1,3-oxazolidin-3-yl]pyridin-2-yl}-2,3-dihydro-1H-pyrrolo[3,4-c]pyridin-1-one | 442.9 | ¹H NMR (400 MHz, DMSO-d₆) δ 8.47 (br. s, 3H) 8.25 (d, J = 8.0 Hz, 1H) 8.01-7.95 (m, 1H) 7.92-7.86 (m, 1H) 6.80 (s, 1H) 5.23-4.92 (m, 5H) 4.89-4.72 (m, 1H) 4.65 (t, J = 8.8 Hz, 1H) 4.52 (dd, J = 3.1, 8.7 Hz, 1H) 4.23-4.16 (m, 2H) 3.49 (q, J = 6.7 Hz, 2H) 1.22-1.13 (m, 9H). |
| 124 (M) | 4-(aminomethyl)-6-[(2R,5R)-2,5-dimethylpyrrolidin-1-yl]-2-{6-[(4R)-4-(fluoromethyl)-2-oxo-1,3-oxazolidin-3-yl]pyridin-2-yl}-2,3-dihydro-1H-pyrrolo[3,4-c]pyridin-1-one | 455.1 | ¹H NMR (400 MHz, DMSO-d₆) δ 8.36 (br. s, 3H) 8.24 (d, J = 7.9 Hz, 1H) 8.01-7.95 (m, 1H) 7.92-7.86 (m, 1H) 6.71 (s, 1H) 5.22-5.08 (m, 2H) 5.07-4.98 (m, 2H) 4.85 (br. d, J = 10.5 Hz, 1H) 4.65 (t, J = 8.9 Hz, 1H) 4.52 (dd, J = 3.1, 8.7 Hz, 1H) 4.28-4.11 (m, 2H) 2.24 (br. d, J = 0.9 Hz, 2H) 2.05-1.94 (m,2H) 1.67 (br. d, J = 5.4 Hz, 2H) 1.19-1.08 (m, 6H). absolute stereochemistry known |
| 125 (T) | 4-(aminomethyl)-2-{6-[(4S)-4-methyl-2-oxo-1,3-oxazolidin-3-yl]pyridin-2-yl}-6-[(2R)-2-methylpyrrolidin-1-yl]-2,3-dihydro-1H-pyrrolo[3,4-c]pyridin-1-one | 423.3 | ¹H NMR (400 MHz, DMSO-d₆) δ 8.45 (br. s, 3H) 8.23 (d, J = 7.8 Hz, 1H) 7.95 (t, J = 8.1 Hz, 1H) 7.82 (d, J = 7.8 Hz, 1H) 6.69 (s, 1H) 5.17-5.00 (m, 2H) 4.96 (dt, J = 2.4, 4.0 Hz, 1H) 4.60 (t, J = 8.3 Hz, 1H) 4.34 (br. s, 1H) 4.22 (br. dd, J = 6.1, 7.8 Hz, 2H) 4.16 (dd, J = 3.8, 8.4 Hz, 1H) 3.63 (br. d, J = 2.6 Hz, 1H) 2.14-1.94 (m, 3H) 1.77-1.70 (m, 1H) 1.49 (d, J = 6.2 Hz, 3H) 1.20 (d, J = 6.2 Hz, 3H). absolute stereochemistry known |
| 126 (S) | 4-(aminomethyl)-6-(1-methylcyclopropyl)-2-{6-[4-(pentan-3-yl)-4H-1,2,4-triazol-3-yl]pyridin-2-yl}-2,3-dihydro-1H-pyrrolo[3,4-c]pyridin-1-one | 432.3 | ¹H NMR (400 MHz, DMSO-d₆) δ 8.92 (s, 1H) 8.64 (d, J = 8.5 Hz, 1H) 8.11 (t, J = 8.0 Hz, 1H) 7.95 (d, J = 7.5 Hz, 1H) 7.55 (s, 1H) 5.38-5.30 (m, 1H) 5.29 (s,2H) 3.97 (s, 2H) 2.10 (br. s, 2H) 2.00-1.82 (m, 4H) 1.56 (s, 3H) 1.30-1.20 (m, 2H) 0.89-0.70 (m, 2H) 0.78 (br. t, J = 7.3 Hz, 6H). |

TABLE 1A-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 127 (AD) | 4-(aminomethyl)-2-[6-(4-ethyl-5-methyl-4H-1,2,4-triazol-3-yl)pyridin-2-yl]-6-(1-methylcyclopropyl)-2,3-dihydro-1H-pyrrolo[3,4-c]pyridin-1-one | 404.3 | ¹H NMR (400 MHz, Methanol-d₄) δ 8.77-8.67 (m, 1H) 8.09-8.0 (m, 1H) 7.99-7.92 (m, 1H) 7.71-7.63 (m, 1H) 5.28-5.20 (m, 2H) 4.66 (q,J = 7.1 Hz, 2H) 4.05 (s, 2H) 2.60 (s, 3H) 1.61 (5, 3H) 1.57 (t, J = 7.2 Hz, 3H) 1.43-1.38 (m, 2H) 0.95-0.89 (m, 2H). |
| 128 (AD) | 4-(aminomethyl)-6-(1-methylcyclopropyl)-2-[6-(5-methyl-4-propyl-4H-1,2,4-triazol-3-yl)pyridin-2-yl]-2,3-dihydro-1H-pyrrolo[3,4-c]pyridin-1-one | 418.5 | ¹H NMR (400 MHz, DMSO-d₆) δ 8.64 (dd, J = 8.4, 0.9 Hz, 1H), 8.32 (s, 3H), 8.12 (dd, J = 8.4, 7.7 Hz, 1H), 7.99 (dd, J = 7.6, 0.9 Hz, 1H), 7.70 (s, 1H), 5.25 (s, 2H), 4.50-4.41 (m, 2H), 4.38 (s, 2H), 2.51 (s, 3H), 1.83 (dt, J = 9.3, 7.3 Hz, 2H), 1.60 (s, 3H), 1.47 (q, J = 3.4 Hz, 2H), 0.97 (t, J = 7.4 Hz, 3H), 0.92 (q, J = 3.5 Hz, 2H). |
| 129 (C) | 4-(aminomethyl)-6-cyclopropyl-2-{6-[4-(pentan-3-yl)-4H-1,2,4-triazol-3-yl]pyridin-2-yl}-2,3-dihydro-1H-pyrrolo[3,4-c]pyridin-1-one | 418.2 | ¹H NMR (600 MHz, DMSO-d₆) δ 8.77-8.86 (m, 1H) 8.50-8.59 (m, 1H) 7.99-8.06 (m, 1H) 7.83-7.94 (m, 1H) 7.41-7.51 (m, 1H) 5.27-5.35 (m, 1H) 5.14-5.24 (m, 2H) 3.85-3.94 (m, 1H) 3.03-3.19 (m, 2H) 2.16-2.33 (m, 1H) 1.76-1.91 (m, 5H) 0.88-0.99 (m, 4H) 0.64-0.77 (m, 6H). |
| 130 (AE) | 6-[ethyl(methyl)amino]-4-[(methylamino)methyl]-2-[6-(5-methyl-4-propyl-4H-1,2,4-triazol-3-yl)pyridin-2-yl]-2,3-dihydro-1H-pyrrolo[3,4-c]pyridin-1-one | 435.5 | ¹H NMR (400 MHz, DMSO-d₆) δ 9.00-8.80 (m, 2H), 8.64 (dd, J = 8.4, 0.9 Hz, 1H), 8.21-8.03 (m, 1H), 7.97 (dd, J = 7.7, 0.9 Hz, 1H), 6.93 (s, 1H), 5.10 (s, 2H), 4.44 (dd, J = 8.7, 6.6 Hz, 2H), 4.35 (t, J = 5.9 Hz, 2H), 3.72 (q, J = 7.0 Hz, 2H), 3.13 (s, 3H), 2.75 (t, J = 5.3 Hz, 3H), 2.53 (s, 3H), 1.80 (q, J = 7.5 Hz, 2H), 1.12 (t, J = 7.0 Hz, 3H), 0.94 (t, J = 7.4 Hz, 3H). |

TABLE 1A-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 131 (C) | 6-[ethyl(methyl)amino]-2-[6-(4-ethyl-4H-1,2,4-triazol-3-yl)pyridin-2-yl]-4-[(methylamino)methyl]-2,3-dihydro-1H-pyrrolo[3,4-c]pyridin-1-one | 407.3 | $^1$H NMR (400 MHz, DMSO-$d_6$) δ 9.20-9.12 (m, 2H) 8.90 (s, 1H) 8.64 (d, J = 8.5 Hz, 1H) 8.13 (t, J = 8.0 Hz, 1H) 8.01 (d, J = 7.8 Hz, 1H) 6.91 (s, 1H) 5.15(s, 2H) 4.64 (q,J = 7.0 Hz, 2H) 4.34 (t, J = 5.8 Hz, 2H) 3.75-3.67 (m, 2H) 3.12 (s, 3H) 2.73 (t, J = 5.4 Hz, 3H) 1.49 (t, J = 7.2 Hz, 3H) 1.12 (t, J = 7.0 Hz, 3H). |
| 132 (M) | 4-(aminomethyl)-2-{6-[(4S)-4-methyl-2-oxo-1,3-oxazolidin-3-yl]pyridin-2-yl}-6-[(2S)-2-methylpyrrolidin-1-yl]-2,3-dihydro-1H-pyrrolo[3,4-c]pyridin-1-one | 423.6 | $^1$H NMR (400 MHz, DMSO-$d_6$) δ 8.31-8.15 (m, 4H), 7.96 (t, J = 8.1 Hz, 1H), 7.86-7.78 (m, 1H), 6.70 (s, 1H), 5.18-4.97 (m, 2H), 4.97-4.90 (m, 1H), 4.61 (t, J = 8.3 Hz, 1H), 4.35 (m, 1H), 4.26 (d, J = 5.8 Hz, 2H), 4.17 (dd, J = 8.4, 3.8 Hz, 1H), 3.64 (t, J = 9.0 Hz, 1H), 3.39 (m, 1H), 2.06 (m, 3H), 1.75 (m, 1H), 1.49 (d, J = 6.2 Hz, 3H), 1.21 (d, J = 6.2 Hz, 3H). absolute stereochemistry known |
| 133 (AF) | 4-(aminomethyl)-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 447.2 | $^1$H NMR (600 MHz, DMSO-$d_6$) δ 8.52 (d, J = 8.25 Hz, 1H) 7.97 (t, J = 7.98 Hz, 1H) 7.88 (d, J = 7.52 Hz, 1H) 6.51 (s, 1H) 5.03 (s, 2H) 4.31-4.44 (m, 2H) 4.13-4.26 (m, 1H) 3.82-3.92 (m, 1H) 3.45-3.55 (m, 4H) 2.41 (s, 3H) 1.93-2.05 (m, 2H) 1.86-1.93 (m, 1H) 1.83 (br. s, 1H) 1.69-1.79 (m, 2H) 1.62-1.67 (m, 1H) 1.13 (d, J = 6.24 Hz, 3H) 0.89 (t, J = 7.34 Hz, 3H). |
| 134 (AE) | 4-[(methylamino)methyl]-2-[6-(5-methyl-4-propyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one | 461.6 | $^1$H NMR (400 MHz, DMSO-$d_6$) δ 8.87 (s, 2H), 8.63 (d, J = 8.4 Hz, 1H), 8.16-8.04 (m, 1H), 7.96 (d, J = 7.6 Hz, 1H), 6.76 (s, 1H), 5.11 (d, J = 1.6 Hz, 2H), 4.49-4.40 (m, 2H), 4.40-4.29 (m, 3H), 3.74-3.59 (m, 2H), 2.77 (t, J = 5.3 Hz, 3H), 2.50 (s, 3H), 2.21-1.94 (m, 3H), 1.79 (dt, J = 15.3, 7.4 Hz, 3H), 1.21 (d, J = 6.2 Hz, 3H), 0.94 (t, J = 7.4 Hz, 3H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 135 (AE) | 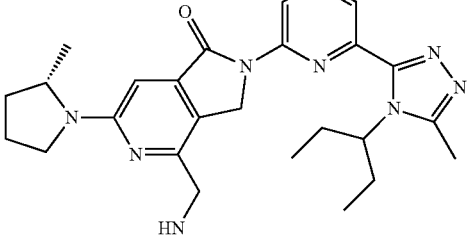<br>4-[(methylamino)methyl]-2-{6-[5-methyl-4-(pentan-3-yl)-4H-1,2,4-triazol-3-yl]pyridin-2-yl}-6-[(2S)-2-methylpyrrolidin-1-yl]-2,3-dihydro-1H-pyrrolo[3,4-c]pyridin-1-one | 489.6 | 1H NMR (700 MHz, DMSO-d6) δ 8.90 (s, 2H), 8.64 (d, J = 8.4 Hz, 1H), 8.11 (t, J = 7.9 Hz, 1H), 7.78 (d, J = 7.5 Hz, 1H), 6.75 (s, 1H), 5.06 (s, 2H), 4.43-4.21 (m, 4H), 3.65 (t, J = 9.2 Hz, 2H), 2.78 (m, 3H), 2.50 (s, 3H). |
| 136 (C) | 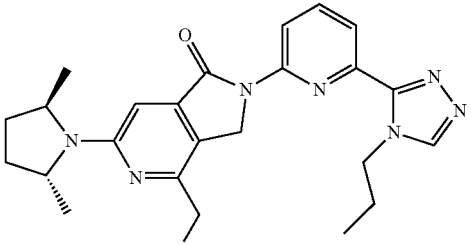<br>4-(aminomethyl)-6-[(2R,5R)-2,5-dimethylpyrrolidin-1-yl]-2-[6-(4-propyl-4H-1,2,4-triazol-3-yl)pyridin-2-yl]-2,3-dihydro-1H-pyrrolo[3,4-c]pyridin-1-one | 447.1 | 1H NMR (400 MHz, DMSO-d6) δ 8.74 (s, 1H), 8.62 (d, J = 7.9 Hz, 1H), 8.08 (t, J = 8.0 Hz, 1H), 8.01 (d, J = 7.3 Hz, 1H), 6.59 (s, 1H), 5.20-5.06 (m, 2H), 4.64-4.49 (m, 2H), 4.27 (s, 2H), 3.84 (s, 2H), 2.24 (m, 2H), 1.88 (m, 2H), 1.65 (m, 2H), 1.14 (d, J = 6.1 Hz, 6H), 0.94 (t, J = 7.4 Hz, 3H). |
| 137 (D) | <br>4-(aminomethyl)-6-[(2R,5R)-2,5-dimethylpyrrolidin-1-yl]-2-{6-[(4S)-4-methyl-2-oxo-1,3-oxazolidin-3-yl]pyridin-2-yl}-2,3-dihydro-1H-pyrrolo[3,4-c]pyridin-1-one | 437.2 | 1H NMR (400 MHz, Methanol-d4) δ 8.32 (t, J = 4.4 Hz, 1H) 7.90 (m, 2H) 6.89 (s, 1H) 5.20-5.03 (m, 3H) 4.63 (t, J = 8.3 Hz, 1H) 4.40 (br. s,2H) 4.37-4.30 (m, 2H) 4.20 (dd, J = 4.0, 8.5 Hz, 1H) 2.37 (br. s, 2H) 1.78 (br. d, J = 5.5 Hz, 2H) 1.57 (d, J = 6.2 Hz, 3H) 1.24 (d, J = 6.1 Hz, 6H).<br>absolute stereochemistry known |
| 138 (C) | 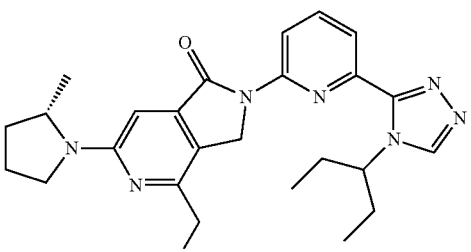<br>4-[(methylamino)methyl]-6-[(2S)-2-methylpyrrolidin-1-yl]-2-{6-[4-(pentan-3-yl)-4H-1,2,4-triazol-3-yl]pyridin-2-yl}-2,3-dihydro-1H-pyrrolo[3,4-c]pyridin-1-one | 475.7 | 1H NMR (700 MHz, DMSO-d6) δ 8.91 (s, 3H), 8.62 (d, J = 8.4 Hz, 1H), 8.11 (t, J = 7.9 Hz, 1H), 7.91 (d, J = 7.5 Hz, 1H), 6.73 (s, 1H), 5.20 (m, 1H), 5.08 (s, 2H), 4.28-4.33 (m, 3H), 3.64 (m, 2H), 2.77 (m, 3H), 2.11-1.97 (m, 3H), 1.92 (m, 4H), 1.73 (m, 1H), 1.20 (d, J = 6.3 Hz, 3H), 0.79 (t, J = 7.3 Hz, 6H). |

TABLE 1A-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 139 (S) | 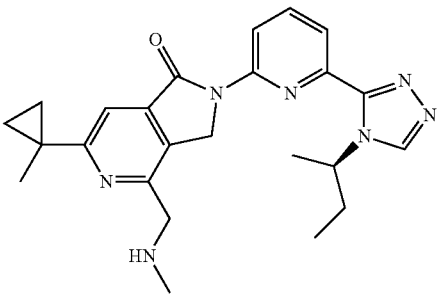<br>2-(6-{4-[(2R)-butan-2-yl]-4H-1,2,4-triazol-3-yl}pyridin-2-yl)-4-[(methylamino)methyl]-6-(1-methylcyclopropyl)-2,3-dihydro-1H-pyrrolo[3,4-c]pyridin-1-one | 432.2 | ¹H NMR (600 MHz, DMSO-d₆) δ 9.14-9.18 (m, 1H) 8.93 (s, 1 H) 8.61 (d, J = 8.44 Hz, 1H) 8.12 (t, J = 7.97 Hz, 1H) 7.93 (d, J = 7.52 Hz, 1H) 7.69 (s, 1H) 5.24-5.31 (m, 1H) 5.18-5.24 (m, 2H) 4.47 (br. s, 2H) 2.77 (s, 3H) 1.87-2.03 (m, 2H) 1.56-1.61 (m, 6H) 1.38-1.49 (m, 2H) 0.89-0.95 (m, 2H) 0.82 (t, J = 7.34 Hz, 3H). absolute stereochemistry known |
| 140 (AG) | 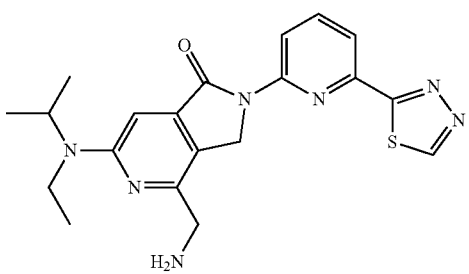<br>4-(aminomethyl)-6-[ethyl(propan-2-yl)amino]-2-[6-(1,3,4-thiadiazol-2-yl)pyridin-2-yl]-2,3-dihydro-1H-pyrrolo[3,4-c]pyridin-1-one | 410.2 | ¹H NMR (400 MHz, DMSO-d₆) δ 9.76 (s, 1H) 8.69 (d, J = 8.0 Hz, 1H) 8.19-8.14 (m, 1H) 8.13-8.09 (m, 1H) 6.77 (s, 1H) 5.70 (br. s, 2H) 5.16 (s, 2H) 4.98-4.88 (m, 1H) 4.08 (s, 2H) 3.52-3.43 (m, 2H) 1.21-1.16 (m, 9H). |
| 141 (AH) | 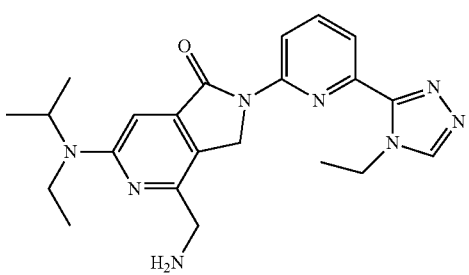<br>4-(aminomethyl)-6-[ethyl(propan-2-yl)amino]-2-[6-(4-ethyl-4H-1,2,4-triazol-3-yl)pyridin-2-yl]-2,3-dihydro-1H-pyrrolo[3,4-c]pyridin-1-one | 421.3 | ¹H NMR (400 MHz, DMSO-d₆) δ 9.17 (s, 1H) 8.67 (d, J = 8.0 Hz, 1H) 8.49 (br. s, 3H) 8.16 (t, J = 8.0 Hz, 1H) 8.03 (d, J = 7.0 Hz, 1H) 6.84 (s, 1H) 5.17 (s,2H) 5.05-4.93 (m, 1H) 4.69 (q, J = 7.2 Hz, 2H) 4.23 (q, J = 5.3 Hz, 2H) 3.50 (q, J = 6.7 Hz, 2H) 1.52 (t, J = 7.2 Hz, 3H) 1.21-1.15 (m, 9H). |
| 142 (C) | 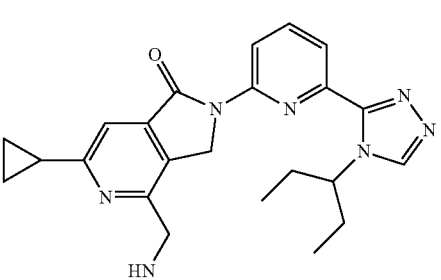<br>6-cyclopropyl-4-[(methylamino)methyl]-2-{6-[4-(pentan-3-yl)-4H-1,2,4-triazol-3-yl]pyridin-2-yl}-2,3-dihydro-1H-pyrrolo[3,4-c]pyridin-1-one | 432.1 | ¹H NMR (600 MHz, DMSO-d₆) δ 8.84-8.92 (m, 1H) 8.54-8.63 (m, 1H) 8.03-8.10 (m, 1H) 7.85-7.94 (m, 1H) 7.48-7.54 (m, 1H) 5.31-5.38 (m, 1H) 5.18-5.23 (m, 2H) 3.85-3.86 (m, 2H) 2.30-2.34 (m, 3H) 2.21-2.27 (m, 1H) 1.83-1.95 (m, 4H) 0.93-1.04 (m, 5H) 0.73-0.79 (m, 6H). |

TABLE 1A-continued

| Ex. No. | Structure/IUPAC name | LCMS [M + H]+ | 1H NMR (ppm); 19F NMR (ppm); optical rotation; stereochem. notes |
|---|---|---|---|
| 143 (R) | 4-(aminomethyl)-6-[(2R)-2-methylpyrrolidin-1-yl]-2-{6-[4-(pentan-3-yl)-4H-1,2,4-triazol-3-yl]pyridin-2-yl}-2,3-dihydro-1H-pyrrolo[3,4-c]pyridin-1-one | 461.4 | 1H NMR (400 MHz, DMSO-d6,) δ 8.84 (s, 1H), 8.57 (d, J = 8.4 Hz, 1H), 8.02 (t, J = 8.0 Hz, 1H), 7.87 (d, J = 7.2 Hz, 1H), 6.50 (s, 1H), 5.3-5.4 (m, 1H), 5.09 (s, 2H), 4.1-4.3 (m, 1H), 3.78 (br. s, 2H), 3.5-3.6 (m, 2H), 2.0-2.1 (m, 2H), 1.7-1.9 (m, 5H), 1.6-1.6 (m, 1H), 1.13 (d, J = 6.1 Hz, 3H), 0.71 (t, J = 7.3 Hz, 6H). |
| 144 (C) | 4-[(methylamino)methyl]-6-[(2R)-2-methylpyrrolidin-1-yl]-2-{6-[4-(pentan-3-yl)-4H-1,2,4-triazol-3-yl]pyridin-2-yl}-2,3-dihydro-1H-pyrrolo[3,4-c]pyridin-1-one | 475.2 | 1H NMR (400 MHz, DMSO-d6) δ 8.91 (s, 1H) 8.64 (d, J = 7.95 Hz, 1H) 8.09 (t, J = 7.95 Hz, 1H) 7.94 (d, J = 7.09 Hz, 1H) 6.60 (s, 1H) 5.32-5.50 (m, 1H) 5.14 (s, 2H) 4.12-4.28 (m, 1H) 3.82 (br. s, 2H) 3.51-3.61 (m, 1 H) 2.27-2.47 (m, 3H) 2.02-2.12 (m, 2H) 1.86-1.99 (m, 6H) 1.62-1.75 (m, 1H) 1.20 (d, J = 6.11 Hz, 3H) 0.79 (t, J = 7.34 Hz, 6H). |
| 145 (AH) | 4-(aminomethyl)-6-[ethyl(propan-2-yl)amino]-2-{6-[4-(propan-2-yl)-4H-1,2,4-triazol-3-yl]pyridin-2-yl}-2,3-dihydro-1H-pyrrolo[3,4-c]pyridin-1-one | 434.9 | 1H NMR (400 MHz, DMSO-d6) δ 9.61 (s, 1H) 8.70 (d, J = 8.3 Hz, 1H) 8.57 (br. s, 3H) 8.18 (t, J = 8.0 Hz, 1H) 7.98 (d, J = 7.3 Hz, 1H) 6.84 (s, 1H) 5.59-5.48 (m, 1H) 5.20 (s, 2H) 5.05-4.90 (m, 1H) 4.20 (br. d, J = 5.5 Hz, 2H) 3.57-3.44 (m, 2H) 1.64 (d, J = 6.8 Hz, 6H) 1.22-1.15 (m, 9H). |
| 146 (AH) | 4-(aminomethyl)-6-[ethyl(propan-2-yl)amino]-2-[6-(4-propyl-4H-1,2,4-triazol-3-yl)pyridin-2-yl]-2,3-dihydro-1H-pyrrolo[3,4-c]pyridin-1-one | 435.3 | 1H NMR (400 MHz, DMSO-d6) δ 9.08 (s, 1H) 8.70-8.64 (m, 1H) 8.46 (br. s, 3H) 8.19-8.11 (m, 1H) 8.03 (dd, J = 0.6, 7.6 Hz, 1H) 6.84 (s, 1H) 5.15 (s,2H) 5.05-4.93 (m, 1H) 4.61 (t, J = 7.3 Hz, 2H) 4.21 (q, J = 5.6 Hz, 2H) 3.50 (q, J = 6.6 Hz, 2H) 1.96-1.84 (m, 2H) 1.24-1.13 (m, 9H) 0.96 (t, J = 7.4 Hz,3H). |

*Use of orl in a structure and ξ for stereochemistry in a name is to identify chiral centers that have been resolved into enantiomers, but the specific enantiomer is not identified; a solid or dashed wedge is drawn in the structure but it could be the other enanatiomer.

TABLE 1B

| Ex. No. | Structure/IUPAC name | LCMS [M + H]+ | $^1$H NMR (ppm); $^{19}$F NMR (ppm); optical rotation; stereochem. notes |
|---|---|---|---|
| 150 (C) | 4-(aminomethyl)-6-[methyl(propan-2-yl)amino]-2-{6-[4-(pentan-3-yl)-4H-1,2,4-triazol-3-yl]pyridin-2-yl}-2,3-dihydro-1H-pyrrolo[3,4-c]pyridin-1-one | 449.3 | $^1$H NMR (400 MHz, Methanol-d$_4$) δ 9.10 (s, 1H), 8.81 (d, J = 8.1 Hz, 1H), 8.10 (d, J = 8.4 Hz, 1H), 7.92 (d, J = 7.1 Hz, 1H), 7.01 (s, 1H), 5.38-5.30 (m, 1H), 5.14 (s, 2H), 5.06 (td, J = 6.7, 13.3 Hz, 1H), 4.33 (s, 2H), 3.02 (s, 3H), 2.14-1.95 (m, 4H), 1.27 (d, J = 6.7 Hz, 6H), 0.93 (t, J = 7.4 Hz, 6H). |
| 151 (C) | 4-(aminomethyl)-6-(2,2-dimethylpyrrolidin-1-yl)-2-{6-[4-(pentan-3-yl)-4H-1,2,4-triazol-3-yl]pyridin-2-yl}-2,3-dihydro-1H-pyrrolo[3,4-c]pyridin-1-one | 475.2 | $^1$H NMR (400 MHz, Methanol-d$_4$) δ 8.93 (s, 1H), 8.79 (d, J = 8.3 Hz, 1H), 8.10 (t, J = 8.1 Hz, 1H), 7.90 (d, J = 7.2 Hz, 1H), 6.95 (s, 1H), 5.29 (s, 1H), 5.14 (s, 2H), 4.32 (s, 2H), 3.70-3.63 (m, 2H), 2.09-1.97 (m, 8H), 1.61 (s, 6H), 0.92 (t, J = 7.4 Hz, 6H). |
| 152 (C) | 4-(aminomethyl)-6-[(2S)-2-methylpyrrolidin-1-yl]-2-{6-[4-(pentan-3-yl)-4H-1,2,4-triazol-3-yl]pyridin-2-yl}-2,3-dihydro-1H-pyrrolo[3,4-c]pyridin-1-one | 461.3 | $^1$H NMR (400 MHz, Methanol-d$_4$) δ 8.89 (s, 1H), 8.78 (d, J = 8.0 Hz, 1H), 8.13-8.07 (m, 1H), 7.90 (d, J = 7.0 Hz, 1H), 6.85 (s, 1H), 5.28 (s, 1H), 5.14 (s, 2H), 4.37-4.31 (m, 3H), 3.72 (br. s, 1H), 3.50 (br. s, 1H), 2.22-1.95 (m, 7H), 1.86 (br. d, J = 4.0 Hz, 1H), 1.31 (d, J = 6.3 Hz, 3H), 0.92 (dt, J = 1.1, 7.3 Hz, 6H). |
| 153 (C) | 4-(aminomethyl)-6-[ethyl(methyl)amino]-2-{6-[4-(pentan-3-yl)-4H-1,2,4-triazol-3-yl]pyridin-2-yl}-2,3-dihydro-1H-pyrrolo[3,4-c]pyridin-1-one | 435.3 | $^1$H NMR (400 MHz, Methanol-d$_4$) δ 9.96 (s, 1H), 8.93 (d, J = 8.4 Hz, 1H), 8.25-8.17 (m, 1H), 8.01 (d, J = 7.3 Hz, 1H), 7.02 (s, 1H), 5.59 (s, 1H), 5.17 (s, 2H), 4.35 (s, 2H), 3.77 (q, J = 7.1 Hz, 2H), 3.21 (s, 3H), 2.24-2.03 (m, 4H), 1.24 (t, J = 7.0 Hz, 3H), 0.99 (t, J = 7.4 Hz, 6H). |

TABLE 1B-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 154 (AI) | 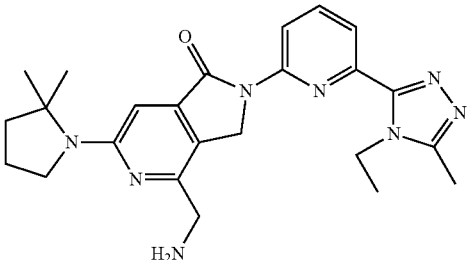<br>4-(aminomethyl)-6-(2,2-dimethylpyrrolidin-1-yl)-2-[6-(4-ethyl-5-methyl-4H-1,2,4-triazol-3-yl)pyridin-2-yl]-2,3-dihydro-1H-pyrrolo[3,4-c]pyridin-1-one | 447.3 | ¹H NMR (400 MHz, Methanol-$d_4$) δ 8.75 (d, J = 8.8 Hz, 1H), 8.15-8.06 (m, 1H), 7.97 (d, J = 7.0 Hz, 1H), 7.02 (s, 1H), 5.18 (s, 2H), 4.65 (q, J = 7.1 Hz, 2H), 4.34 (s, 2H), 3.02 (s, 3H), 2.62 (s, 3H), 1.55 (t, J = 7.2 Hz, 3H), 1.27 (d, J = 6.8 Hz, 6H). |
| 155 (AI) | 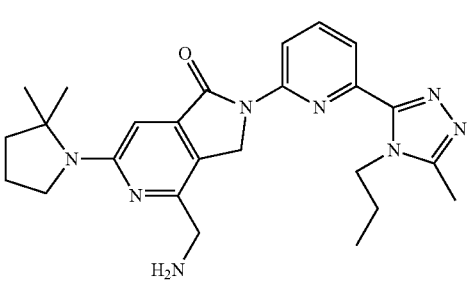<br>4-(aminomethyl)-6-(2,2-dimethylpyrrolidin-1-yl)-2-[6-(5-methyl-4-propyl-4H-1,2,4-triazol-3-yl)pyridin-2-yl]-2,3-dihydro-1H-pyrrolo[3,4-c]pyridin-1-one | 461.3 | ¹H NMR (400 MHz, Methanol-$d_4$) δ 8.85 (d, J = 8.4 Hz, 1H), 8.13 (d, J = 8.2 Hz, 1H), 8.02 (d, J = 7.6 Hz, 1H), 6.95 (s, 1H), 5.18 (s, 2H), 4.74-4.68 (m, 2H), 4.36 (s, 2H), 3.67 (s, 2H), 2.78 (s, 3H), 2.08-1.95 (m, 6H), 1.62 (s, 6H), 1.10 (t, J = 7.5 Hz, 3H). |
| 156 (AI) | 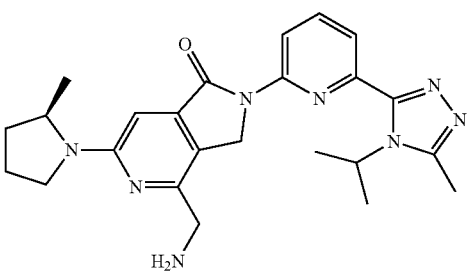 [SMILES: CCCn1c(C)nnc1-c1cccc(N2Cc3c(cc(N4CCC[C@H]4C)nc3CN)C2=O)n1]<br>4-(aminomethyl)-{6-[5-methyl-4-(propan-2-yl)-4H-1,2,4-triazol-3-yl]pyridin-2-yl}-6-[(2R)-2-methylpyrrolidin-1-yl]-2,3-dihydro-1H-pyrrolo[3,4-c]pyridin-1-one | 447.3 | ¹H NMR (400 MHz, Methanol-$d_4$) δ 8.91 (d, J = 8.3 Hz, 1H), 8.23-8.14 (m, 1H), 7.89 (d, J = 7.0 Hz, 1H), 6.87 (s, 1H), 5.72 (quin, J = 7.0 Hz, 1H), 5.17 (s, 2H), 4.35 (s, 3H), 3.78-3.66 (m, 1H), 3.56-3.47 (m, 1H), 2.96 (s, 3H), 2.26-2.05 (m, 3H), 1.91 -1.83 (m, 1H), 1.78 (d, J = 7.0 Hz, 6H), 1.31 (d, J = 6.3 Hz, 3H). |
| 157 (AI) | 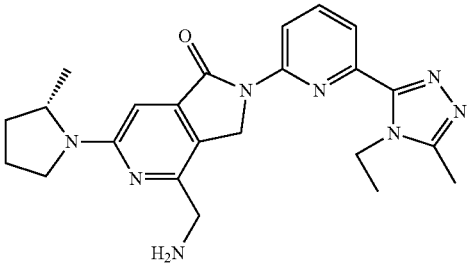 [SMILES: CCCn1c(C)nnc1-c1cccc(N2Cc3c(cc(N4CCC[C@@H]4C)nc3CN)C2=O)n1]<br>4-(aminomethyl)-2-[6-(4-ethyl-5-methyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one | 433.2 | ¹H NMR (400 MHz, Methanol-$d_4$) δ 8.84 (d, J = 8.0 Hz, 1H), 8.15 (t, J = 8.0 Hz, 1H), 8.03 (d, J = 7.3 Hz, 1H), 6.85 (s, 1H), 5.19 (s, 2H), 4.84-4.78 (m, 2H), 4.37 (s, 2H), 4.33 (br. d, J = 6.5 Hz, 1H), 3.71 (br. dd, J = 7.9, 10.4 Hz, 1H), 3.56-3.44 (m, 1H), 2.82 (s, 3H), 2.26-2.04 (m, 3H), 1.89- 1.80 (m, 1H), 1.63 (t, J = 7.2 Hz, 3H), 1.30 (d, J = 6.3 Hz, 3H). |

TABLE 1B-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 158 (AI) | 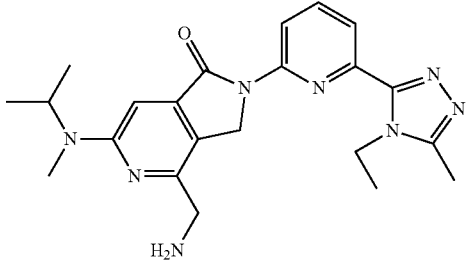<br>4-(aminomethyl)-2-[6-(4-ethyl-5-methyl-4H-1,2,4-triazol-3-yl)pyridin-2-yl]-6-[methyl(propan-2-yl)amino]-2,3-dihydro-1H-pyrrolo[3,4-c]pyridin-1-one | 421.3 | ¹H NMR (400 MHz, Methanol-d₄) δ 8.75 (d, J = 8.8 Hz, 1H), 8.15-8.06 (m, 1H), 7.97 (d, J = 7.0 Hz, 1H), 7.02 (s, 1H), 5.18 (s, 2H), 4.65 (q, J = 7.1 Hz, 2H), 4.34 (s, 2H), 3.02 (s, 3H), 2.62 (s, 3H), 1.55 (t, J = 7.2 Hz, 3H), 1.27 (d, J = 6.8 Hz, 6H). |
| 159 (AI) | 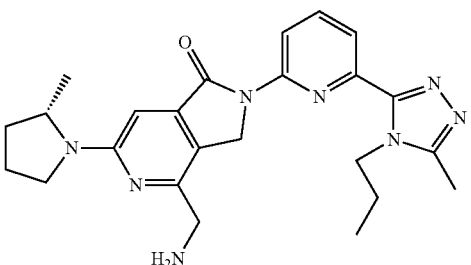<br>4-(aminomethyl)-2-[6-(5-methyl-4-propyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one | 447.3 | ¹H NMR (400 MHz, Methanol-d₄) δ 8.86 (d, J = 8.4 Hz, 1H), 8.14 (t, J = 8.1 Hz, 1H), 8.02 (d, J = 7.5 Hz, 1H), 6.87 (s, 1H), 5.17 (s, 2H), 4.74-4.65 (m, 2H), 4.36 (s, 3H), 3.72 (br. d, J = 2.6 Hz, 1H), 3.51 (br. d, J = 9.9 Hz, 1H), 2.78 (s, 3H), 2.29-1.94 (m, 5H), 1.86 (br. s, 1H), 1.31 (d, J = 6.4 Hz, 3H), 1.10 (t, J = 7.4 Hz, 3H). |
| 160 (AI) | 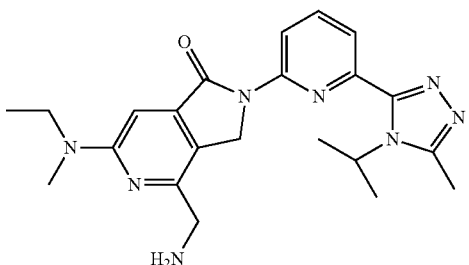<br>4-(aminomethyl)-6-[ethyl(methyl)amino]-2-{6-[5-methyl-4-(propan-2-yl)-4H-1,2,4-triazol-3-yl]pyridin-2-yl}-2,3-dihydro-1H-pyrrolo[3,4-c]pyridin-1-one | 421.2 | ¹H NMR (400 MHz, Methanol-d₄) δ 8.89 (d, J = 8.5 Hz, 1H), 8.22-8.13 (m, 1H), 7.88 (d, J = 7.5 Hz, 1H), 7.00 (s, 1H), 5.68 (quin, J = 7.1 Hz, 1H), 5.16 (s, 2H), 4.35 (s, 2H), 3.77 (q, J = 7.1 Hz, 2H), 3.20 (s, 3H), 2.92 (s, 3H), 1.76 (d, J = 7.0 Hz, 6H), 1.24 (t, J = 7.0 Hz, 3H). |

TABLE 1B-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 161 (AI) | 4-(aminomethyl)-6-[ethyl(methyl)amino]-2-[6-(5-methyl-4-propyl-4H-1,2,4-triazol-3-yl)pyridin-2-yl]-2,3-dihydro-1H-pyrrolo[3,4-c]pyridin-1-one | 421.2 | $^1$H NMR (400 MHz, Methanol-$d_4$) δ 8.90 (dd, J = 0.7, 8.6 Hz, 1H), 8.21-8.13 (m, 1H), 8.05 (dd, J = 0.7, 7.6 Hz, 1H), 7.01 (s, 1H), 5.18 (s, 2H), 4.81-4.74 (m, 2H), 4.38 (s, 2H), 3.77 (d, J = 7.1 Hz, 2H), 3.21 (s, 3H), 2.90-2.83 (m, 3H), 2.03 (s, 2H), 1.24 (t, J = 7.1 Hz, 3H), 1.13 (t, J = 7.4 Hz, 3H). |
| 162 (AI) | 4-(aminomethyl)-2-{6-[5-methyl-4-(propan-2-yl)-4H-1,2,4-triazol-3-yl]pyridin-2-yl}-6-[(2S)-2-methylpyrrolidin-1-yl]-2,3-dihydro-1H-pyrrolo[3,4-c]pyridin-1-one | 447.3 | $^1$H NMR (400 MHz, Methanol-$d_4$) δ 8.65 (d, J = 8.5 Hz, 1H), 7.96 (t, J = 8.1 Hz, 1H), 7.65 (d, J = 7.6 Hz, 1H), 6.73 (s, 1H), 5.30 (td, J = 7.0, 14.1 Hz, 1H), 5.01 (s, 2H), 4.20 (s, 3H), 3.65-3.55 (m, 1H), 3.44-3.35 (m, 1H), 2.59 (s, 3H), 2.13-1.92 (m, 3H), 1.73 (br. s, 1H), 1.54 (d, J = 7.1 Hz, 6H), 1.18 (d, J = 6.3 Hz, 3H). |
| 163 (AI) | 4-(aminomethyl)-6-(diethylamino)-2-[6-(4-ethyl-5-methyl-4H-1,2,4-triazol-3-yl)pyridin-2-yl]-2,3-dihydro-1H-pyrrolo[3,4-c]pyridin-1-one | 421.3 | $^1$H NMR (400 MHz, Methanol-$d_4$) δ 8.88 (d, J = 8.4 Hz, 1H), 8.16 (t, J = 8.1 Hz, 1H), 8.04 (d, J = 7.5 Hz, 1H), 6.99 (s, 1H), 5.19 (s, 2H), 4.37 (s, 2H), 3.71 (q, J = 6.9 Hz, 4H), 2.83 (s, 3H), 1.64 (t, J = 7.2 Hz, 3H), 1.27 (t, J = 7.0 Hz, 6H). $^1$H NMR (400 MHz, Methanol-$d_4$ + $D_2O$) δ 8.85 (d, J = 8.3 Hz, 1H), 8.19-8.12 (m, 1H), 8.07-8.00 (m, 1H), 6.98 (s, 1H), 5.19 (s, 2H), 4.83-4.75 (m, 2H), 4.36 (s, 2H), 3.71 (q, J = 7.0 Hz, 4H), 2.80 (s, 3H), 1.63 (t, J = 7.2 Hz, 3H), 1.27 (t, J = 7.0 Hz, 6H) |
| 164 (AI) | 4-(aminomethyl)-6-(2,2-dimethylpyrrolidin-1-yl)-2-{6-[5-methyl-4-(propan-2-yl)-4H-1,2,4-triazol-3-yl]pyridin-2-yl}-2,3-dihydro-1H-pyrrolo[3,4-c]pyridin-1-one | 483.5 | $^1$H NMR (400 MHz, Methanol-$d_4$) δ 8.88 (d, J = 8.3 Hz, 1H), 8.16 (t, J = 8.0 Hz, 1H), 7.86 (d, J = 7.0 Hz, 1H), 6.96 (s, 1H), 5.62 (br. d, J = 7.5 Hz, 1H), 5.15 (s, 3H), 4.33 (s, 2H), 3.67 (s, 2H), 2.88 (s, 3H), 2.05 (s, 4H), 1.74 (d, J = 7.0 Hz, 6H), 1.61 (s, 6H). |

TABLE 1B-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 165 (AI) | 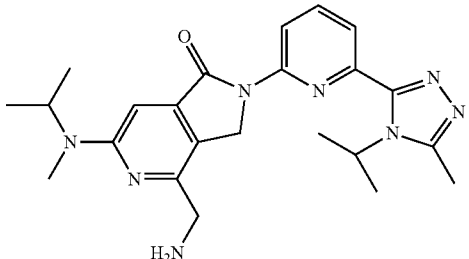<br>4-(aminomethyl)-6-[methyl(propan-2-yl)amino]-2-{6-[5-methyl-4-(propan-2-yl)-4H-1,2,4-triazol-3-yl]pyridin-2-yl}-2,3-dihydro-1H-pyrrolo[3,4-c]pyridin-1-one | 435.4 | ¹H NMR (400 MHz, Methanol-d₄) δ 8.91 (d, J = 7.8 Hz, 1H), 8.22-8.13 (m, 1H), 7.88 (d, J = 7.5 Hz, 1H), 7.02 (s, 1H), 5.73-5.62 (m, 1H), 5.16 (s, 2H), 5.09-5.05 (m, 1H), 4.34 (s, 2H), 3.02 (s, 3H), 2.93 (s, 3H), 1.76 (d, J = 7.0 Hz, 6H), 1.27 (d, J = 6.5 Hz, 6H). |
| 166 (AI) | 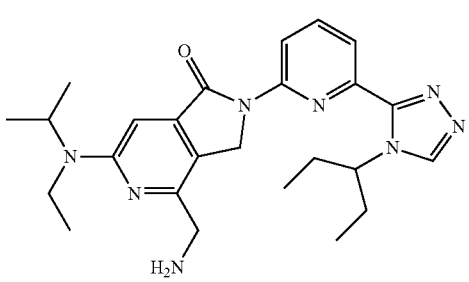<br>4-(aminomethyl)-6-[ethyl(propan-2-yl)amino]-2-{6-[4-(pentan-3-yl)-4H-1,2,4-triazol-3-yl]pyridin-2-yl}-2,3-dihydro-1H-pyrrolo[3,4-c]pyridin-1-one | 463.2 | ¹H NMR (400 MHz, Methanol-d₄) δ 9.40 (s, 1H), 8.86 (d, J = 8.4 Hz, 1H), 8.15 (dd J = 7.7, 8.4 Hz, 1H), 7.96 (d, J = 7.6 Hz, 1H), 7.00 (s, 1H), 5.49-5.38 (m, 1H), 5.16 (s, 2H), 5.11-5.03 (m, 1H), 4.33 (s, 2H), 3.57 (q, J = 6.9 Hz, 2H), 2.15-2.00 (m, 4H), 1.29 (d, J = 6.7 Hz, 9H), 0.95 (t, J = 7.3 Hz, 6H). |
| 167 (AI) | 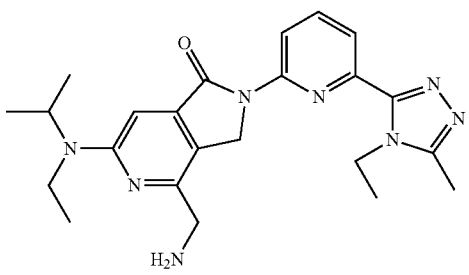 [SMILES: CCN(c1cc2c(c(CN)n1)CN(c1cccc(-c3nncs3)n1)C2=O)C(C)C]<br>4-(aminomethyl)-2-[6-(4-ethyl-5-methyl-4H-1,2,4-triazol-3-yl)pyridin-2-yl]-6-[ethyl(propan-2-yl)amino]-2,3-dihydro-1H-pyrrolo[3,4-c]pyridin-1-one | 435.3 | ¹H NMR (400 MHz, Methanol-d₄) δ 8.92 (d, J = 8.5 Hz, 1H), 8.19 (t, J = 8.0 Hz, 1H), 7.90 (d, J = 7.3 Hz, 1H), 7.05 (br. s, 1H), 5.81-5.68 (m, 1H), 5.19 (s, 2H), 5.03 (br. s, 1H), 4.36 (s, 2H), 3.58 (br d, J = 7.3 Hz, 2H), 2.97 (s, 3H), 1.79 (br. d, J = 7.0 Hz, 6H), 1.36-1.26 (m, 8H), 1.36-1.26 (m, 1H). |
| 168 (AI) | 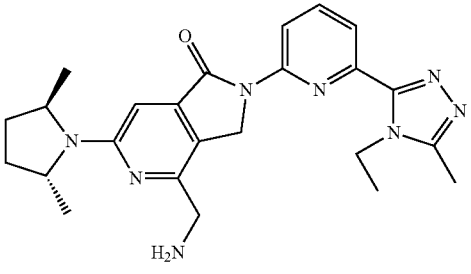<br>4-(aminomethyl)-6-[(2R,5R)-2,5-dimethylpyrrolidin-1-yl]-2-[6-(4-ethyl-5-methyl-4H-1,2,4-triazol-3-yl)pyridin-2-yl]-2,3-dihydro-1H-pyrrolo[3,4-c]pyridin-1-one | 447.3 | ¹H NMR (400 MHz, DMSO-d₆) δ 8.71 (dd, J = 4.9, 8.3 Hz, 1H), 8.18 (dt, J = 3.5, 8.0 Hz, 1H), 7.98 (dd, J = 1.6, 7.6 Hz, 1H), 6.72 (s, 1H), 5.12 (br. s, 2H), 4.63 (br. d, J = 6.4 Hz, 2H), 4.52-4.15 (m, 4H), 2.72 (br. d, J = 5.9 Hz, 3H), 2.23 (br. s, 2H), 1.66 (br. d, J = 5.3 Hz, 2H), 1.57-1.45 (m, 3H), 1.12 (br. d, J = 5.9 Hz, 6H). |

TABLE 1B-continued

| Ex. No. | Structure/IUPAC name | LCMS [M + H]+ | 1H NMR (ppm); 19F NMR (ppm); optical rotation; stereochem. notes |
|---|---|---|---|
| 169 (AI) | 4-(aminomethyl)-6-[(2R,5R)-2,5-dimethylpyrrolidin-1-yl]-2-{6-[5-methyl-4-(propan-2-yl)-4H-1,2,4-triazol-3-yl]pyridin-2-yl}-2,3-dihydro-1H-pyrrolo[3,4-c]pyridin-1-one | 461.1 | 1H NMR (400 MHz, Methanol-d4) δ 8.79 (d, J = 8.5 Hz, 1H), 8.16 (dd, J = 7.8, 8.5 Hz, 1H), 7.84 (d, J = 7.5 Hz, 1H), 6.87 (s, 1H), 5.53 (quin, J = 7.0 Hz,1H), 5.16 (s, 2H), 4.83-4.77 (m, 2H), 4.56-4.21 (m, 4H), 2.86 (s, 3H), 2.35 (br. s, 2H), 1.77 (br. d, J = 5.5 Hz, 2H), 1.72 (d, J = 7.0 Hz, 6H), 1.23 (d, J = 6.3 Hz, 6H). |
| 170 (AI) | 4-(aminomethyl)-6-(diethylamino)-2-[6-(5-methyl-4-propyl-4H-1,2,4-triazol-3-yl)pyridin-2-yl]-2,3-dihydro-1H-pyrrolo[3,4-c]pyridin-1-one | 435.2 | 1H NMR (400 MHz, Methanol-d4) δ 8.86 (d, J = 8.5 Hz, 1H), 8.14 (t, J = 8.0 Hz, 1H), 8.02 (d, J = 7.0 Hz, 1H), 6.99 (s, 1H), 5.17 (s, 2H), 4.73-4.65 (m, 2H), 4.35 (s, 2H), 3.71 (q, J = 7.0 Hz, 4H), 2.77 (s, 3H), 2.00 (br. d, J = 7.8 Hz, 2H), 1.27 (t, J = 7.0 Hz, 6H), 1.10 (t, J = 7.4 Hz, 3H). |
| 171 (AI) | 4-(aminomethyl)-6-[ethyl(methyl)amino]-2-[6-(4-ethyl-5-methyl-4H-1,2,4-triazol-3-yl)pyridin-2-yl]-2,3-dihydro-1H-pyrrolo[3,4-c]pyridin-1-one | 407.3 | 1H NMR (400 MHz, Methanol-d4) δ 8.88-8.82 (m, 1H), 8.19-8.10 (m, 1H), 8.07-8.00 (m, 1H), 7.00 (s, 1H), 5.19 (s, 2H), 4.83-4.76 (m, 2H), 4.37 (s, 2H), 3.77 (q, J = 7.0 Hz, 2H), 3.20 (s, 3H), 2.81 (s, 3H), 1.63 (t, J = 7.3 Hz, 3H), 1.24 (t, J = 7.0 Hz, 3H). |
| 172 (AI) | 4-(aminomethyl)-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one | 435.1 | 1H NMR (400 MHz, Methanol-d4) δ 8.91 (d, J = 7.9 Hz, 1H), 8.17 (d, J = 8.5 Hz, 1H), 8.05 (d, J = 7.0 Hz, 1H), 7.03 (s, 1H), 5.19 (s, 2H), 5.06 (td, J = 6.7, 13.1 Hz, 1H), 4.83-4.76 (m, 2H), 4.38 (s, 2H), 3.02 (s, 3H), 2.88 (s, 3H), 2.05 (br. d, J = 7.5 Hz, 2H), 1.28 (d, J = 6.8 Hz, 6H), 1.13 (t, J = 7.4 Hz, 3H). |

TABLE 1B-continued

| Ex. No. | Structure/IUPAC name | LCMS [M + H]+ | 1H NMR (ppm); 19F NMR (ppm); optical rotation; stereochem. notes |
|---|---|---|---|
| 173 (C) | 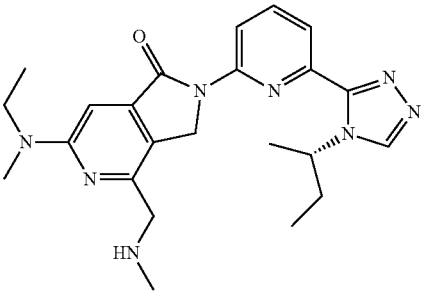<br>2-(6-{4-[(2S)-butan-2-yl]-4H-1,2,4-triazol-3-yl}pyridin-2-yl)-6-[ethyl(methyl)amino]-4-[(methylamino)methyl]-2,3-dihydro-1H-pyrrolo[3,4-c]pyridin-1-one | 435.3 | 1H NMR (400 MHz, DMSO-d6) δ 9.29 (br. s, 2H), 9.19 (s, 1H), 8.66 (d, J = 8.5 Hz, 1H), 8.15 (t, J = 8.0 Hz, 1H), 7.95 (d, J = 7.5 Hz, 1H), 6.92 (s, 1H), 5.33 (q, J = 7.0 Hz, 1H), 5.15 (s, 2H), 4.37-4.24 (m, 2H), 3.72 (q, J = 6.8 Hz, 2H), 3.12 (s, 3H), 2.78-2.69 (m, 3H), 2.04-1.87 (m, 2H), 1.60 (d, J = 6.6 Hz, 3H), 1.12 (t, J = 7.0 Hz, 3H), 0.83 (t, J = 7.4 Hz, 3H). |
| 174 (H) | 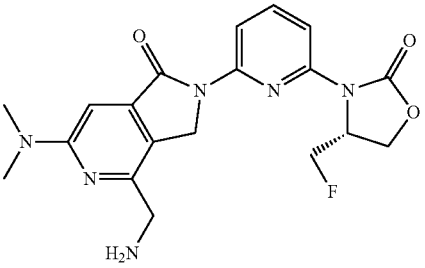<br>4-(aminomethyl)-6-(dimethylamino)-2-{6-[(4R)-4-(fluoromethyl)-2-oxo-1,3-oxazolidin-3-yl]pyridin-2-yl}-2,3-dihydro-1H-pyrrolo[3,4-c]pyridin-1-one | 401.1 | 1H NMR (400 MHz, DMSO-d6) δ 8.54 (br. s, 2H), 8.24 (d, J = 7.5 Hz, 1H), 8.01-7.94 (m, 1H), 7.91-7.87 (m, 1H), 6.87 (s, 1H), 5.22-5.09 (m, 2H), 5.08-4.97 (m, 2H), 4.88-4.71 (m, 1H), 4.65 (t, J = 8.9 Hz, 1H), 4.52 (dd, J = 3.3, 8.7 Hz, 1H), 4.27-4.17 (m, 2H), 3.16 (s, 6H). absolute stereochemistry known |
| 175 (AD) | 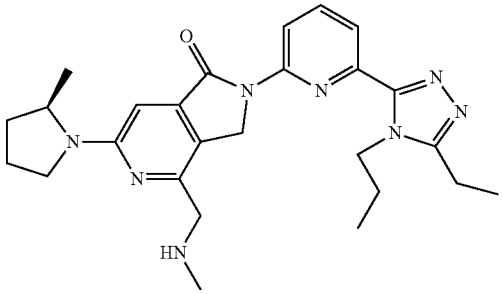<br>2-[6-(5-ethyl-4-propyl-4H-1,2,4-triazol-3-yl)pyridin-2-yl]-4-[(methylamino)methyl]-6-[(2R)-2-methylpyrrolidin-1-yl]-2,3-dihydro-1H-pyrrolo[3,4-c]pyridin-1-one | 475.2 | 1H NMR (400 MHz, DMSO-d6) δ 9.43-9.24 (m, 2H), 8.70 (d, J = 8.3 Hz, 1H), 8.16 (t, J = 7.8 Hz, 1H), 7.99 (d, J = 7.8 Hz, 1H), 6.75 (s, 1H), 5.15 (s, 2H), 4.59-4.46 (m, 2H), 4.38-4.33 (m, 1H), 4.29 (br. t, J = 5.1 Hz, 2H), 3.70-3.52 (m, 1H), 3.41 (br. d, J = 9.8 Hz, 1H), 3.01 (q, J = 7.5 Hz, 2H), 2.77-2.69 (m, 3H), 2.14-1.96 (m, 3H), 1.88-1.71 (m, 3H), 1.41 (t, J = 7.5 Hz, 3H), 1.20 (d, J = 6.0 Hz, 3H), 0.96 (t, J = 7.4 Hz, 3H). |

TABLE 1B-continued

| Ex. No. | Structure/IUPAC name | LCMS [M + H]+ | 1H NMR (ppm); 19F NMR (ppm); optical rotation; stereochem. notes |
|---|---|---|---|
| 176 (AD) | 4-[(methylamino)methyl]-2-{6-[5-methyl-4-(2-methylpropyl)-4H-1,2,4-triazol-3-yl]pyridin-2-yl}-6-[(2R)-2-methylpyrrolidin-1-yl]-2,3-dihydro-1H-pyrrolo[3,4-c]pyridin-1-one | 475.2 | 1H NMR (400 MHz, DMSO-$d_6$) δ 9.53-9.28 (m, 2H), 8.68 (d, J = 8.1 Hz, 1H), 8.17 (t, J = 8.1 Hz, 1H), 7.96 (d, J = 7.1 Hz, 1H), 6.74 (s, 1H), 5.14 (s, 2H), 4.50 (br. d, J = 7.7 Hz, 2H), 4.35 (br. d, J = 6.0 Hz, 1H), 4.28 (br. t, J = 5.2 Hz, 2H), 3.64 (br. t, J = 8.4 Hz, 1H), 3.46-3.32 (m, 1H), 2.71 (t, J = 5.3 Hz, 3H), 2.67 (s, 3H), 2.15-1.93 (m, 4H), 1.74 (br. d, J = 7.3 Hz, 1H), 1.20 (d, J = 6.2 Hz, 3H), 0.84 (d, J = 6.6 Hz, 6H). |
| 177 (B) | 6-(aminomethyl)-4-[(methylamino)methyl]-2-{6-[4-(2-methylpropyl)-4H-1,2,4-triazol-3-yl]pyridin-2-yl}-2,3-dihydro-1H-pyrrolo[3,4-c]pyridin-1-one | 421.1 | 1H NMR (600 MHz, DMSO-$d_6$) δ ppm 9.05-9.08 (m, 1 H) 8.67 (s, 1 H) 8.53 (d, J = 8.44 Hz, 1 H) 8.00 (t, J = 7.98 Hz, 1 H) 7.91 (d, J = 7.52 Hz, 1 H) 6.83 (s, 1 H) 5.01 (s, 2 H) 4.39 (br d, J = 7.52 Hz, 2 H) 4.29 (br s, 2 H) 3.09 (s, 6 H) 2.69 (s, 3 H) 2.05 (s, 1 H) 0.79 (d, J = 6.42 Hz, 6 H). |
| 178 (B) | 6-(aminomethyl)-4-[(methylamino)methyl]-2-(6-{4-[(2S)-3-methylbutan-2-yl]-4H-1,2,4-triazol-3-yl}pyridin-2-yl)-2,3-dihydro-1H-pyrrolo[3,4-c]pyridin-1-one | 435.1 | 1H NMR (400 MHz, DMSO-$d_6$) δ 9.31 (br. s, 2H), 9.10 (s, 1H), 8.64 (dd, J = 0.6, 8.4 Hz, 1H), 8.18-8.08 (m, 1H), 7.95 (dd, J = 0.6, 7.6 Hz, 1H), 6.94 (s, 1H), 5.25-5.04 (m, 3H), 4.27 (br. t, J = 5.4 Hz, 2H), 3.17 (s, 6H), 2.71 (t, J = 5.4 Hz, 3H), 2.18 (qd, J = 6.7, 15.4 Hz, 1H), 1.58 (d, J = 6.8 Hz, 3H), 0.98 (d, J = 6.7 Hz, 3H), 0.73 (d, J = 6.7 Hz, 3H). absolute stereochemistry known |

| Ex. No. | Structure/IUPAC name | LCMS [M + H]⁺ | ¹H NMR (ppm); ¹⁹F NMR (ppm); optical rotation; stereochem. notes |
|---|---|---|---|
| 179 (AJ) | 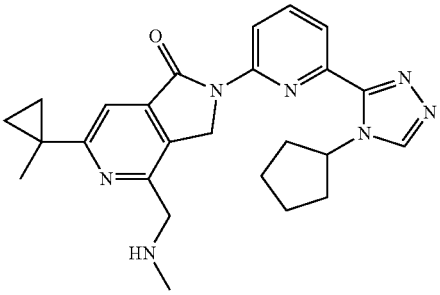 2-[6-(4-cyclopentyl-4H-1,2,4-triazol-3-yl)pyridin-2-yl]-4-[(methylamino)methyl]-6-(1-methylcyclopropyl)-2,3-dihydro-1H-pyrrolo[3,4-c]pyridin-1-one | 444.2 | ¹H NMR (400 MHz, DMSO-d₆) δ 9.37 (br. d, J = 4.3 Hz, 2H), 9.19 (s, 1H), 8.67 (d, J = 8.4 Hz, 1H), 8.17 (t, J = 8.0 Hz, 1H), 7.98 (d, J = 7.5 Hz, 1H), 7.71 (s, 1H), 5.67-5.54 (m, 1H), 5.30 (s, 2H), 4.42 (br. t, J = 5.7 Hz, 2H), 2.71 (br. t, J = 5.2 Hz, 3H), 2.35-2.26 (m, 2H), 2.00-1.85 (m, 4H), 1.79 (br. s, 2H), 1.60 (s, 3H), 1.46 (br. d, J = 2.2 Hz, 2H), 0.96-0.87 (m, 2H). |
| 180 (S) | 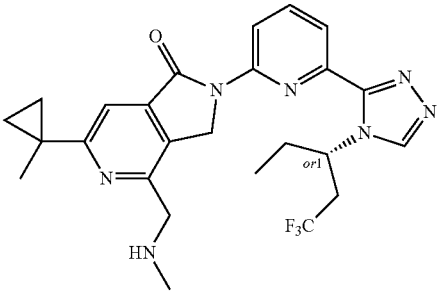 4-[(methylamino)methyl]-6-(1-methylcyclopropyl)-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 500.1 | ¹H NMR (400 MHz, DMSO-d₆) δ 9.08 (s, 1H), 8.67-8.63 (m, 1H), 8.12 (t, J = 8.0 Hz, 1H), 7.99 (d, J = 7.0 Hz, 1H), 7.57 (s, 1H), 6.07 (br. s, 1H), 5.24 (d, J = 6.5 Hz, 2H), 3.90 (s, 2H), 3.18 (s, 1H), 3.05-2.90 (m, 1H), 2.32 (s, 3H), 2.10-1.95 (m, 2H), 1.56 (s, 3H), 1.29-1.22 (m, 2H), 0.90-0.78 (m, 5H). absolute stereochemistry unknown* |
| 181 (S) | 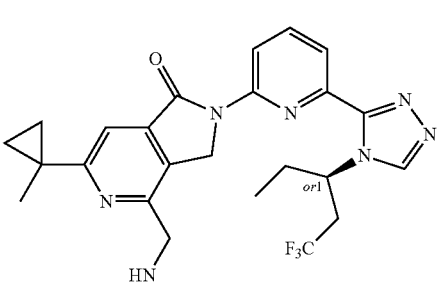 4-[(methylamino)methyl]-6-(1-methylcyclopropyl)-2-(6-{4-[(3ξ)-1,1,1-trifluoropentan-3-yl]-4H-1,2,4-triazol-3-yl}pyridin-2-yl)-2,3-dihydro-1H-pyrrolo[3,4-c]pyridin-1-one | 500.1 | ¹H NMR (400 MHz, DMSO-d₆) δ 9.08 (s, 1H), 8.65 (d, J = 7.8 Hz, 1H), 8.12 (t, J = 8.0 Hz, 1H), 7.99 (d, J = 7.5 Hz, 1H), 7.57 (s, 1H), 6.13-6.00 (m, 1H), 5.30-5.14 (m, 2H), 3.91 (s, 2H), 3.27-3.11 (m, 1H), 3.01 (br. d, J = 11.5 Hz, 1H), 2.33 (s, 3H), 2.09-1.94 (m, 2H), 1.56 (s, 3H), 1.29-1.22 (m, 2H), 0.91-0.78 (m, 5H). absolute stereochemistry unknown* |

US 11,142,525 B2

TABLE 1B-continued

| Ex. No. | Structure/IUPAC name | LCMS [M + H]⁺ | ¹H NMR (ppm); ¹⁹F NMR (ppm); optical rotation; stereochem. notes |
|---|---|---|---|
| 182 (B) | 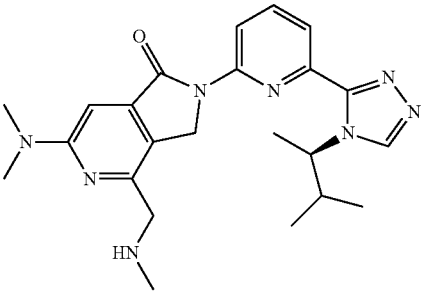<br>6-(aminomethyl)-4-[(methylamino)methyl]-2-(6-{4-[(2R)-3-methylbutan-2-yl]-4H-1,2,4-triazol-3-yl}pyridin-2-yl)-2,3-dihydro-1H-pyrrolo[3,4-c]pyridin-1-one | 435.3 | ¹H NMR (400 MHz, DMSO-$d_6$) δ 9.33 (br. s, 2H), 9.07 (s, 1H), 8.64 (d, J = 7.9 Hz, 1H), 8.13 (t, J = 8.0 Hz, 1H), 7.94 (d, J = 7.1 Hz, 1H), 6.93 (s, 1H), 5.25-5.05 (m, 3H), 4.35-4.17 (m, 2H), 3.17 (s, 6H), 2.71 (t, J = 5.4 Hz, 3H), 2.17 (qd, J = 6.6, 15.3 Hz, 1H), 1.58 (d, J = 6.8 Hz, 3H), 0.98 (d, J = 6.7 Hz, 3H), 0.73 (d, J = 6.6 Hz, 3H).<br>absolute stereochemistry known |
| 183 (S) | 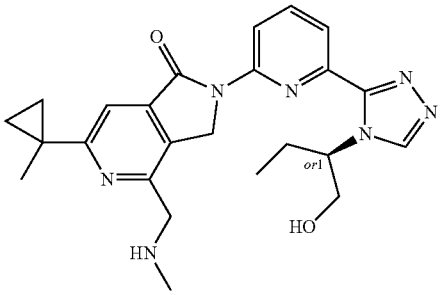<br>2-(6-{4-[(2ξ)-1-hydroxybutan-2-yl]-4H-1,2,4-triazol-3-yl}pyridin-2-yl)-4-[(methylamino)methyl]-6-(1-methylcyclopropyl)-2,3-dihydro-1H-pyrrolo[3,4-c]pyridin-1-one | 448.2 | ¹H NMR (400 MHz, DMSO-$d_6$) δ 8.82 (s, 1H), 8.63 (d, J = 8.3 Hz, 1H), 8.11 (t, J = 7.8 Hz, 1H), 7.96 (d, J = 7.5 Hz, 1H), 7.57 (s, 1H), 5.51-5.35 (m, 1H), 5.25 (s, 2H), 5.06 (br. S, 1H), 3.90 (s, 2H), 3.78 (br. D, J = 12.3 Hz, 2H), 2.34 (s, 3H), 2.08-1.92 (m, 2H), 1.56 (s, 3H), 1.28-1.22 (m, 2H), 0.92-0.84 (m, 5H).<br>absolute stereochemistry unknown* |
| 184 (S) | 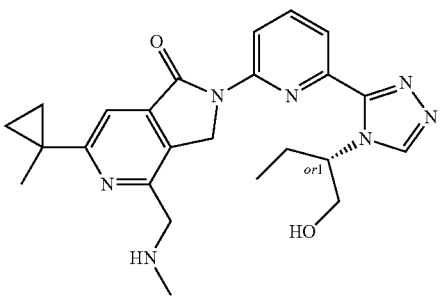<br>2-(6-{4-[(2ξ)-1-hydroxybutan-2-yl]-4H-1,2,4-triazol-3-yl}pyridin-2-yl)-4-[(methylamino)methyl]-6-(1-methylcyclopropyl)-2,3-dihydro-1H-pyrrolo[3,4-c]pyridin-1-one | 448.2 | ¹H NMR (400 MHz, DMSO-$d_6$) δ 8.83-8.80 (m, 1H), 8.63 (d, J = 8.3 Hz, 1H), 8.11 (t, J = 7.9 Hz, 1H), 7.96 (d, J = 7.3 Hz, 1H), 7.57 (s, 1H), 5.49-5.42 (m, 1H), 5.25 (s, 2H), 5.07 (br. D, J = 6.3 Hz, 1H), 3.90 (s, 2H), 3.84-3.70 (m, 2H), 2.34 (s, 3H), 2.05-1.92 (m, 2H), 1.56 (s, 3H), 1.28-1.22 (m, 2H), 0.92-0.84 (m, 5H).<br>absolute stereochemistry unknown* |

TABLE 1B-continued

| Ex. No. | Structure/IUPAC name | LCMS [M + H]+ | $^1$H NMR (ppm); $^{19}$F NMR (ppm); optical rotation; stereochem. notes |
|---|---|---|---|
| 185 (AD) | 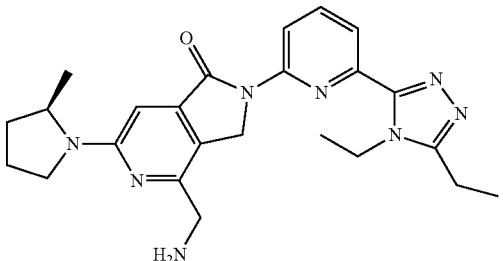<br>4-(aminomethyl)-2-[6-(4,5-diethyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 447.3 | $^1$H NMR (400 MHz, DMSO-d$_6$) δ 8.69 (d, J = 8.3 Hz, 1H), 8.40 (br. S, 3H), 8.16 (t, J = 8.2 Hz, 1H), 7.99 (d, J = 7.5 Hz, 1H), 6.72 (s, 1H), 5.17 (s, 2H), 4.59 (q, J = 7.0 Hz, 2H), 4.46-4.30 (m, 1H), 4.29-4.18 (m, 2H), 3.86-3.60 (m, 1H), 3.00 (q, J = 7.3 Hz, 2H), 2.57 (br. Dd, J = 1.8, 3.8 Hz, 1H), 2.16-1.96 (m, 3H), 1.77-1.70 (m, 1H), 1.47 (t, J = 7.0 Hz, 3H), 1.40 (t, J = 7.4 Hz, 3H), 1.21 (d, J = 6.3 Hz, 3H). |
| 186 (AD) | 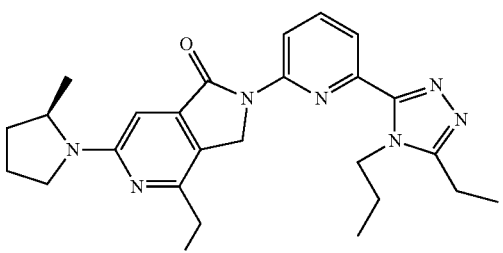<br>4-(aminomethyl)-2-[6-(5-ethyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one | 461.3 | $^1$H NMR (400 MHz, DMSO-d$_6$) δ 8.69 (d, J = 8.5 Hz, 1H), 8.43 (br. S, 3H), 8.15 (t, J = 8.0 Hz, 1H), 7.99 (d, J = 7.5 Hz, 1H), 6.72 (s, 1H), 5.15 (s,2H), 4.54-4.48 (m, 2H), 4.40-4.33 (m, 1H), 4.24-4.16 (m, 2H), 3.66 (br. D, J = 8.5 Hz, 1H), 3.45-3.38 (m, 1H), 2.98 (q, J = 7.5 Hz, 2H), 2.13-1.96 (m, 3H), 1.88-1.79 (m, 2H), 1.77-1.72 (m, 1H), 1.40 (t, J = 7.4 Hz, 3H), 1.21 (d, J = 6.0 Hz, 3H), 0.98 (t, J = 7.4 Hz, 3H). |
| 187 (AD) | 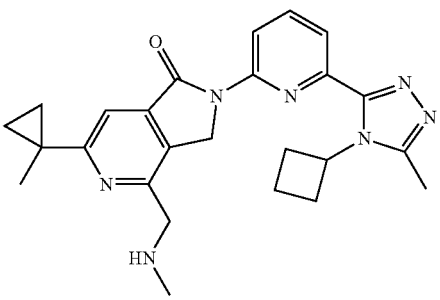<br>2-[6-(4-cyclobutyl-5-methyl-4H-1,2,4-triazol-3-yl)pyridin-2-yl]-4-[(methylamino)methyl]-6-(1-methylcyclopropyl)-2,3-dihydro-1H-pyrrolo[3,4-c]pyridin-1-one | 444.2 | $^1$H NMR (400 MHz, CDCl$_3$) δ 8.78-8.70 (m, 1H), 7.99-7.91 (m, 1H), 7.91-7.82 (m, 1H), 7.71 (s, 1H), 5.57 (quin, J = 9.0 Hz, 1H), 5.19 (s, 2H), 3.99 (s, 2H), 2.73 (s, 3H), 2.63-2.54 (m, 2H), 2.53 (s, 3H), 2.50-2.42 (m, 2H), 1.98-1.80 (m, 2H), 1.61 (s, 3H), 1.40-1.32 (m, 2H), 0.95-0.87 (m, 2H). |

TABLE 1B-continued

| Ex. No. | Structure/IUPAC name | LCMS [M + H]+ | 1H NMR (ppm); 19F NMR (ppm); optical rotation; stereochem. notes |
|---|---|---|---|
| 188 (AD) | 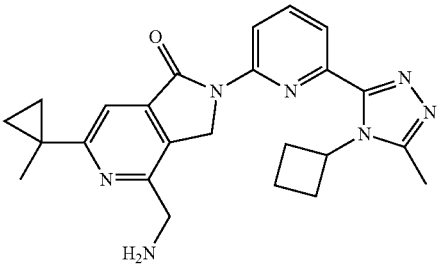<br>4-(aminomethyl)-2-[6-(4-cyclobutyl-5-methyl-4H-1,2,4-triazol-3-yl)pyridin-2-yl]-6-(1-methylcyclopropyl)-2,3-dihydro-1H-pyrrolo[3,4-c]pyridin-1-one | 430.0 | 1H NMR (400 MHz, CDCl$_3$) δ 8.72 (d, J = 8.3 Hz, 1H), 7.93 (t, J = 7.9 Hz, 1H), 7.83 (d, J = 6.9 Hz, 1H), 7.69 (s, 1H), 5.51 (t, J = 8.9 Hz, 1H), 5.14 (s, 2H), 4.09 (s, 2H), 2.71 (s, 3H), 2.62-2.39 (m, 4H), 1.95-1.79 (m, 2H), 1.61 (s, 3H), 1.38-1.33 (m, 2H), 0.92-0.87 (m, 2H). |

*Use of orl in a structure and ξ for stereochemistry in a name is to identify chiral centers that have been resolved into enantiomers, but the specific enantiomer is not identified; a solid or dashed wedge is drawn in the structure but it could be the other enantiomer.

Biological Assays and Data
HPK1 Biochemical Enzyme Assay

HPK1 enzyme inhibition was measured using a microfluidic mobility shift assay (MSA). The reactions were conducted in 50 μL volumes in 96-well plates, and contained 0.5 nM human full-length recombinant HPK1, 3 μM phosphoacceptor peptide, 5FAM-AKRRRLSSLRA-COOH (CPC Scientific, Sunnyvale, Calif.), test compound (11-dose 3-fold serial dilutions, 2% DMSO final) or DMSO only, 0.002% Tween-20, 1 mM DTT and 2.5 mM MgCl$_2$ in 50 mM MOPS (3-(N-morpholino)propanesulfonic acid), pH 7.8, buffer and were initiated by addition of 75 μM ATP, following a 20-min preincubation. The reactions were conducted for 60 min at 37° C., stopped by the addition of 50 μL of 0.015 M EDTA, pH 8, and the extent of reactions (~15-20% conversion with no inhibitor) was determined after electrophoretic separation of the fluorescently labeled peptide substrate and phosphorylated product on an LabChip EZ Reader II (PerkinElmer, Inc., Waltham, Mass.).

Inhibition of HPK1 was also measured using the fluorescence based chelation-enhanced fluorescence (CHEF) method (1), using a proprietary fluorescent peptide substrate, in which a cysteine residue is alkylated with a sulfonamido-oxine based derivative to afford an amino acid termed C-Sox (CSx). The assay was conducted similarly as described for the MSA method above, but using 3 μM Ac-[CSx]HSL-PRFNR-amide peptide substrate (also known as AQT0178 when purchased from AssayQuant Technologies Inc., Hopkinton, Mass.) and 45 μM ATP. Initial reaction velocities were determined by following the peptide fluorescence ($\lambda_{ex}$=360 nm, $\lambda_{em}$=500 nm) at 30° C. for 15 min in a Tecan M1000 plate reader (Tecan Group Ltd., Männedorf, Zürich, Switzerland). The inhibition constant ($K_i$) values were calculated by fitting the % conversion based (MSA method) or fluorescence based initial velocities (CHEF method) to the Morrison equation (2) for tight-binding competitive inhibition using non-linear regression method and an experimentally measured ATP $K_m$ (29 μM by MSA and 19 μM by CHEF, respectively). The inhibitors were shown to be ATP-competitive from kinetic and crystallographic studies. HPK1 protein was produced in-house and preactivated by autophosphorylation of enzyme with MgATP as described in the section "Production of recombinant autophosphorylated full-length HPK1".

Cell Based Assays
Phospho-SLP-76 (Ser376) Homogeneous Time Resolved Fluorescence (HTRF) Assay Jurkat cells were seeded at 90,000 cells/well in 90 uL of RPMI1640 growth medium containing 10% FBS and incubated at 37° C. with 5% CO$_2$ overnight. The following day, compounds were serially diluted from a 10 mM top dose for an 11-point 3 fold dilution curve in DMSO. Compounds were intermediately diluted 1:100 into growth media prior to diluting 1:10 on cells for final concentration 10 μM to 0.1 nM in 0.1% DMSO. After 30 minutes pre-treatment with compounds, the cells were stimulated using 200 μg/mL of F(ab)2 complexed anti-CD3 (clone UCTH1) for 15 min at 37° C. with 5% CO$_2$. Stimulation was stopped with ice cold PBS and cells were harvested by centrifugation before lysis in Cisbio lysis buffer (Cisbio, Bedford, Mass.). Lysates were transferred to white, low-volume plates containing anti-phospho-SLP-76-Cryptate plus anti-phospho-SLP-76-d2 HTRF antibodies and incubated overnight at room temperature protected from light according to the manufacturer's protocol (Cisbio, Bedford, Mass.). HTRF was measured on a Perkin Elmer Envision and IC50 values were calculated by concentration-response curve fitting utilizing four-parameter nonlinear regression analyses.

Biological activity data for selected compounds in the HPK1 mobility shift assays and the Phospho-SLP-76 (Ser376) Homogeneous Time Resolved Fluorescence (HTRF) assays are provided in are provided in Table 2 as IC$_{50}$ (μM).

TABLE 2

| Example # | HPK1 Enzyme Assay_Ki (μM) | Number of runs ("n") | SLP76 Assay_IC$_{50}$ (μM) | Number of runs ("n") |
|---|---|---|---|---|
| 1 | 0.00015 | 6 | 0.112 | 11 |
| 2 | 0.00028 | 3 | 0.086 | 5 |
| 3 | 0.00077 | 1 | — | — |
| 4 | 0.00039 | 3 | 0.106 | 4 |
| 5 | 0.00039 | 1 | 0.186 | 2 |
| 6 | 0.00013 | 1 | 0.039 | 3 |
| 7 | 0.00146 | 1 | 0.73 | 2 |
| 8 | 0.00025 | 1 | 0.089 | 3 |
| 9 | 0.00027 | 2 | 0.088 | 3 |
| 10 | 0.00026 | 2 | 0.0976 | 2 |

TABLE 2-continued

| Example # | HPK1 Enzyme Assay_Ki (µM) | Number of runs ("n") | SLP76 Assay_IC$_{50}$ (µM) | Number of runs ("n") |
|---|---|---|---|---|
| 11 | 0.00009 | 3 | 0.159 | 3 |
| 12 | 0.0002 | 2 | 0.155 | 3 |
| 13 | <0.00008 | 5 | 0.085 | 4 |
| 14 | 0.00017 | 2 | 0.102 | 3 |
| 15 | <0.00007 | 2 | 0.134 | 3 |
| 16 | 0.00056 | 2 | 0.358 | 2 |
| 17 | <0.00005 | 7 | 0.07 | 5 |
| 18 | <0.00005 | 3 | 0.101 | 3 |
| 19 | 0.0069 | 2 | >10 | 1 |
| 20 | 0.0028 | 2 | 0.158 | 4 |
| 21 | 0.00062 | 2 | 0.245 | 3 |
| 22 | 0.0004 | 1 | 0.105 | 2 |
| 23 | 0.14 | 1 | — | — |
| 24 | 0.00072 | 2 | 0.488 | 1 |
| 25 | 0.001 | 1 | — | — |
| 26 | 0.0009 | 2 | 0.439 | 4 |
| 27 | 0.00019 | 1 | — | — |
| 28 | 0.00041 | 4 | 0.119 | 5 |
| 29 | 0.0032 | 2 | 0.396 | 3 |
| 30 | 0.0021 | 3 | 0.573 | 1 |
| 31 | 0.00066 | 1 | — | — |
| 32 | 0.00034 | 2 | 0.21 | 3 |
| 33 | 0.00028 | 2 | 0.134 | 2 |
| 34 | 0.00132 | 1 | 0.379 | 2 |
| 35 | 0.00012 | 1 | 0.183 | 3 |
| 36 | 0.0051 | 1 | 1.11 | 2 |
| 37 | 0.0015 | 1 | 0.487 | 2 |
| 38 | 0.00038 | 2 | 0.147 | 5 |
| 39 | 0.0018 | 2 | 0.672 | 1 |
| 40 | 0.00081 | 3 | 0.137 | 2 |
| 41 | 0.0046 | 1 | 0.315 | 1 |
| 42 | 0.00033 | 2 | 0.192 | 1 |
| 43 | 0.00192 | 3 | 0.561 | 1 |
| 44 | 0.0004 | 1 | 0.244 | 1 |
| 45 | 0.00017 | 1 | 0.173 | 5 |
| 46 | 0.00014 | 1 | 0.094 | 4 |
| 47 | 0.0071 | 1 | 1.52 | 2 |
| 48 | 0.00014 | 1 | 0.094 | 4 |
| 49 | 0.00146 | 1 | 0.73 | 2 |
| 50 | 0.00014 | 1 | 0.094 | 4 |
| 51 | 0.0071 | 1 | 1.52 | 2 |
| 52 | 0.0899 | 1 | — | — |
| 53 | 0.00061 | 3 | 0.489 | 1 |

Biological activity data in the HPK1 mobility shift assays and the Phospho-SLP-76 (Ser376) Homogeneous Time Resolved Fluorescence (HTRF) assays are provided in Table 3 for Examples 55 to 68.

TABLE 3

| Example # | HPK1 Enzyme Assay_Ki (µM) | Number of runs ("n") | SLP76 Assay_IC$_{50}$ (µM) | Number of runs ("n") |
|---|---|---|---|---|
| 55 | <0.00006 | 2 | 0.034 | 3 |
| 56 | 0.00034 | 1 | 0.139 | 3 |
| 57 | 0.00021 | 2 | 0.074 | 4 |
| 58 | 0.00016 | 1 | 0.103 | 1 |
| 59 | 0.00019 | 1 | 0.059 | 2 |
| 60 | 0.00017 | 2 | 0.070 | 2 |
| 61 | 0.00018 | 2 | 0.088 | 4 |
| 62 | 0.00009 | 1 | 0.042 | 2 |
| 63 | <0.00009 | 2 | 0.087 | 4 |
| 64 | <0.00017 | 10 | 0.091 | 11 |
| 65 | 0.00035 | 1 | 0.114 | 2 |
| 66 | 0.00052 | 1 | 0.108 | 2 |
| 67 | 0.00129 | 1 | ND | NA |
| 68 | <0.00007 | 3 | 0.05 | 2 |

In Tables 3 to 5, ND means not determined, with NA (not applicable) in the column for the number of runs.

Biological activity data in the HPK1 mobility shift assays and the Phospho-SLP-76 (Ser376) Homogeneous Time Resolved Fluorescence (HTRF) assays are provided in Table 4 for Examples in Table 1A.

TABLE 4

| Example # | HPK1 Enzyme Assay_Ki (µM) | Number of runs ("n") | SLP76 Assay_IC$_{50}$ (µM) | Number of runs ("n") |
|---|---|---|---|---|
| 69 | 0.00053 | 1 | 0.248 | 3 |
| 70 | 0.00016 | 1 | 0.062 | 2 |
| 71 | 0.00018 | 2 | 0.040 | 4 |
| 72 | 0.00448 | 1 | 1.02 | 2 |
| 73 | 0.00022 | 1 | 0.061 | 3 |
| 74 | 0.00006 | 1 | 0.077 | 2 |
| 75 | 0.00052 | 1 | 0.118 | 2 |
| 76 | 0.00064 | 1 | 0.583 | 1 |
| 77 | 0.00068 | 1 | ND | NA |
| 78 | 0.00073 | 1 | 0.307 | 1 |
| 79 | <0.00005 | 1 | 0.048 | 2 |
| 80 | 0.00016 | 1 | 0.184 | 2 |
| 81 | 0.00058 | 1 | 0.406 | 1 |
| 82 | 0.00012 | 1 | 0.095 | 2 |
| 83 | 0.0352 | 1 | 6.64 | 1 |
| 84 | 0.00014 | 1 | 0.138 | 2 |
| 85 | 0.00111 | 1 | 0.345 | 2 |
| 86 | 0.00304 | 1 | 0.652 | 2 |
| 87 | 0.00144 | 1 | 0.299 | 2 |
| 88 | 0.00252 | 1 | 2.682 | 2 |
| 89 | <0.00008 | 3 | 0.054 | 3 |
| 90 | 0.00146 | 1 | 0.694 | 1 |
| 91 | 0.00033 | 1 | 0.257 | 2 |
| 92 | 0.00043 | 1 | 0.226 | 2 |
| 93 | 0.00042 | 1 | 0.713 | 1 |
| 94 | 0.00034 | 1 | 0.280 | 1 |
| 95 | 0.00051 | 1 | 0.168 | 1 |
| 96 | 0.00040 | 1 | 0.142 | 1 |
| 97 | 0.00034 | 1 | 0.186 | 2 |
| 98 | 0.00096 | 1 | 0.514 | 1 |
| 99 | 0.00083 | 1 | ND | NA |
| 100 | <0.00005 | 1 | 0.034 | 3 |
| 101 | 0.00094 | 1 | 0.217 | 1 |
| 102 | 0.00029 | 1 | 0.074 | 2 |
| 103 | 0.00115 | 1 | 0.199 | 1 |
| 104 | 0.00013 | 2 | 0.051 | 1 |
| 105 | 0.00021 | 1 | 0.064 | 3 |
| 106 | 0.00026 | 2 | 0.083 | 2 |
| 107 | 0.00004 | 1 | 0.022 | 2 |
| 108 | 0.00370 | 1 | 0.583 | 1 |
| 109 | 0.00006 | 1 | 0.012 | 1 |
| 110 | 0.00032 | 1 | 0.086 | 2 |
| 111 | 0.00101 | 1 | 0.147 | 1 |
| 112 | 0.00149 | 1 | 0.431 | 1 |
| 113 | 0.00022 | 2 | 0.083 | 1 |
| 114 | 0.00012 | 2 | 0.037 | 2 |
| 115 | <0.00009 | 3 | 0.021 | 2 |
| 116 | 0.00104 | 2 | 0.381 | 1 |
| 117 | 0.00046 | 1 | 0.089 | 2 |
| 118 | 0.00089 | 1 | 0.149 | 1 |
| 119 | 0.00052 | 1 | 0.104 | 2 |
| 120 | <0.00009 | 2 | 0.056 | 1 |
| 121 | 0.00009 | 1 | 0.062 | 3 |
| 122 | 0.00041 | 1 | 0.070 | 1 |
| 123 | 0.00103 | 1 | 0.273 | 1 |
| 124 | 0.00150 | 1 | 0.375 | 1 |
| 125 | 0.00010 | 2 | 0.050 | 2 |
| 126 | 0.00080 | 1 | 0.114 | 2 |
| 127 | 0.00152 | 2 | 0.435 | 1 |
| 128 | 0.00063 | 1 | 0.874 | 1 |
| 129 | 0.00031 | 1 | 0.093 | 1 |
| 130 | 0.00078 | 1 | 0.201 | 1 |
| 131 | 0.00011 | 1 | 0.057 | 2 |
| 132 | 0.00020 | 1 | 0.067 | 1 |
| 133 | 0.00028 | 2 | 0.232 | 1 |
| 134 | 0.00047 | 1 | 0.053 | 2 |
| 135 | 0.00080 | 1 | >10 | 1 |
| 136 | 0.00073 | 2 | 0.106 | 1 |
| 137 | 0.00028 | 1 | 0.076 | 2 |
| 138 | 0.00009 | 1 | >10 | 1 |

TABLE 4-continued

| Example # | HPK1 Enzyme Assay_Ki (μM) | Number of runs ("n") | SLP76 Assay_IC50 (μM) | Number of runs ("n") |
|---|---|---|---|---|
| 139 | 0.00046 | 1 | 0.266 | 1 |
| 140 | 0.00207 | 1 | 0.464 | 1 |
| 141 | 0.00074 | 1 | 0.122 | 2 |
| 142 | 0.00052 | 1 | 0.239 | 1 |
| 143 | 0.00009 | 1 | 0.028 | 3 |
| 144 | <0.00005 | 1 | 0.015 | 3 |
| 145 | 0.00047 | 1 | 0.061 | 2 |
| 146 | 0.00091 | 1 | 0.106 | 2 |

Biological activity data in the HPK1 mobility shift assays and the Phospho-SLP-76 (Ser376) Homogeneous Time Resolved Fluorescence (HTRF) assays are provided in Table 5 for Examples in Table 1B.

TABLE 5

| Example # | HPK1 Enzyme Assay_Ki (μM) | Number of runs ("n") | SLP76 Assay_IC50 (μM) | Number of runs ("n") |
|---|---|---|---|---|
| 150 | 0.00006 | 1 | 0.033 | 1 |
| 151 | 0.0001 | 1 | 0.014 | 1 |
| 152 | 0.00012 | 1 | 0.046 | 1 |
| 153 | 0.00014 | 1 | 0.065 | 1 |
| 154 | 0.00015 | 1 | 0.151 | 1 |
| 155 | 0.00016 | 1 | 0.055 | 1 |
| 156 | 0.00019 | 1 | 0.104 | 1 |
| 157 | 0.00023 | 1 | 0.085 | 1 |
| 158 | 0.00038 | 1 | 0.083 | 1 |
| 159 | 0.00045 | 1 | 0.112 | 1 |
| 160 | 0.00048 | 1 | 0.272 | 1 |
| 161 | 0.00068 | 1 | 0.217 | 1 |
| 162 | 0.00076 | 1 | 0.136 | 1 |
| 163 | 0.00088 | 1 | 0.196 | 1 |
| 164 | 0.0001 | 1 | 0.065 | 2 |
| 165 | 0.00028 | 1 | 0.114 | 2 |
| 166 | 0.0005 | 1 | 0.104 | 1 |
| 167 | 0.0007 | 1 | 0.391 | 1 |
| 168 | 0.00076 | 1 | 0.3 | 1 |
| 169 | 0.00095 | 1 | 0.179 | 1 |
| 170 | 0.00036 | 1 | 0.264 | 1 |
| 171 | 0.00034 | 1 | 0.18 | 1 |
| 172 | 0.00055 | 1 | 0.085 | 2 |
| 173 | 0.00006 | 1 | 0.043 | 1 |
| 174 | 0.00037 | 1 | 0.207 | 1 |
| 175 | 0.00094 | 1 | 0.185 | 1 |
| 176 | 0.00022 | 2 | 0.64 | 1 |
| 177 | 0.00026 | 1 | 0.152 | 1 |
| 178 | 0.00017 | 2 | ND | NA |
| 179 | 0.00047 | 2 | ND | NA |
| 180 | 0.02509 | 1 | ND | NA |
| 181 | 0.00013 | 1 | ND | NA |
| 182 | 0.00037 | 1 | ND | NA |
| 183 | 0.00035 | 1 | ND | NA |
| 184 | 0.00115 | 1 | ND | NA |
| 185 | 0.00079 | 1 | 0.136 | 2 |
| 186 | 0.00191 | 2 | ND | NA |
| 187 | 0.026 | 1 | ND | NA |
| 188 | 0.041 | 1 | ND | NA |

All publications and patent applications cited in the specification are herein incorporated by reference in their entirety. It will be apparent to those of ordinary skill in the art that certain changes and modifications may be made thereto without departing from the spirit or scope of the appended claims.

What is claimed is:

1. A compound of Formula I

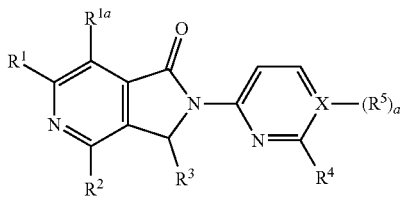

or a pharmaceutically acceptable salt thereof, wherein:
$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, —N($R^6$)($R^7$), and $(C_3-C_6)$cycloalkyl, wherein said $(C_1-C_6)$alkyl, halo$(C_1-C_6)$alkyl, and $(C_3-C_6)$cycloalkyl are optionally substituted with one to three substituents selected from the group consisting of halogen, hydroxy, cyano, $(C_1-C_6)$alkyl, and $(C_1-C_6)$alkoxy;
$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl, and halo$(C_1-C_6)$alkyl are optionally substituted with one to three substituents selected from the group consisting of halogen, hydroxy, cyano, $(C_1-C_6)$alkyl, and $(C_1-C_6)$alkoxy;
$R^{1a}$ is selected from the group consisting of hydrogen and halogen;
$R^2$ is:
i) —$(CH_2)_m$N($R^8$)($R^9$), wherein m is an integer selected from 0, 1, 2, or 3, and $R^8$ and $R^9$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^8$ and $R^9$ taken together with the nitrogen to which they are attached form a (4- to 6-membered)heterocycloalkyl that is optionally substituted with one to three substituents selected from the group consisting of halogen, hydroxy, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy;
ii) $(C_1-C_6)$alkyl, wherein said $(C_1-C_6)$alkyl is optionally substituted with 1 to 3 substituents selected from the group consisting of halogen, $(C_1-C_6)$alkoxy, —N($R^6$)($R^7$), cyano, and hydroxy, wherein $R^6$ and $R^7$ are each independently selected from the group consisting of hydrogen and $(C_1-C_6)$alkyl; or
iii) a (4- to 6-membered)heterocycloalkyl, wherein said heterocycloalkyl is optionally substituted with one to three substituents selected from the group consisting of halogen, hydroxy, cyano, $(C_1-C_6)$alkyl, halo$(C_1-$ $C_6$)alkyl, $(C_1-C_6)$alkyl, $(C_1-C_6)$alkoxy, and halo$(C_1-C_6)$alkoxy, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy;

$R^3$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy;

X is carbon or nitrogen;

$R^4$ is a (4- to 6-membered)heterocycloalkyl or a (5- to 10-membered)heteroaryl, wherein said (4- to 6-membered)heterocycloalkyl and (5- to 10-membered)heteroaryl are optionally substituted with 1 to 3 substituents selected from the group consisting of halogen, cyano, oxo, hydroxy, —N($R^{10}$)($R^{11}$), $(C_1-C_6)$alkyl, halo$(C_1-C_6)$alkyl, $(C_1-C_6)$alkoxy, halo$(C_1-C_6)$alkoxy, and —$(CH_2)_n(C_3-C_6)$cycloalkyl, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy, and wherein n is an integer selected from 0, 1, or 2; and wherein $R^{10}$ and $R^{11}$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy;

$R^5$ is selected from the group consisting of hydrogen, halogen, hydroxy, $(C_1-C_6)$alkyl, halo$(C_1-C_6)$alkyl, $(C_1-C_6)$alkoxy, and halo$(C_1-C_6)$alkoxy; and a is an integer selected from 0 or 1, provided that when X is nitrogen a is 0.

2. The compound according to claim 1, or a pharmaceutically acceptable salt thereof, wherein $R^1$ is —N($R^6$)($R^7$), and $R^6$ and $R^7$ are each independently selected from the group consisting of hydrogen and $(C_1-C_6)$alkyl, wherein said $(C_1-C_6)$alkyl is optionally substituted with 1 to 3 halogen.

3. The compound according to claim 2, or a pharmaceutically acceptable salt thereof, wherein $R^6$ and $R^7$ are each methyl.

4. The compound according to claim 1, or a pharmaceutically acceptable salt thereof, wherein $R^1$ is —N($R^6$)($R^7$) and $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

5. The compound according to claim 4, or a pharmaceutically acceptable salt thereof, wherein the (4- to 8-membered)heterocycloalkyl is azetidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

6. The compound according to claim 4, or a pharmaceutically acceptable salt thereof, wherein the (4- to 8-membered)heterocycloalkyl is pyrrolidinyl optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

7. The compound according to claim 1, or a pharmaceutically acceptable salt thereof, wherein $R^1$ is a $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy.

8. The compound according to claim 7, or a pharmaceutically acceptable salt thereof, wherein said $(C_3-C_6)$cycloalkyl is cyclopropyl.

9. The compound of claim 1, or a pharmaceutically acceptable salt thereof, wherein $R^3$ is hydrogen.

10. The compound of claim 1, or a pharmaceutically acceptable salt thereof, wherein $R^4$ is a (5- to 6-membered) heteroaryl optionally substituted with 1 to 3 substituents selected from the group consisting of halogen, cyano, hydroxy, —N($R^{10}$)($R^{11}$), $(C_1-C_6)$alkyl, halo$(C_1-C_6)$alkyl, $(C_1-C_6)$alkoxy, halo$(C_1-C_6)$alkoxy, and —$(CH_2)_n(C_3-C_6)$cycloalkyl, wherein n is an integer selected from 0, 1, or 2; and wherein $R^{10}$ and $R^{11}$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy.

11. The compound according to claim 10, or a pharmaceutically acceptable salt thereof, wherein the (5- to 6-membered)heteroaryl is 1, 2, 3-triazolyl, 1, 2, 4-triazolyl or pyrazolyl.

12. The compound of claim 1, or a pharmaceutically acceptable salt thereof, wherein X is carbon, a is 1 and $R^5$ is hydrogen or halogen.

13. The compound according to claim 12, or a pharmaceutically acceptable salt thereof, wherein $R^5$ is halogen and the halogen is fluoro.

14. A compound of Formula II

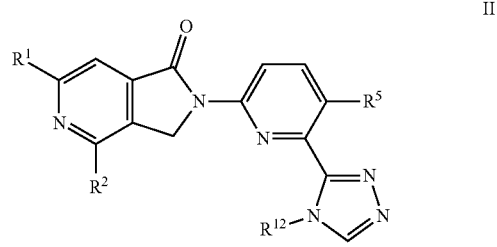

or a pharmaceutically acceptable salt thereof, wherein:

$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, —N($R^6$)($R^7$), and $(C_3-C_6)$cycloalkyl, wherein said $(C_3-C_6)$cycloalkyl is optionally substituted with one to three substituents selected from the group consisting of halogen, hydroxy, $(C_1-C_6)$alkyl, and $(C_1-C_6)$alkoxy;

$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy;

R² is:
i) a —(CH₂)ₘN(R⁸)(R⁹), wherein m is an integer selected from 0, 1, 2, or 3, and R⁸ and R⁹ are each independently selected from the group consisting of hydrogen and (C₁-C₆)alkyl, wherein said (C₁-C₆)alkyl is optionally substituted with 1 to 3 substituents selected from the group consisting of halogen and hydroxy, or R⁸ and R⁹ taken together with the nitrogen to which they are attached form a (4- to 6-membered)heterocycloalkyl that is optionally substituted with one to three substituents selected from the group consisting of halogen, (C₁-C₆)alkyl, halo(C₁-C₆)alkyl, (C₁-C₆)alkoxy, and halo(C₁-C₆)alkoxy; or ii) a (4- to 6-membered)heterocycloalkyl, wherein said heterocycloalkyl is optionally substituted with one to three substituents selected from the group consisting of halogen, (C₁-C₆)alkyl, halo(C₁-C₆)alkyl, (C₁-C₆)alkoxy, and halo(C₁-C₆)alkoxy;

R⁵ is selected from the group consisting of hydrogen, halogen, hydroxy, (C₁-C₆)alkyl, halo(C₁-C₆)alkyl, (C₁-C₆)alkoxy, and halo(C₁-C₆)alkoxy; and R¹² is selected from the group consisting of (C₁-C₆)alkyl, halo(C₁-C₆)alkyl, and —(CH₂)ₙ(C₃-C₆)cycloalkyl, wherein n is an integer 0 or 1.

15. The compound according to claim 14, or a pharmaceutically acceptable salt thereof, wherein R¹ is —N(R⁶)(R⁷), and R⁶ and R⁷ are each independently selected from the group consisting of hydrogen and (C₁-C₆)alkyl, wherein said (C₁-C₆)alkyl is optionally substituted with 1 to 3 halogen.

16. The compound according to claim 15, or a pharmaceutically acceptable salt thereof, wherein R⁶ and R⁷ are each methyl.

17. The compound according to claim 15, or a pharmaceutically acceptable salt thereof, wherein one of R⁶ and R⁷ is hydrogen and the other is methyl.

18. The compound according to claim 15, or a pharmaceutically acceptable salt thereof, wherein one of R⁶ and R⁷ is methyl and the other is ethyl.

19. The compound according to claim 14, or a pharmaceutically acceptable salt thereof, wherein R¹ is —N(R⁶)(R⁷) and R⁶ and R⁷ taken together with the nitrogen to which they are attached form the (4- to 8-membered)heterocycloalkyl that is optionally substituted with one to three substituents selected from the group consisting of halogen, (C₁-C₆)alkyl, halo(C₁-C₆)alkyl, (C₁-C₆)alkoxy, and halo(C₁-C₆)alkoxy.

20. The compound according to claim 19, or a pharmaceutically acceptable salt thereof, wherein the (4- to 8-membered)heterocycloalkyl is azetidinyl optionally substituted with one to three substituents selected from the group consisting of halogen, (C₁-C₆)alkyl, halo(C₁-C₆)alkyl, (C₁-C₆)alkoxy, and halo(C₁-C₆)alkoxy.

21. The compound according to claim 19, or a pharmaceutically acceptable salt thereof, wherein the (4- to 8-membered)heterocycloalkyl is pyrrolidinyl optionally substituted with one to three substituents selected from the group consisting of halogen, (C₁-C₆)alkyl, halo(C₁-C₆)alkyl, (C₁-C₆)alkoxy, and halo(C₁-C₆)alkoxy.

22. A compound of Formula III

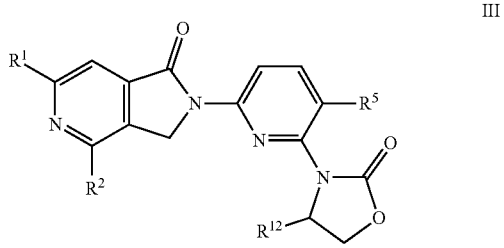

III or a pharmaceutically acceptable salt thereof, wherein:
R¹ is selected from the group consisting of hydrogen, halogen, (C₁-C₆)alkyl, halo(C₁-C₆)alkyl, (C₁-C₆)alkoxy, halo(C₁-C₆)alkoxy, —N(R⁶)(R⁷), and (C₃-C₆)cycloalkyl, wherein said (C₃-C₆)cycloalkyl is optionally substituted with one to three substituents selected from the group consisting of halogen, hydroxy, (C₁-C₆)alkyl, and (C₁-C₆)alkoxy;

R⁶ and R⁷ are each independently selected from the group consisting of hydrogen and (C₁-C₆)alkyl, wherein said (C₁-C₆)alkyl is optionally substituted with 1 to 3 substituents selected from the group consisting of halogen and hydroxy, or R⁶ and R⁷ taken together with the nitrogen to which they are attached form a (4- to 8-membered)heterocycloalkyl that is optionally substituted with one to three substituents selected from the group consisting of halogen, (C₁-C₆)alkyl, halo(C₁-C₆)alkyl, (C₁-C₆)alkoxy, and halo(C₁-C₆)alkoxy;

R² is:
i) a —(CH₂)ₘN(R⁸)(R⁹), wherein m is an integer selected from 0, 1, 2, or 3, and R⁸ and R⁹ are each independently selected from the group consisting of hydrogen and (C₁-C₆)alkyl, wherein said (C₁-C₆)alkyl is optionally substituted with 1 to 3 substituents selected from the group consisting of halogen and hydroxy, or R⁸ and R⁹ taken together with the nitrogen to which they are attached form a (4- to 6-membered)heterocycloalkyl that is optionally substituted with one to three substituents selected from the group consisting of halogen, (C₁-C₆)alkyl, halo(C₁-C₆)alkyl, (C₁-C₆)alkoxy, and halo(C₁-C₆)alkoxy; or ii) a (4- to 6-membered)heterocycloalkyl, wherein said heterocycloalkyl is optionally substituted with one to three substituents selected from the group consisting of halogen, (C₁-C₆)alkyl, halo(C₁-C₆)alkyl, (C₁-C₆)alkoxy, and halo(C₁-C₆)alkoxy;

R⁵ is selected from the group consisting of hydrogen, halogen, hydroxy, (C₁-C₆)alkyl, halo(C₁-C₆)alkyl, (C₁-C₆)alkoxy, and halo(C₁-C₆)alkoxy; and R¹² is selected from the group consisting of (C₁-C₆)alkyl, halo(C₁-C₆)alkyl, and —(CH₂)ₙ(C₃-C₆)cycloalkyl, wherein n is an integer 0 or 1.

23. The compound according to claim 22, or a pharmaceutically acceptable salt thereof, wherein R¹ is —N(R⁶)(R⁷), and R⁶ and R⁷ are each independently selected from the group consisting of hydrogen and (C₁-C₆)alkyl, wherein said (C₁-C₆)alkyl is optionally substituted with 1 to 3 halogen.

24. The compound according to claim 22, or a pharmaceutically acceptable salt thereof, wherein R¹ is —N(R⁶)(R⁷) and R⁶ and R⁷ taken together with the nitrogen to which they are attached form the (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy.

25. The compound of claim 22, or a pharmaceutically acceptable salt thereof, wherein $R^2$ is $-(CH_2)_mN(R^8)(R^9)$, m is 1 and one of $R^8$ and $R^9$ is hydrogen and the other is methyl.

26. The compound of claim 22, or a pharmaceutically acceptable salt thereof, wherein $R^{12}$ is $(C_1-C_6)$alkyl selected from the group consisting of ethyl, propyl, isopropyl, butyl, and tert-butyl.

27. The compound of claim 22, or a pharmaceutically acceptable salt thereof, wherein $R^{12}$ is halo$(C_1-C_6)$alkyl selected from the group consisting of fluoromethyl, fluoroethyl, difluoromethyl, difluoroethyl, trifluoromethyl, triflourobutanyl, and trifluoropentanyl.

28. A compound of Formula I

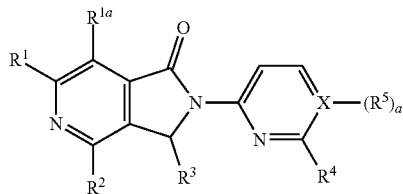

or a pharmaceutically acceptable salt thereof, wherein:
$R^1$ is selected from the group consisting of hydrogen, halogen, $(C_1-C_6)$alkyl, halo$(C_1-C_6)$alkyl, $(C_1-C_6)$alkoxy, halo$(C_1-C_6)$alkoxy, $-N(R^6)(R^7)$, and $(C_3-C_6)$cycloalkyl, wherein said $(C_1-C_6)$alkyl, halo$(C_1-C_6)$alkyl, and $(C_3-C_6)$cycloalkyl are optionally substituted with one to three substituents selected from the group consisting of halogen, hydroxy, cyano, $(C_1-C_6)$alkyl, and $(C_1-C_6)$alkoxy;
$R^6$ and $R^7$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^6$ and $R^7$ taken together with the nitrogen to which they are attached form a (4- to 8-membered)heterocycloalkyl that is optionally substituted with one to three substituents selected from the group consisting of halogen, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl, and halo$(C_1-C_6)$alkyl are optionally substituted with one to three substituents selected from the group consisting of halogen, hydroxy, cyano, $(C_1-C_6)$alkyl, and $(C_1-C_6)$alkoxy;
$R^{1a}$ is H;
$R^2$ is $CH_2N(R^8)(R^9)$, wherein $R^8$ and $R^9$ are each independently selected from the group consisting of hydrogen and $(C_1-C_6)$alkyl, wherein said $(C_1-C_6)$alkyl is optionally substituted with 1 to 3 substituents selected from the group consisting of halogen, $(C_1-C_6)$alkoxy, cyano, and hydroxy, or $R^8$ and $R^9$ taken together with the nitrogen to which they are attached form a (4- to 6-membered)heterocycloalkyl that is optionally substituted with one to three substituents selected from the group consisting of halogen, hydroxy, $(C_1-C_6)$alkyl, halo$(C_1-C_6)$alkyl, $(C_1-C_6)$alkoxy, and halo$(C_1-C_6)$alkoxy, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy; and
$R^3$ is H;
X is carbon;
$R^5$ is hydrogen;
a is 1; and
$R^4$ is a (4- to 6-membered)heterocycloalkyl or a (5- to 10-membered)heteroaryl, wherein said (4- to 6-membered)heterocycloalkyl and (5- to 10-membered)heteroaryl are optionally substituted with 1 to 3 substituents selected from the group consisting of halogen, cyano, oxo, hydroxy, $-N(R^{10})(R^{11})$, $(C_1-C_6)$alkyl, halo$(C_1-C_6)$alkyl, $(C_1-C_6)$alkoxy, halo$(C_1-C_6)$alkoxy, and $-(CH_2)_n(C_3-C_6)$cycloalkyl, wherein said $(C_1-C_6)$alkyl and halo$(C_1-C_6)$alkyl are optionally substituted with one to three substituents selected from the group consisting of halogen, hydroxy, cyano, and $(C_1-C_6)$alkoxy, and wherein n is an integer selected from 0, 1, or 2; and wherein $R^{10}$ and $R^{11}$ are each independently selected from the group consisting of hydrogen and $(C_1-C_6)$alkyl, wherein said $(C_1-C_6)$alkyl is optionally substituted with 1 to 3 substituents selected from the group consisting of halogen and hydroxy.

29. The compound of claim 28, or a pharmaceutically acceptable salt thereof, wherein:
$R^1$ is selected from the group consisting of $(C_1-C_4)$alkyl, $CF_3$, $-N(R^6)(R^7)$, and $(C_3-C_4)$cycloalkyl, wherein said $(C_3-C_4)$cycloalkyl is optionally substituted with one $CH_3$;
$R^6$ and $R^7$ are each independently selected from the group consisting of hydrogen and $(C_1-C_3)$alkyl, or
$R^6$ and $R^7$ taken together with the nitrogen to which they are attached form the (4- to 5-membered)heterocycloalkyl that is optionally substituted with one to two $CH_3$ substituents;
$R^2$ is $CH_2N(R^8)(R^9)$, wherein $R^8$ is hydrogen and $R^9$ is selected from the group consisting of hydrogen and $CH_3$; and
$R^4$ is a (5-membered)heterocycloalkyl or a (5-membered) heteroaryl, wherein said (5-membered)heterocycloalkyl is 1,3-oxazolidin-3-yl and said (5-membered)heteroaryl is 1H-pyrazolyl or triazolyl, each optionally substituted with 1 to 2 substituents selected from the group consisting of oxo, $(C_1-C_5)$alkyl, halo$(C_1-C_5)$alkyl, and $-CH_2$-cyclopropyl.

30. The compound of claim 28, or a pharmaceutically acceptable salt thereof, wherein:
$R^1$ is selected from the group consisting of $(C_1-C_4)$alkyl, $CF_3$, $-N(R^6)(R^7)$, and $(C_3-C_4)$cycloalkyl, wherein said $(C_3-C_4)$cycloalkyl is optionally substituted with one $CH_3$;
$R^6$ and $R^7$ are each independently selected from the group consisting of hydrogen and $(C_1-C_3)$alkyl, or
$R^6$ and $R^7$ taken together with the nitrogen to which they are attached form the (4- to 5-membered)heterocycloalkyl that is optionally substituted with one to two $CH_3$ substituents;
$R^2$ is $CH_2N(R^8)(R^9)$, wherein $R^8$ is hydrogen and $R^9$ is selected from the group consisting of hydrogen and $CH_3$; and
$R^4$ is a (5-membered)heterocycloalkyl or a (5-membered) heteroaryl, wherein said (5-membered)heterocycloalkyl is 2-oxo-1,3-oxazolidin-3-yl, optionally substituted with 1 $CH_3$, $CH_2F$, $CHF_2$, or $CF_3$, and said (5-membered)heteroaryl is 1H-pyrazolyl or triazolyl, optionally substituted with 1 to 2 substituents selected from the group consisting of ($C_1$-$C_5$)alkyl, halo($C_1$-$C_5$)alkyl, and —$CH_2$-cyclopropyl.

31. The compound of claim 28, or a pharmaceutically acceptable salt thereof, wherein:
$R^1$ is selected from the group consisting of —N($R^6$)($R^7$), and ($C_3$-$C_4$)cycloalkyl, wherein said ($C_3$-$C_4$)cycloalkyl is optionally substituted with one $CH_3$;
$R^6$ and $R^7$ are each independently selected from the group consisting of hydrogen and ($C_1$-$C_3$)alkyl, or
$R^6$ and $R^7$ taken together with the nitrogen to which they are attached form a (4- to 5-membered)heterocycloalkyl that is optionally substituted with one to two substituents selected from the group consisting of $CH_3$, or halo($C_1$)alkyl;
$R^2$ is —$CH_2$N($R^8$)($R^9$), wherein $R^8$ and $R^9$ are each independently selected from the group consisting of hydrogen and $CH_3$; and
$R^4$ is a (5-membered)heterocycloalkyl or a (5-membered) heteroaryl, wherein said (5-membered)heterocycloalkyl is 2-oxo-1,3-oxazolidin-3-yl, optionally substituted with 1 substituent selected from the group consisting of $CH_3$, $CHF_2$, and $CH_2F$, and said (5-membered)heteroaryl is imidazolyl, 1H-pyrazolyl, thiadiazolyl, or triazolyl, optionally substituted with 1 to 2 substituents independently selected from the group consisting of ($C_1$-$C_5$)alkyl, halo($C_1$-$C_6$)alkyl, and —($C_4$-$C_5$)cycloalkyl, wherein said ($C_1$-$C_5$)alkyl is optionally substituted with one hydroxy.

32. The compound of claim 28, or a pharmaceutically acceptable salt thereof, wherein:
$R^1$ is —N($R^6$)($R^7$);
$R^6$ and $R^7$ are each independently selected from the group consisting of hydrogen and ($C_1$-$C_3$)alkyl, or
$R^6$ and $R^7$ taken together with the nitrogen to which they are attached form pyrrolidin-1-yl, optionally substituted with 1 to 2 $CH_3$;
$R^2$ is —$CH_2$N($R^8$)($R^9$), wherein $R^8$ and $R^9$ are each independently selected from the group consisting of hydrogen and $CH_3$; and
$R^4$ is triazol-3-yl, substituted with 1 to 2 substituents independently selected from the group consisting of $CH_3$, $CH_3$—$CH_2$—, and $CH_3$—$CH_2$—$CH_2$—.

33. A compound or pharmaceutically acceptable salt thereof, wherein the compound is selected from the group consisting of
4-[(methylamino)methyl]-6-[methyl(propan-2-yl) amino]-2-[6-(4-propyl-4H-1,2,4-triazol-3-yl)pyridin-2-yl]-2,3-dihydro-1H-pyrrolo[3,4-c]pyridin-1-one;
4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one;
4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one;
4-[(methylamino)methyl]-6-[methyl(propan-2-yl) amino]-2-[6-(5-methyl-4-propyl-4H-1,2,4-triazol-3-yl) pyridin-2-yl]-2,3-dihydro-1H-pyrrolo[3,4-c]pyridin-1-one; and
4-(aminomethyl)-2-[6-(4-ethyl-5-methyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one.

34. The compound of claim 33, or pharmaceutically acceptable salt thereof, wherein the compound is 4-[(methylamino)methyl]-6-[methyl(propan-2-yl)amino]-2-[6-(4-propyl-4H-1,2,4-triazol-3-yl)pyridin-2-yl]-2,3-dihydro-1H-pyrrolo[3,4-c]pyridin-1-one.

35. The compound of claim 33, or pharmaceutically acceptable salt thereof, wherein the compound is 4-[(methylamino)methyl]-6-[(2R)-2-methylpyrrolidin-1-yl]-2-[6-(4-propyl-4H-1,2,4-triazol-3-yl)pyridin-2-yl]-2,3-dihydro-1H-pyrrolo[3,4-c]pyridin-1-one.

36. The compound of claim 33, or pharmaceutically acceptable salt thereof, wherein the compound is 4-[(methylamino)methyl]-2-[6-(5-methyl-4-propyl-4H-1,2,4-triazol-3-yl)pyridin-2-yl]-6-[(2R)-2-methylpyrrolidin-1-yl]-2,3-dihydro-1H-pyrrolo[3,4-c]pyridin-1-one.

37. The compound of claim 33, or pharmaceutically acceptable salt thereof, wherein the compound is 4-[(methylamino)methyl]-6-[methyl(propan-2-yl)amino]-2-[6-(5-methyl-4-propyl-4H-1,2,4-triazol-3-yl)pyridin-2-yl]-2,3-dihydro-1H-pyrrolo[3,4-c]pyridin-1-one.

38. The compound of claim 33, or pharmaceutically acceptable salt thereof, wherein the compound is 4-(aminomethyl)-2-[6-(4-ethyl-5-methyl-4H-1,2,4-triazol-3-yl)pyridin-2-yl]-6-[(2S)-2-methylpyrrolidin-1-yl]-2,3-dihydro-1H-pyrrolo[3,4-c]pyridin-1-one.

39. A pharmaceutical composition comprising a compound of claim 1, or a pharmaceutically acceptable salt thereof, and a pharmaceutically acceptable carrier or excipient.

40. A method for reversing, alleviating, or inhibiting abnormal cell growth in a mammal, comprising administering to the mammal a therapeutically effective amount of a compound of claim 1, or a pharmaceutically acceptable salt thereof.

* * * * *